United States Patent
Wong et al.

(10) Patent No.: US 7,566,718 B2
(45) Date of Patent: *Jul. 28, 2009

(54) AMINE-LINKED PYRIDYL AND PHENYL SUBSTITUTED PIPERAZINE-PIPERIDINES WITH CXCR3 ANTAGONIST ACTIVITY

(75) Inventors: Michael K. C. Wong, North Brunswick, NJ (US); Youheng Shu, Blue Bell, PA (US); Wensheng Yu, Edison, NJ (US); Stuart B. Rosenblum, West Orange, NJ (US); Joseph A. Kozlowski, Princeton, NJ (US); Brian F. McGuinness, Plainsboro, NJ (US); Yuefei Shao, Princeton, NJ (US); Douglas W. Hobbs, Yardley, PA (US)

(73) Assignees: Schering Corporation, Kenilworth, NJ (US); Pharmacopeia Drug Discovery, Inc., Princeton, NJ (US)

( * ) Notice: Subject to any disclaimer, the term of this patent is extended or adjusted under 35 U.S.C. 154(b) by 264 days.

This patent is subject to a terminal disclaimer.

(21) Appl. No.: 11/354,328

(22) Filed: Feb. 14, 2006

(65) Prior Publication Data

US 2006/0276480 A1 Dec. 7, 2006

Related U.S. Application Data

(60) Provisional application No. 60/653,339, filed on Feb. 16, 2005.

(51) Int. Cl.
*A61K 31/497* (2006.01)
*C07D 401/00* (2006.01)
*C07D 403/00* (2006.01)
*C07D 405/00* (2006.01)
*C07D 409/00* (2006.01)

(52) U.S. Cl. .................. 514/253.01; 544/360; 544/364

(58) Field of Classification Search ............ 514/253.01; 544/364
See application file for complete search history.

(56) References Cited

U.S. PATENT DOCUMENTS

2006/0217392 A1 * 9/2006 Anilkumar et al. ..... 514/253.01

FOREIGN PATENT DOCUMENTS

WO WO 2004/113323 * 12/2004
WO WO 2005/003127 1/2005

OTHER PUBLICATIONS

West, Anthony R., Solid State Chemistry and Its Applications, Wiley, New York, 1988, 358.*
Machii et al.: "Preparation of 5-cyanopyrimidine derivatives as anti-inflammatory agents", Database Caplus Chemical Abstracts Service, Columbus, Ohio—2pgs. XP002384407.
International Search Report for International Application No. PCT/US2006/005266, mailed Jun. 28, 2006—5pgs.

* cited by examiner

*Primary Examiner*—James O Wilson
*Assistant Examiner*—Erich A Leeser
(74) *Attorney, Agent, or Firm*—Krishna G. Banerjee; Palaiyur S. Kalyanaraman

(57) ABSTRACT

The present application discloses a compound, or enantiomers, stereoisomers, rotamers, tautomers, racemates or prodrug of said compound, or pharmaceutically acceptable salts, solvates or esters of said compound, or of said prodrug, said compound having the general structure shown in Formula 1:

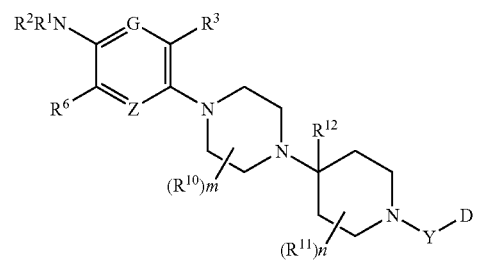

Formula 1 and the pharmaceutically acceptable salts, solvates and esters thereof. Also disclosed is a method of treating chemokine mediated diseases, such as, palliative therapy, curative therapy, prophylactic therapy of certain diseases and conditions such as inflammatory diseases (non-limiting example(s) include, psoriasis), autoimmune diseases (non-limiting example(s) include, rheumatoid arthritis, multiple sclerosis), graft rejection (non-limiting example(s) include, allograft rejection, xenograft rejection), infectious diseases (e.g. tuberculoid leprosy), fixed drug eruptions, cutaneous delayed-type hypersensitivity responses, ophthalmic inflammation, type I diabetes, viral meningitis and tumors using a compound of Formula 1.

41 Claims, No Drawings

AMINE-LINKED PYRIDYL AND PHENYL SUBSTITUTED PIPERAZINE-PIPERIDINES WITH CXCR3 ANTAGONIST ACTIVITY

REFERENCE TO PRIORITY APPLICATIONS

This Application claims the benefit of U.S. Provisional Application Ser. No. 60/653,339 filed Feb. 16, 2005, which is incorporated herein in its entirety by reference.

FIELD OF THE INVENTION

The present invention relates to novel pyridyl and phenyl substituted piperazine-piperidines with CXCR3 antagonist activity, pharmaceutical compositions containing one or more such antagonists, one or more such antagonists in combination with other compounds with chemokine activity, one or more such antagonists in combination with known immunosuppressive agents, non-limiting example(s) include Methotrexate, interferon, cyclosporin, FK-506 and FTY720, methods of preparing such antagonists and methods of using such antagonists to modulate CXCR3 activity. This invention also discloses methods of using such CXCR3 antagonists for the treatment (non-limiting examples include palliative, curative and prophylactic therapies) of diseases and conditions where CXCR3 has been implicated. Diseases and conditions where CXCR3 has been implicated include but are not limited to inflammatory conditions (psoriasis and inflammatory bowel disease), autoimmune disease (multiple sclerosis, rheumatoid arthritis), fixed drug eruptions, cutaneous delayed-type hypersensitivity responses, type I diabetes, viral meningitis and tuberculoid leprosy. CXCR3 antagonist activity has also been indicated as a therapy for tumor growth suppression as well as graft rejection (allograft and zenograft rejections for example).

BACKGROUND OF THE INVENTION

Chemokines constitute a family of small cytokines that are produced in inflammation and regulate leukocyte recruitment (Baggiolini, M. et al., *Adv. Immunol.*, 55: 97-179 (1994); Springer, T. A., *Annu. Rev. Physio.*, 57: 827-872 (1995); and Schall, T. J. and K. B. Bacon, *Curr. Opin. Immunol*, 6: 865-873 (1994)). Chemokines are capable of selectively inducing chemotaxis of the formed elements of the blood (other than red blood cells), including leukocytes such as neutrophils, monocytes, macrophages, eosinophils, basophils, mast cells, and lymphocytes, such as T cells and B cells. In addition to stimulating chemotaxis, other changes can be selectively induced by chemokines in responsive cells, including changes in cell shape, transient rises in the concentration of intracellular free calcium ions ($[Ca^{2+}]_i$), granule exocytosis, integrin upregulation, formation of bioactive lipids (e.g., leukotrienes) and respiratory burst, associated with leukocyte activation. Thus, the chemokines are early triggers of the inflammatory response, causing inflammatory mediator release, chemotaxis and extravasation to sites of infection or inflammation.

The chemokines are related in primary structure and share four conserved cysteines, which form disulfide bonds. Based upon this conserved cysteine motif, the family can be divided into distinct branches, including the C—X—C chemokines (β-chemokines) in which the first two conserved cysteines are separated by an intervening residue (e.g., IL-8, IP-10, Mig, I-TAC, PF4, ENA-78, GCP-2, GROα, GROβ, GROδ, NAP-2, NAP-4), and the C—C chemokines (β-chemokines), in which the first two conserved cysteines are adjacent residues (e.g., MIP-1α, MIP-1β, RANTES, MCP-1, MCP-2, MCP-3, 1-309) (Baggiolini, M. and Dahinden, C. A., *Immunology Today*, 15: 127-133 (1994)). Most CXC-chemokines attract neutrophil leukocytes. For example, the CXC-chemokines interleukin 8 (IL-8), GRO alpha (GROα), and neutrophil-activating peptide 2 (NAP-2) are potent chemoattractants and activators of neutrophils. The CXC-chemokines designated Mig (monokine induced by gamma interferon) and IP-10 (interferon-gamma inducible 10 kDa protein) are particularly active in inducing chemotaxis of activated peripheral blood lymphocytes. CC-chemokines are generally less selective and can attract a variety of leukocyte cell types, including monocytes, eosinophils, basophils, T lymphocytes and natural killer cells. CC-chemokines such as human monocyte chemotactic proteins 1-3 (MCP-1, MCP-2 and MCP-3), RANTES (Regulated on Activation, Normal T Expressed and Secreted), and the macrophage inflammatory proteins 1α and 1β (MIP-1α and MIP-1β) have been characterized as chemoattractants and activators of monocytes or lymphocytes, but do not appear to be chemoattractants for neutrophils.

A chemokine receptor that binds the CXC-chemokines IP-10 and Mig has been cloned and characterized (Loetscher, M. et al., *J. Exp. Med.*, 184: 963-969 (1996)). CXCR3 is a G-protein coupled receptor with seven transmembrane-spanning domains and has been shown to be restrictively expressed in activated T cells, preferentially human Th1 cells. On binding of the appropriate ligand, chemokine receptors transduce an intracellular signal through the associated G-protein resulting in a rapid increase in intracellular calcium concentration.

The receptor mediates $Ca^{2+}$ (calcium ion) mobilization and chemotaxis in response to IP-10 and Mig. CXCR3 expressing cells show no significant response to the CXC-chemokines IL-8, GROα, NAP-2, GCP-2 (granulocyte chemotactic protein-2), ENA78 (epithelial-derived neutrophil-activating peptide 78), PF4 (platelet factor 4), or the CC-chemokines MCP-1, MCP-2, MCP-3, MCP-4, MIP-1α, MIP-1β, RANTES, I309, eotaxin or lymphotactin. Moreover, a third ligand for CXCR3, I-TAC (Interferon-inducible T cell Alpha Chemoattractant), has also been found to bind to the receptor with high affinity and mediate functional responses (Cole, K. E. et al., *J. Exp. Med.*, 187: 2009-2021 (1998)).

The restricted expression of human CXCR3 in activated T lymphocytes and the ligand selectivity of CXCR3 are noteworthy. The human receptor is highly expressed in IL-2 activated T lymphocytes but was not detected in resting T lymphocytes, monocytes or granulocytes (Qin, S. et al., *J. Clin. Invest.*, 101: 746-754 (1998)). Additional studies of receptor distribution indicate that it is mostly $CD3^+$ cells that express CXCR3, including cells which are $CD95^+$, $CD45RO^+$, and $CD45RA^{low}$, a phenotype consistent with previous activation, although a proportion of $CD20^+$ (B) cells and $CD56^+$ (NK) cells also express this receptor. The selective expression in activated T lymphocytes is of interest, because other receptors for chemokines which have been reported to attract lymphocytes (e.g., MCP-1, MCP-2, MCP-3, MIP-1α, MIP-1β, RANTES) are also expressed by granulocytes, such as neutrophils, eosinophils, and basophils, as well as monocytes. These results suggest that the CXCR3 receptor is involved in the selective recruitment of effector T cells.

CXCR3 recognizes unusual CXC-chemokines, designated IP-10, Mig and I-TAC. Although these belong to the CXC-subfamily, in contrast to IL-8 and other CXC-chemokines which are potent chemoattractants for neutrophils, the primary targets of IP-10, Mig and I-TAC are lymphocytes, particularly effector cells such as activated or stimulated T lymphocytes and natural killer (NK) cells (Taub, D. D. et al., *J. Exp. Med.*, 177: 18090-1814 (1993); Taub, D. D. et al., *J. Immunol.*, 155: 3877-3888 (1995); Cole, K. E. et al., *J. Exp. Med.*, 187: 2009-2021 (1998)). (NK cells are large granular lymphocytes, which lack a specific T cell receptor for antigen recognition, but possess cytolytic activity against cells such as tumor cells and virally infected cells.) Consistently, IP-10, Mig and I-TAC lack the ELR motif, an essential binding epitope in those CXC-chemokines that efficiently induce neutrophil chemotaxis (Clark-Lewis, I. et al., *J. Biol. Chem.* 266: 23128-23134 (1991); Hebert, C. A. et al., *J. Biol. Chem.*, 266: 18989-18994 (1991); and Clark-Lewis, 1. et al., *Proc. Natl. Acad. Sci. USA*, 90: 3574-3577 (1993)). In addition, both recombinant human Mig and recombinant human IP-10 have been reported to induce calcium flux in tumor infiltrating lymphocytes (TIL) (Liao, F. et al., *J. Exp. Med*, 182: 1301-1314 (1995)). While IP-10 has been reported to induce chemotaxis of monocytes in vitro (Taub, D. D. et al., *J. Exp. Med.*, 177: 1809-1814 (1993), the receptor responsible has not been identified), human Mig and I-TAC appear highly selective, and do not show such an effect (Liao, F. et al., *J. Exp. Med.*, 182: 1301-1314 (1995); Cole, K. E. et al., *J. Exp. Med.*, 187: 2009-2021 (1998)). IP-10 expression is induced in a variety of tissues in inflammatory conditions such as psoriasis, fixed drug eruptions, cutaneous delayed-type hypersensitivity responses and tuberculoid leprosy as well as tumors and in animal model studies, for example, experimental glomerulonephritis, and experimental allergic encephalomyelitis. IP-10 has a potent in vivo antitumor effect that is T cell dependent, is reported to be an inhibitor of angiogenesis in vivo and can induce chemotaxis and degranulation of NK cells in vitro, suggesting a role as a mediator of NK cell recruitment and degranulation (in tumor cell destruction, for example) (Luster, A. D. and P. Leder, *J. Exp. Med.*, 178: 1057-1065 (1993); Luster, A. D. et al., *J. Exp. Med.* 182: 219-231 (1995); Angiolillo, A. L. et al., *J. Exp. Med.*, 182: 155-162 (1995); Taub, D. D. et al., *J. Immunol.*, 155: 3877-3888 (1995)). The expression patterns of IP-10, Mig and I-TAC are also distinct from that of other CXC chemokines in that expression of each is induced by interferon-gamma (IFNδ), while the expression of IL-8 is down-regulated by IFNδ (Luster, A. D. et al., *Nature*, 315: 672-676 (1985); Farber, J. M., *Proc. Natl. Acad. Sci. USA*, 87: 5238-5242 (1990); Farber, J. M., *Biochem. Biophys. Res. Commun.*, 192 (1): 223-230 (1993), Liao, F. et al., *J. Exp. Med.*, 182: 1301-1314 (1995); Seitz, M. et al., *J. Clin. Invest.*, 87: 463-469 (1991); Galy, A. H. M. and H. Spits, *J. Immunol.*, 147: 3823-3830 (1991); Cole, K. E. et al., *J. Exp. Med.*, 187: 2009-2021 (1998)).

Chemokines are recognized as the long-sought mediators for the recruitment of lymphocytes. Several CC-chemokines were found to elicit lymphocyte chemotaxis (Loetscher, P. et al., *FASEB J.*, 8: 1055-1060 (1994)), however, they are also active on granulocytes and monocytes (Uguccioni, M. et al., *Eur. J. Immunol.*, 25: 64-68 (1995); Baggiolini, M. and C. A. Dahinden, *Immunol. Today*, 15: 127-133 (1994)). The situation is different for IP-10, Mig and I-TAC, which are selective in their action on lymphocytes, including activated T lymphocytes and NK cells, and which bind CXCR3, a receptor which does not recognize numerous other chemokines and which displays a selective pattern of expression.

In view of these observations, it is reasonable to conclude that the formation of the characteristic infiltrates in inflammatory lesions, such as, for example, delayed-type hypersensitivity lesions, sites of viral infection and certain tumors is a process mediated via CXCR3 and regulated by CXCR3 expression. Lymphocytes, particularly T lymphocytes, bearing a CXCR3 receptor as a result of activation can be recruited into inflammatory lesions, sites of infection and/or tumors by IP-10, Mig and/or I-TAC, which can be induced locally by interferon-gamma. Thus, CXCR3 plays a role in the selective recruitment of lymphocytes, particularly effector cells such as activated or stimulated T lymphocytes. Accordingly, activated and effector T cells have been implicated in a number of disease states such as graft-rejection, inflammation, rheumatoid arthritis, multiple sclerosis, inflammatory bowel disease (such as Crohn's disease and ulcerative colitis) and psoriasis. Thus, CXCR3 represents a promising target for the development of novel therapeutics.

Reference is made to PCT Publication No. WO 93/10091 (Applicant: Glaxo Group Limited, Published May 27, 1993) which discloses piperidine acetic acid derivatives as inhibitors of fibrinogen-dependent blood platelet aggregation having the formula:

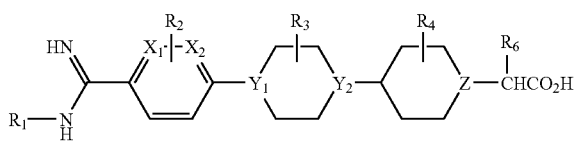

An illustrative compound of that series is:

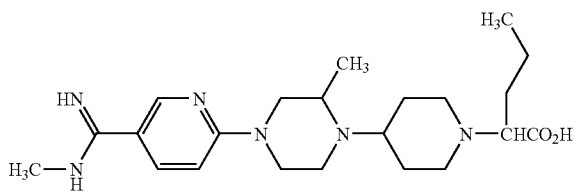

Reference is also made to PCT Publication No. WO 9/20606 (Applicant: J. Uriach & CIA. S.A., Published Apr. 29, 1999) which discloses piperazines as platelet aggregation inhibitors having the formula:

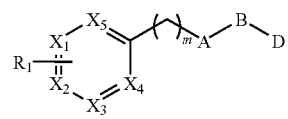

Reference is also made to US Patent Application No. US 2002/0018776 A1 (Applicant: Hancock, et al. Published Feb. 14, 2002) which discloses methods of treating graft rejection.

Reference is also made to PCT Publication No. WO 03/098185 A2 (Applicant: Renovar, Inc., Published Nov. 27, 2003) which discloses methods of diagnosing and predicting organ transplant rejection by detection of chemokines, for example, CXCR3 and CCL chemokines in urine.

Reference is also made to PCT Publication No. WO 03/082335 A1 (Applicant: Sumitomo Pharmaceuticals Co. Ltd., Published Oct. 9, 2003) which discloses methods of screening a CXCR3 ligand and methods of diagnosing type 2 diabetes by detecting the expression dose of a CXCR3 ligand in a biological sample.

Reference is also made to PCT Publication No. WO 02/085861 (Applicant: Millennium Pharmaceuticals, Inc.

Published Oct. 31, 2002) which discloses imidazolidine compounds and their use as CXCR3 antagonists having the formula:

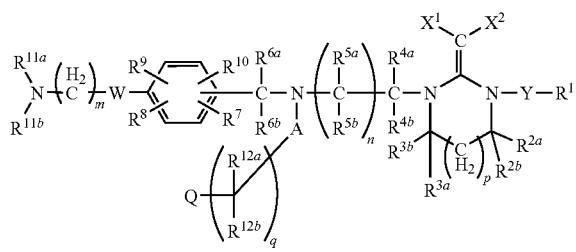

An illustrative compound of that series is:

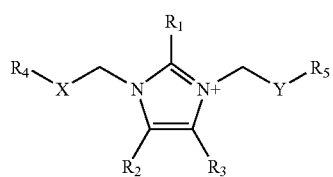

Reference is also made to PCT Publication No. WO 03/101970 (Applicant: SmithKline Beecham Corporation, Published Dec. 11, 2003) which discloses imidazolium compounds and their use as CXCR3 antagonists having the formula:

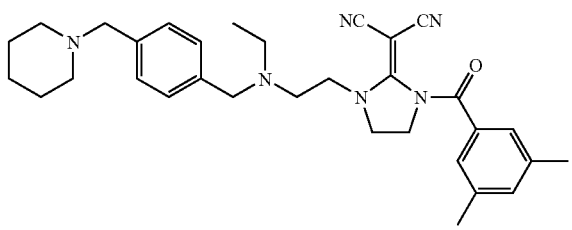

An illustrative example of that series is:

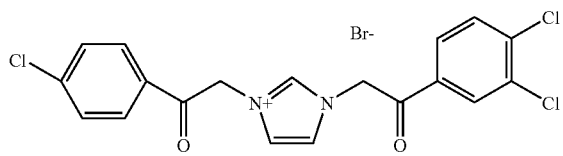

Reference is also made to US Patent Application No. US 2003/0055054 A1 (Applicant: Medina et al, *Published Mar. 20, 2003*) which discloses compounds having the formula:

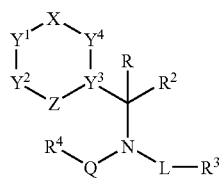

An illustrative compound of that series is:

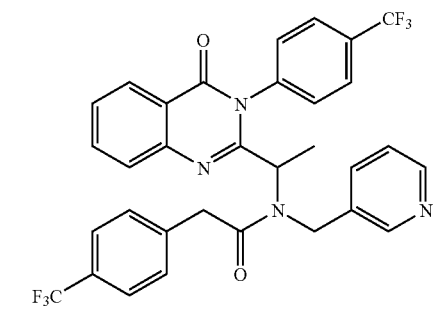

Reference is also made to U.S. Pat. No. 6,124,319 (Applicant: MacCoss et al., issued Sep. 6, 2000) which discloses compounds useful as chemokine receptor modulators having the formula:

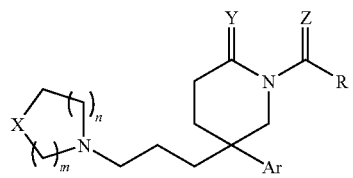

Reference is also made to PCT Publication WO 03/070242 A1 (Applicant: CELLTECH R&D limited, Published Aug. 28, 2003) which discloses compounds useful as "chemokine receptor inhibitors for the treatment of inflammatory diseases" having the formula:

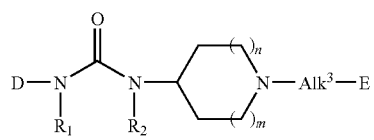

There is a need for compounds that are capable of modulating CXCR3 activity. For example, there is a need for new treatments and therapies for diseases and conditions associated with CXCR3 such as inflammatory conditions (psoriasis and inflammatory bowel disease), autoimmune disease (multiple sclerosis, rheumatoid arthritis) and graft rejection (allograft and zenograft rejections for example) as well as infectious diseases, cancers and tumors, fixed drug eruptions, cutaneous delayed-type hypersensitivity responses, type I diabetes, viral meningitis and tuberculoid leprosy.

There is a need for methods of treatment or prevention or amelioration of one or more symptoms of diseases and conditions associated with CXCR3. There is a need for methods for modulating CXCR3 activity using the compounds provided herein.

SUMMARY OF THE INVENTION

In its many embodiments, the invention provides novel compounds of the Formula 1:

Formula 1

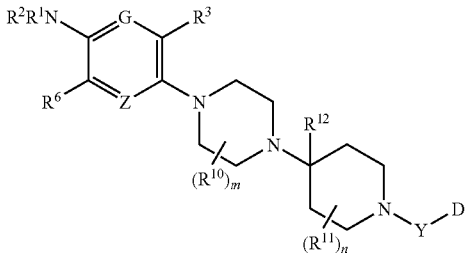

or pharmaceutically acceptable salts, solvates or esters thereof wherein:

Z is N, $C(R^{29})$, NO or NOH;

G is N, $C(R^4)$, NO or NOH;

$R^1$ and $R^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N≡CH, =NCN, —$(CH_2)_qOH$, —$(CH_2)_qOR^{31}$, —$(CH_2)_qNH_2$, —$(CH_2)_qNHR^{31}$, —$(CH_2)_qN(R^{31})_2$, —$(CH_2)_qC(=O)NHR^{31}$, —$(CH_2)_qSO_2R^{31}$, —$(CH_2)_qNHSO_2R^{31}$, —$(CH_2)_qSO_2NHR^{31}$, —C(=S)N(H)alkyl, —N(H)—S(O)$_2$-alkyl, —N(H)C(=O)N(H)-alkyl, —S(O)$_2$alkyl, —S(O)$_2$NH$_2$, —S(O)$_2$N(H)alkyl, —S(O)$_2$N(alkyl)$_2$, —S(O)$_2$aryl, —S(O)$_2$heteroaryl, —S(O)$_2$heterocyclyl, —C(=S)N(H)cycloalkyl, —C(=O)N(H)NH$_2$, —C(=O)alkyl, —C(=O)heteroaryl, —C(=O)heterocyclyl, -heteroaryl, heterocyclyl, and heterocyclenyl; or alternatively the N taken together with the $R^1$ and $R^2$ forms a heterocyyl, heteroaryl or —N=C(NH$_2$)$_2$;

$R^3$, $R^4$, $R^6$ and $R^{29}$ moieties can be the same or different, each being independently selected from the group consisting of H, alkyl, alkylaryl, aralkyl, —CN, CF$_3$, haloalkyl, cycloalkyl, halogen, hydroxyalkyl, —N=CH—$(R^{31})$, —C(=O)N(R$^{30}$)$_2$, —N(R$^{30}$)$_2$, —OR$^{30}$, —SO$_2$(R$^{31}$), —N(R$^{30}$)C(=O)N(R$^{30}$)$_2$ and —N(R$^{30}$)C(=O)R$^{31}$;

the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(=O)N(R$^{30}$)$_2$, —(CH$_2$)$_q$OH, —(CH$_2$)$_q$OR$^{31}$—(CH$_2$)$_q$NHR$^{31}$, —(CH$_2$)$_q$N(R$^{31}$)$_2$, —OR$^{30}$, halogen, =O, and —C(=O)R$^{31}$;

the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, CO$_2$H, —(CH$_2$)$_q$OH, —(CH$_2$)$_q$OR$^{31}$—(CH$_2$)$_q$NHR$^{31}$—(CH$_2$)$_q$N(R$^{31}$)$_2$, —OR$^{30}$, halogen, =O, and —C(=O)R$^{31}$;

the $R^{12}$ moieties can be the same or different, each being independently selected from the group consisting of H, alkyl, —CN, —C(=O)N(R$^{30}$)$_2$, (CH$_2$)$_q$OH, —(CH$_2$)$_q$OR$^{31}$—(CH$_2$)$_q$NHR$^{31}$, —(CH$_2$)$_q$N(R$^{31}$)$_2$, and —S(O$_2$)R$^{31}$;

D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$; or alternatively two R$^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 R$^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$—C(=NR$^{30}$)NHR$^{30}$, —C(=NOH)N(R$^{30}$)$_2$, —C(=NOR$^{31}$)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)SO$_2$(R$^{31}$), —N(R$^{30}$)C(=O)N(R$^{30}$)$_2$, —N(R$^{30}$)SO$_2$(R$^{31}$), —N(R$^{30}$)S(O)$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$;

Y is selected from the group consisting of —(CR$^{13}$R$^{13}$)$_r$—, —CHR$^{13}$C(=O)—, —(CHR$^{13}$)$_r$O—, —(CHR$^{13}$)$_r$N(R$^{30}$)—, —C(=O)—, —C(=NR$^{30}$)—, —C(=N—OR$^{30}$)—, —CH(C(=O)NHR$^{30}$)—, CH-heteroaryl-, —C(R$^{13}$R$^{13}$)$_r$C(R$^{13}$)=C(R$^{13}$)—, —(CHR$^{13}$)$_r$C(=O)— and —(CHR$^{13}$)$_r$N(H)C(=O)—; or alternatively Y is cycloalkyl, heterocyclenyl, or heterocyclyl wherein the cycloalkyl, heterocyclenyl, or heterocyclyl is fused with ring D;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —CO$_2$H, —C(=O)R$^{30}$, —C(=O)N(R$^{30}$)$_2$, —(CHR$^{30}$)$_q$OH, —(CHR$^{30}$)$_q$OR$^{31}$, —(CHR$^{30}$)$_q$NH$_2$, —(CH R$^{30}$)$_q$NHR$^{31}$, —(CH$_2$)$_q$C(=O)NHR$^{30}$, —(CH$_2$)$_q$SO$_2$R$^{31}$, —(CH$_2$)$_q$NSO$_2$R$^{31}$, —(CH$_2$)$_q$SO$_2$NHR$^{31}$, —NH$_2$, —N(R$^{30}$)$_2$, —N(R$^{30}$)C(=O)N(R$^{30}$)$_2$, —N(R$^{30}$)SO$_2$(R$^{31}$), —OH, OR$^{30}$, —SO$_2$N(R$^{30}$)$_2$, and —SO$_2$(R$^{31}$);

the $R^{30}$ moieties can be the same or different, each being independently selected from the group consisting of H, alkyl, alkylaryl, aryl, aralkyl, cycloalkyl, CN, —(CH$_2$)$_q$OH, —(CH$_2$)$_q$Oalkyl, —(CH$_2$)$_q$Oalkylaryl, —(CH$_2$)$_q$Oaryl, —(CH$_2$)$_q$Oaralkyl, —(CH$_2$)$_q$Ocycloalkyl, —(CH$_2$)$_q$NH$_2$, —(CH$_2$)$_q$NHalkyl, —(CH$_2$)$_q$N(alkyl)$_2$, —(CH$_2$)$_q$NHalkylaryl, —(CH₂)qNHaryl, —(CH₂)qNHaralkyl, —(CH₂)qNHcycloalkyl, —(CH₂)qC(=O)NHalkyl, —(CH₂)qC(=O)N(alkyl)₂, —(CH₂)qC(=O)NHalkylaryl, —(CH₂)qC(=O)NHaryl, —(CH₂)qC(=O)NHaralkyl, —(CH₂)qC(=O)NHcycloalkyl, —(CH₂)qSO₂alkyl, —(CH₂)qSO₂alkylaryl, —(CH₂)qSO₂aryl, —(CH₂)qSO₂aralkyl, —(CH₂)qSO₂cycloalkyl, —(CH₂)qNSO₂alkyl, —(CH₂)q NSO₂alkylaryl, —(CH₂)qNSO₂aryl, —(CH₂)q NSO₂aralkyl, —(CH₂)qNSO₂cycloalkyl, —(CH₂)q SO₂NHalkyl, —(CH₂)q SO₂NHalkylaryl, —(CH₂)q SO₂NHaryl, —(CH₂)q SO₂NHaralkyl, —(CH₂)q SO₂NHcycloalkyl, heterocyclenyl, heterocyclyl, and heteroaryl;

the R³¹ moieties can be the same or different, each being independently selected from the group consisting of alkyl, alkylaryl, aryl, aralkyl, cycloalkyl, —(CH₂)qOH, —(CH₂)q Oalkyl, —(CH₂)qOalkylaryl, —(CH₂)qOaryl, —(CH₂)q Oaralkyl, —(CH₂)qOcycloalkyl, —(CH₂)qNH₂, —(CH₂)q NHalkyl, —(CH₂)qN(alkyl)₂, —(CH₂)qNHalkylaryl, —(CH₂)qNHaryl, —(CH₂)qNHaralkyl, —(CH₂)qNHcycloalkyl, —(CH₂)qC(=O)NHalkyl, —(CH₂)qC(=O)N(alkyl)₂, —(CH₂)qC(=O)NHalkylaryl, —(CH₂)qC(=O)NHaryl, —(CH₂)qC(=O)NHaralkyl, —(CH₂)qC(=O)NHcycloalkyl, —(CH₂)qSO₂alkyl, —(CH₂)qSO₂alkylaryl, —(CH₂)qSO₂aryl, —(CH₂)qSO₂aralkyl, —(CH₂)q SO₂cycloalkyl, —(CH₂)qNSO₂alkyl, —(CH₂)q NSO₂alkylaryl, —(CH₂)qNSO₂aryl, —(CH₂)q NSO₂aralkyl, —(CH₂)qNSO₂cycloalkyl, —(CH₂)q SO₂NHalkyl, —(CH₂)q SO₂NHalkylaryl, —(CH₂)q SO₂NHaryl, —(CH₂)q SO₂NHaralkyl, —(CH₂)q SO₂NHcycloalkyl, heterocyclenyl, heterocyclyl, and heteroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

A further feature of the invention is a pharmaceutical composition containing as active ingredient at least one compound of Formula 1 together with at least one pharmaceutically acceptable carrier or excipient.

The invention provides methods of preparing compounds of Formula 1, as well as methods for treating diseases, for example, treatment (e.g., palliative therapy, curative therapy, prophylactic therapy) of certain diseases and conditions e.g., inflammatory diseases (e.g., psoriasis, inflammatory bowel disease), autoimmune diseases (e.g., rheumatoid arthritis, multiple sclerosis), graft rejection (e.g., allograft rejection, xenograft rejection), ophthalmic inflammation or dry eye, infectious diseases and tumors. The invention provides a method of treating a CXCR3 chemokine mediated disease in a patient in need of such treatment comprising administering to the patient a therapeutically effective amount of at least one compound of Formula 1, or a pharmaceutically acceptable salt, solvate or ester thereof.

The invention provides methods of treating diseases, for example, treatment (e.g., palliative therapy, curative therapy, prophylactic therapy) of certain diseases and conditions such as inflammatory diseases (e.g., psoriasis, inflammatory bowel disease), autoimmune diseases (e.g., rheumatoid arthritis, multiple sclerosis), graft rejection (e.g., allograft rejection, xenograft rejection), infectious diseases as well as cancers and tumors, fixed drug eruptions, cutaneous delayed-type hypersensitivity responses, ophthalmic inflammation or dry eye, type I diabetes, viral meningitis and tuberculoid leprosy comprising administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics.

The invention also provides a method of modulating (inhibiting or promoting) an inflammatory response in an individual in need of such therapy. The method comprises administering a therapeutically effective amount of a compound (e.g., small organic molecule) which inhibits or promotes mammalian CXCR3 function in an individual in need thereof. Also disclosed is a method of inhibiting or blocking T-cell mediated chemotaxis in a patient in need of such treatment comprising administering to the patient a therapeutically effective amount of a compound of Formula 1 or a pharmaceutically acceptable salt, solvate or ester thereof.

Also disclosed is a method of treating inflammatory bowel disease (such Crohn's disease, ulcerative colitis) in a patient in need of such treatment comprising administering to the patient a therapeutically effective amount of at least one compound of Formula 1, or a pharmaceutically acceptable salt, solvate or ester thereof.

Also disclosed is a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Also disclosed is a method of treating graft rejection in a patient in need of such treatment comprising administering to the patient a therapeutically effective amount of at least one compound of Formula 1, or a pharmaceutically acceptable salt, solvate or ester thereof.

Also disclosed is a method of treating graft rejection in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

Also disclosed is a method of treating multiple sclerosis in a patient in need of such treatment the method comprising administering to the patient a therapeutically effective amount of: (a) a therapeutically effective amount of at least one compound of Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Also disclosed is a method of treating rheumatoid arthritis in a patient in need of such treatment the method comprising administering to the patient a therapeutically effective amount of: (a) at least one compound of Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Also disclosed is a method of treating psoriasis in a patient in need of such treatment the method comprising administering to the patient a therapeutically effective amount of: a) at least one compound of Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Also disclosed is a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Also disclosed is a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

The invention also provides a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

DETAILED DESCRIPTION OF THE INVENTION

The terms used herein have their ordinary meaning and the meaning of such terms is independent at each occurrence thereof. That notwithstanding and except where stated otherwise, the following definitions apply throughout the specification and claims. Chemical names, common names, and chemical structures may be used interchangeably to describe the same structure. These definitions apply regardless of whether a term is used by itself or in combination with other terms, unless otherwise indicated. Hence, the definition of "alkyl" applies to "alkyl" as well as the "alkyl" portions of "hydroxyalkyl," "haloalkyl," "alkoxy," etc.

As used above, and throughout the specification, the following terms, unless otherwise indicated, shall be understood to have the following meanings:

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. The alkenyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl, amino, aminosulfonyl, halo, carboxyl, carboxyalkyl (non-limiting example(s) include ester), alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), —NHC(=O)alkyl, urea (e.g. —NH(C=O)NH$_2$, —NH(C=O)NH(alkyl), —NH(C=O)NH(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, alkylthiocarboxy, —S(O)$_2$ alkyl, —S(O)$_2$aryl, —OS(O)$_2$alkyl, —OS(O)$_2$aryl, sulfonyl urea (non-limiting example(s) include NHC(=S)NHalkyl). Non-limiting examples of suitable alkenyl groups include ethenyl, propenyl, n-butenyl, 3-methylbut-2-enyl, n-pentenyl, octenyl and decenyl.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl group may be substituted by one or more substituents which may be the same or different, each substituent being independently selected from the group consisting of alkyl, alkenyl, alkynyl, alkoxyl, aryl, aryloxy, cycloalkyl, cycloalkenyl, cyano, heteroaryl, heterocyclyl, heterocyclenyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), alkoxycarbonyl, hydroxyalkyl, carbonyl (non-limiting example(s) include ketone), —C(=O)heterocyclyl, formyl, carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl)), —NHC(=O)alkyl, amidinyl, hydrazidyl, hydroxamate, —NHC(=O)H, —NHC(=O)alkyl, urea (non-limiting example(s) include —NH(C=O)NH$_2$, —NH(C=O)NH (alkyl), —NH(C=O)N(alkyl)$_2$, —NH(C=O)NH(heteroaryl), —NH(C=O)NH(heterocyclyl)), guanidinyl, —NHC(=NCN)NH$_2$, —NHC(=NCN)N(alkyl)$_2$, carbamoyl (i.e., —CO$_2$NH$_2$), —NHC(=O)Oalkyl, —CO$_2$N(alkyl)$_2$, —NHC(=O)NH—S(O)$_2$alkyl, —NHC(=O)N (alkyl)-S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthio, alkylthiocarboxy, —S(O)alkyl, —S(O)$_2$alkyl, —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$. Non-limiting examples of suitable alkyl groups include methyl, ethyl, n-propyl, isopropyl, n-butyl, t-butyl, n-pentyl, heptyl, nonyl, decyl, fluoromethyl, trifluoromethyl and cyclopropylmethyl.

"Alkylheteroaryl" means an alkyl-heteroaryl-group wherein the alkyl is as previously described and the bond to the parent moiety is through the heteroaryl group.

"Alkylamino" means an —NH$_2$ or —NH$_3$+group in which one or more of the hydrogen atoms on the nitrogen is replaced by an alkyl group as defined above. The bond to the parent is through the nitrogen.

"Alkylaryl" means an alkyl-aryl-group in which the alkyl and aryl are as described herein. Preferred alkylaryls comprise a lower alkyl group. Non-limiting examples of suitable alkylaryl groups include o-tolyl, p-tolyl and xylyl. The bond to the parent moiety is through the aryl.

"Alkylthio" means an alkyl-S— group in which the alkyl group is as described herein. Non-limiting examples of suitable alkylthio groups include methylthio, ethylthio, i-propylthio and heptylthio. The bond to the parent moiety is through the sulfur.

"Alkylthiocarboxy" means an alkyl-S—C(=O)O— group. Preferred groups are those in which the alkyl group is lower alkyl. The bond to the parent moiety is through the carboxy.

"Alkylsulfonyl" means an alkyl-S(O)$_2$— group. Preferred groups are those in which the alkyl group is lower alkyl. The bond to the parent moiety is through the sulfonyl.

"Alkylsulfinyl" means an alkyl-S(O)— group. Preferred groups are those in which the alkyl group is lower alkyl. The bond to the parent moiety is through the sulfinyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl, 3-methylbutynyl, n-pentynyl, and decynyl. The alkynyl group may be substituted by one or more substituents which may be the same or different, each substituent being independently selected from the group consisting of alkyl, alkoxyl, aryl, aryloxy, cycloalkyl, cycloalkenyl, cyano, heteroaryl, heterocyclyl, heterocyclenyl, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, alkoxycarbonyl, hydroxyalkyl, carbonyl (non-limiting example(s) include ketone), —C(=O)heterocyclyl, carboxamido (i.e. amido, —C(=O)NH$_2$, —C(=O)N(alkyl)$_2$, —C(=O)NH(alkyl), —C(=O)N(cycloalkyl)$_2$, —C(=O)NH(cycloalkyl)), alkylC(=O)NH—, —NHC(=O)alkyl), urea (e.g. —NH (C=O)NH$_2$), —NH(C=O)NH(alkyl), —NH(C=O)NH (alkyl)$_2$, —NH(C=O)NH(heteroaryl), —NH(C=O)NH (heterocyclyl), —S(O)$_2$alkyl, and —S(O)$_2$aryl.

"Alkoxy" means an alkyl-O— group in which the alkyl group is as previously described. Non-limiting examples of suitable alkoxy groups include methoxy, ethoxy, n-propoxy, isopropoxy, n-butoxy, heptoxy and methylhydroxy. The bond to the parent moiety is through the ether oxygen.

"Alkoxycarbonyl" means an alkyl-O—C(=O)— group. Non-limiting examples of suitable alkoxycarbonyl groups include methoxycarbonyl and ethoxycarbonyl. The bond to the parent moiety is through the carbonyl.

"Aminoalkyl" means an amine-alkyl-group in which alkyl is as previously defined. Preferred aminoalkyls contain lower alkyl. Non-limiting examples of suitable aminoalkyl groups include aminomethyl and 2-Dimethlylamino-2-ethyl. The bond to the parent moiety is through the alkyl.

"Amidinyl" means —C(=NR)NHR group. The R groups are defined as H, alkyl, alkylaryl, heteroaryl, hydroxyl, alkoxy, amino, ester, CN, —NHSO$_2$alkyl, —NHSO$_2$Aryl, —NHC(=O)NHalkyl, and —NHalkyl. The bond to the parent moiety is through the carbon.

"Aralkyl" or "arylalkyl" means an aryl-alkyl-group in which the aryl and alkyl are as previously described. Preferred aralkyls comprise a lower alkyl group attached to the aryl group. Non-limiting examples of suitable aralkyl groups include phenymethylene, 2-phenethyl and naphthalenylmethyl. The bond to the parent moiety is through the alkyl.

"Aralkenyl" means an aryl-alkenyl-group in which the aryl and alkenyl are as previously described. Preferred aralkenyls contain a lower alkenyl group. Non-limiting examples of suitable aralkenyl groups include 2-phenethenyl and 2-naphthylethenyl. The bond to the parent moiety is through the alkenyl.

"Aralkylthio" means an aralkyl-S— group in which the aralkyl group is as previously described. Non-limiting example of a suitable aralkylthio group is benzylthio. The bond to the parent moiety is through the sulfur.

"Aralkoxy" means an aralkyl-O— group in which the aralkyl group is as described above. The bond to the parent moiety is through the oxygen group.

"Aralkoxycarbonyl" means an aralkyl-O—C(=O)— group. Non-limiting example of a suitable aralkoxycarbonyl group is benzyloxycarbonyl. The bond to the parent moiety is through the carbonyl.

"Aroyl" means an aryl-C(=O)— group in which the aryl group is as previously described. The bond to the parent moiety is through the carbonyl. Non-limiting examples of suitable groups include benzoyl and 1- and 2-naphthoyl.

"Aryl" (sometimes abbreviated "Ar") means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Aryloxy" means an aryl-O— group in which the aryl group is as previously described. Non-limiting examples of suitable aryloxy groups include phenoxy and naphthoxy. The bond to the parent moiety is through the ether-oxygen.

"Aryloxycarbonyl" means an aryl-O—C(=O)— group. Non-limiting examples of suitable aryloxycarbonyl groups include phenoxycarbonyl and naphthoxycarbonyl. The bond to the parent moiety is through the carbonyl.

"Arylsulfonyl" means an aryl-S(O)$_2$— group. The bond to the parent moiety is through the sulfonyl.

"Arylsulfinyl" means an aryl-S(O)— group. The bond to the parent moiety is through the sulfinyl.

"Arylthio" means an aryl-S— group in which the aryl group is as previously described. Non-limiting examples of suitable arylthio groups include phenylthio and naphthylthio. The bond to the parent moiety is through the sulfur.

"Carboxyalkyl" means an alkyl-C(=O)O— group. The bond to the parent moiety is through the carboxy.

"Carboxamido" means —C(=O)NRR wherein R is H, alkyl, amino, aryl, cycloalkyl, heterocyclenyl, heteroaryl and carboxamido. The bond to the parent moiety is through the carboxy.

Carbamates and urea substituents refer to groups with oxygens and nitrogens respectively adjacent an amide; representative carbamate and urea substituents include the following:

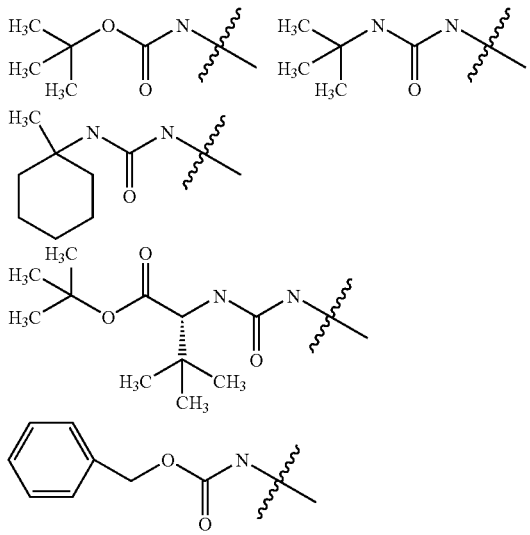

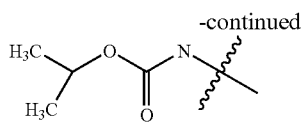

-continued

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples can include bicyclic cycloalkyls such as bicycloheptane. Non-limiting examples of suitable multicyclic cycloalkyls include 1-decalin, norbornyl, adamantyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cycloheptenyl, and the like. Non-limiting example of a suitable multicyclic cycloalkenyl is norbornylenyl. The term "cycloalkenyl" additionally means moieties such as cyclobutenedione, cyclopentenone, cyclopentenedione and the like.

"Halogen" (or halo) means fluorine, chlorine, bromine, or iodine. Preferred are fluorine, chlorine and bromine.

"Haloalkyl" means an alkyl as defined above wherein one or more hydrogen atoms on the alkyl is replaced by a halo group defined above.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. The nitrogen or sulfur atom of the heteroaryl can be optionally oxidized to the corresponding N-oxide, S-oxide or S,S-dioxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, oxazolidinyl, imidazolidinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, dihydro-2-pyrrolinyl, dihydro-3-pyrrolinyl, dihydro-2-imidazolinyl, dihydro-2-pyrazolinyl, dihydro-4,5-trizolyl and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include thiophenyl, dihydrothiophenyl, dihydrothiopyranyl, and the like.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, 2-(furan-3-yl)ethyl and quinolin-(3-yl)methyl. The bond to the parent moiety is through the alkyl.

"Heteroaralkenyl" means an heteroaryl-alkenyl-group in which the heteroaryl and alkenyl are as previously described. Preferred heteroaralkenyls contain a lower alkenyl group. Non-limiting examples of suitable heteroaralkenyl groups include 2-(pyrid-3-yl)ethenyl and 2-(quinolin-3-yl)ethenyl. The bond to the parent moiety is through the alkenyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl. The bond to the parent moiety is through the alkyl.

"Hydroxamate" means an alkyl-C(=O)NH—O— group. The bond to the parent moiety is through the oxygen group.

"Spiroalkyl" means an alkylene group wherein two carbon atoms of an alkyl group are attached to one carbon atom of a parent molecular group thereby forming a carbocyclic or heterocyclic ring of three to eleven atoms. Representative structures include examples such as:

The spiroalkyl groups of this invention:

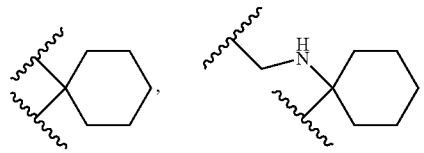

can be optionally substituted by one or more ring system substituents, wherein "ring system substituent" is as defined herein.

"Ring system substituent" means a substituent attached to an aromatic or non-aromatic ring system which, for example, replaces an available hydrogen on the ring system. Ring system substituents may be the same or different, each being independently selected from the group consisting of H, alkyl, alkenyl, alkynyl, alkoxyl, aryl, aroyl, aryloxy, cycloalkyl, cycloalkenyl, heteroaryl, heterocyclyl, heterocyclenyl, alkylaryl, alkylheteroaryl, aralkyl, aralkenyl, aralkoxy, aralkoxycarbonyl, amino, —NH(alkyl), —N(alkyl)$_2$, —NH(cycloalkyl), —N(cycloalkyl)$_2$, —NH(aryl), —N(aryl)$_2$, —NH(heteroaryl), —N(heteroaryl)$_2$, —NH(heterocyclyl), N(heterocyclyl)$_2$, halo, hydroxy, carboxyl, carboxyalkyl (non-limiting example(s) include ester), cyano, alkoxycarbonyl, hydroxyalkyl, carbonyl (non-limiting example(s) include ketone), —C(=O)heterocyclyl, formyl (non-limiting example(s) include aldehyde), carboxamido (i.e. amido, —C(=O)NH$_2$), —C(=O)N(alkyl)$_2$, —C(=O)NH(alkyl), —C(=O)N(cycloalkyl)$_2$, —C(=O)NH(cycloalkyl), alkylC(=O)NH—, -amidino, hydrazido, hydroxamate, —NHC(=O)H, —NHC(=O)alkyl, urea (e.g. —NH(C=O)NH$_2$), —NH(C=O)NH(alkyl), —NH(C=O)NH(alkyl)$_2$, —NH(C=O)NH(heteroaryl), —NH(C=O)NH(heterocyclyl), guanidinyl, —NHC(=NCN)NH$_2$, —NHC(=NCN)N(alkyl)$_2$, carbamoyl (i.e. —CO$_2$NH$_2$), NHC(=O)Oalkyl, —CO$_2$N(alkyl)$_2$, —NHC(=O))NH—S(O)$_2$alkyl, —NHC(=O)N(alkyl)$_2$—S(O)$_2$alkyl, —NH—S(O)$_2$alkyl, —NH—S(O)$_2$heteroaryl, —N(alkyl)-S(O)$_2$alkyl, —NH—S(O)$_2$aryl, —N(alkyl)-S(O)$_2$aryl, —NH—S(O)$_2$NH$_2$, —NH—S(O)$_2$NHalkyl, —NH—S(O)$_2$N(alkyl)$_2$, thio, alkylthiocarboxy, —S(O)$_2$alkyl —S(O)$_2$aryl, —OS(O)$_2$alkyl, —OS(O)$_2$aryl, sulfonyl urea (non-limiting example(s) include —NHC(=S)NHalkyl) and OSi(alkyl)$_3$.

"Ring system substituent" also means a cyclic ring of 3 to 7 ring atoms of which may contain 1 or 2 heteroatoms, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

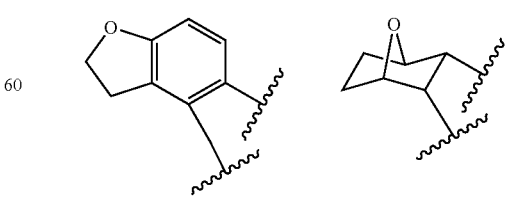

and the like.

The term "optionally substituted" means optional substitution with the specified groups, radicals or moieties, in available position or positions.

With reference to the number of moieties (non-limiting example(s) include, substituents, groups or rings) in a compound, unless otherwise defined, the phrases "one or more" and "at least one" mean that, there can be as many moieties as chemically permitted, and the determination of the maximum number of such moieties is well within the knowledge of those skilled in the art. Preferably, there are one to three substituents, or more preferably, one to two substituents, with at least one in the para position.

As used herein, the term "composition" is intended to encompass a product comprising the specified ingredients in the specified amounts, as well as any product which results, directly or indirectly, from combination of the specified ingredients in the specified amounts.

The straight line ——— as a bond generally indicates a mixture of, or either of, the possible isomers, non-limiting example(s) include, containing (R)- and (S)-stereochemistry. For example,

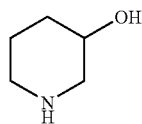

means containing both

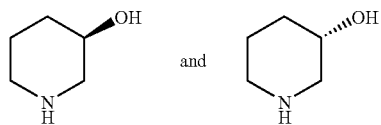

Lines drawn into the ring systems, such as, for example:

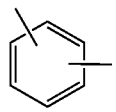

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

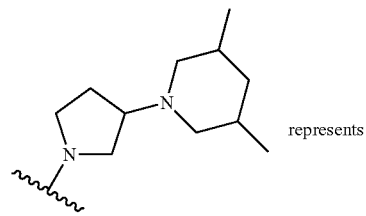 represents

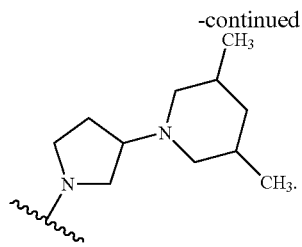

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula 1 or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

Metabolic conjugates, for example, glucoronides and sulfates which can under reversible conversion to compounds of Formula 1 are contemplated in this application.

"Effective amount" or "therapeutically effective amount" is meant to describe an amount of compound or a composition of the present invention effective to antagonize CXCR3 and thus produce the desired therapeutic effect in a suitable patient.

"Mammal" means humans and other mammalian animals.

"Patient" includes both human and animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

The compounds of Formula 1 form salts which are also within the scope of this invention. Reference to a compound of Formula 1 herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula 1 contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (non-limiting example(s) include, non-toxic, physiologically acceptable) salts are preferred, although other salts are also useful. Salts of the compounds of the Formula 1 may be formed, for example, by reacting a compound of Formula 1 with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in The Orange Book (Food & Drug Administration, Washington, D.C. on their website); and P. Heinrich Stahl, Camille G. Wermuth (Eds.), *Handbook of Pharmaceutical Salts: Properties, Selection, and Use*, (2002) *Int'l. Union of Pure and Applied Chemistry*, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis (dehydroabietyl)ethylened iamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (non-limiting example(s) include methyl, ethyl, propyl, and butyl chlorides, bromides and iodides), dialkyl sulfates (non-limiting example(s) include dimethyl, diethyl, dibutyl, and diamyl sulfates), long chain halides (non-limiting example(s) include decyl, lauryl, myristyl and stearyl chlorides, bromides and iodides), aralkyl halides (non-limiting example(s) include benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$)acyl glycerol.

Compounds of Formula 1, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention.

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

It should also be noted that throughout the specification and Claims appended hereto any formula, compound, moiety or chemical illustration with unsatisfied valences is assumed to have the hydrogen atom to satisfy the valences unless the context indicates a bond.

In one embodiment, the present invention discloses compounds of Formula 1, having CXCR3 antagonist activity, or a pharmaceutically acceptable derivative thereof, where the various definitions are given above.

In another embodiment of the present invention, $R^1$ and $R^2$ are independently absent or present, and if present each is independently selected from the group consisting of H, alkyl, aryl, amino, alkoxy, halogen, hydroxy, cycloalkyl, cycloalkenyl, arylalkyl, amidinyl, carboxamido, heteroaryl, heterocyclyl, heterocyclenyl, urea, —S(O)$_2$alkyl, —S(O)$_2$N(H)alkyl, —S(O)$_2$heteroaryl, —S(O)$_2$heterocyclyl, —C(=O)heteroaryl, —C(=O)heterocyclyl, —S(O)$_2$N(alkyl)$_2$, and —C(=S)N(H)cycloalkyl.

In another embodiment of the present invention, $R^1$ and $R^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutylhydroxy, cyclopentyl, and cyclopentylhydroxy; and q is an integer from 1 to 5.

In another embodiment of the present invention, $R^1$ and $R^2$ are independently absent or present, and if present each is independently selected from the group consisting of H, —CH$_3$, fluorophenylmethylene, trifluoromethylphenylmethylene, indanyl, cyanophenylmethylene, difluorophenylmethylene, bromophenylmethylene, chlorophenylmethylene, —CH$_2$CH$_2$O phenyl, cyclopentyl, bromochlorophenylmethylene, fluorochlorophenylmethylene, dichlorophenylmethylene, phenylmethylene, —(CH$_2$)$_3$phenyl, —CH$_2$CF$_3$, methoxylphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$-NH$_2$, —CH$_2$CH$_2$OCH$_3$, cyclopropyl, isoxazolyl, —CH$_2$CH$_2$OH, —CH$_2$CH$_2$O phenyl, —CH$_2$CH$_2$CH$_3$, —NH$_2$, —(CH$_2$)$_2$ NH₂, pyrazolyl, 5-methyl-isoxazolyl, —CH₂CH(OCH₂CH₃)₂, —OCH₃, —NHC(=O)NH₂, chloropyridyl, pyridylmethylene, —C(=O)NHcyclopropyl, —C(=O)N(H)C₂H₅, —C(=O)N(H)CH₂CF₃, —C(=O)N(H)C(CH₃)₃, —C(=S)N(H)cyclopropyl, —C(=O)NH₂, —C(=O)N(H)CH₃, —S(O)₂CH₃, —S(O)₂N(CH₃)₂, —S(O)₂CH₂CH₃, —C(=O)CH₃, —S(O)₂(CH₂)₂CH₃, —C(=O)N(H)cyclohexyl, —C(=NH)NH₂, —C(=O)N(H)NH₂, —C(=O)N(H)CH(CH₃)₂, thiazolyl, —C(=O)N(CH₃)₂, —S(O)₂CH₂CF₃, cyclopropyl, —S(O)₂CF₃, —CH₂CH(OCH₃)₂,

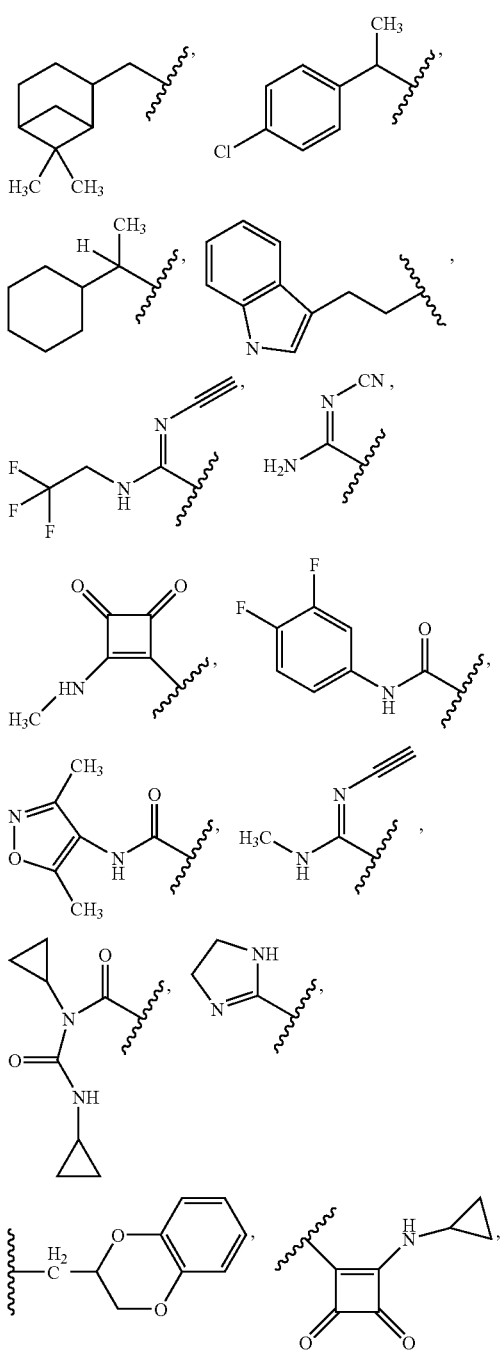

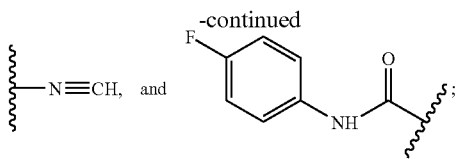

or when X is N, the N taken together with the R¹ and R² to which X is shown attached, forms a —N-cyclopropyl, —N-cyclobutyl, —N-cyclohexyl or

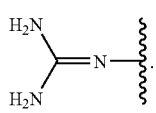

In another embodiment of the present invention, R¹ and R² are independently absent or present, and if present each is independently selected from the group consisting of H, —CH₃, —C₂H₅, difluorophenylmethylene, cyclopropyl, dichlorophenylmethylene, —CH(CH₃)₂, cyclohexylmethylene, cyclohexyl, isoxazolyl, difluorophenyl, —CH₂CH₂OH, —CH₂—CH₂—N(CH₃))₂, —C(=O)N(H)cyclopropyl, —C(=O)N(H)C₂H₅, —C(=O)N(H)CH₂CF₃, —C(=O)N(H)CH(CH₃)₂, —C(=O)N(H)C(CH₃)₃, —C(=S)N(H)cyclopropyl, —C(=O)NH₂, —C(=O)N(H)CH₃, —S(O)₂CH₃, —S(O)₂N(CH₃)₂, —S(O)₂CH₂CH₃, —C(=O)CH₃, —S(O)₂(CH₂)₂CH₃, —C(=O)N(H)cyclohexyl, —C(=NH)NH₂, —C(=O)N(H)NH₂, thiazolyl,

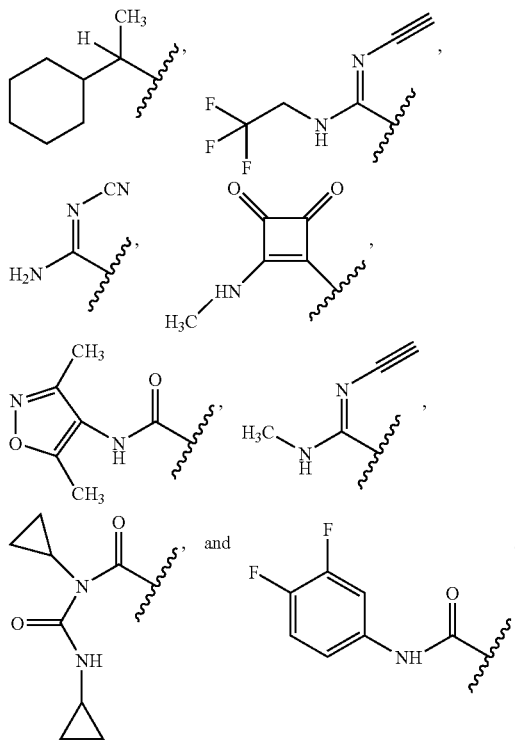

In another embodiment of the invention, Z is N or C(R²⁹).
In another embodiment of the invention, Z is N.

In another embodiment of the invention, Z is C(H), C(alkyl), C(halogen), C(CF$_3$) or C(N(R$^{30}$)$_2$).

In another embodiment of the invention Z is C(alkyl), C(F) or C(NH$_2$).

In another embodiment of the invention, G is N or C(R$^4$).

In another embodiment of the invention, G is N.

In another embodiment of the invention, G is C(R$^4$).

In another embodiment of the invention, G is C(H), C(alkyl), C(halogen), C(CF$_3$) or C(N(R$^{30}$)$_2$).

In another embodiment of the invention, G and Z are the same.

In another embodiment of the invention, G and Z are different.

In another embodiment of the invention, G and Z are both N.

In another embodiment of the invention, G is R$^4$ and Z is C(R$^{29}$), wherein R$^4$=R$^{29}$.

In another embodiment of the invention, G is N and Z is C(R$^{29}$).

In another embodiment of the invention, G is C(R$^4$) and Z is N.

In another embodiment of the invention, R$^3$ is selected from the group consisting of H, alkyl, haloalkyl, hydroxyalkyl, halogen, —N(R$^{30}$)$_2$, —OR$^{30}$ and —CF$_3$.

In another embodiment of the invention, R$^3$ is selected from the group consisting of H, —CH$_3$, —CH$_2$CH$_3$, cyclopropyl, —F, —Cl, OCH$_3$, OCF$_3$ and CF$_3$.

In another embodiment of the invention, Z is N and R$^4$ is selected from the group consisting of H, alkyl, hydroxyalkyl, halogen, OR$^{30}$, or CF$_3$.

In another embodiment of the invention, R$^6$ is selected from the group consisting of H, alkyl, halogen, hydroxyalkyl, —CN, —N(R$^{30}$)$_2$, —OR$^{30}$, —N=CH-alkyl, and —NR$^{30}$C(=O)alkyl.

In another embodiment of the invention, R$^6$ is selected from the group consisting of H, —NH$_2$, —CH$_3$, —CN and —F.

In another embodiment of the invention, R$^{10}$ is selected from the group consisting of H, alkyl, aralkyl, hydroxyalkyl, and carbonyl.

In another embodiment of the invention, R$^{10}$ is selected from the group consisting of —CH$_3$, —CH$_2$CH$_3$ and —CH$_2$CH$_2$CH$_3$, and m is 0-2.

In another embodiment of the invention, R$^{11}$ is selected from the group consisting of H, alkyl, hydroxyalkyl and carbonyl.

In another embodiment of the invention, R$^{11}$ is H or —CH$_3$.

In another embodiment of the invention, R$^{12}$ is selected from the group consisting of H, CN, —C(=O)N(R$^{30}$)$_2$ and alkyl.

In another embodiment of the invention, R$^{12}$ is selected from the group consisting of H, —CH$_3$, CN and —CH$_2$CH$_3$.

In another embodiment of the invention, the ring atoms of ring D are independently C or N and substituted by independently selected 0-4 R$^{20}$ moieties.

In another embodiment of the invention, ring D is a 5 to 6 membered aryl, heteroaryl, heterocyclenyl, or heterocyclyl ring and substituted by independently selected 0-4 R$^{20}$ moieties.

In another embodiment of the invention, the R$^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, aralkoxy, aryl, aryloxy, cyano, cycloalkyl, cycloalkenyl, halogen, haloalkyl, heteroalkyl, heteroaryl, heterocyclyl, hydroxyalkyl, trifluoromethyl, trifluoromethoxy, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)N(R$^{30}$)$_2$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —N(R$^{30}$)SO$_2$(R$^{31}$), —N(R$^{30}$)SO$_2$N(R$^{30}$)$_2$, —OR$^{30}$, —OC(=O)N(R$^{30}$)$_2$, —SR$^{30}$, —SO$_2$N(R$^{30}$)$_2$, —SO$_2$(R$^{31}$), —OSO$_2$(R$^{31}$), and —OSi(R$^{30}$)$_3$.

In another embodiment of the invention, the R$^{20}$ moieties can be the same or different, each being independently selected from the group consisting of H, alkyl, amino, halogen, CN, CH$_3$, CF$_3$, OCF$_3$, —(CH$_2$)$_q$OR$^{31}$, —(CH$_2$)$_q$NHR$^{31}$, —(CH$_2$)$_q$C(=O)NHR$^{31}$, —(CH$_2$)$_q$SO$_2$R$^{31}$, —(CH$_2$)$_q$NSO$_2$R$^{31}$, —(CH$_2$)$_q$SO$_2$NHR$^{31}$, -alkynylC(R$^{31}$)$_2$OR$^{31}$, —C(=O)R$^{30}$, —C(=O)OR$^{30}$, —N(R$^{30}$)$_2$, —N(R$^{30}$)C(=O)R$^{31}$, —NHC(=O)N(R$^{30}$)$_2$, —N(R$^{30}$)C(=O)OR$^{31}$, —N(R$^{30}$)C(=NCN)N(R$^{30}$)$_2$, —N(R$^{30}$)C(=O)N(R$^{30}$)$_2$, —OR$^{30}$, —OC(=O)N(R$^{30}$)$_2$, and —OSO$_2$(R$^{31}$).

In another embodiment of the invention, two R$^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 R$^{21}$ moieties.

In another embodiment of the invention, the R$^{20}$ moieties can be the same or different, each being independently selected from the group consisting of H, —CN, —CH$_3$, —CF$_3$, —CH$_2$OH, —CO$_2$H, —CO$_2$CH$_3$, —NH$_2$, —NHCH$_3$, —OCF$_3$, —OH, F, Cl, Br, —C(=NOH)NH$_2$, —OCH$_2$CH$_2$S(O$_2$)CH$_3$, —C(=O)NH$_2$,

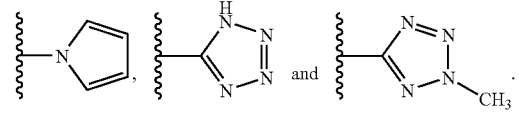

In another embodiment of the invention, Y is selected from the group consisting of: —(CHR$^{13}$)$_r$—, —(CR$^{13}$R$^{13}$)$_r$—, —C(=O)— and —CHR$^{13}$C(=O)—.

In another embodiment of the invention, Y is selected from the group consisting of: —CH$_2$—, —CH(CH$_3$)—, —CH(CH$_2$OH)—, —C(=O)— and —CH(CO$_2$alkyl)-.

In another embodiment of the invention, m is 0-3.

In another embodiment of the invention, n is 0-2.

In another embodiment of the invention, q is 1, 2 or 3.

In another embodiment of the invention, r is 1 or 2.

In another embodiment of the invention, Z is N, C(H), C(alkyl), C(F) or C(NH$_2$);

G is N or C(R$^4$);

R$^1$ and R$^2$ are independently absent or present, and if present each is independently selected from the group consisting of H, alkylaryl, aryl, heteroaryl, —(CH$_2$)$_q$CF$_3$, —(CH$_2$)$_q$OH, —(CH$_2$)$_q$OR$^{31}$, —(CH$_2$)$_q$NH$_2$, —(CH$_2$)$_q$NHR$^{31}$, —(CH$_2$)$_q$—N(R$^{31}$)$_2$, —(CH$_2$)$_q$C(=O)NHR$^{31}$, —(CH$_2$)$_q$SO$_2$R$^{31}$, —(CH$_2$)$_q$NHSO$_2$R$^{31}$, —(CH$_2$)$_q$SO$_2$NHR$^{31}$, —(CH$_2$)$_q$-amidinyl, cyclopropyl, cyclopropylhydroxyl, cyclobutyl, cyclobutyihydroxy, cyclopentyl, and cyclopentylhydroxy;

R$^3$ is selected from the group consisting of H, alkyl, haloalkyl, hydroxyalkyl, halogen, —N(R$^{30}$)$_2$, —OR$^{30}$ and —CF$_3$;

R⁴ is selected from the group consisting of H, alkyl, haloalkyl, hydroxyalkyl, halogen, —N(R³⁰)₂, —OR³⁰ and —CF₃;

R⁶ is selected from the group consisting of H, alkyl, halogen, hydroxyalkyl, —CN, —N(R³⁰)₂, —OR³⁰, —N=CH-alkyl, and —NR³⁰C(=O)alkyl;

R¹⁰ is selected from the group consisting of H, alkyl, aralkyl, hydroxyalkyl, and carbonyl;

R¹¹ is selected from the group consisting of H, alkyl, hydroxyalkyl, and carbonyl;

R¹² is selected from the group consisting of H, CN, —C(=O)N(R³⁰)₂ and alkyl;

ring D is a 5 to 6 membered aryl, heteroaryl, heterocyclenyl, or heterocyclyl ring and substituted by 0-4 R²⁰ moieties;

the R²⁰ moieties can be the same or different, each being independently selected from the group consisting of H, alkyl, amino, halogen, CN, CH₃, CF₃, OCF₃, —(CH₂)qOR³¹, —(CH₂)qNHR³¹, —(CH₂)qC(=O)NHR³¹, —(CH₂)qSO₂R³¹, —(CH₂)qNSO₂R³¹, —(CH₂)qSO₂NHR³¹, -alkynylC(R³¹)₂OR³¹, —C(=O)R³⁰, —C(=O)OR³⁰, —N(R³⁰)₂, —N(R³⁰)C(=O)R³¹, —NHC(=O)N(R¹⁰)₂, —N(R³⁰)C(=O)OR³¹, —N(R³⁰)C(=NCN)N(R³⁰)₂, —N(R³⁰)C(=O)N(R³⁰)₂, —OR³⁰, —OC(=O)N(R³⁰)₂,

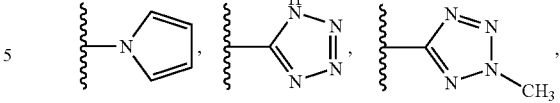

and —OSO₂(R³¹);

Y is selected from the group consisting of: —CH₂—, —CH(CH₃)—, —CH(CH₂OH)—, —C(=O)— and —CH(CO₂alkyl)-;

m is 0-2;
n is 0-2;
q is 1 or 2; and
r is 1 or 2.

In still another embodiment of the present invention, a compound is selected from the following structures in Table 1 below (or a pharmaceutically acceptable salt or solvate thereof) which are shown along with their IC₅₀ ratings. The IC₅₀ values are rated, "A" for IC₅₀ values less than about 25 nanomolar (nM), "B" for IC₅₀ values in the range of from about 25 to about 100 nM and "C" for IC₅₀ values greater than about 100 nM. For example, Compound Number 1 has an IC₅₀ value of 0.8 nM.

TABLE 1

| Compound No. | STRUCTURE | IC₅₀ |
|---|---|---|
| 1 | 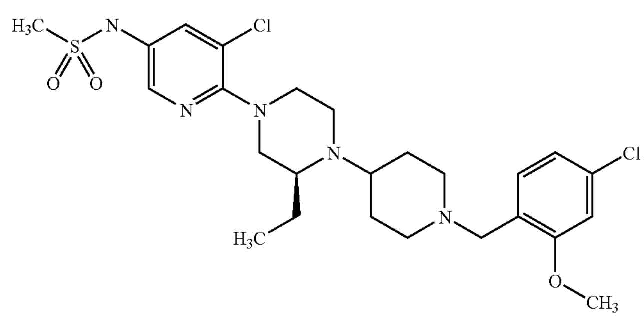 | A |
| 2 | 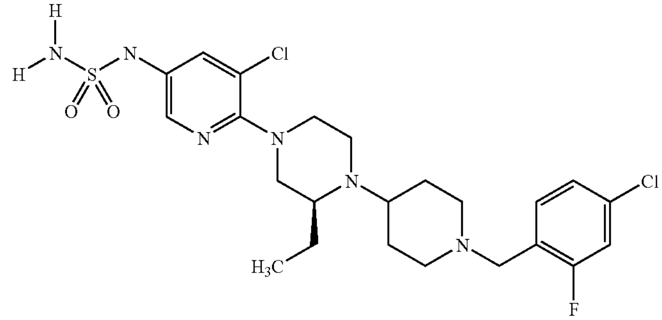 | A |

TABLE 1-continued

| Compound No. | STRUCTURE | IC$_{50}$ |
|---|---|---|
| 3 | 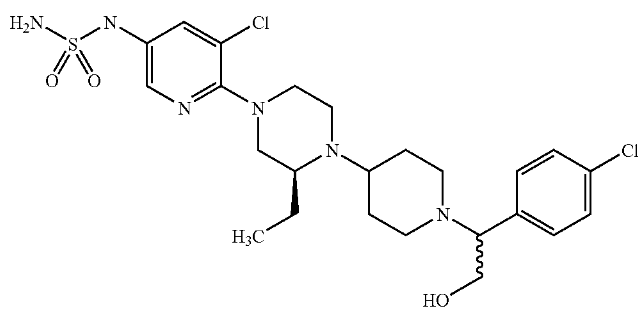 | A |
| 4 | 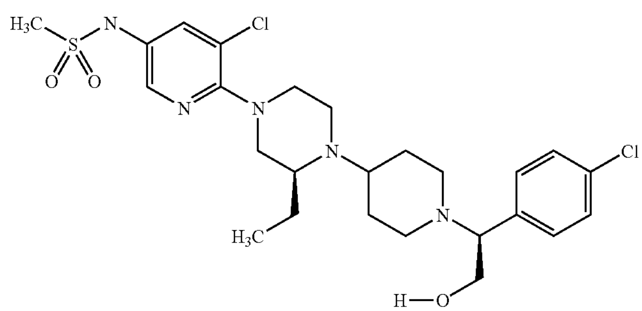 | A |
| 5 | 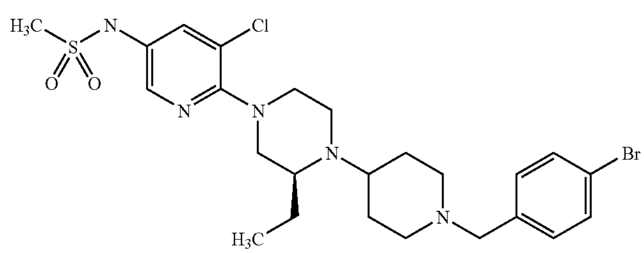 | A |
| 6 | 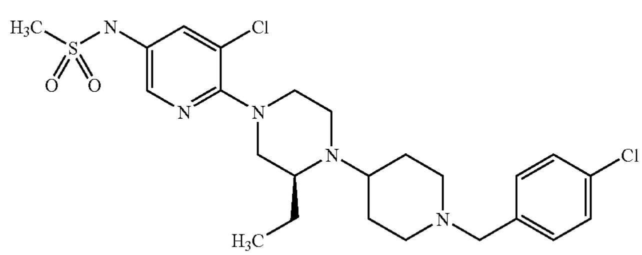 | A |
| 7 | 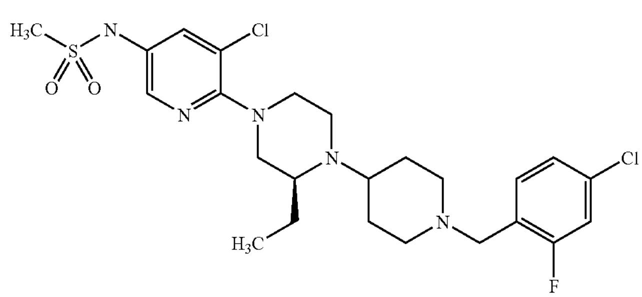 | A |

TABLE 1-continued
| Compound No. | STRUCTURE | IC$_{50}$ |
|---|---|---|
| 8 | 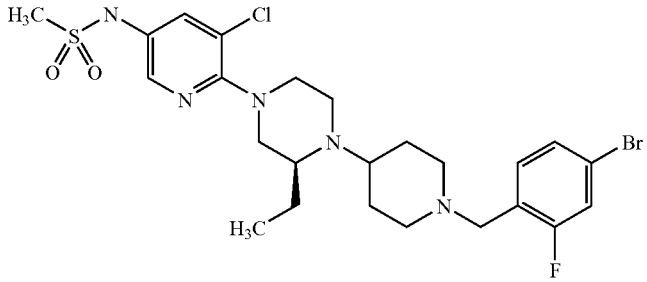 | A |
| 9 | 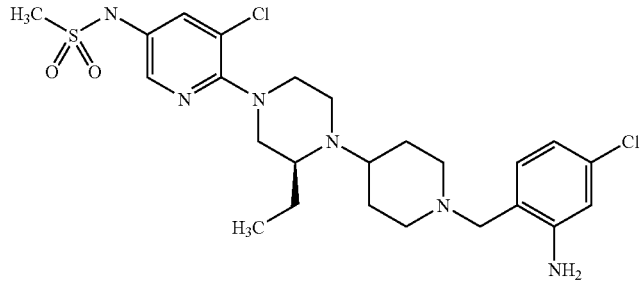 | A |
| 10 | 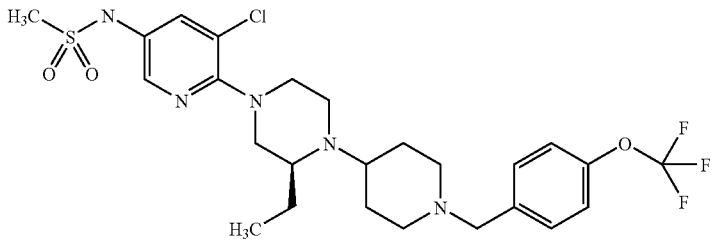 | A |
| 11 | 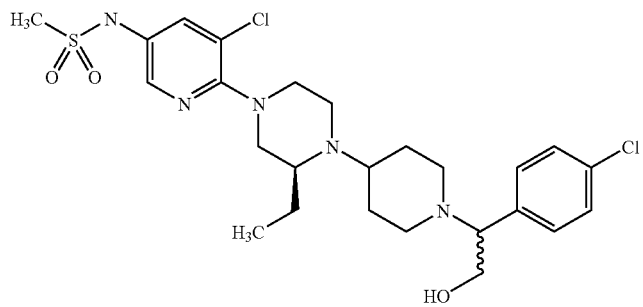 | A |
| 12 | 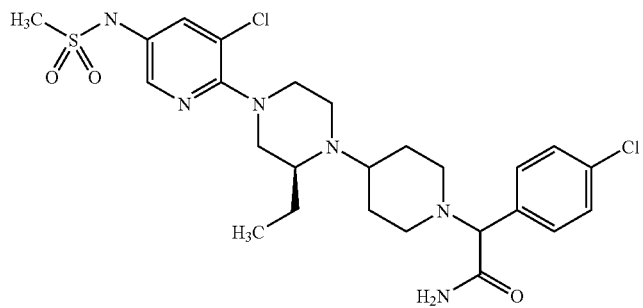 | A |

TABLE 1-continued
| Compound No. | STRUCTURE | IC$_{50}$ |
|---|---|---|
| 13 | 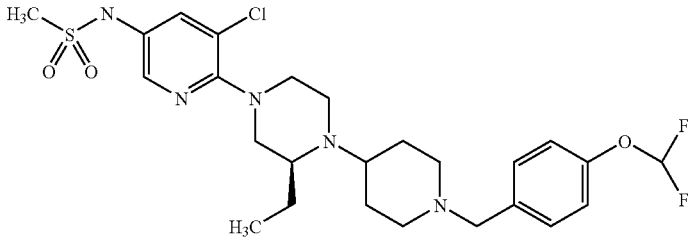 | A |
| 14 | 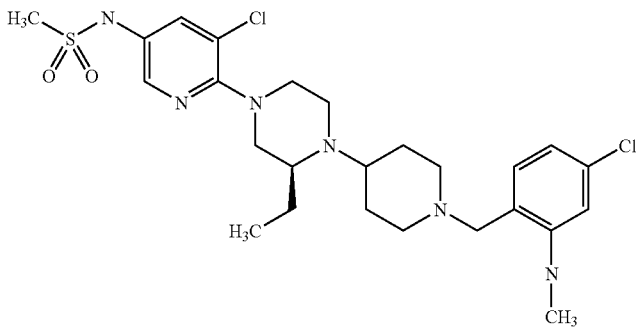 | A |
| 15 | 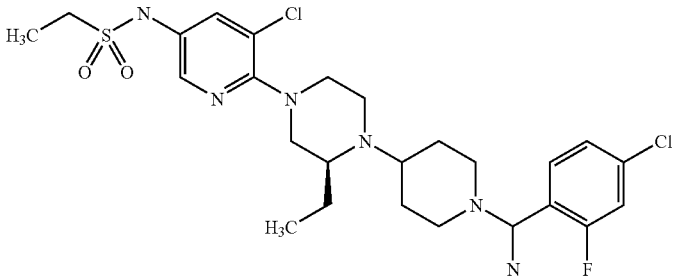 | A |
| 16 | 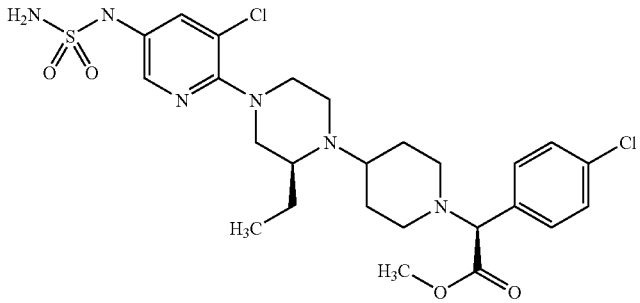 | A |
| 17 | 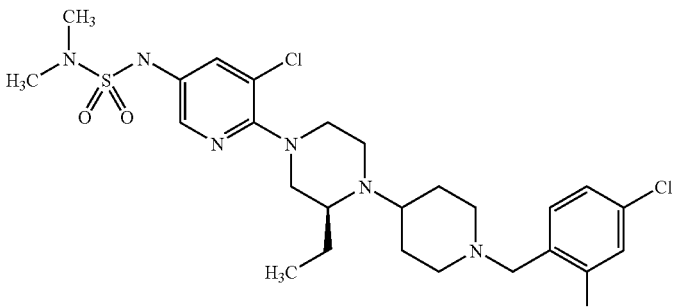 | A |

TABLE 1-continued
| Compound No. | STRUCTURE | IC$_{50}$ |
|---|---|---|
| 18 | 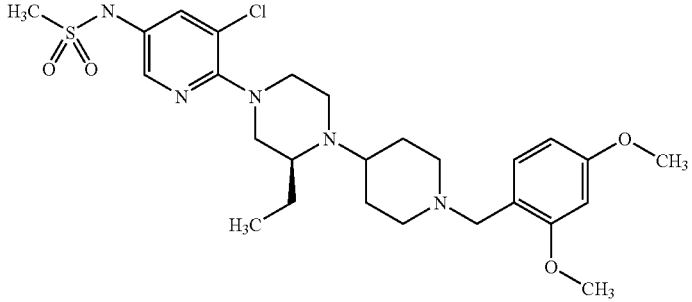 | A |
| 19 | 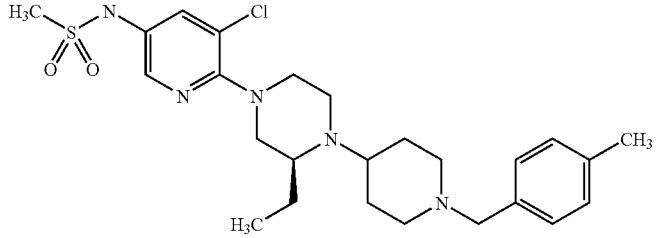 | A |
| 20 | 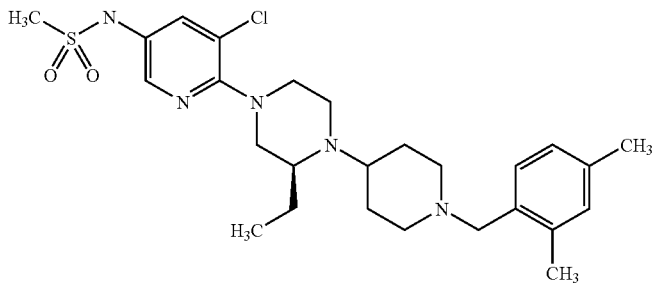 | A |
| 21 | 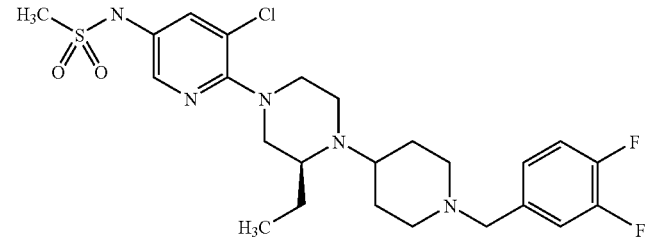 | A |
| 22 | 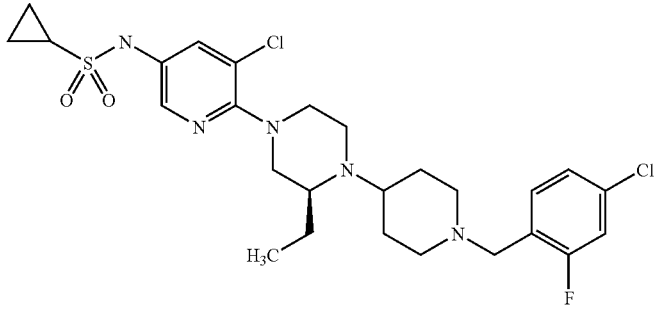 | A |

TABLE 1-continued
| Compound No. | STRUCTURE | IC$_{50}$ |
|---|---|---|
| 23 | 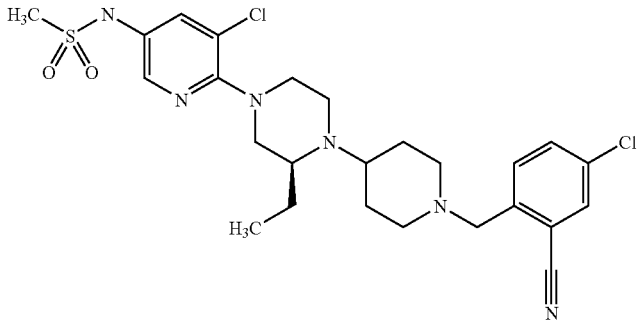 | A |
| 24 | 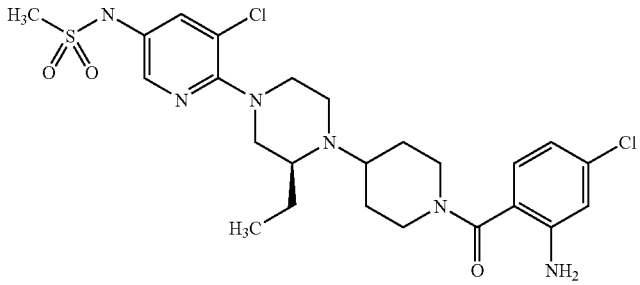 | B |
| 25 | 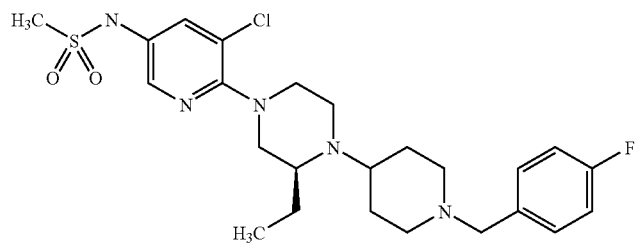 | B |
| 26 | 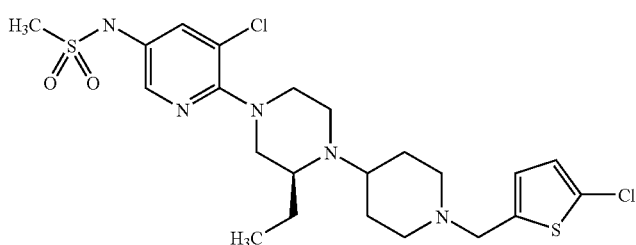 | B |
| 27 | 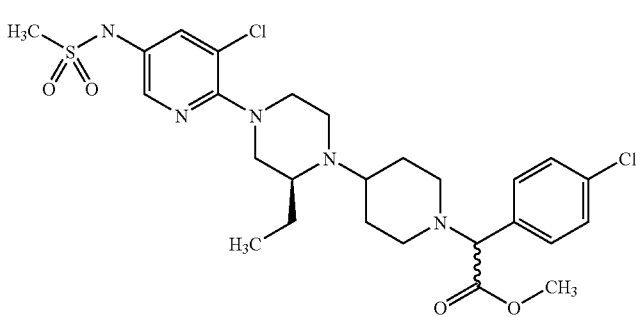 | B |

TABLE 1-continued
| Compound No. | STRUCTURE | IC$_{50}$ |
|---|---|---|
| 28 | 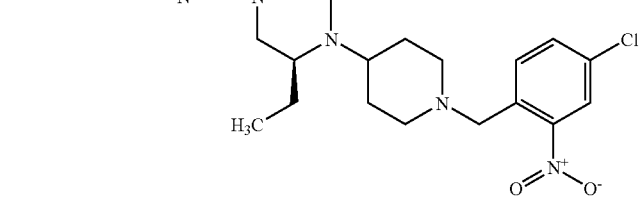 | B |
| 29 | 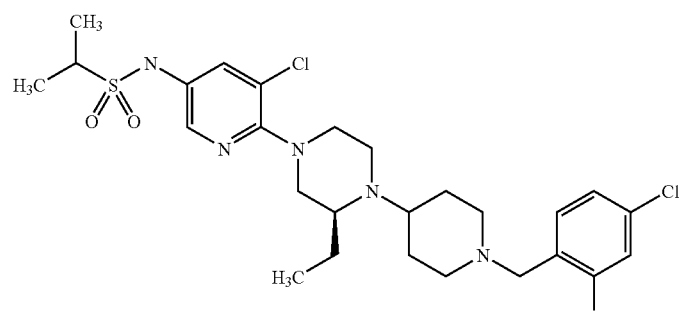 | B |
| 30 | 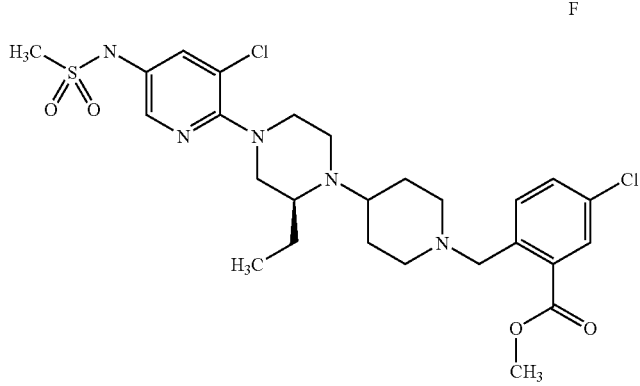 | B |
| 31 | 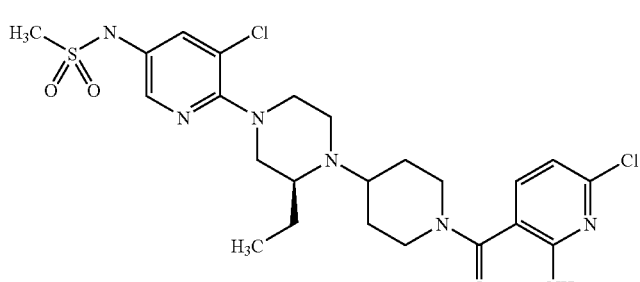 | B |
| 32 | 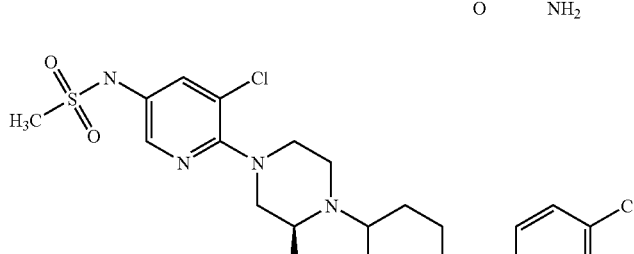 | B |

TABLE 1-continued

| Compound No. | STRUCTURE | IC$_{50}$ |
|---|---|---|
| 33 | 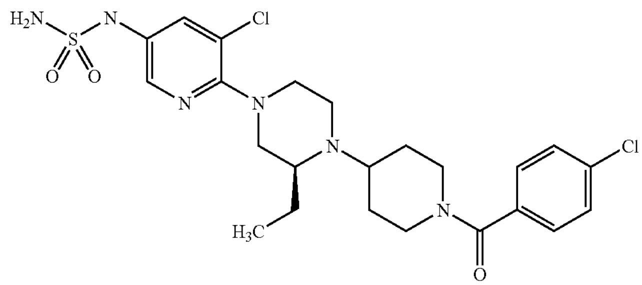 | B |
| 34 | 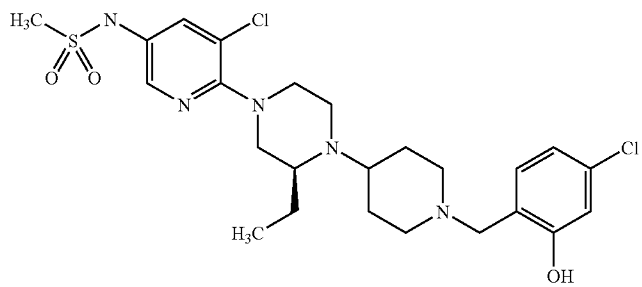 | B |
| 35 | 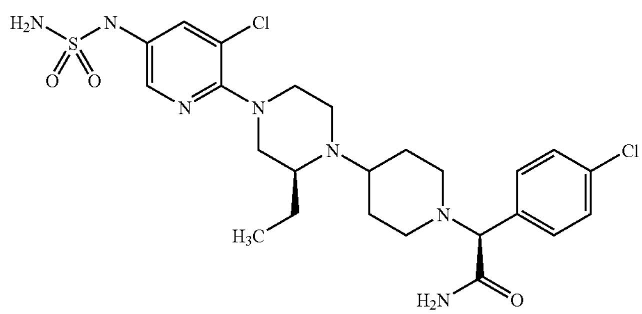 | B |
| 36 | 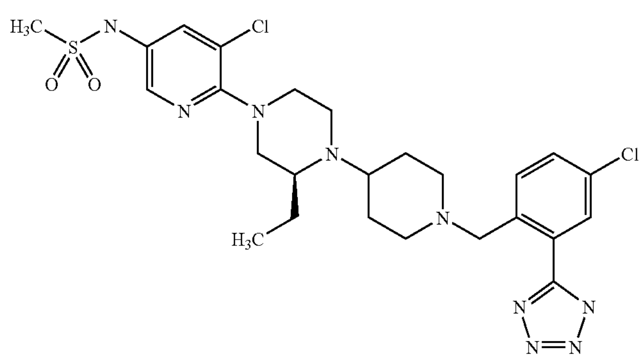 | B |
| 37 | 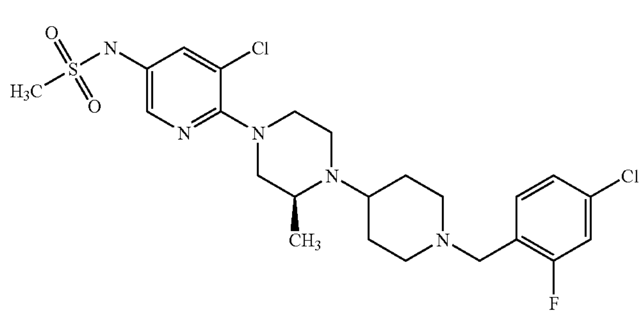 | B |

TABLE 1-continued
| Compound No. | STRUCTURE | IC$_{50}$ |
|---|---|---|
| 38 | 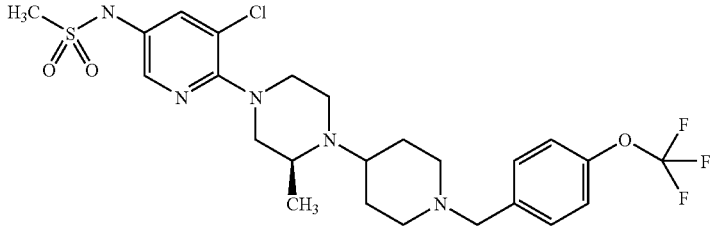 | B |
| 39 | 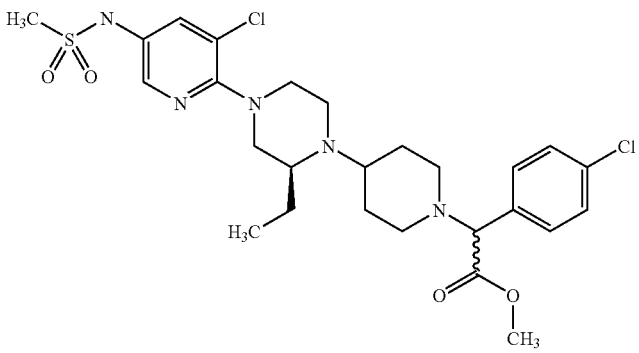 | B |
| 40 | 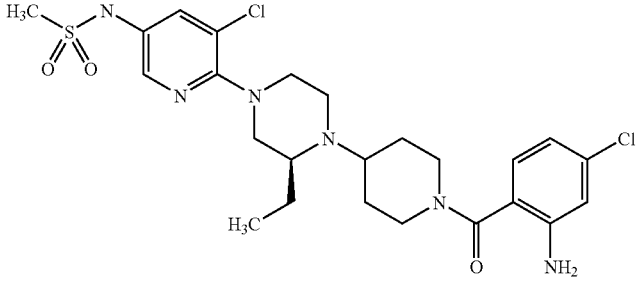 | B |
| 41 | 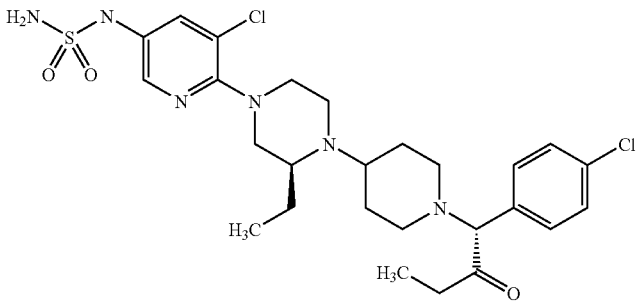 | C |
| 42 | 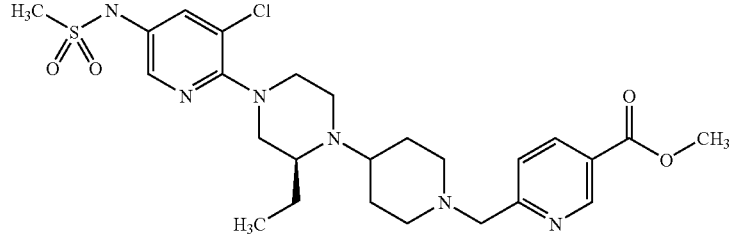 | C |

TABLE 1-continued
| Compound No. | STRUCTURE | IC$_{50}$ |
|---|---|---|
| 43 | 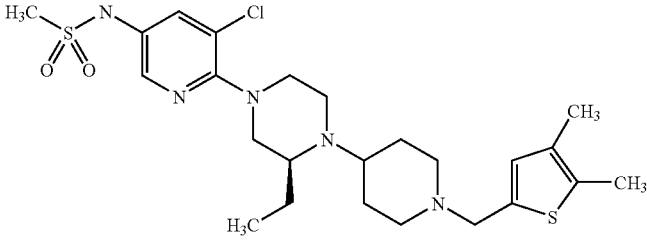 | C |
| 44 | 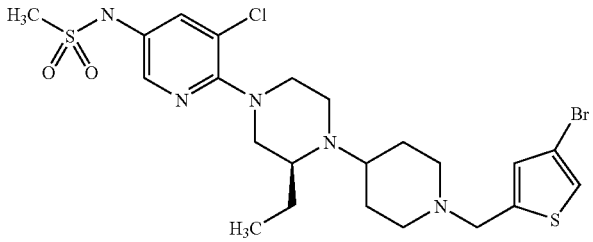 | C |
| 45 | 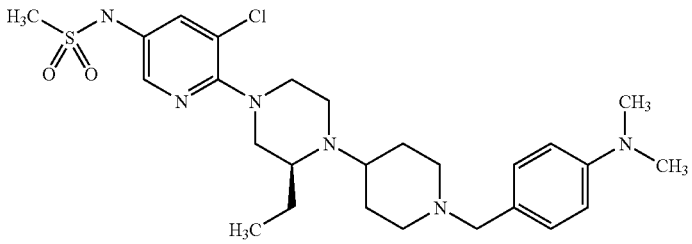 | C |
| 46 | 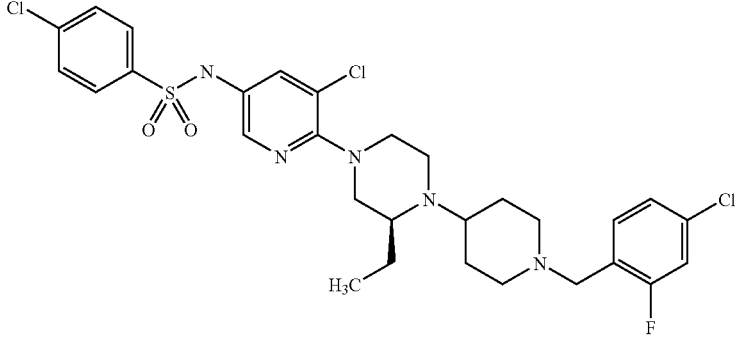 | C |
| 47 | 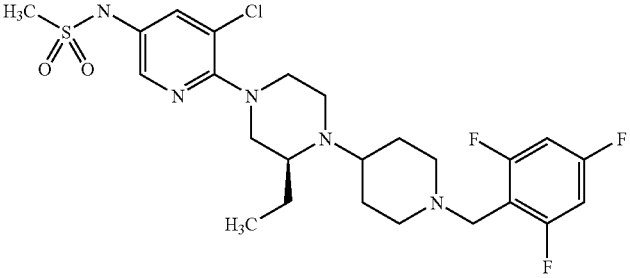 | C |

TABLE 1-continued

| Compound No. | STRUCTURE | IC$_{50}$ |
|---|---|---|
| 48 | 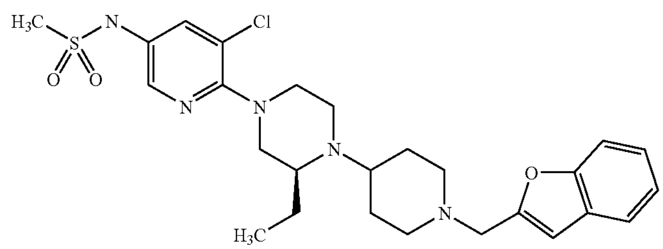 | C |
| 49 | 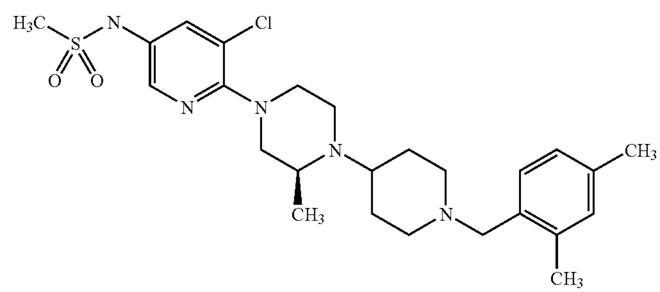 | C |
| 50 | 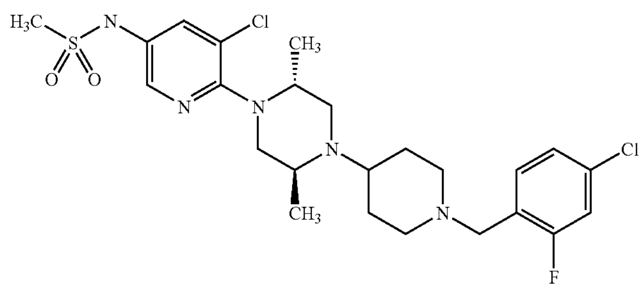 | C |
| 51 | 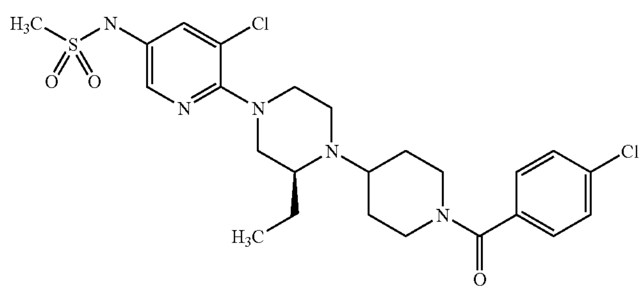 | C |
| 52 | 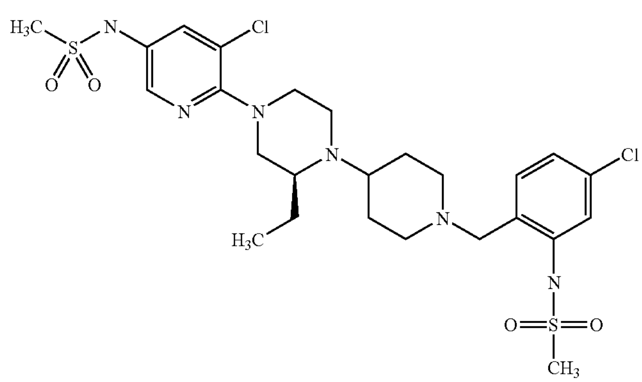 | C |

TABLE 1-continued

| Compound No. | STRUCTURE | IC$_{50}$ |
|---|---|---|
| 53 | 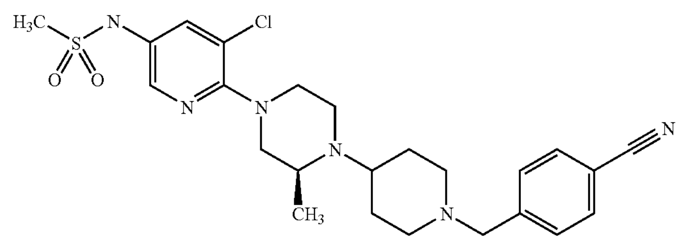 | C |
| 54 | 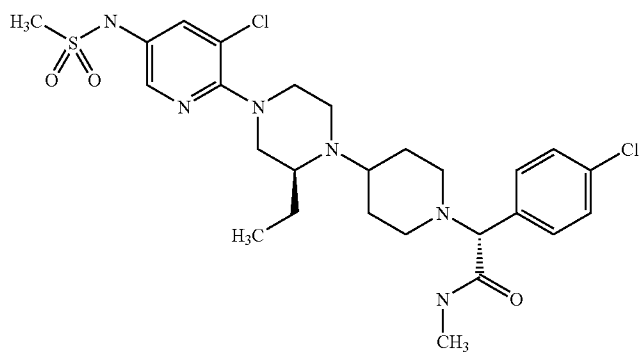 | C |
| 55 | 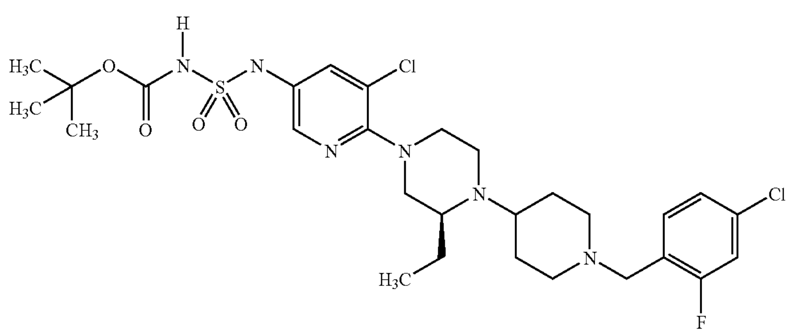 | C |
| 56 | 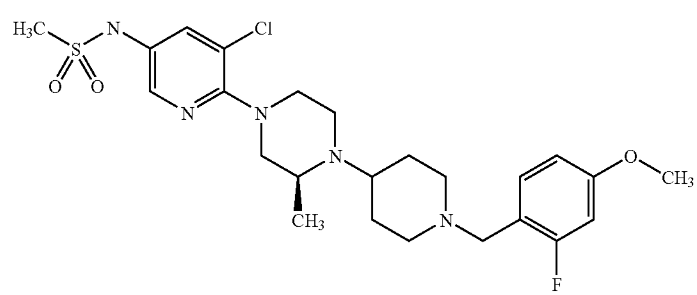 | C |
| 57 | 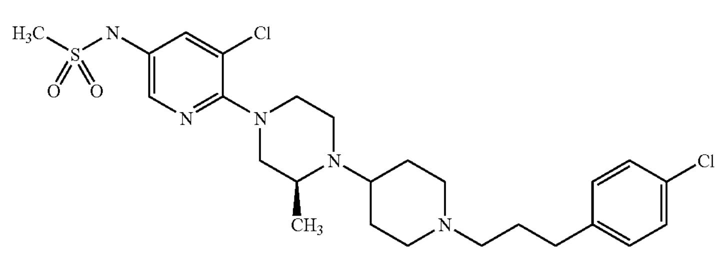 | C |

TABLE 1-continued

| Compound No. | STRUCTURE | IC$_{50}$ |
|---|---|---|
| 58 | 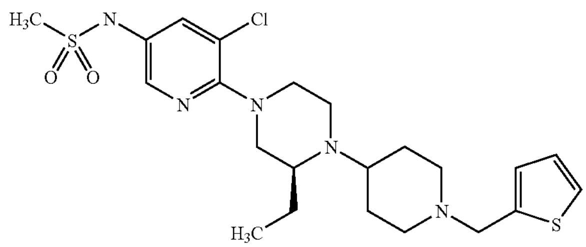 | C |
| 59 | 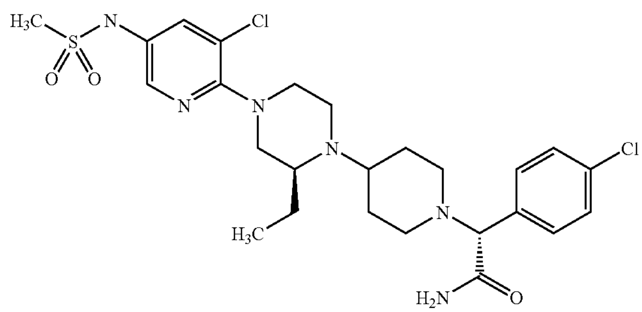 | C |
| 60 | 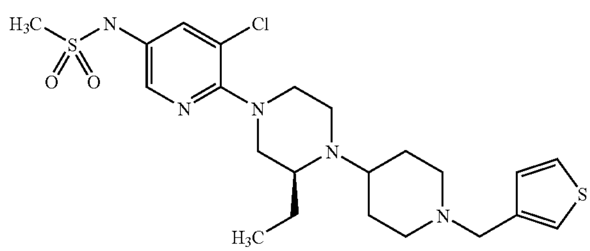 | C |
| 61 | 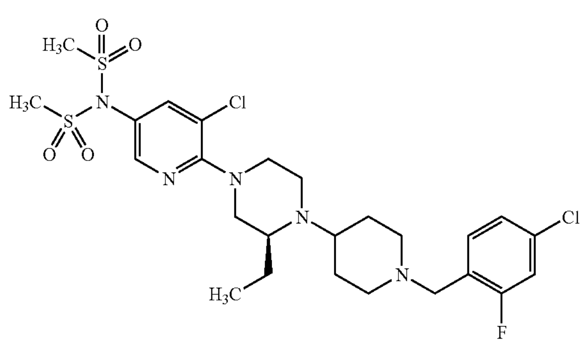 | C |
| 62 | 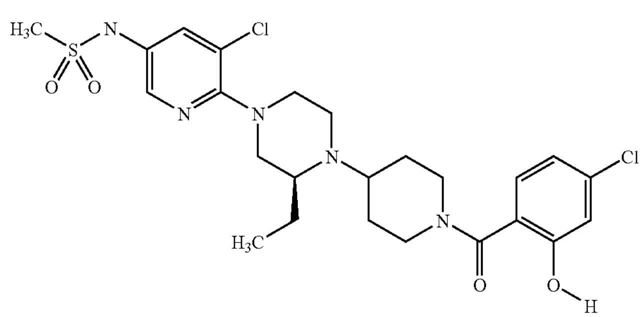 | C |

TABLE 1-continued
| Compound No. | STRUCTURE | IC$_{50}$ |
|---|---|---|
| 63 | 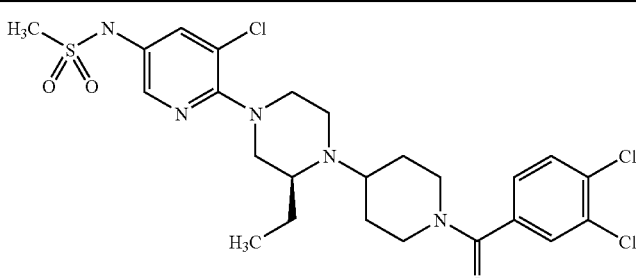 | C |
| 64 | 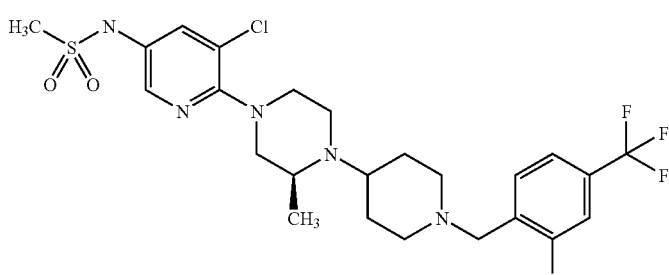 | C |
| 65 | 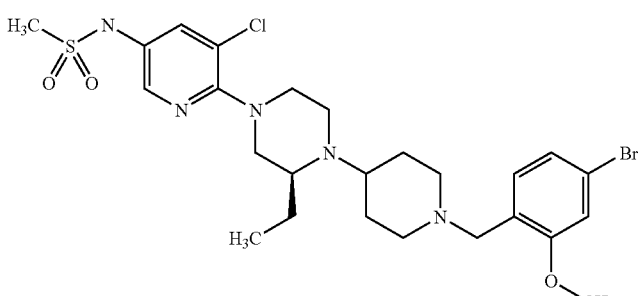 | C |
| 66 | 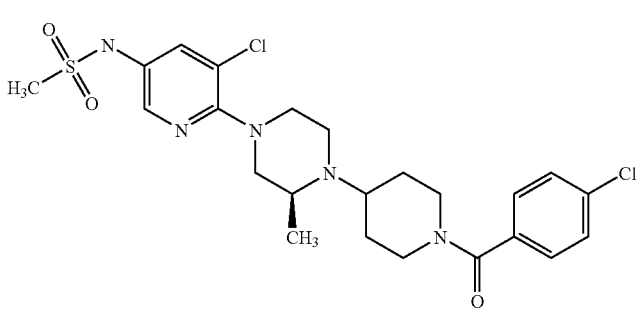 | C |
| 67 | 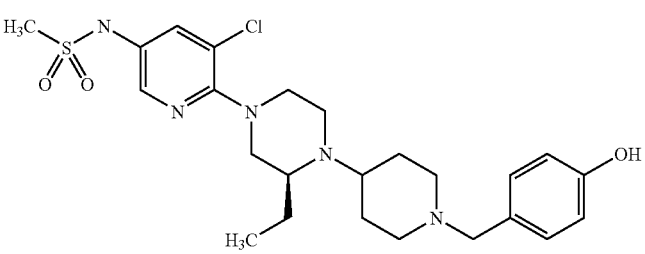 | C |

TABLE 1-continued
| Compound No. | STRUCTURE | IC$_{50}$ |
|---|---|---|
| 68 | 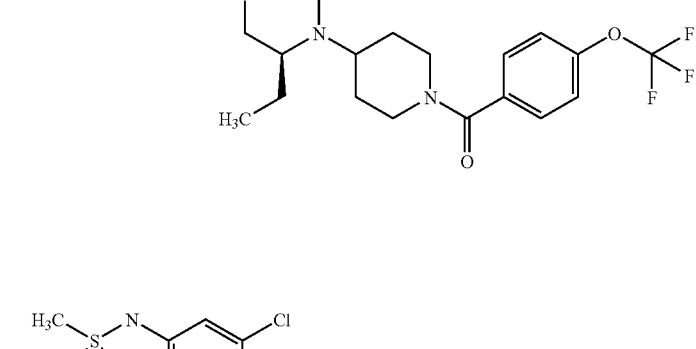 | C |
| 69 | 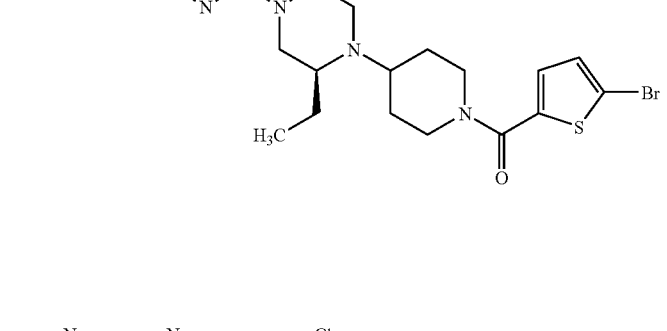 | C |
| 70 | 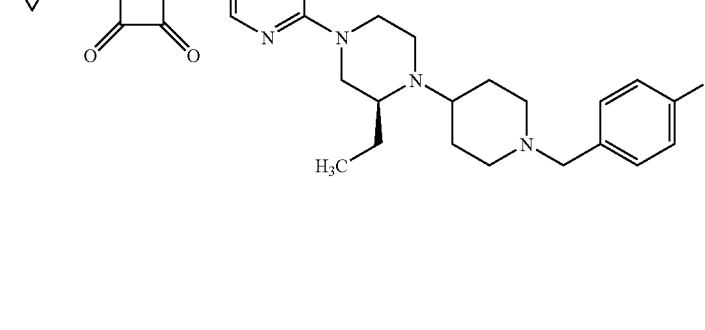 | A |
| 71 | 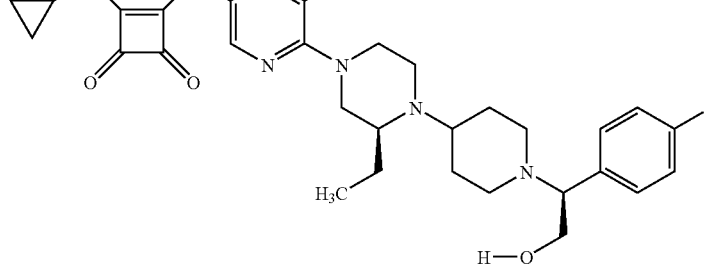 | A |

TABLE 1-continued

| Compound No. | STRUCTURE | IC$_{50}$ |
|---|---|---|
| 72 | 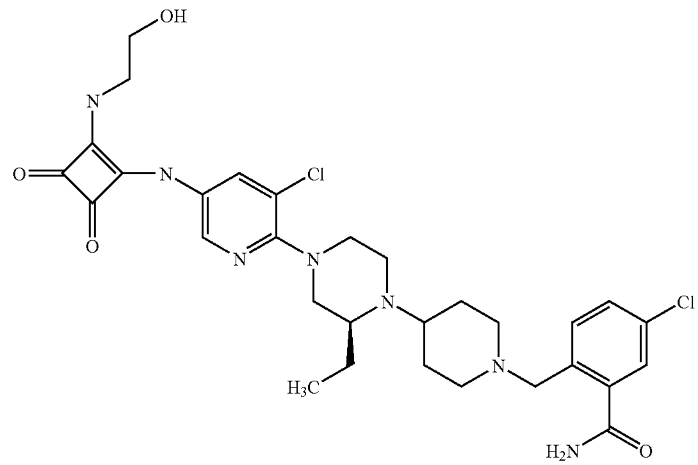 | A |
| 73 | 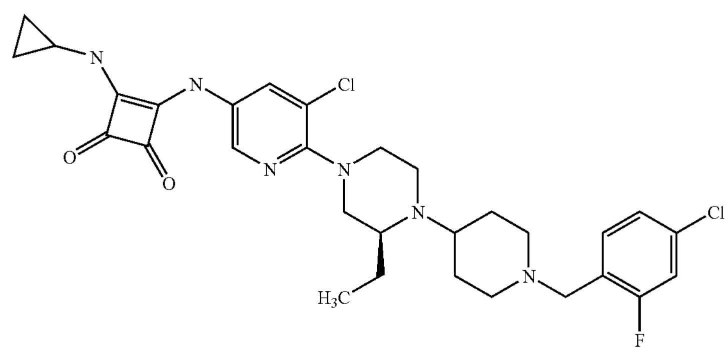 | A |
| 74 | 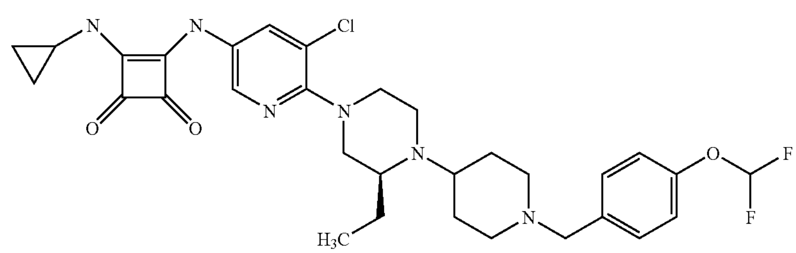 | A |
| 75 | 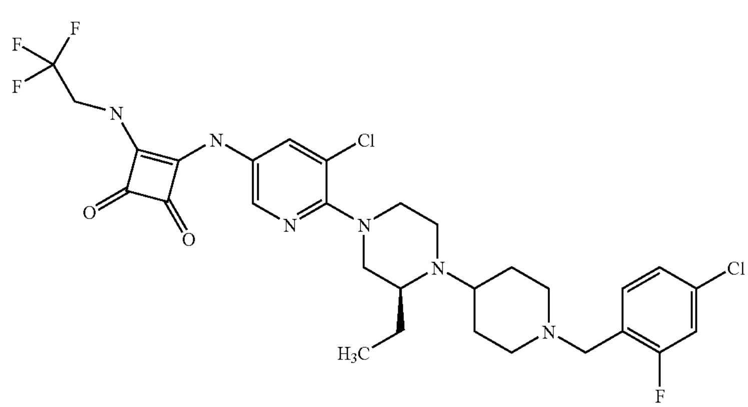 | A |

TABLE 1-continued
| Compound No. | STRUCTURE | IC$_{50}$ |
|---|---|---|
| 76 | 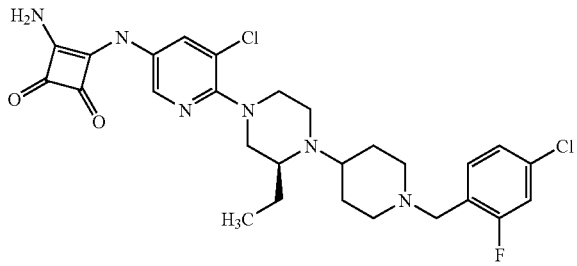 | A |
| 77 | 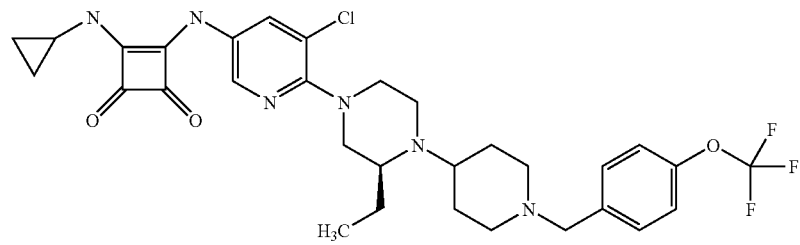 | A |
| 78 | 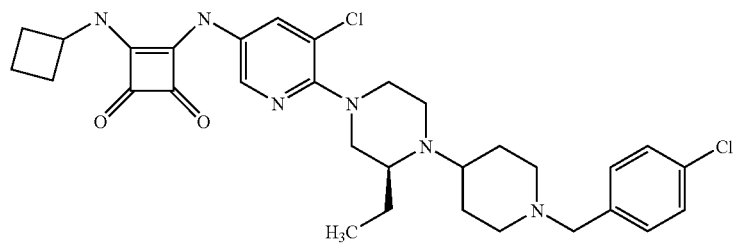 | A |
| 79 | 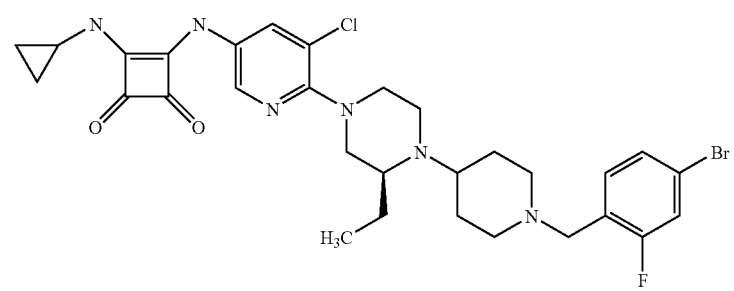 | A |
| 80 | 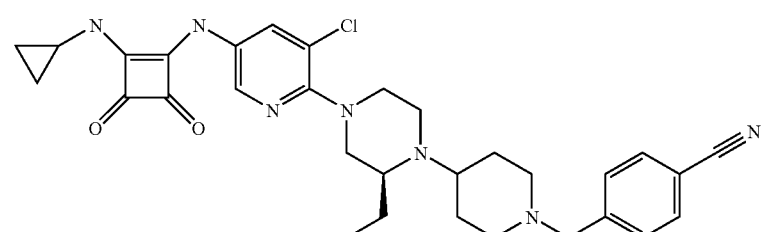 | A |

TABLE 1-continued

| Compound No. | STRUCTURE | IC$_{50}$ |
|---|---|---|
| 81 | 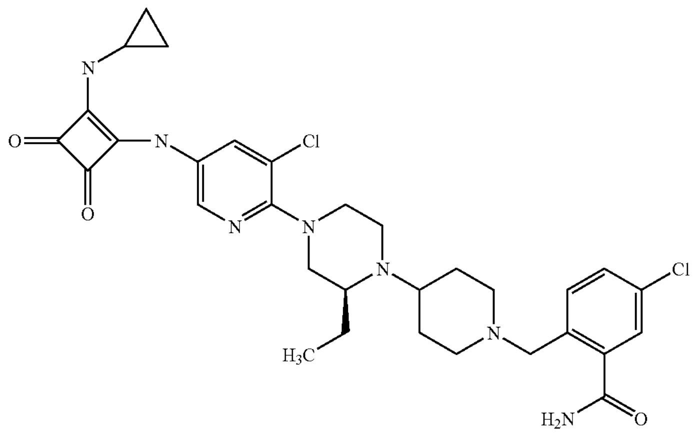 | A |
| 82 | 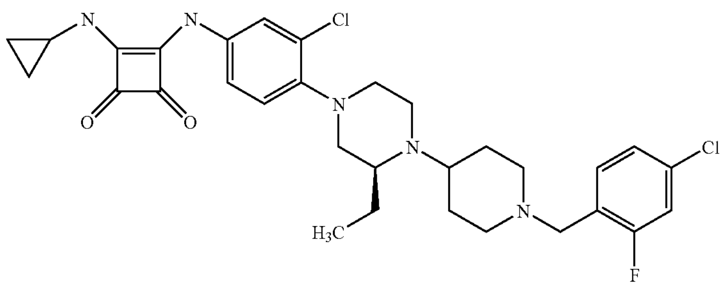 | A |
| 83 | 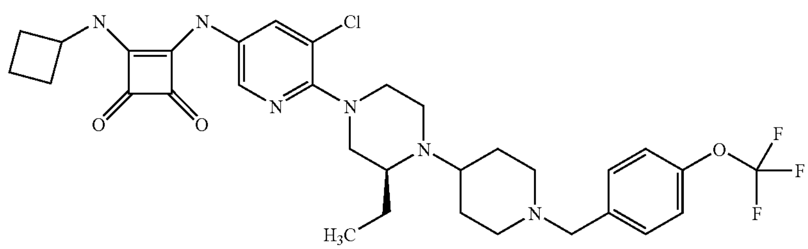 | A |
| 84 | 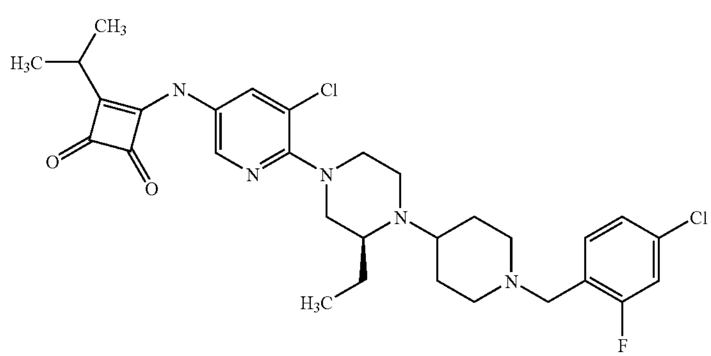 | A |

TABLE 1-continued
| Compound No. | STRUCTURE | IC$_{50}$ |
|---|---|---|
| 85 | 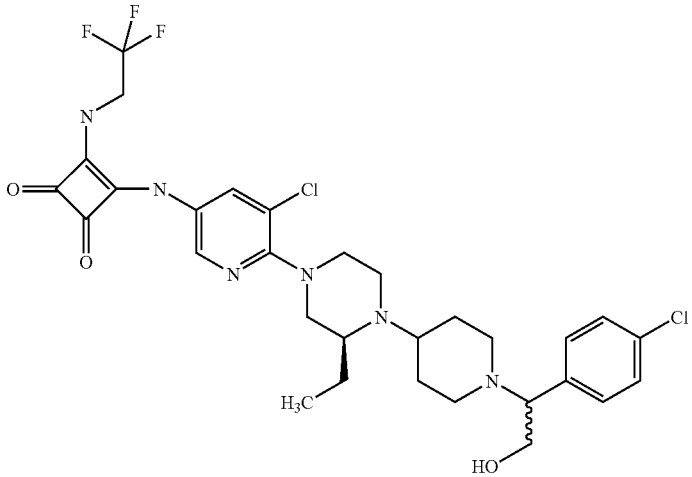 | A |
| 86 | 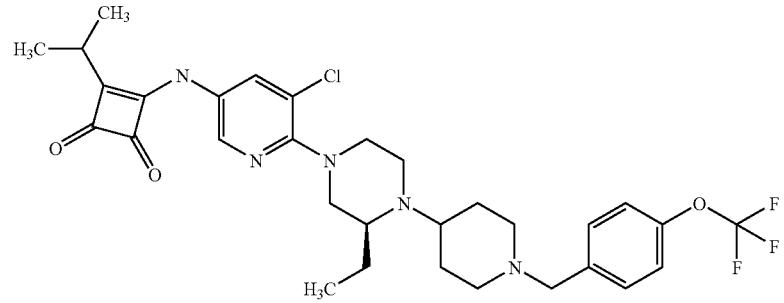 | A |
| 87 | 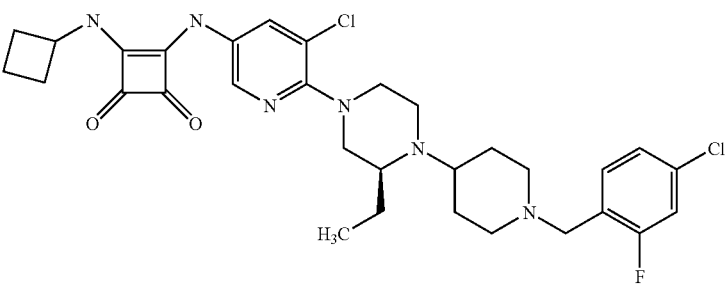 | A |
| 88 | 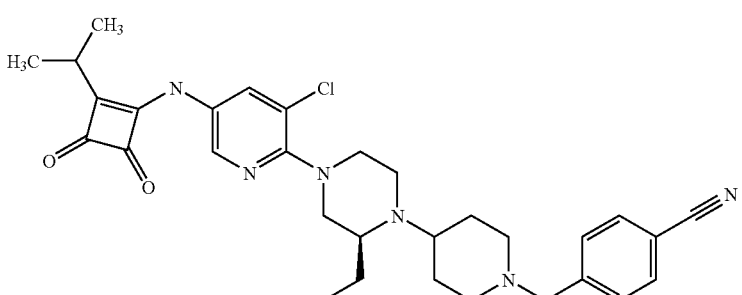 | A |

TABLE 1-continued

| Compound No. | STRUCTURE | IC$_{50}$ |
| --- | --- | --- |
| 89 | 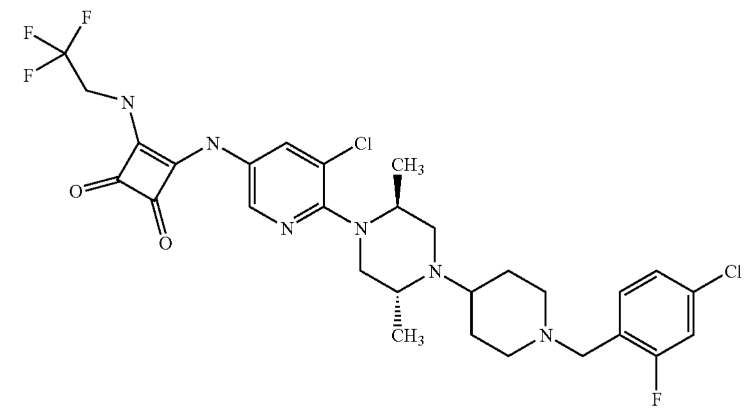 | A |
| 90 | 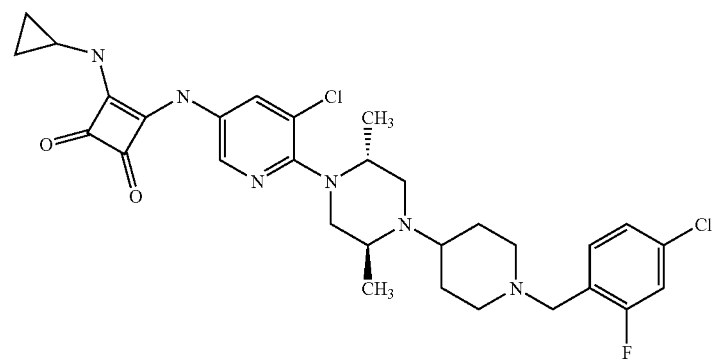 | A |
| 91 | 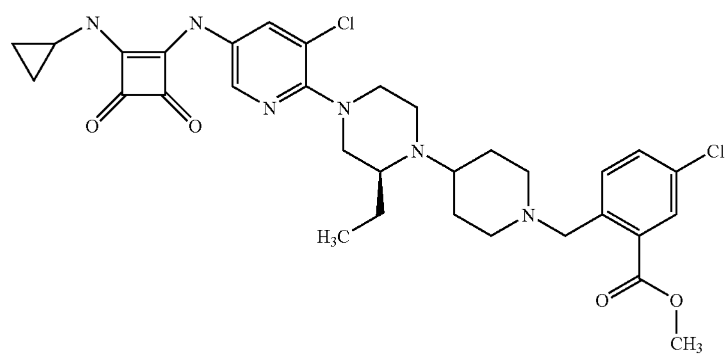 | A |
| 92 | 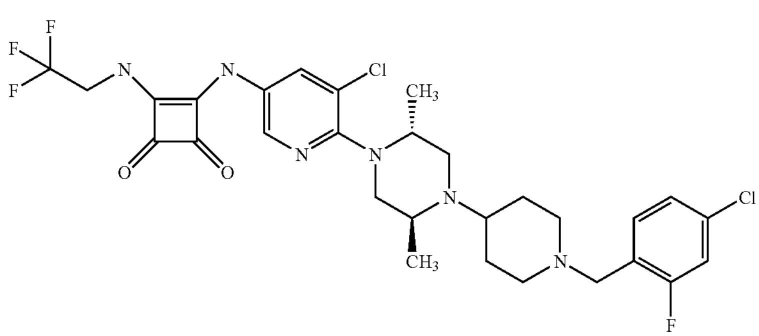 | A |

TABLE 1-continued

| Compound No. | STRUCTURE | IC$_{50}$ |
|---|---|---|
| 93 | 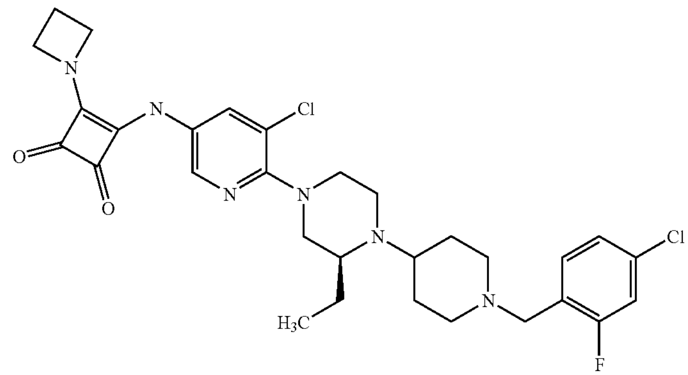 | A |
| 94 | 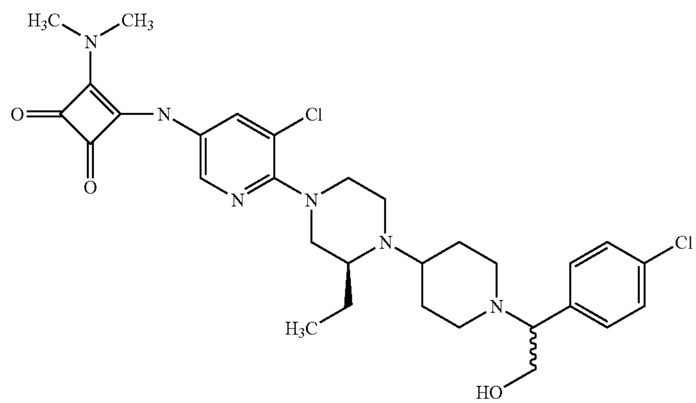 | A |
| 95 | 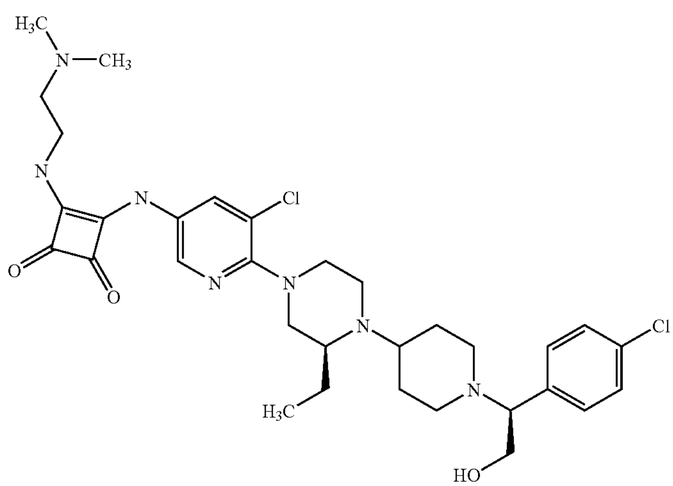 | A |

TABLE 1-continued

| Compound No. | STRUCTURE | IC$_{50}$ |
|---|---|---|
| 96 | 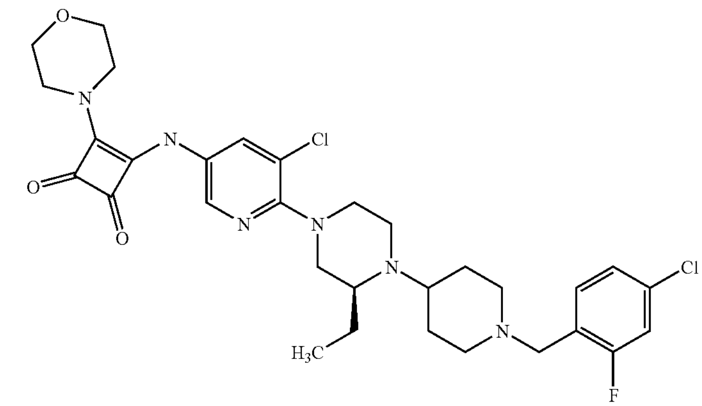 | A |
| 97 | 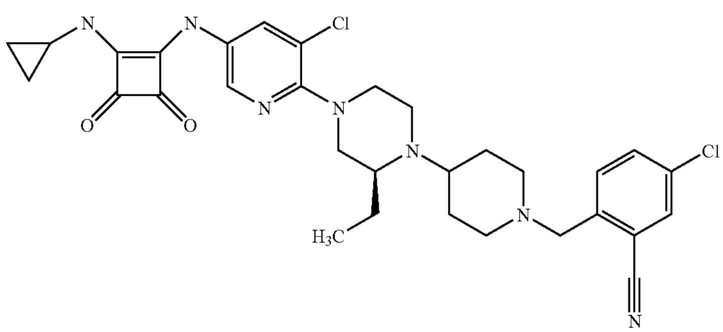 | A |
| 98 | 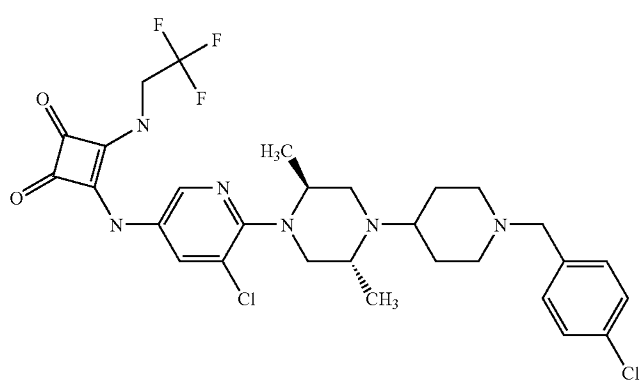 | A |
| 99 | 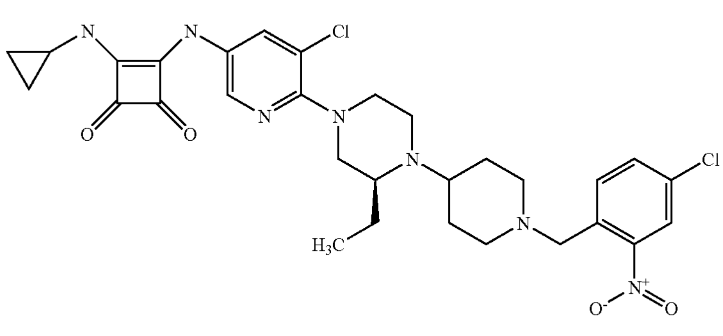 | A |

TABLE 1-continued
| Compound No. | STRUCTURE | IC$_{50}$ |
|---|---|---|
| 100 | 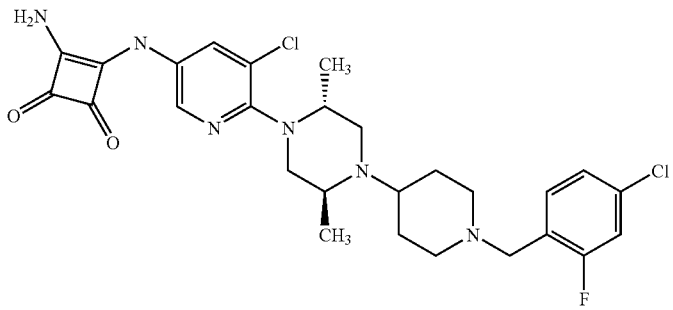 | A |
| 101 | 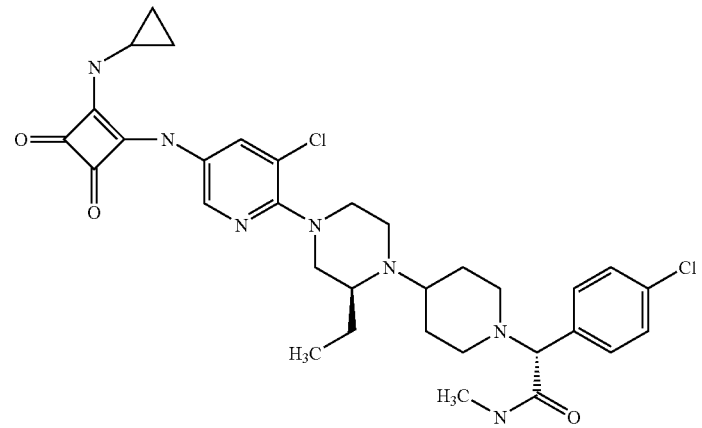 | A |
| 102 | 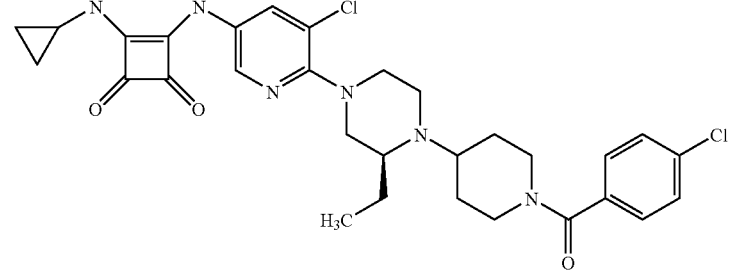 | A |
| 103 | 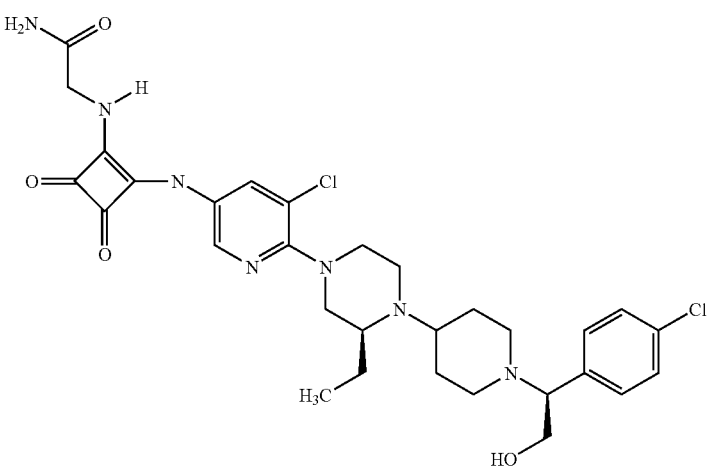 | B |

TABLE 1-continued

| Compound No. | STRUCTURE | IC$_{50}$ |
|---|---|---|
| 104 | 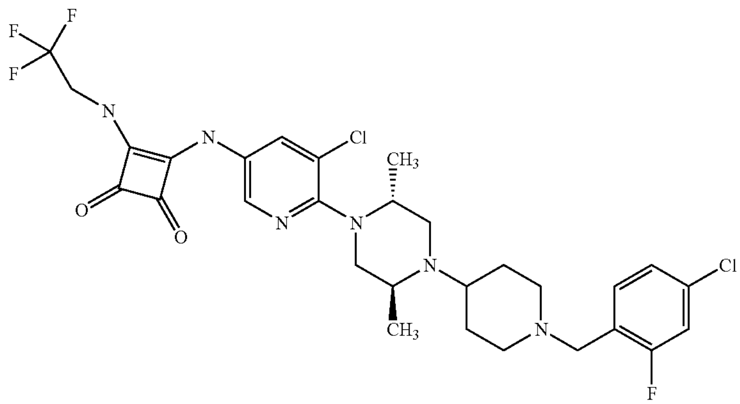 | B |
| 105 | 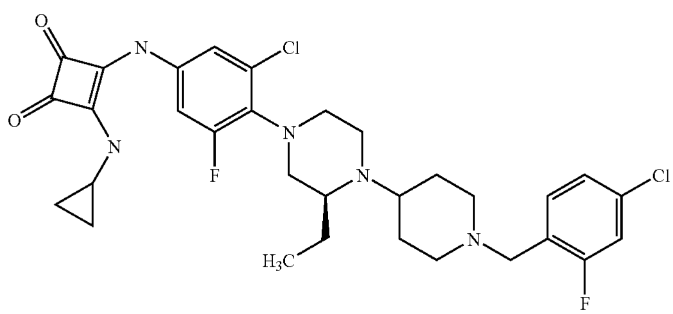 | B |
| 106 | 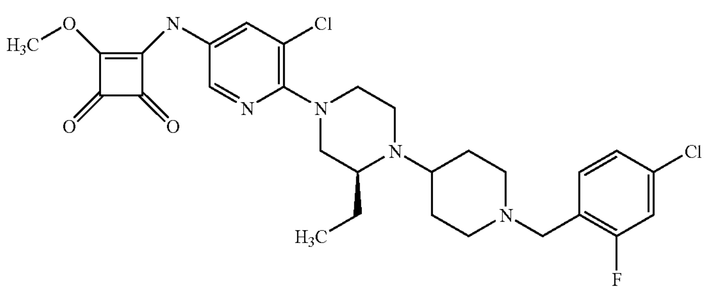 | B |
| 107 | 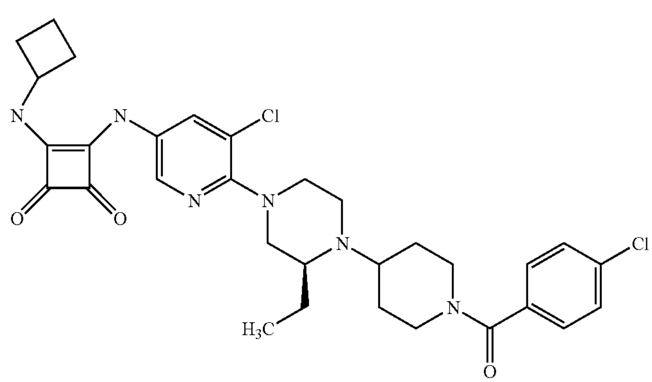 | B |

TABLE 1-continued

| Compound No. | STRUCTURE | IC$_{50}$ |
|---|---|---|
| 108 | 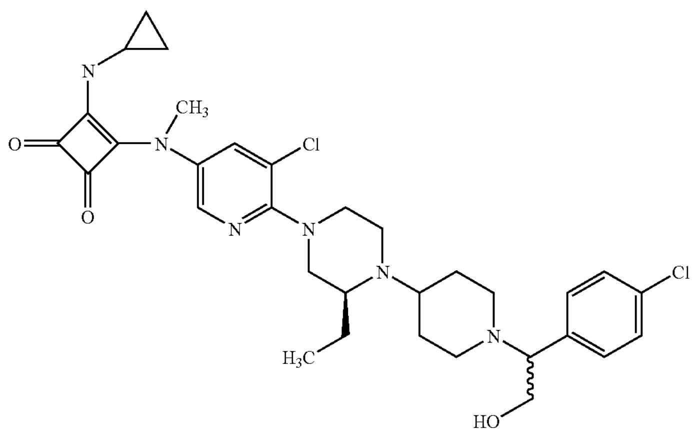 | B |
| 109 | 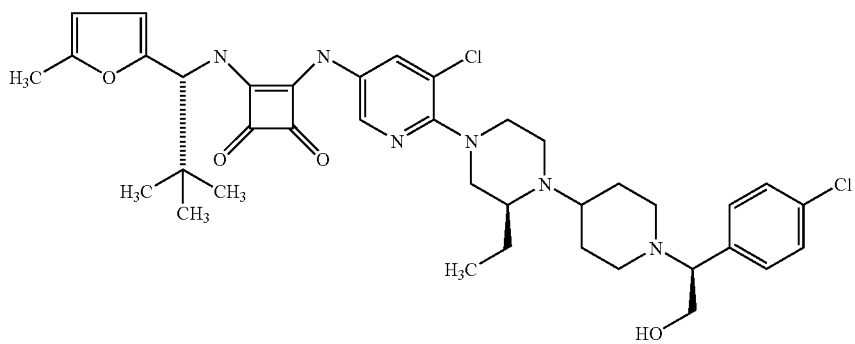 | B |
| 110 | 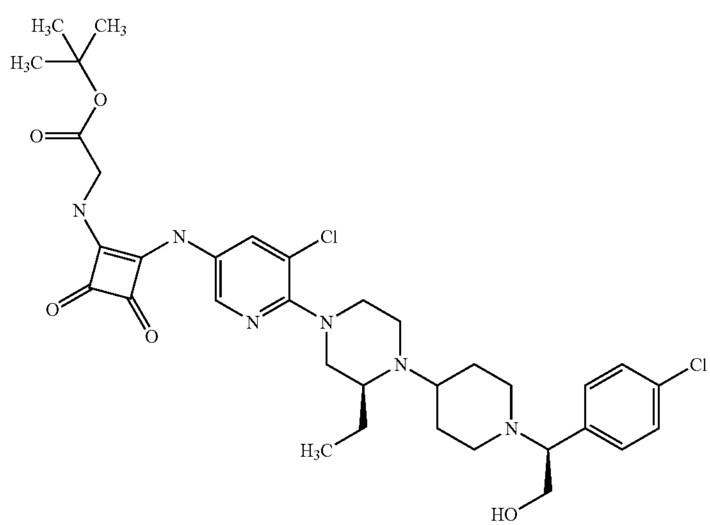 | B |

TABLE 1-continued

| Compound No. | STRUCTURE | IC$_{50}$ |
|---|---|---|
| 111 | 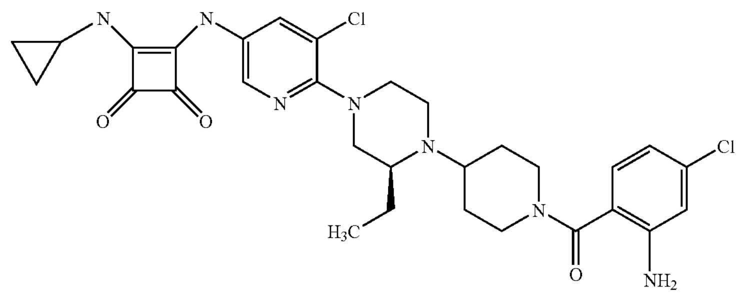 | B |
| 112 | 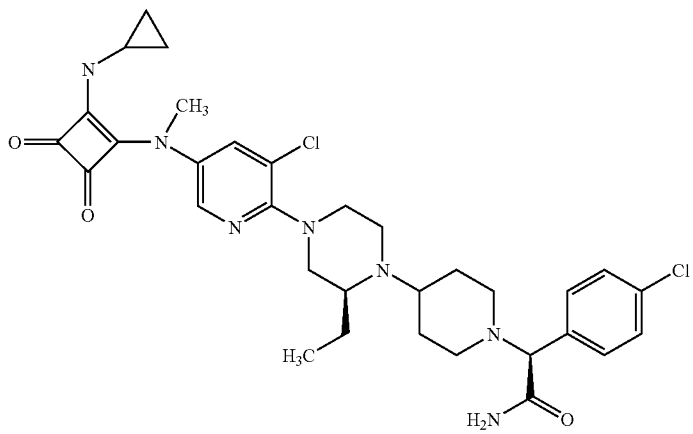 | B |
| 113 | 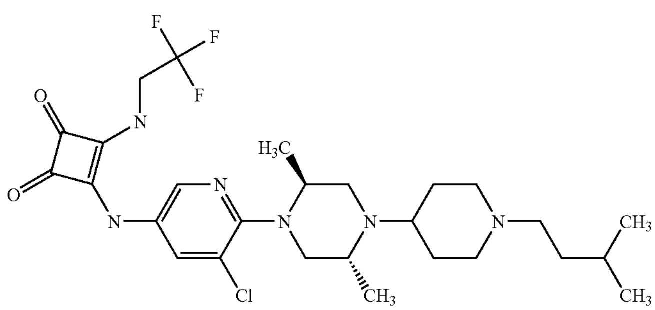 | C |
| 114 | 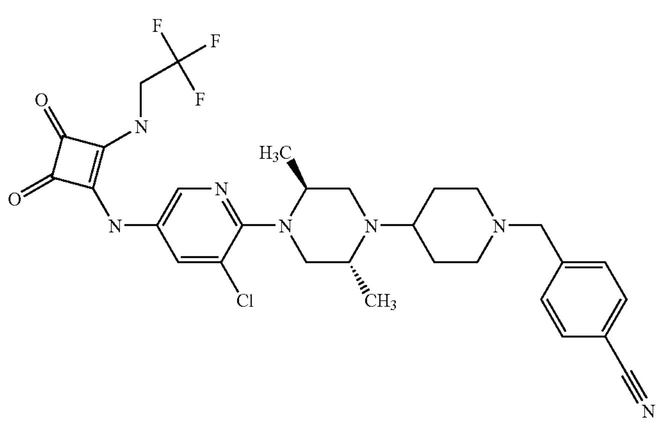 | C |

TABLE 1-continued

| Compound No. | STRUCTURE | IC$_{50}$ |
|---|---|---|
| 115 | 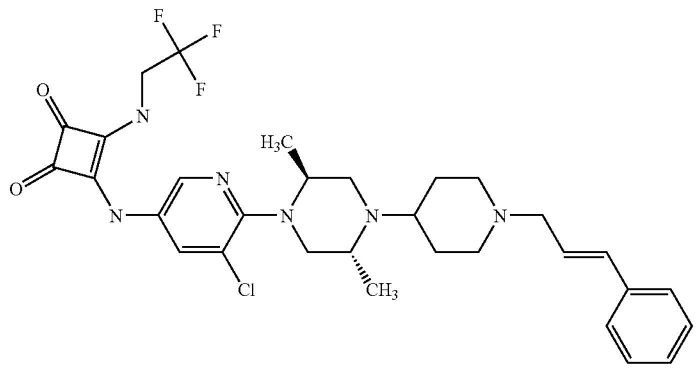 | C |
| 116 | 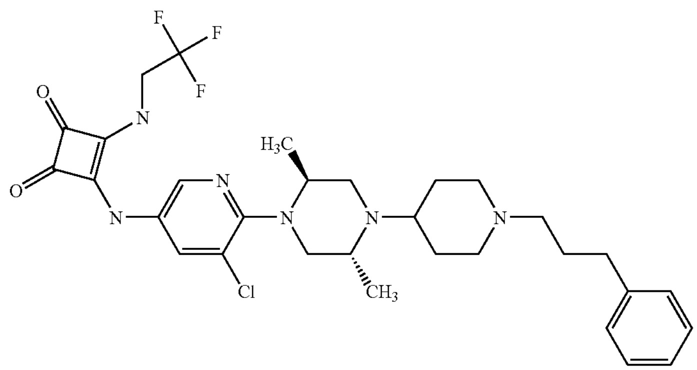 | C |
| 117 | 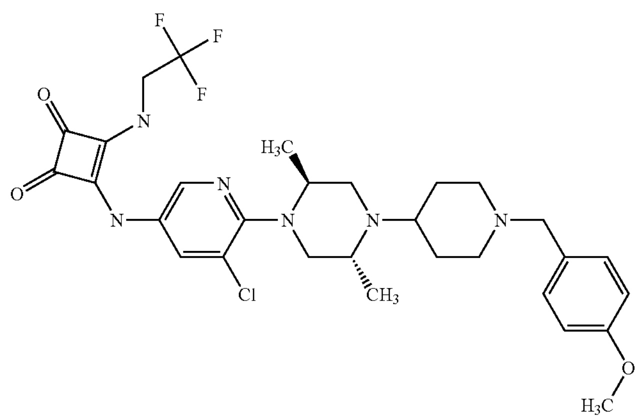 | C |
| 118 | 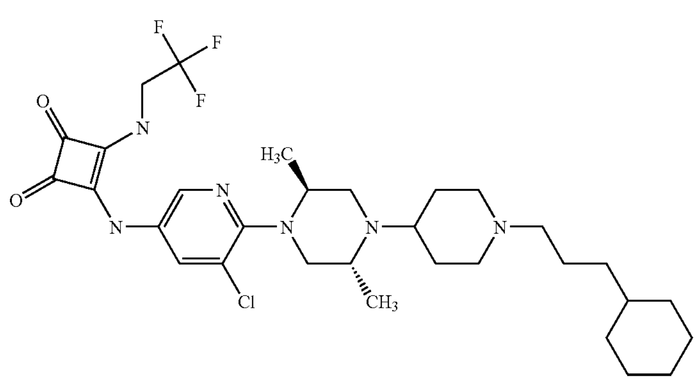 | C |

TABLE 1-continued
| Compound No. | STRUCTURE | IC$_{50}$ |
|---|---|---|
| 119 | 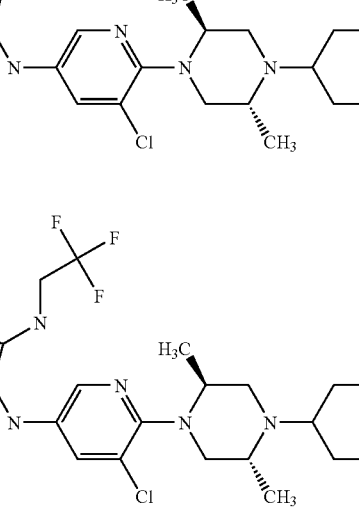 | C |
| 120 | 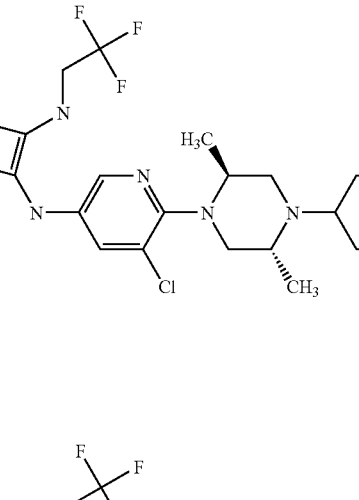 | C |
| 121 | 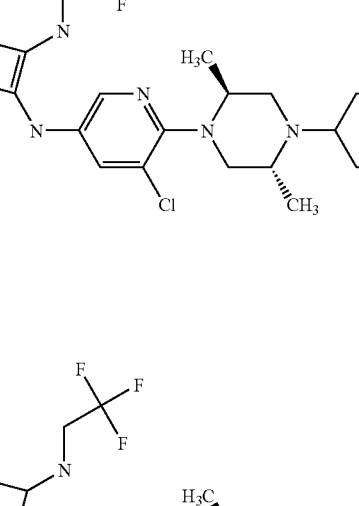 | C |
| 122 | 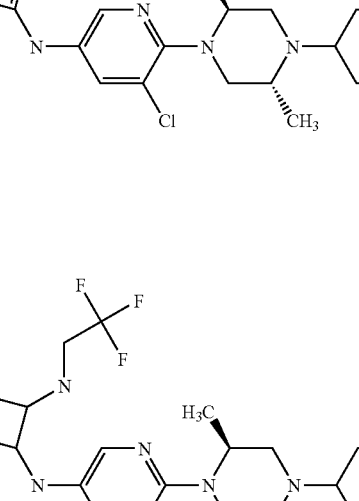 | C |

TABLE 1-continued
| Compound No. | STRUCTURE | IC$_{50}$ |
|---|---|---|
| 123 | 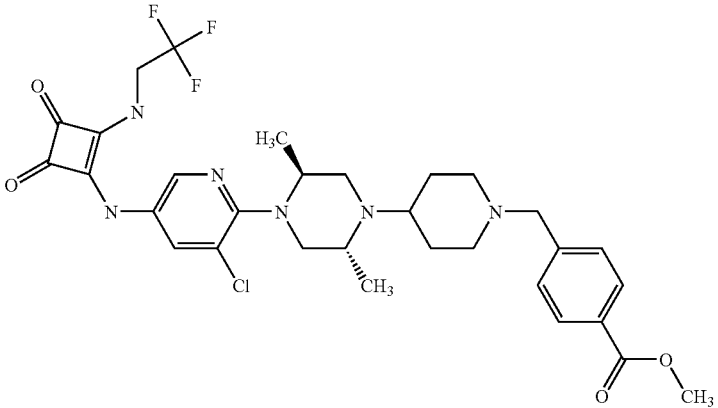 | C |
| 124 | 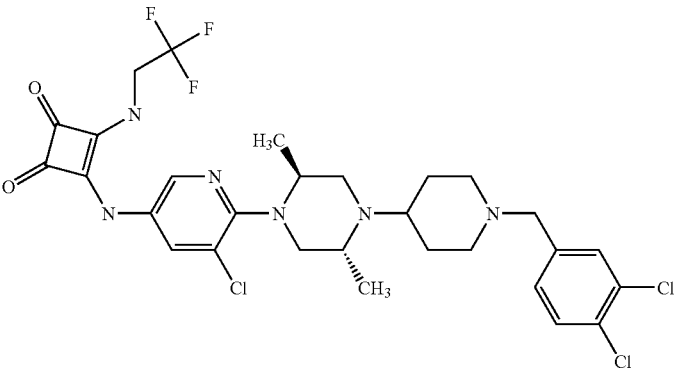 | C |
| 125 | 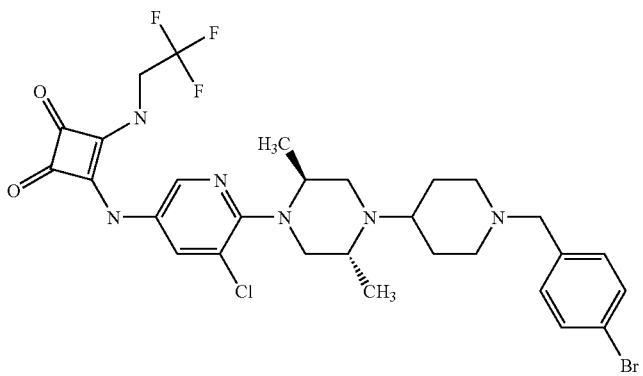 | C |

TABLE 1-continued

| Compound No. | STRUCTURE | IC$_{50}$ |
|---|---|---|
| 126 | 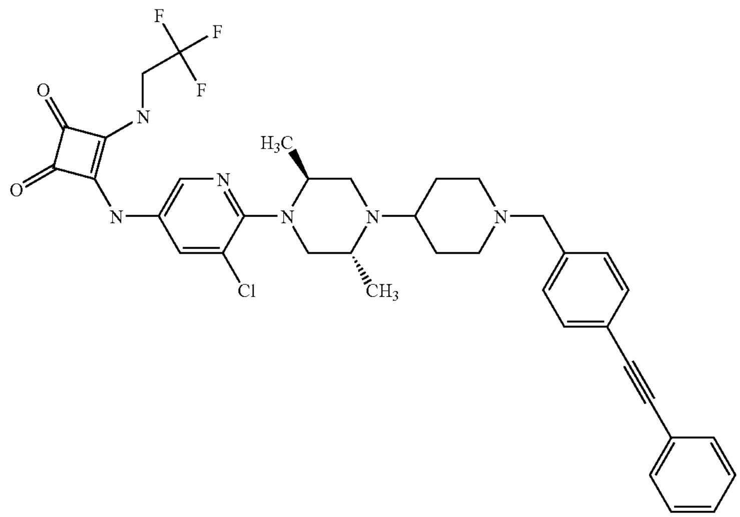 | C |
| 127 | 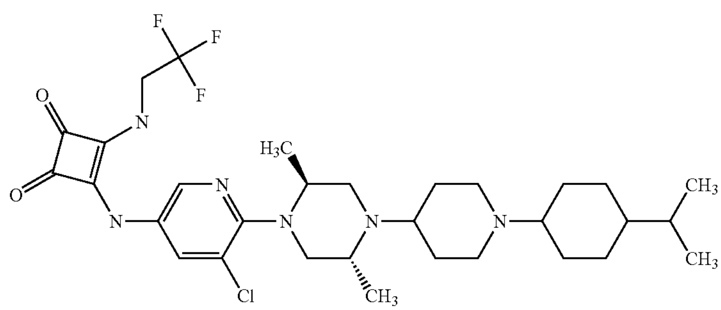 | C |
| 128 | 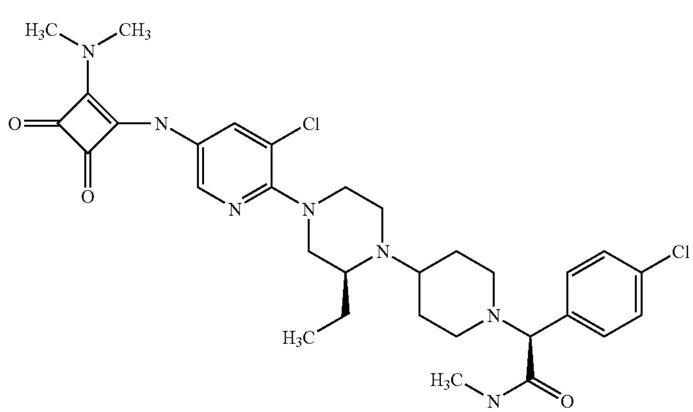 | C |

TABLE 1-continued
| Compound No. | STRUCTURE | IC$_{50}$ |
|---|---|---|
| 129 | 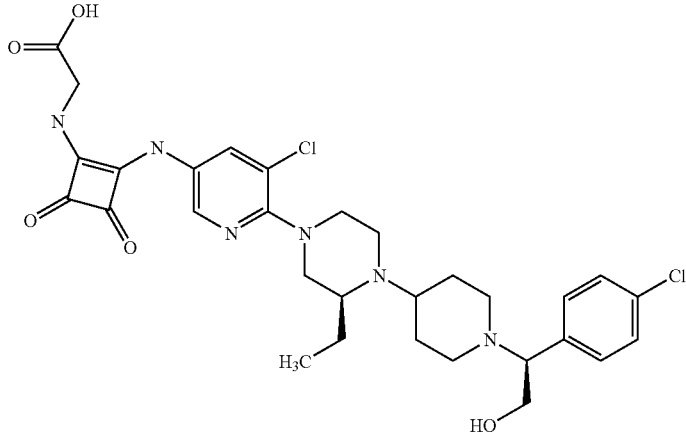 | C |
| 130 | 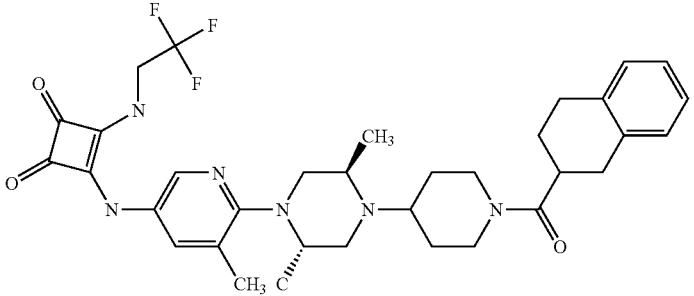 | C |
| 131 | 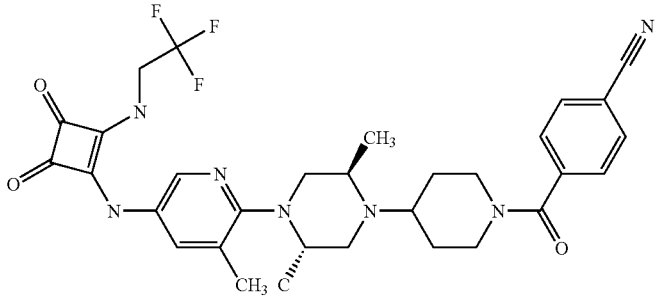 | C |
| 132 | 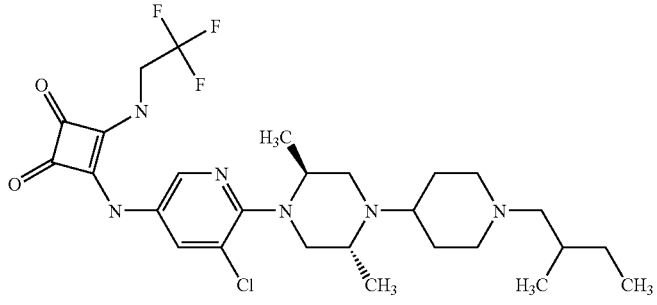 | C |

TABLE 1-continued
| Compound No. | STRUCTURE | IC$_{50}$ |
|---|---|---|
| 133 | 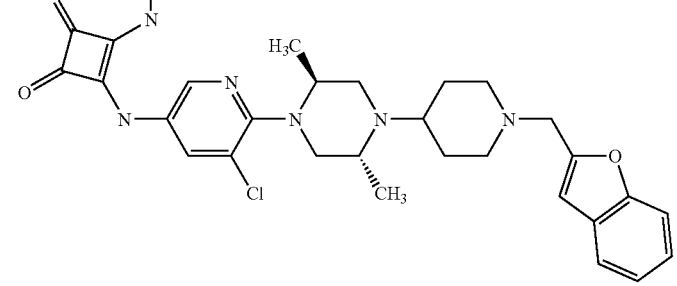 | C |
| 134 | 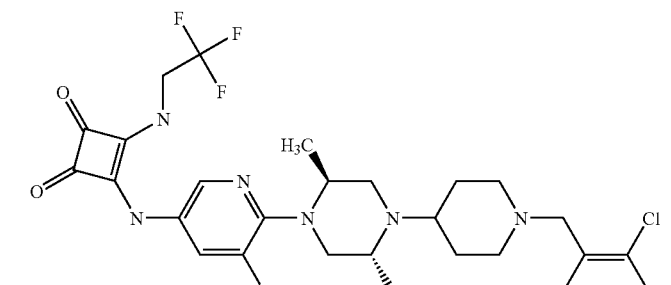 | C |
| 135 | 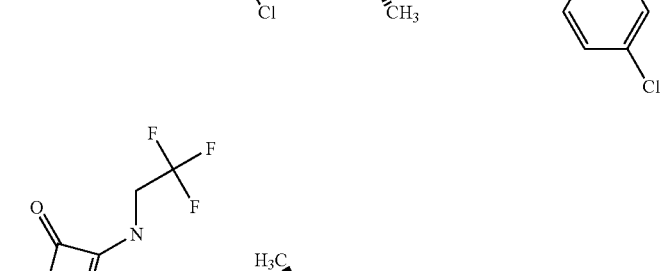 | C |
| 136 | 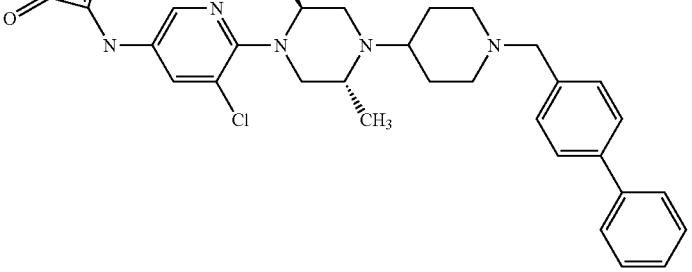 | C |

TABLE 1-continued

| Compound No. | STRUCTURE | IC$_{50}$ |
|---|---|---|
| 137 | 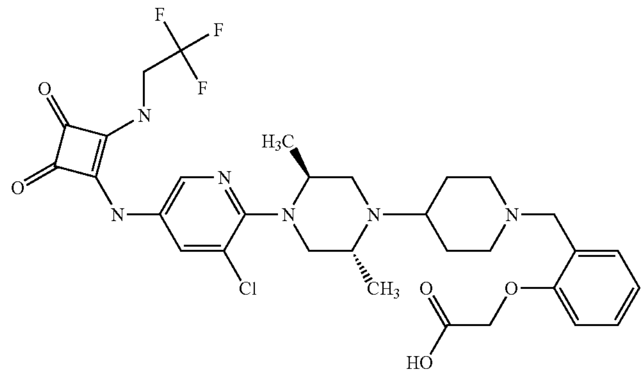 | C |
| 138 | 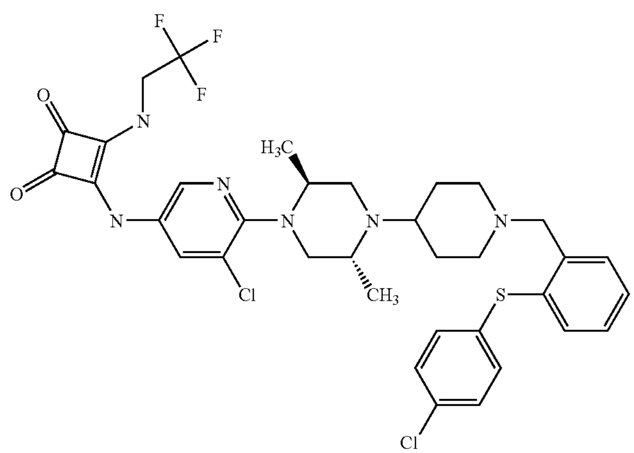 | C |
| 139 | 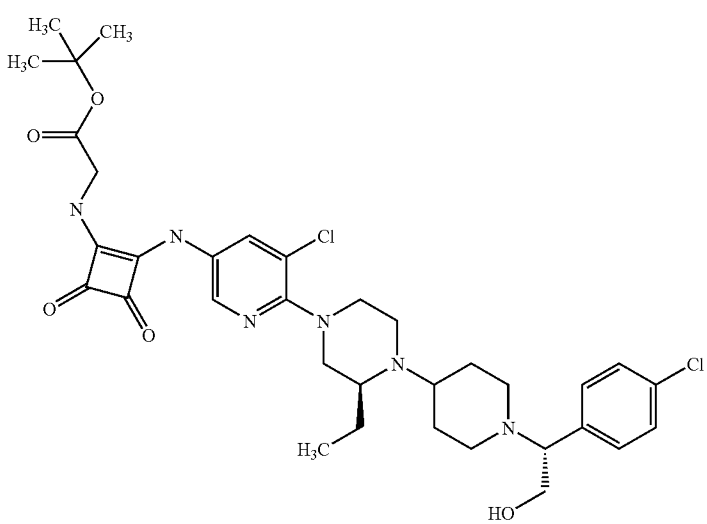 | C |

TABLE 1-continued

| Compound No. | STRUCTURE | IC$_{50}$ |
|---|---|---|
| 140 | 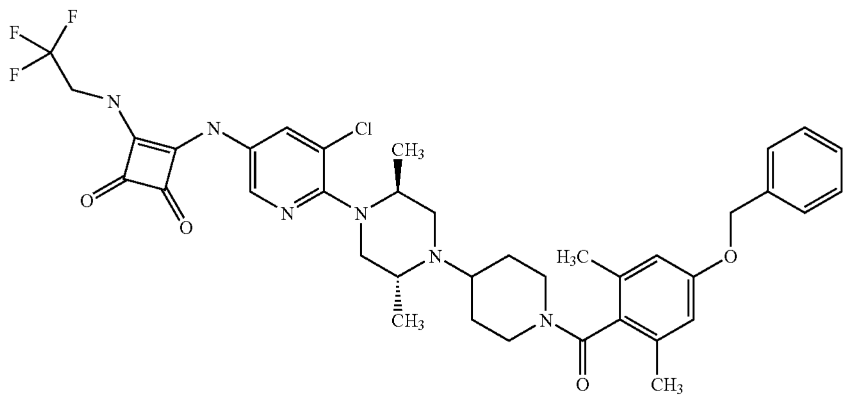 | C |
| 141 | 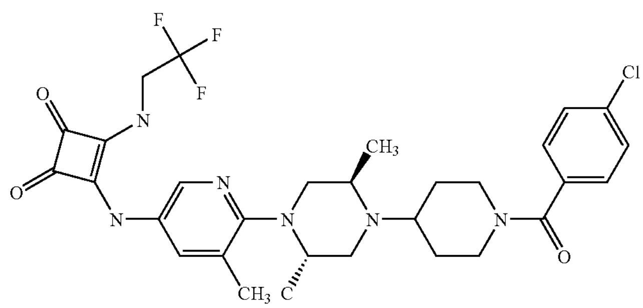 | C |
| 142 | 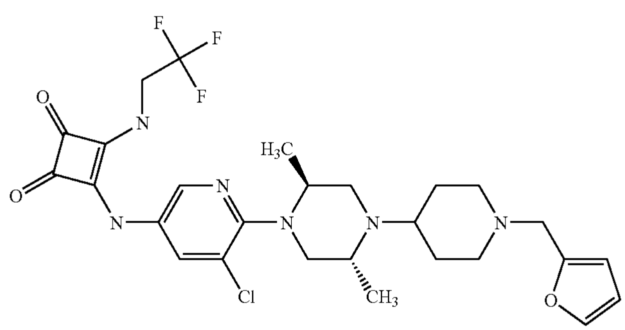 | C |
| 143 | 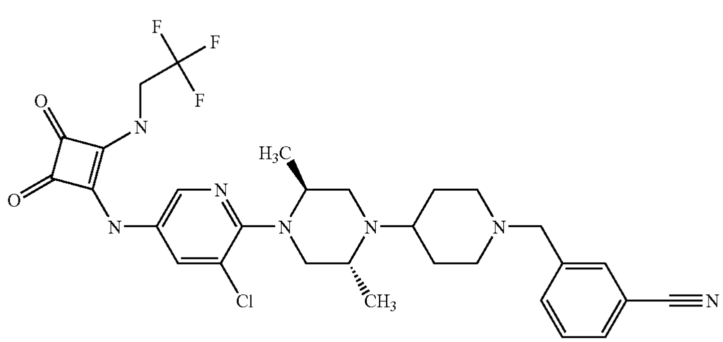 | C |

TABLE 1-continued

| Compound No. | STRUCTURE | IC$_{50}$ |
|---|---|---|
| 144 | 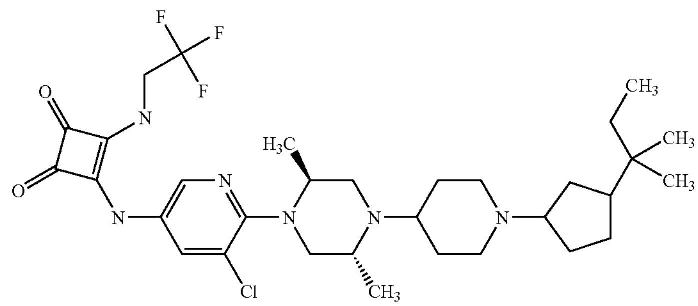 | C |
| 145 | 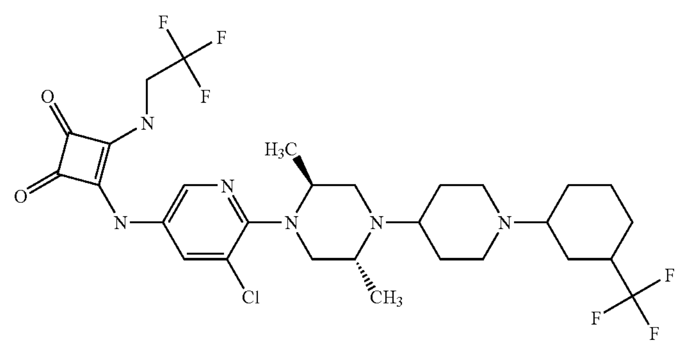 | C |
| 146 | 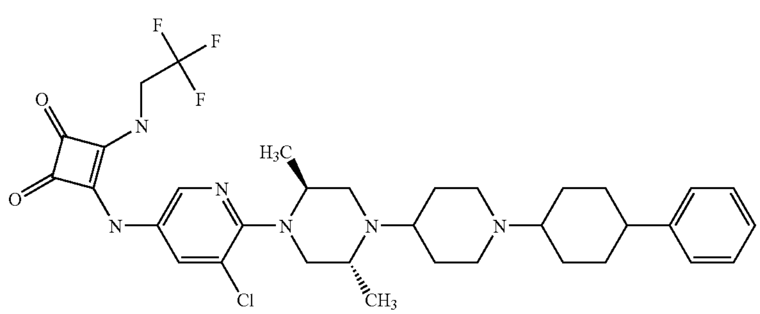 | C |
| 147 | 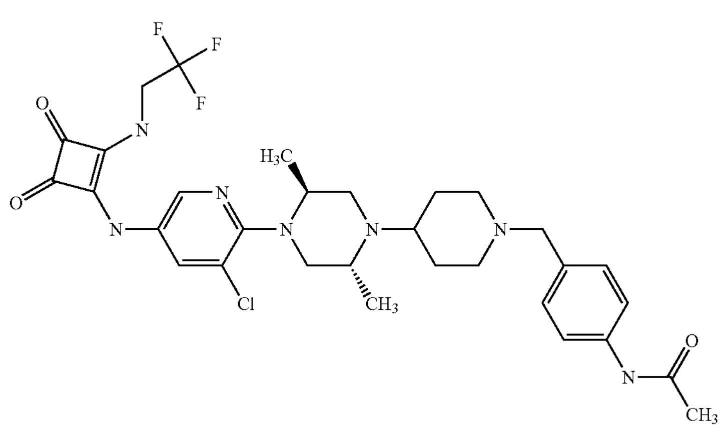 | C |

TABLE 1-continued

| Compound No. | STRUCTURE | IC$_{50}$ |
|---|---|---|
| 148 | 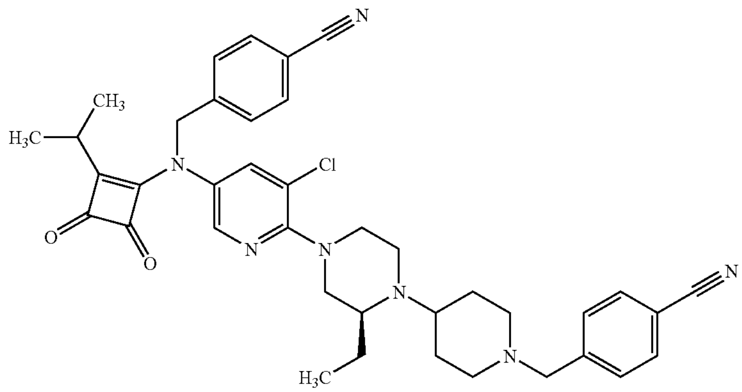 | C |
| 149 | 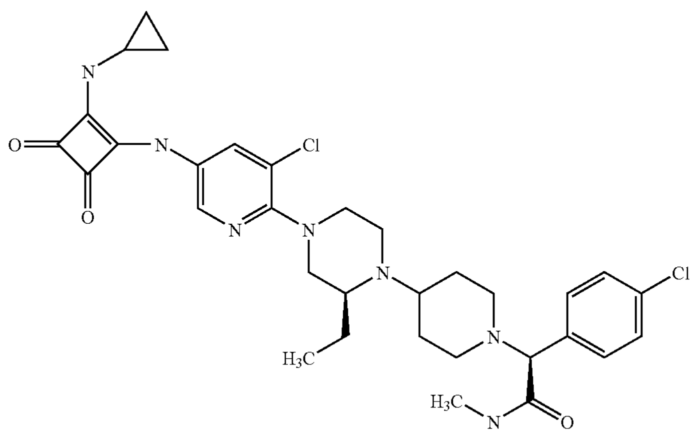 | C |
| 150 | 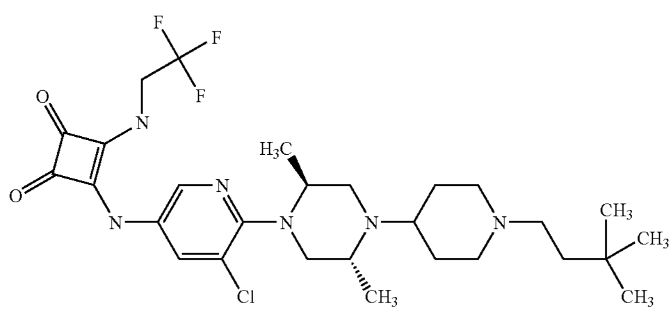 | C |
| 151 | 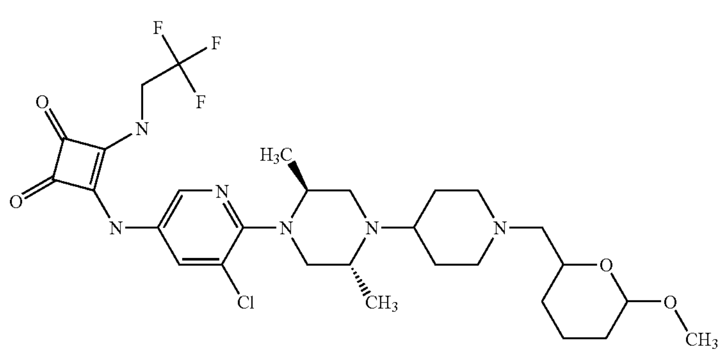 | C |

TABLE 1-continued

| Compound No. | STRUCTURE | IC$_{50}$ |
|---|---|---|
| 152 | 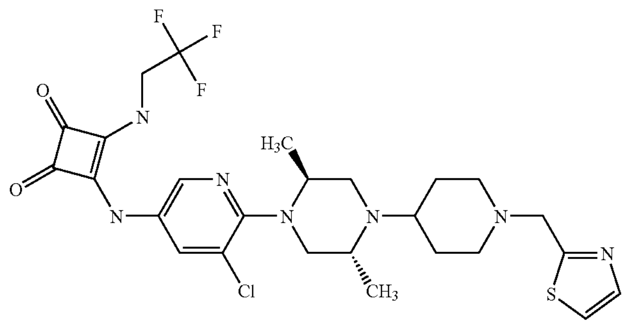 | C |
| 153 | 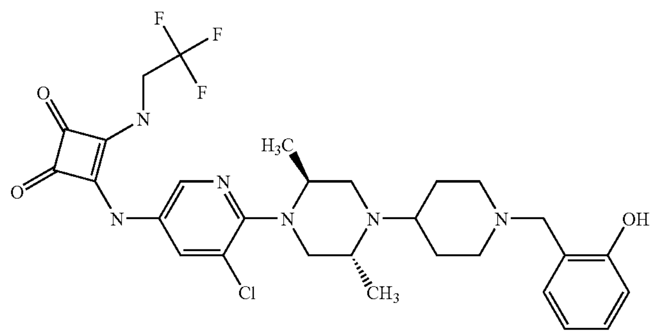 | C |
| 154 | 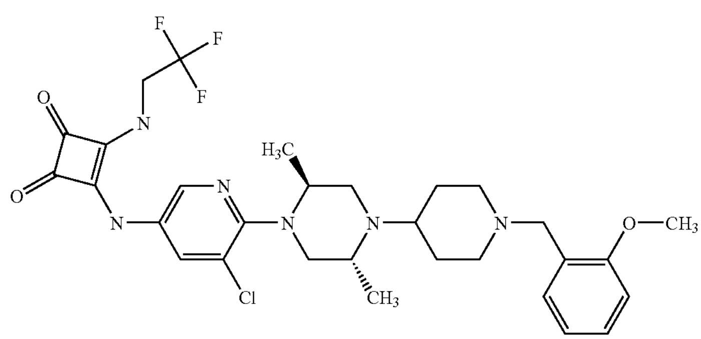 | C |
| 155 | 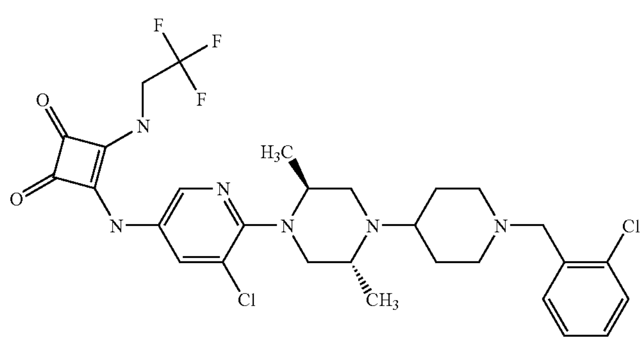 | C |

TABLE 1-continued

| Compound No. | STRUCTURE | IC$_{50}$ |
|---|---|---|
| 156 | 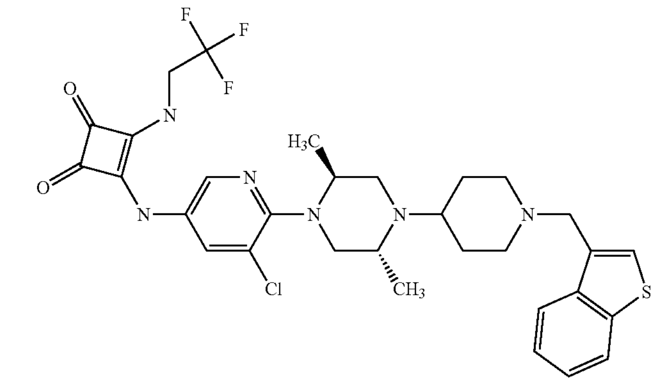 | C |
| 157 | 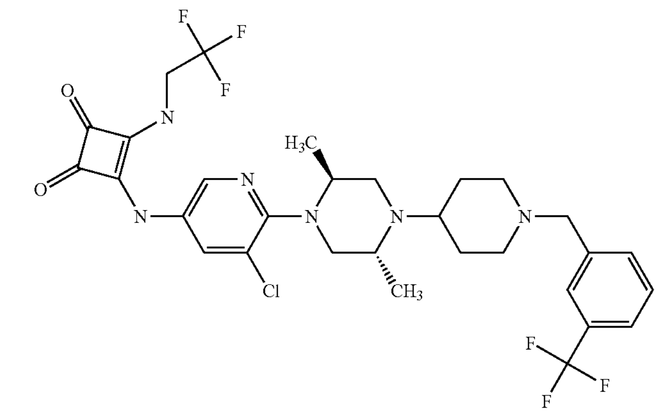 | C |
| 158 | 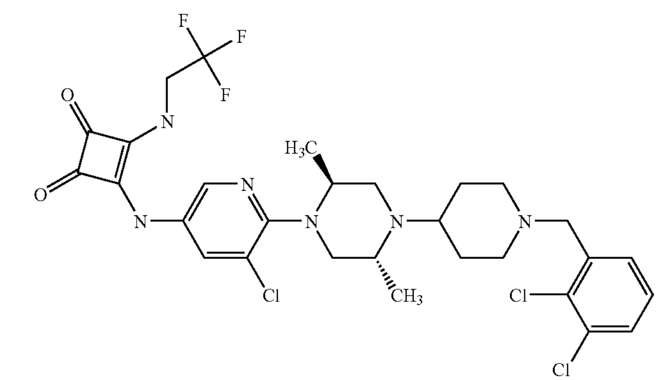 | C |
| 159 | 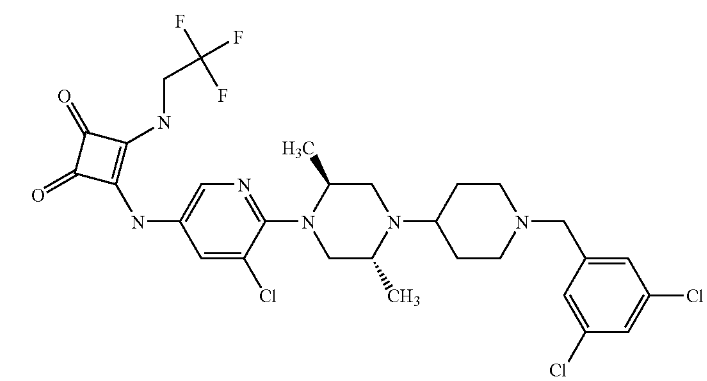 | C |

TABLE 1-continued

| Compound No. | STRUCTURE | IC$_{50}$ |
|---|---|---|
| 160 | 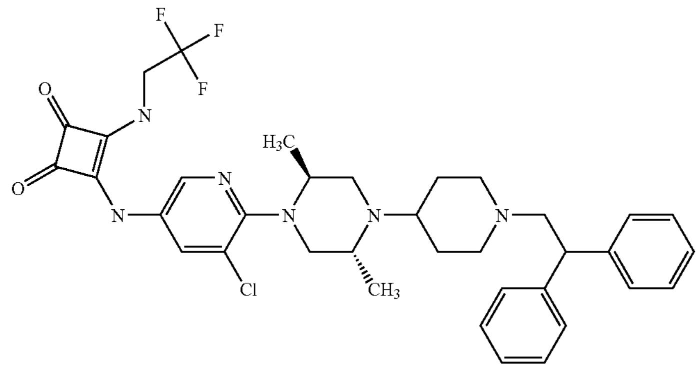 | C |
| 161 | 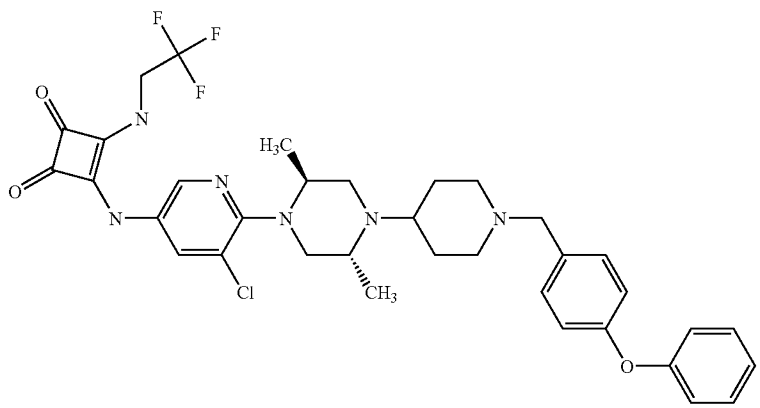 | C |
| 162 | 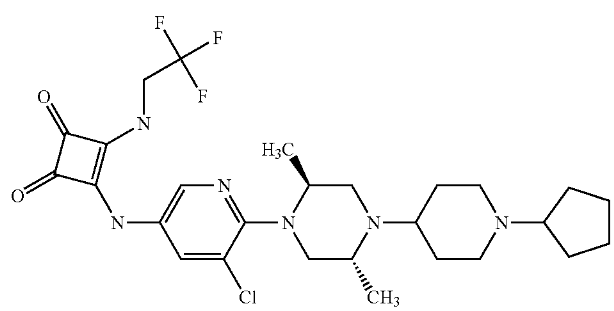 | C |
| 163 | 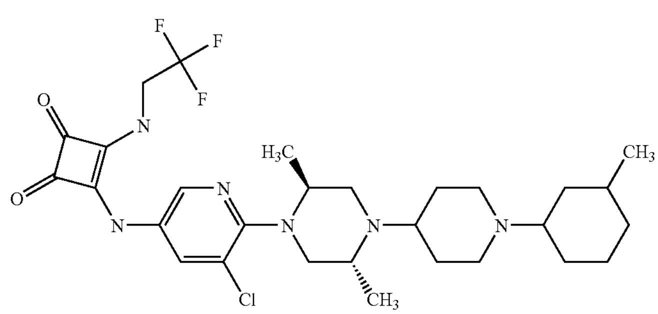 | C |

TABLE 1-continued

| Compound No. | STRUCTURE | IC$_{50}$ |
|---|---|---|
| 164 | 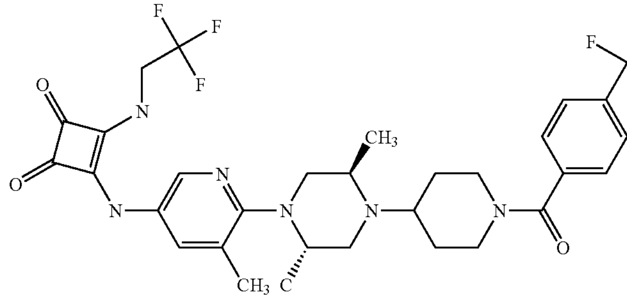 | C |
| 165 | 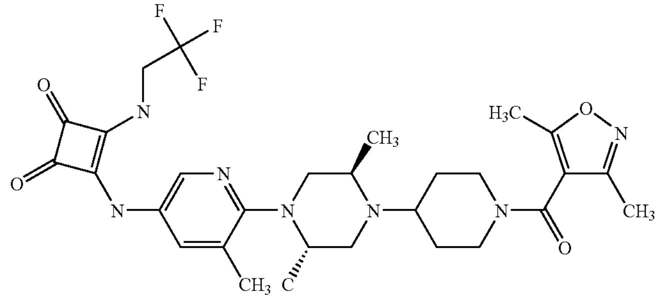 | C |
| 166 | 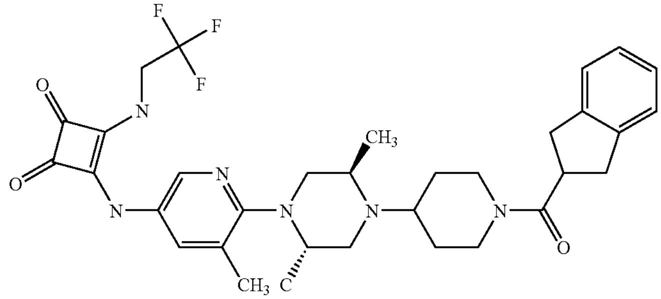 | C |
| 167 | 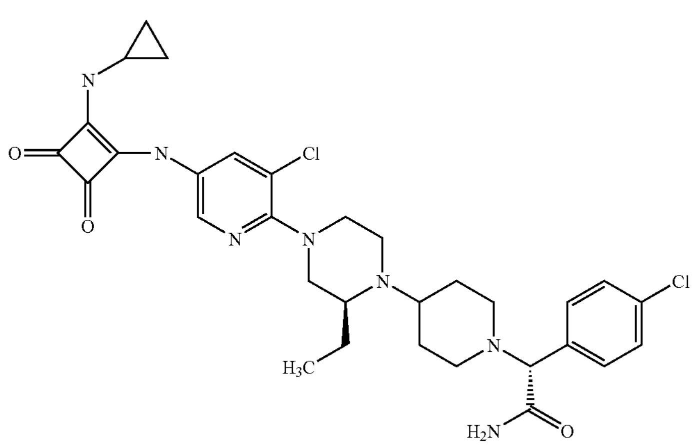 | C |

TABLE 1-continued

| Compound No. | STRUCTURE | IC$_{50}$ |
|---|---|---|
| 168 | 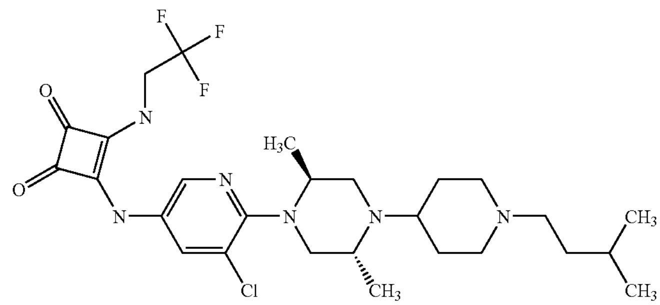 | C |
| 169 | 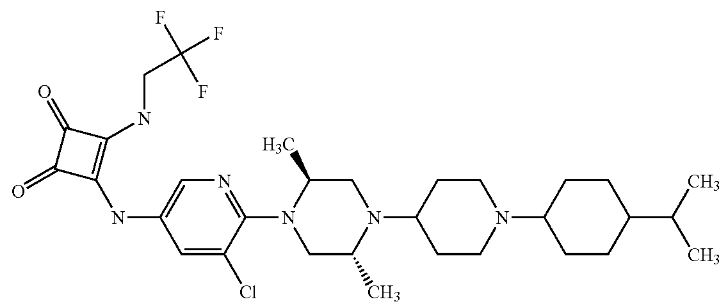 | C |
| 170 | 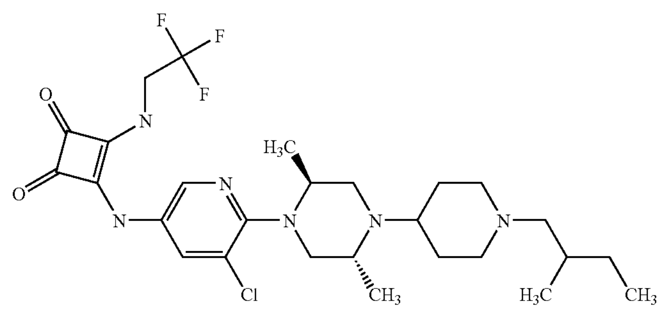 | C |
| 171 | 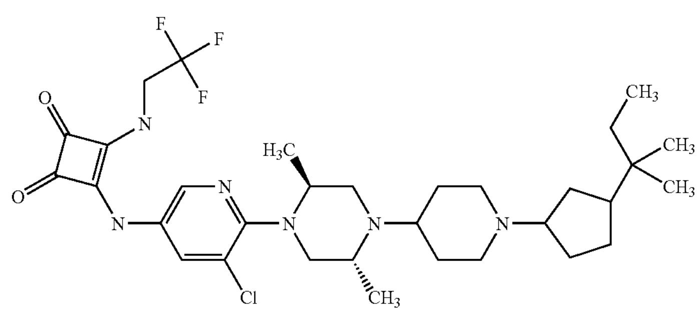 | C |

TABLE 1-continued

| Compound No. | STRUCTURE | IC$_{50}$ |
|---|---|---|
| 172 | 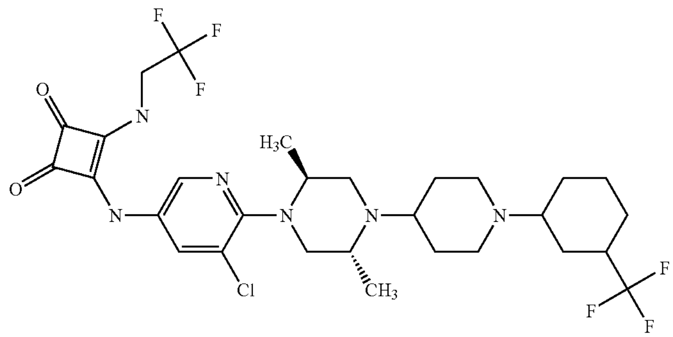 | C |
| 173 | 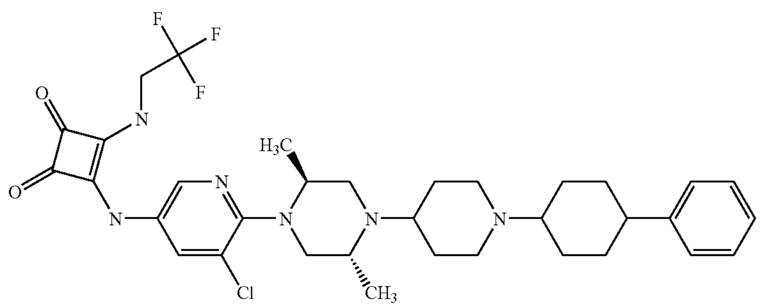 | C |
| 174 | 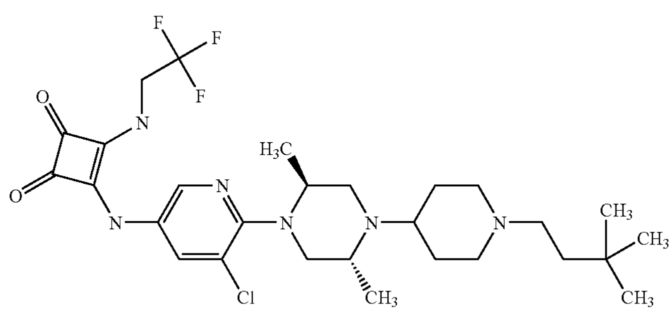 | C |
| 175 | 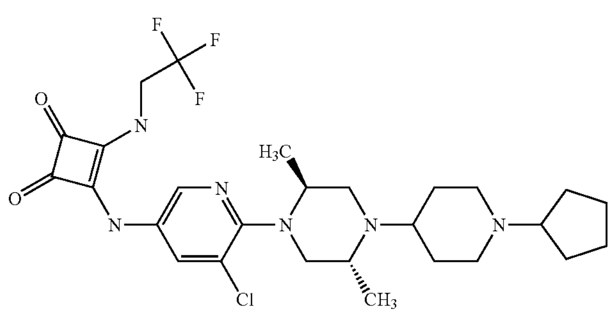 | C |

TABLE 1-continued

| Compound No. | STRUCTURE | IC$_{50}$ |
|---|---|---|
| 176 | 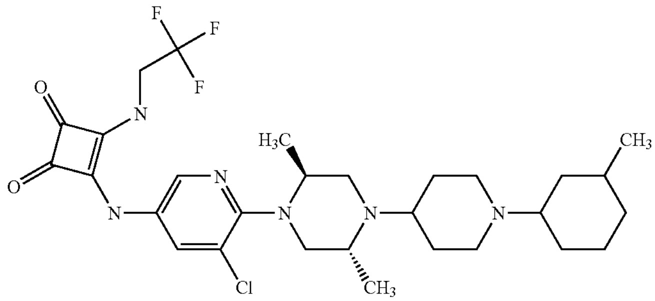 | C |
| 177 | 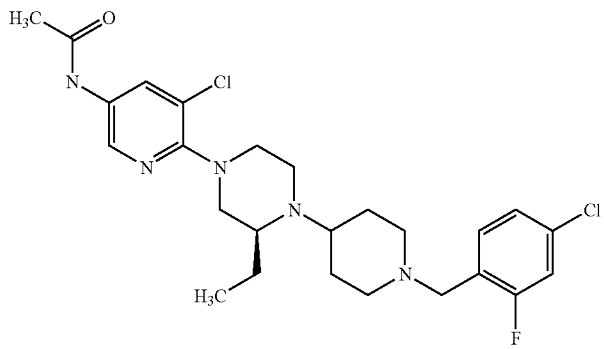 | A |
| 178 | 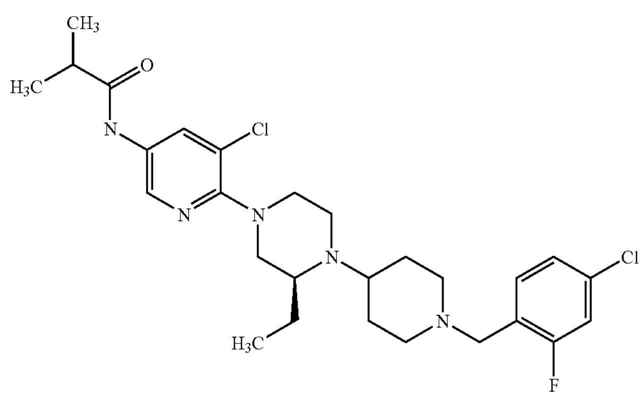 | A |
| 179 | 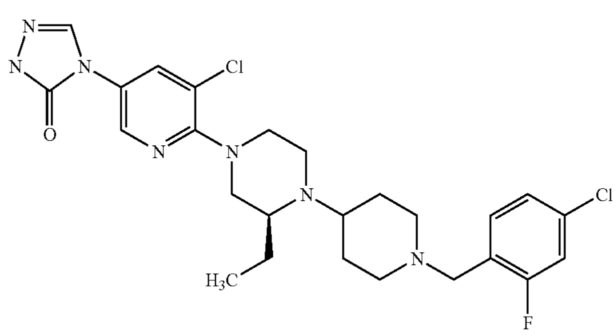 | A |

TABLE 1-continued
| Compound No. | STRUCTURE | IC50 |
|---|---|---|
| 180 | 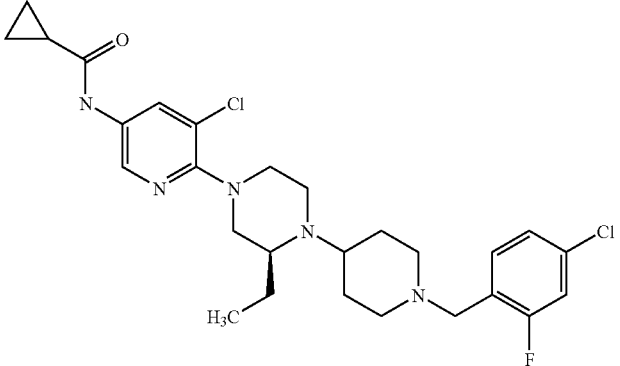 | A |
| 181 | 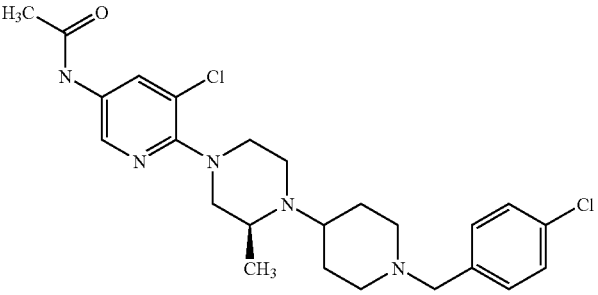 | A |
| 182 | 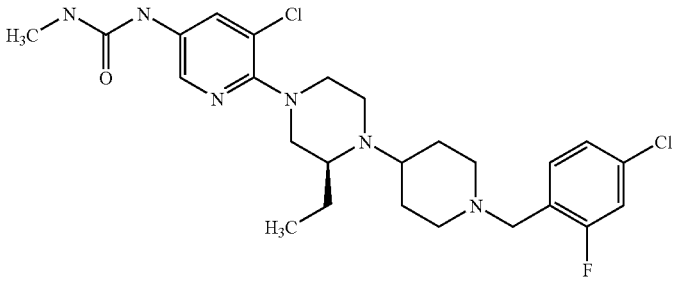 | A |
| 183 | 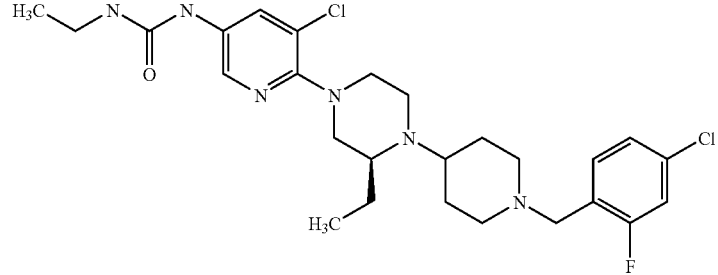 | A |

TABLE 1-continued
| Compound No. | STRUCTURE | IC$_{50}$ |
|---|---|---|
| 184 | 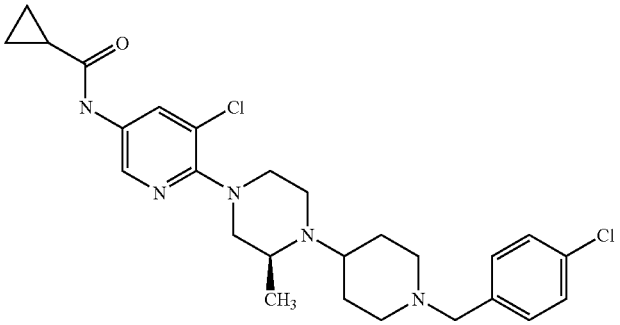 | A |
| 185 | 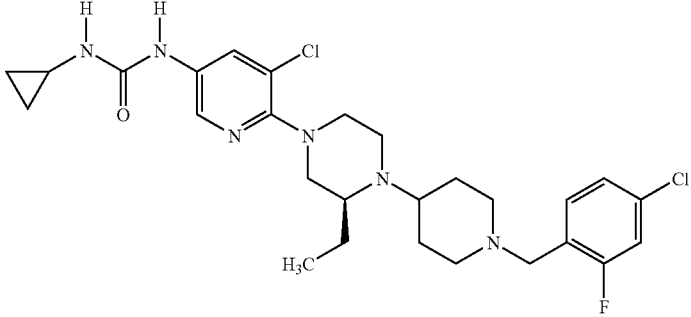 | A |
| 186 | 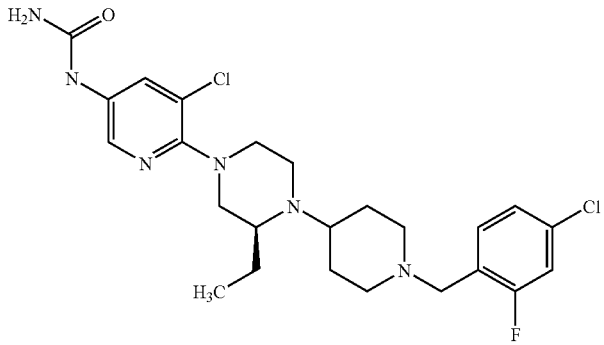 | B |
| 187 | 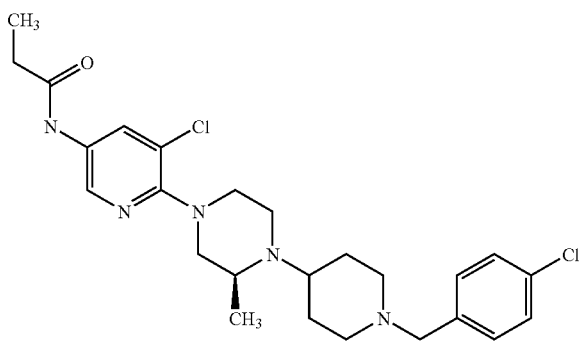 | B |

TABLE 1-continued

| Compound No. | STRUCTURE | IC$_{50}$ |
|---|---|---|
| 188 | 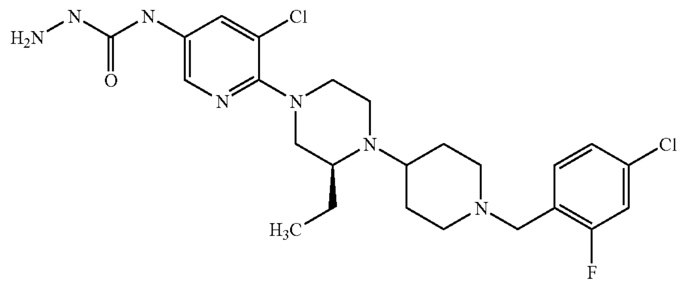 | B |
| 189 | 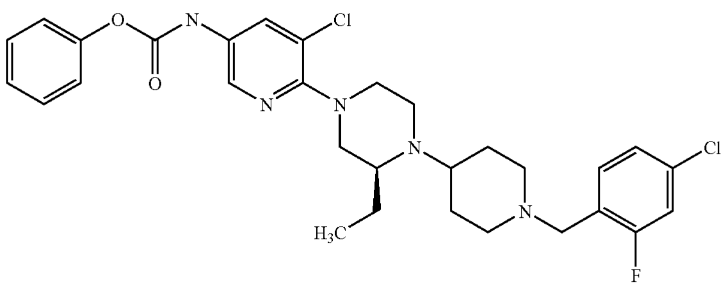 | B |
| 190 | 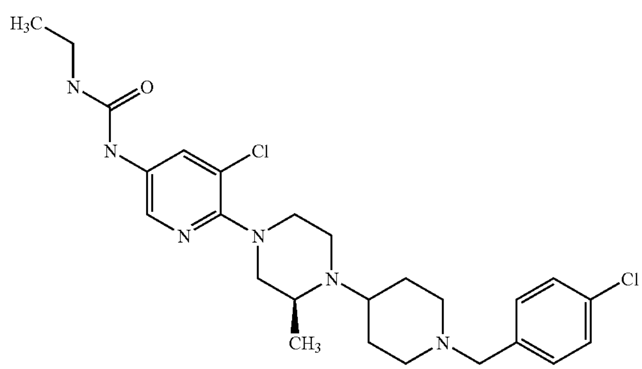 | B |
| 191 | 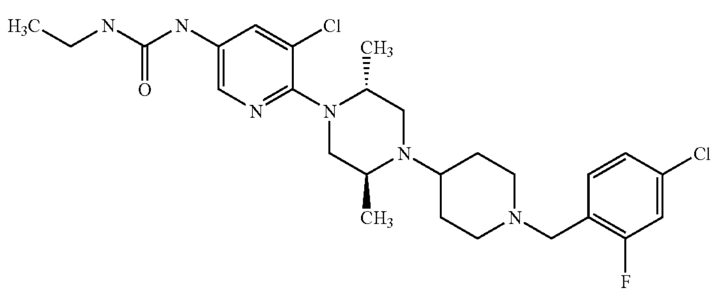 | C |
| 192 | 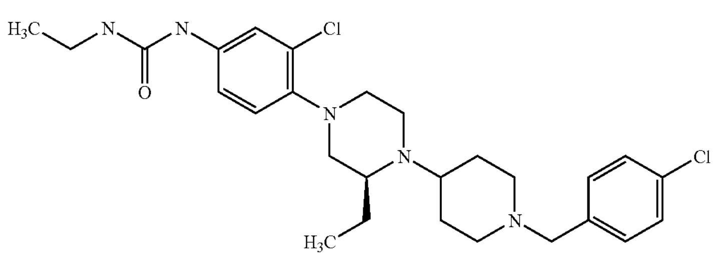 | C |

TABLE 1-continued

| Compound No. | STRUCTURE | IC$_{50}$ |
|---|---|---|
| 193 | 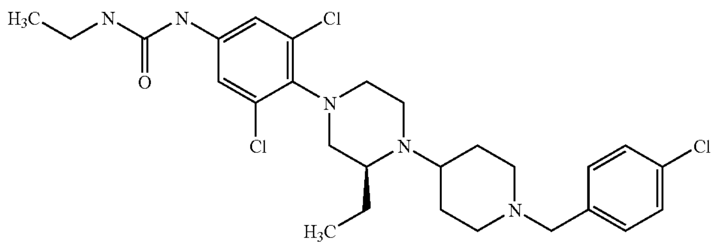 | C |
| 194 | 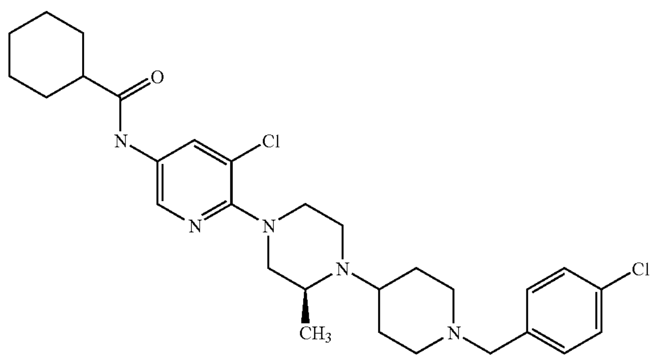 | C |
| 195 | 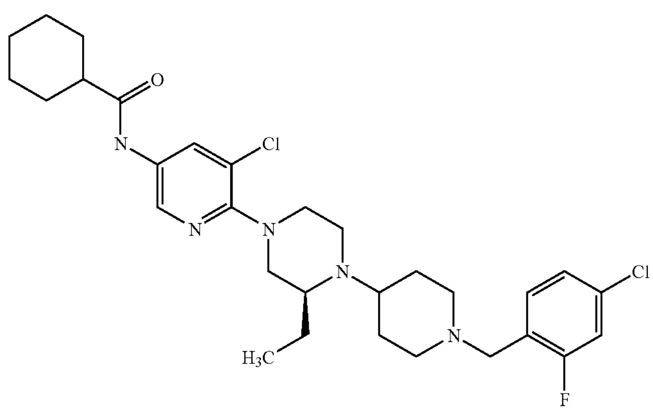 | C |
| 196 | 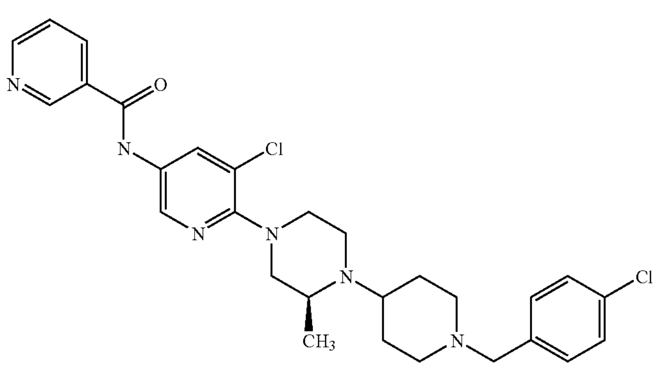 | C |

TABLE 1-continued

| Compound No. | STRUCTURE | IC$_{50}$ |
|---|---|---|
| 197 | 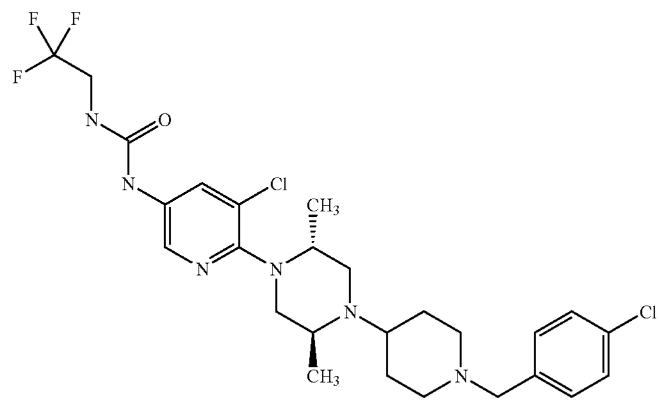 | C |
| 198 | 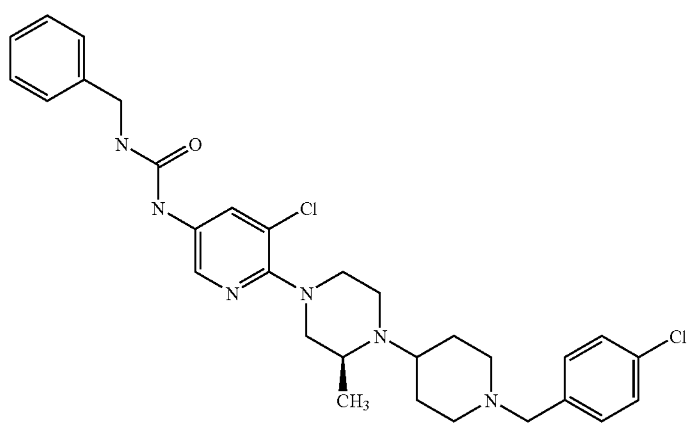 | C |
| 199 | 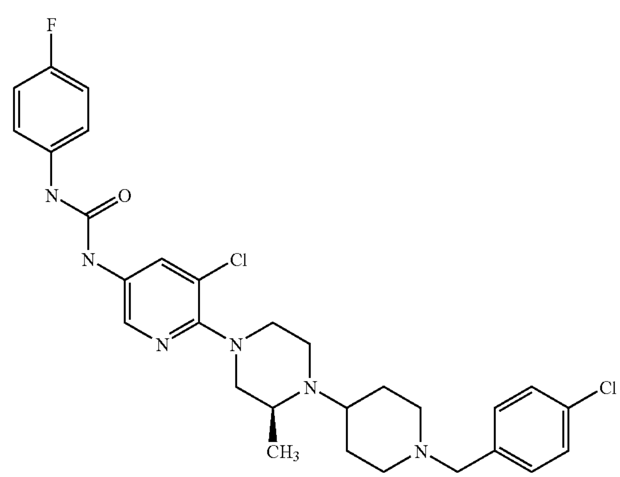 | C |

TABLE 1-continued

| Compound No. | STRUCTURE | IC$_{50}$ |
|---|---|---|
| 200 | 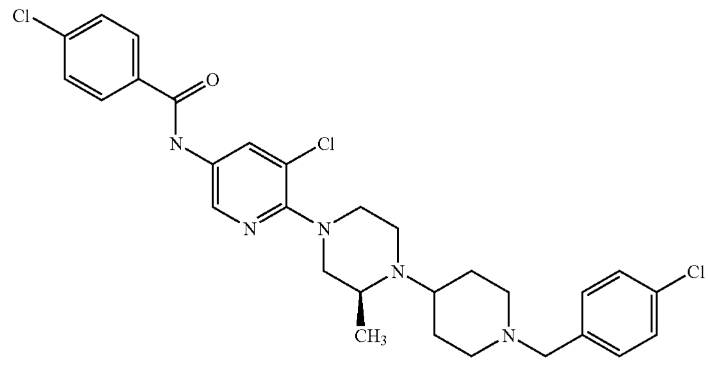 | C |
| 201 | 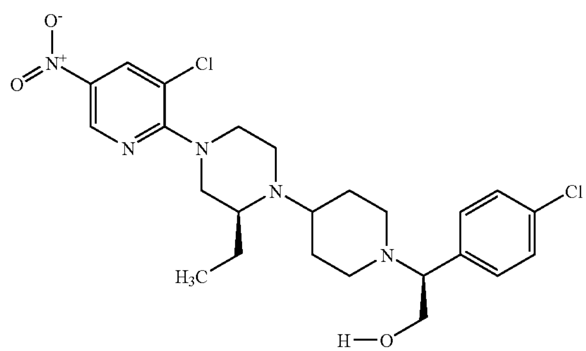 | A |
| 202 | 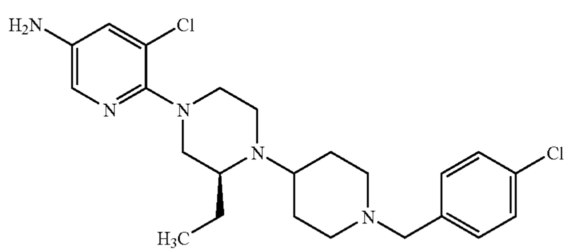 | A |
| 203 | 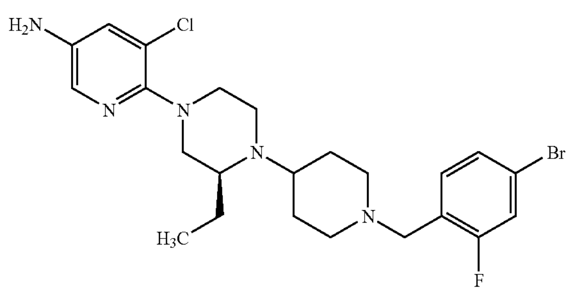 | A |
| 204 | 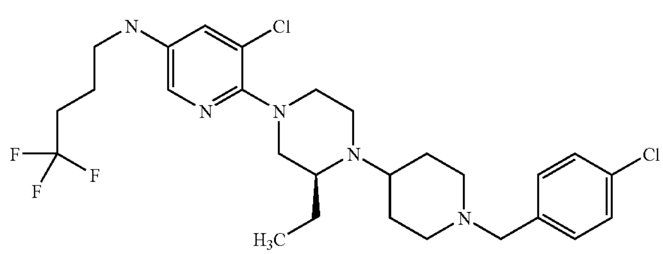 | B |

TABLE 1-continued

| Compound No. | STRUCTURE | IC$_{50}$ |
|---|---|---|
| 205 | 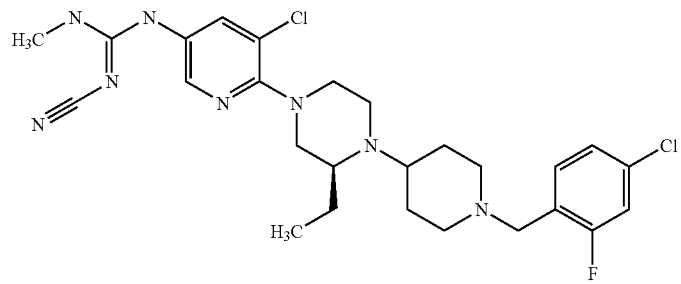 | B |
| 206 | 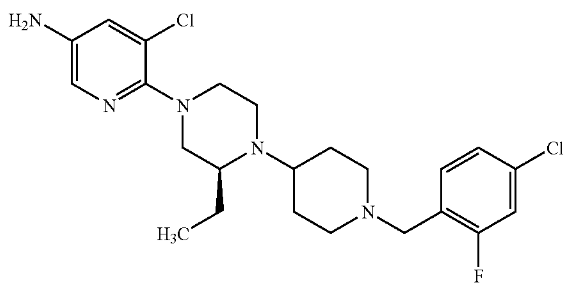 | B |
| 207 | 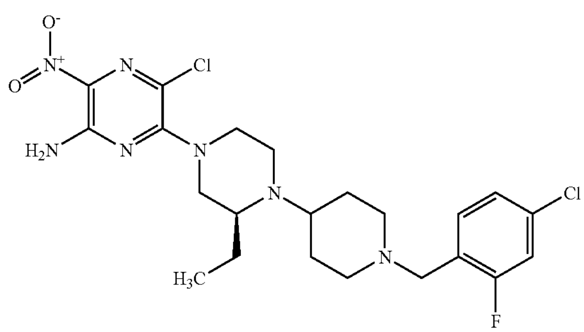 | B |
| 208 | 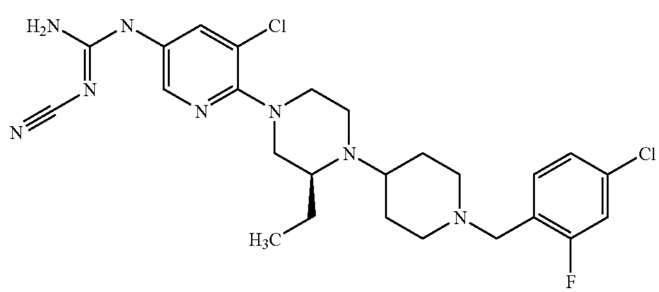 | B |
| 209 | 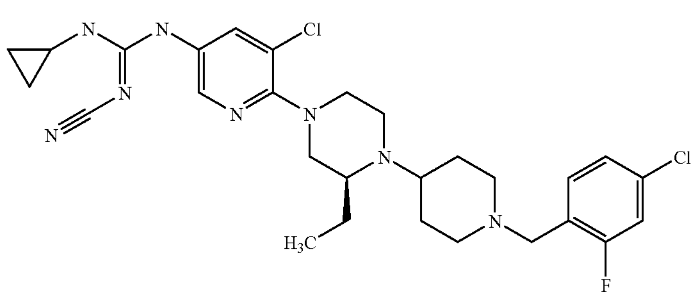 | B |

TABLE 1-continued

| Compound No. | STRUCTURE | IC$_{50}$ |
|---|---|---|
| 210 | 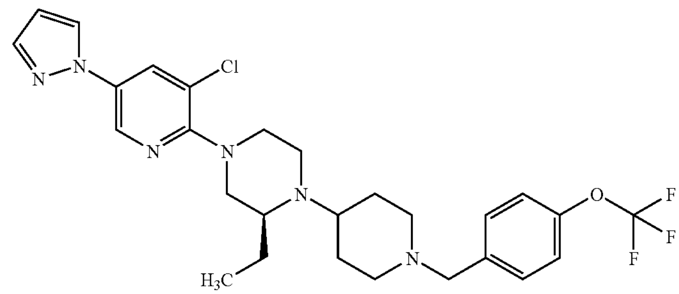 | B |
| 211 | 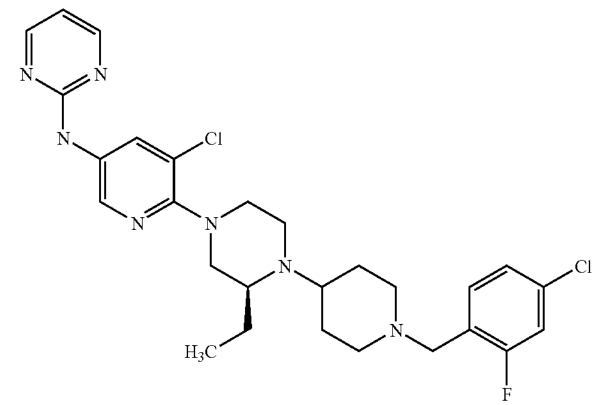 | B |
| 212 | 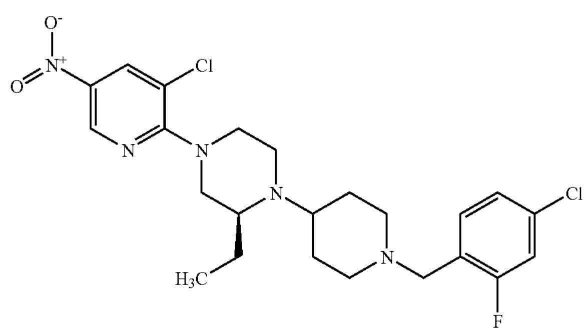 | B |
| 213 | 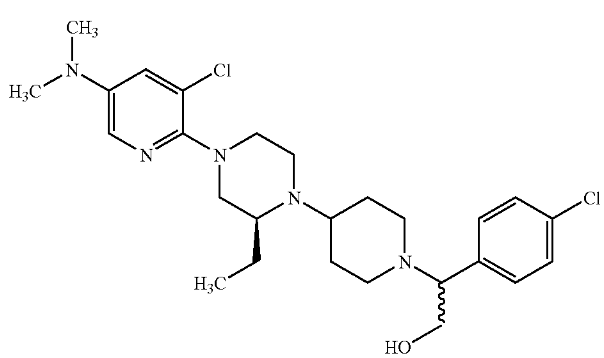 | B |

TABLE 1-continued

| Compound No. | STRUCTURE | IC$_{50}$ |
| --- | --- | --- |
| 214 | 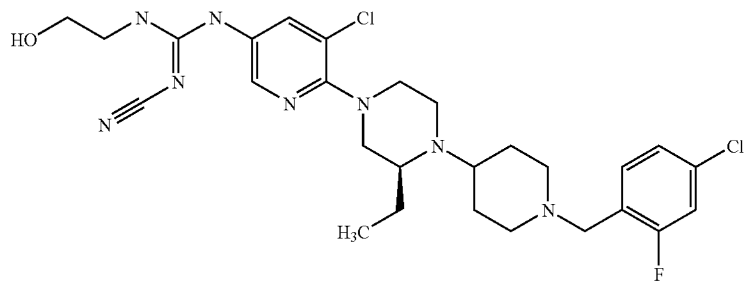 | C |
| 215 | 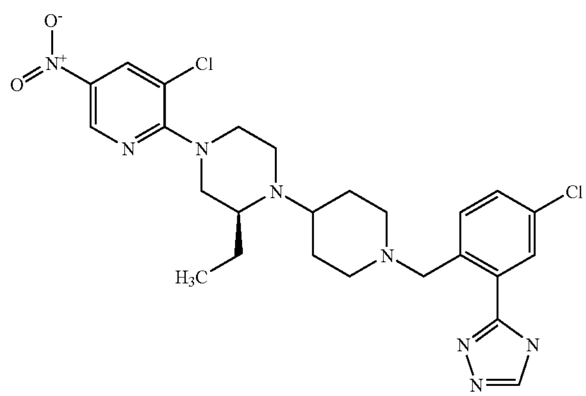 | C |
| 216 | 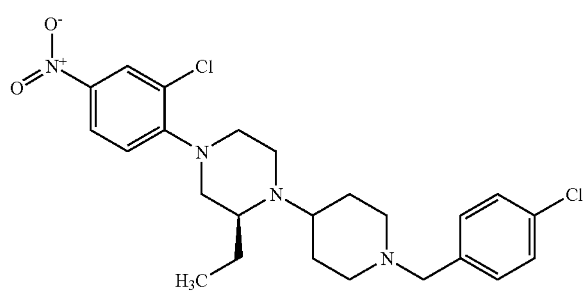 | C |
| 217 | 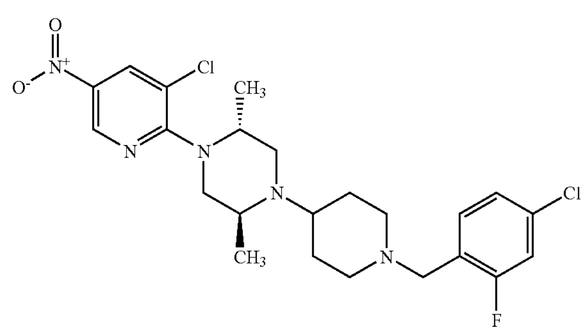 | C |
| 218 | 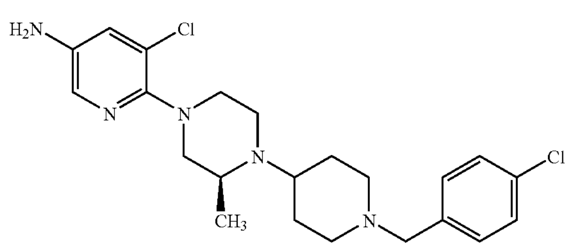 | C |

TABLE 1-continued

| Compound No. | STRUCTURE | IC$_{50}$ |
|---|---|---|
| 219 | 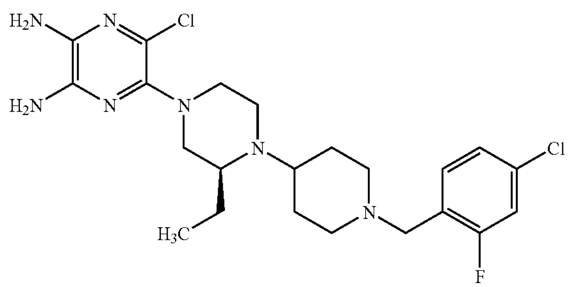 | C |
| 220 | 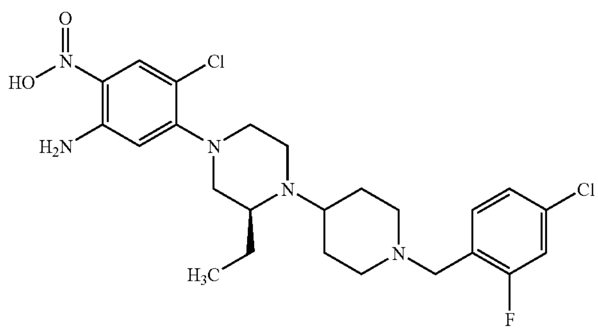 | C |
| 221 | 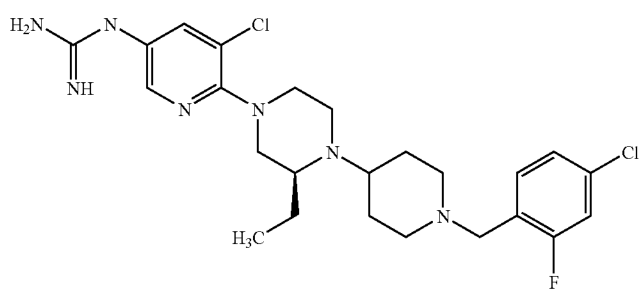 | C |
| 222 | 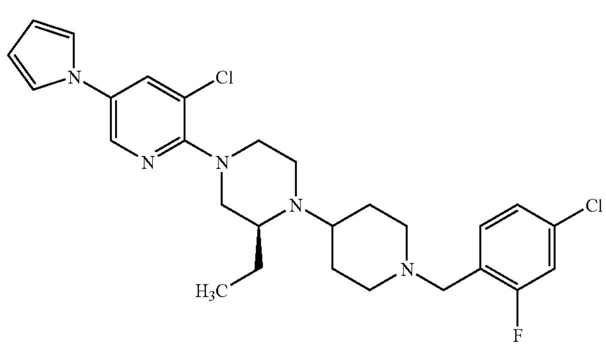 | C |

TABLE 1-continued
| Compound No. | STRUCTURE | IC$_{50}$ |
|---|---|---|
| 223 | 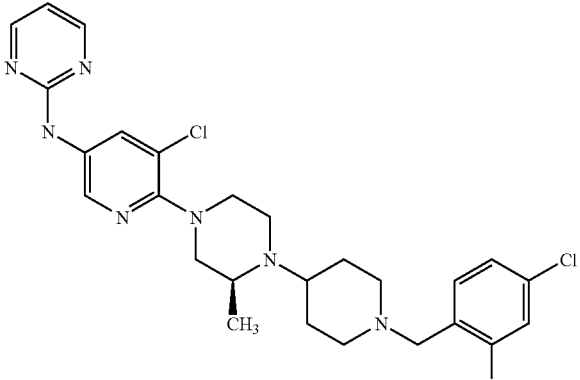 | C |
| 224 | 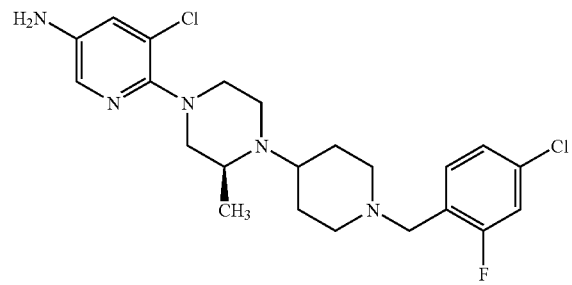 | C |
| 225 | 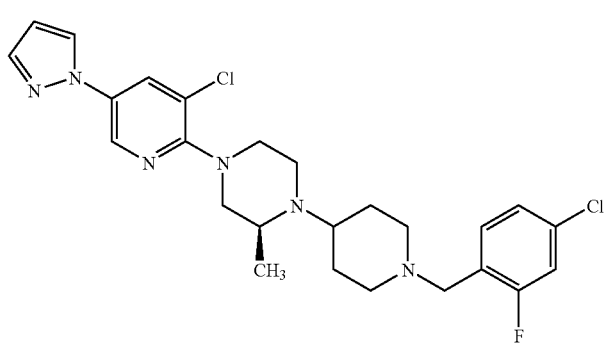 | C |
| 226 | 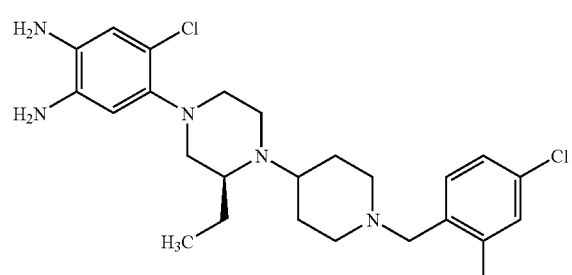 | C |

TABLE 1-continued

| Compound No. | STRUCTURE | IC$_{50}$ |
|---|---|---|
| 227 | 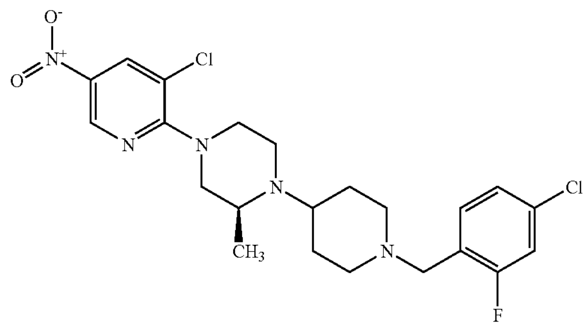 | C |
| 228 | 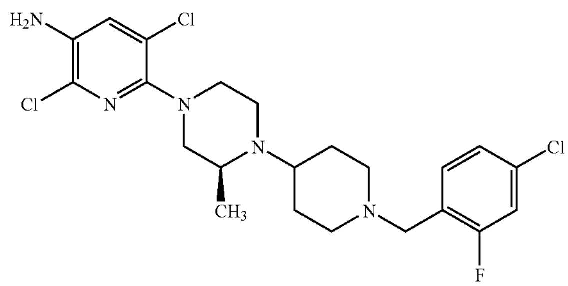 | C |
| 229 | 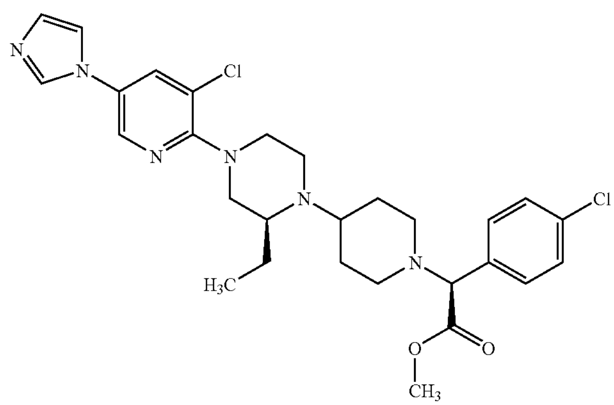 | C |
| 230 | 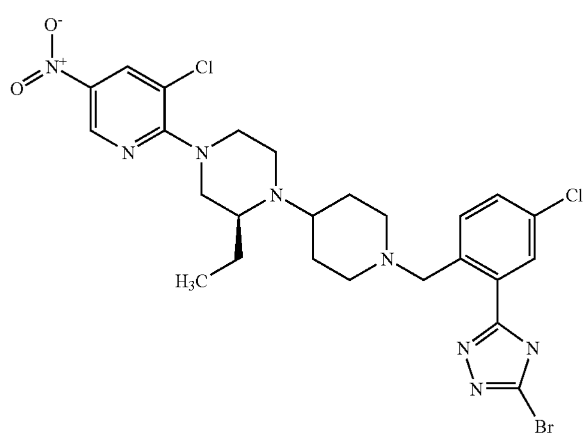 | C |

TABLE 1-continued

| Compound No. | STRUCTURE | IC$_{50}$ |
|---|---|---|
| 231 | [structure] | C |
| 232 | [structure] | C |
| 233 | [structure] | C |
| 234 | [structure] | A |

| Compound No. | STRUCTURE | IC$_{50}$ |
|---|---|---|
| 235 | 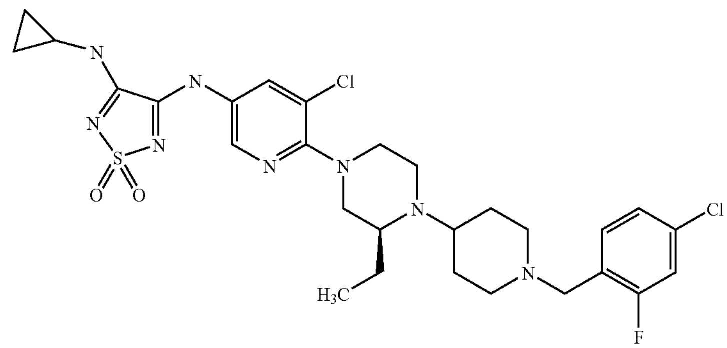 | A |
| 236 | 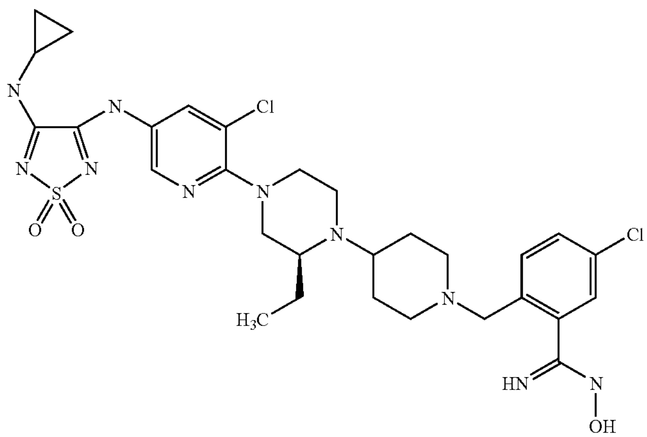 | A |
| 237 | 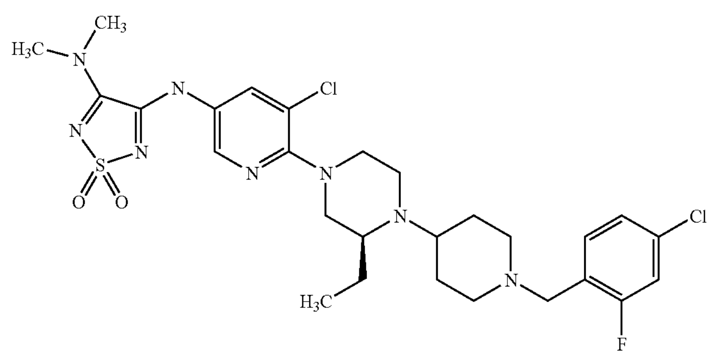 | A |
| 238 | 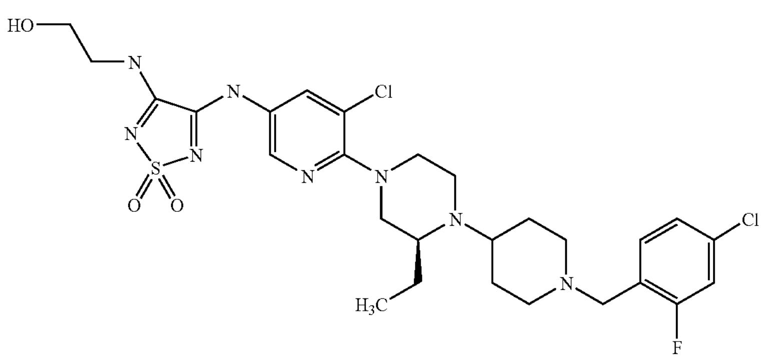 | A |

TABLE 1-continued

| Compound No. | STRUCTURE | IC$_{50}$ |
|---|---|---|
| 239 | 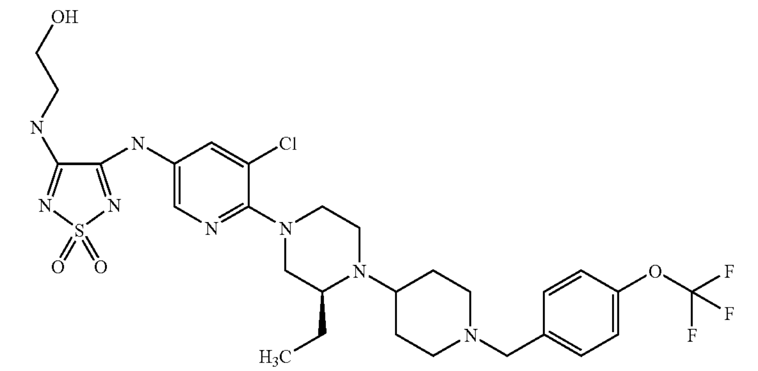 | A |
| 240 | 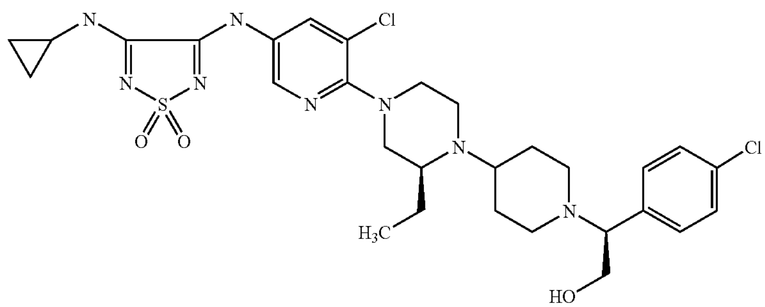 | A |
| 241 | 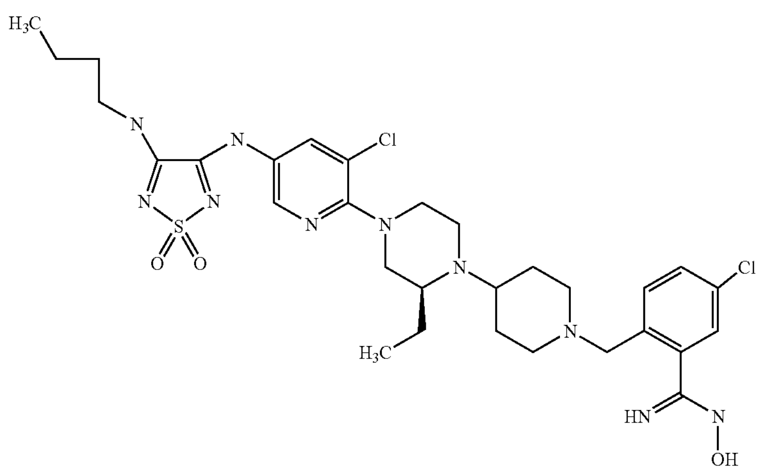 | A |
| 242 | 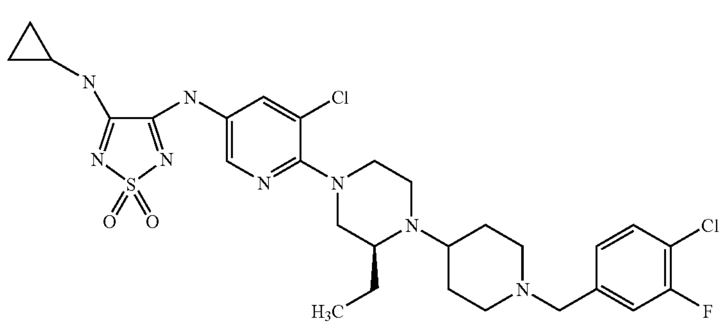 | A |

TABLE 1-continued
| Compound No. | STRUCTURE | IC$_{50}$ |
|---|---|---|
| 243 | 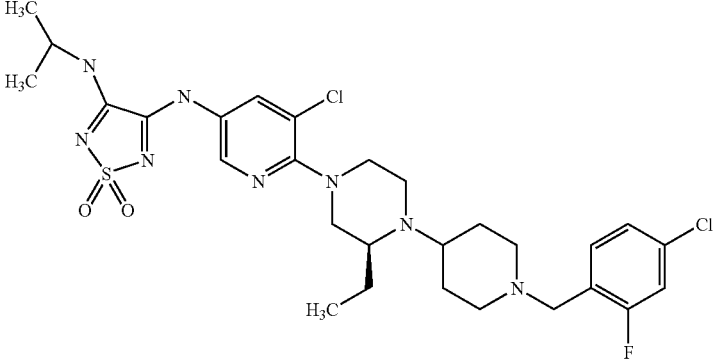 | A |
| 244 | 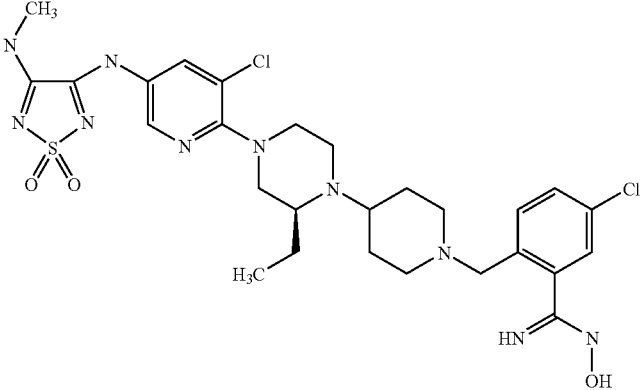 | A |
| 245 | 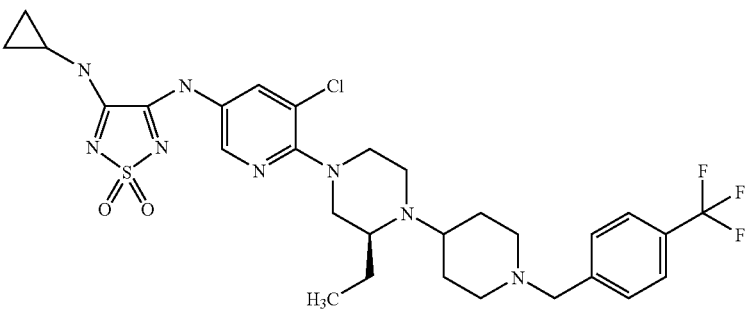 | A |
| 246 | 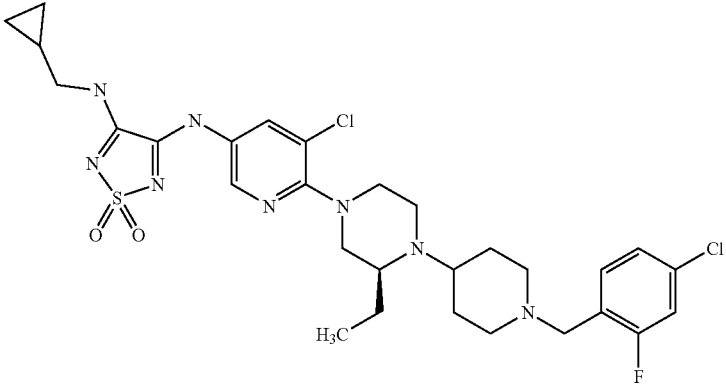 | A |

TABLE 1-continued

| Compound No. | STRUCTURE | IC$_{50}$ |
|---|---|---|
| 247 | 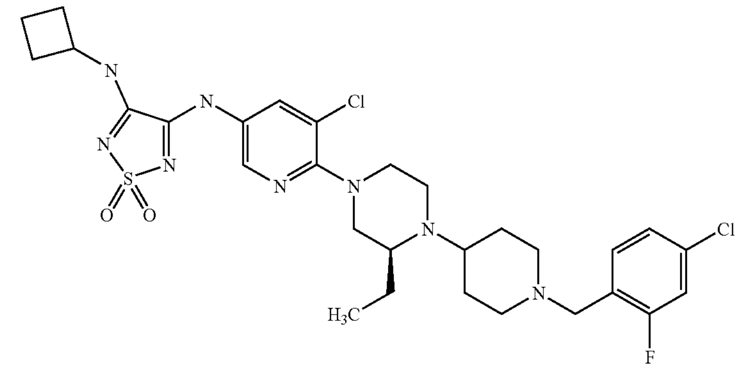 | A |
| 248 | 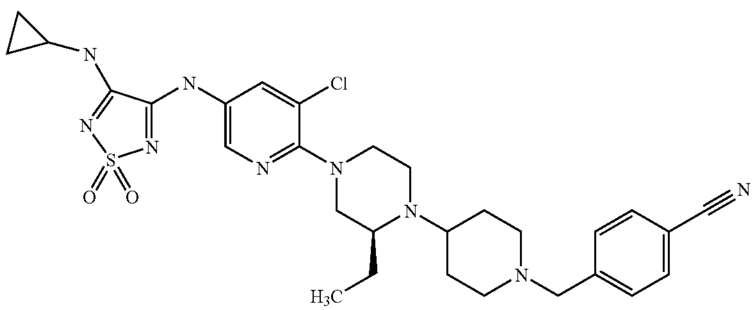 | A |
| 249 | 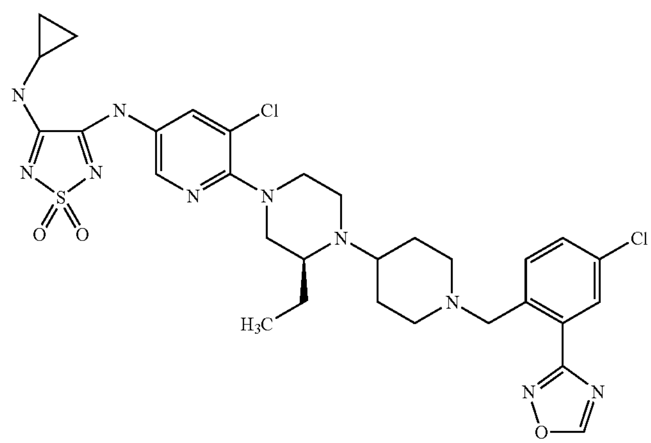 | A |
| 250 | 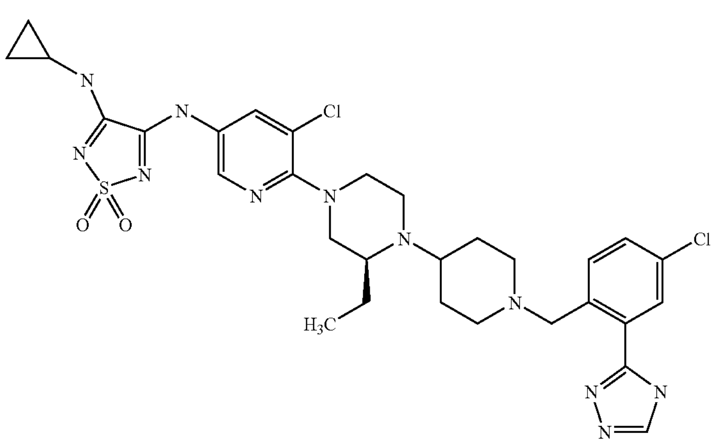 | A |

TABLE 1-continued

| Compound No. | STRUCTURE | IC$_{50}$ |
|---|---|---|
| 251 | 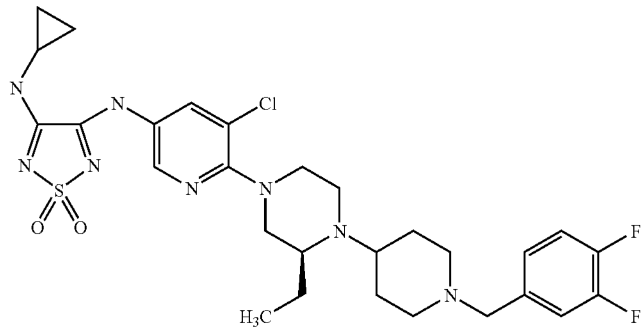 | A |
| 252 | 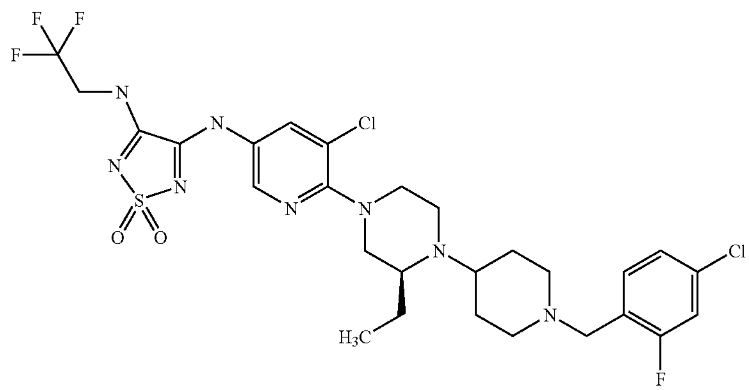 | A |
| 253 | 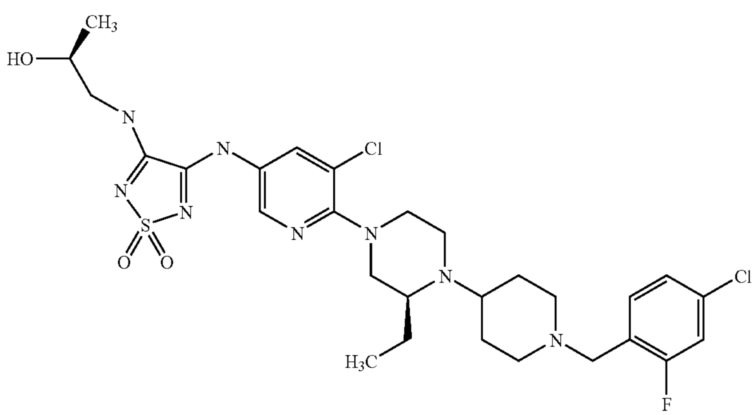 | A |
| 254 | 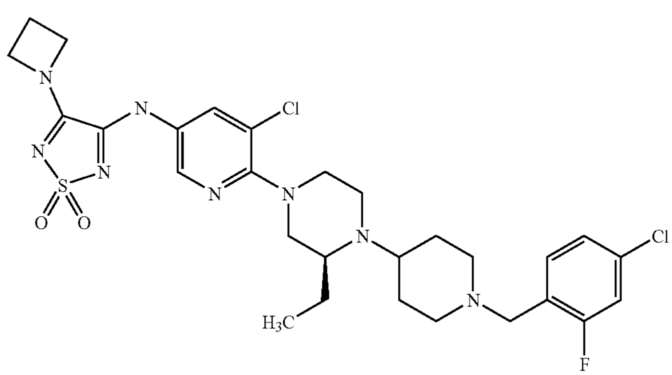 | A |

TABLE 1-continued
| Compound No. | STRUCTURE | IC$_{50}$ |
|---|---|---|
| 255 | 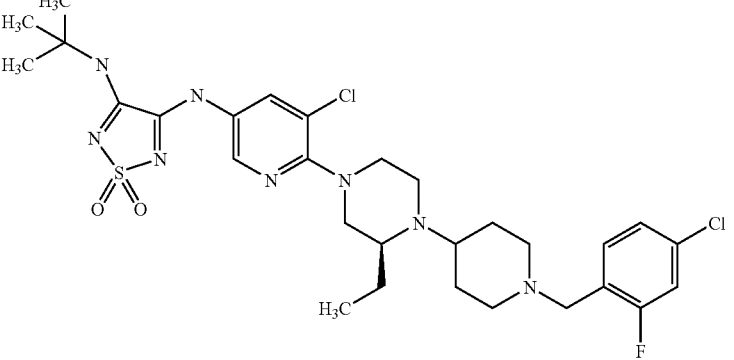 | B |
| 256 | 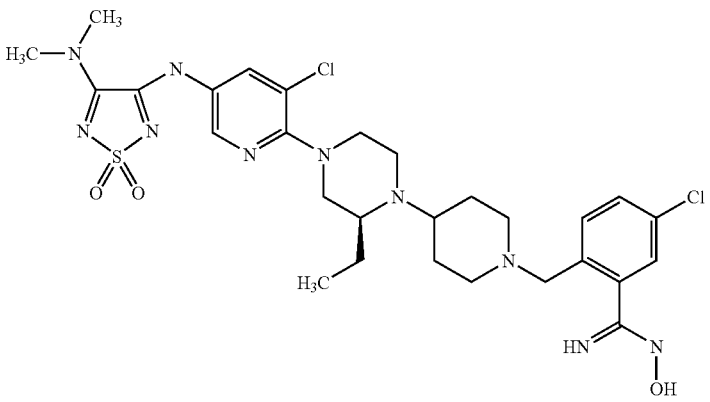 | B |
| 257 | 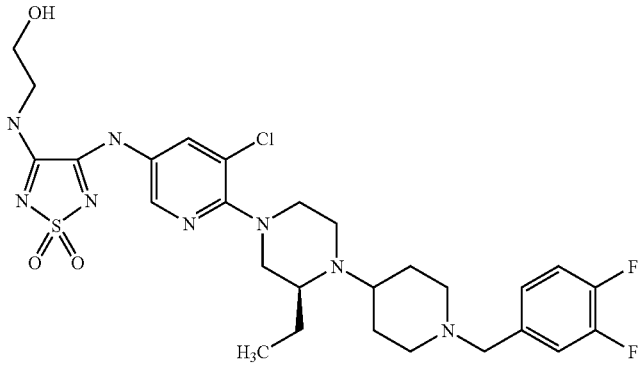 | B |
| 258 | 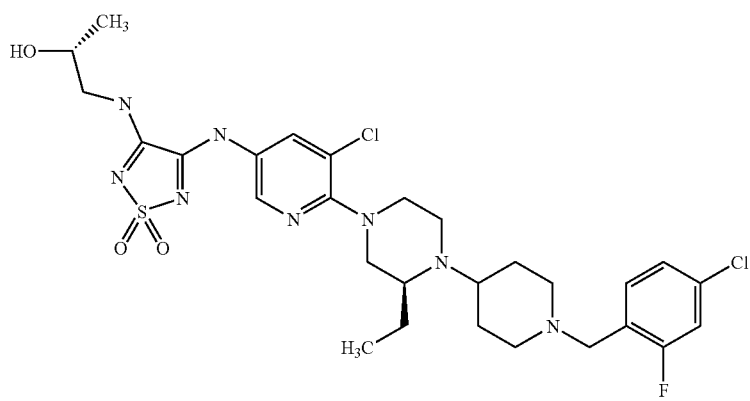 | B |

TABLE 1-continued

| Compound No. | STRUCTURE | IC$_{50}$ |
|---|---|---|
| 259 | 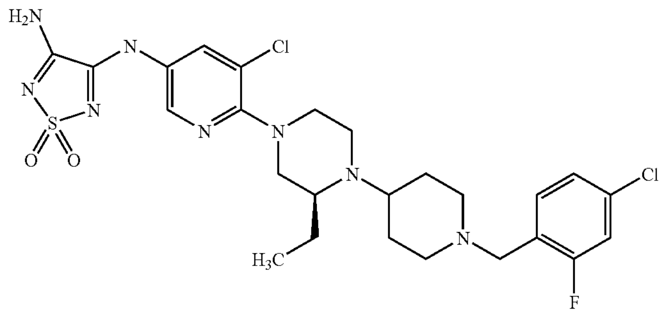 | B |
| 260 | 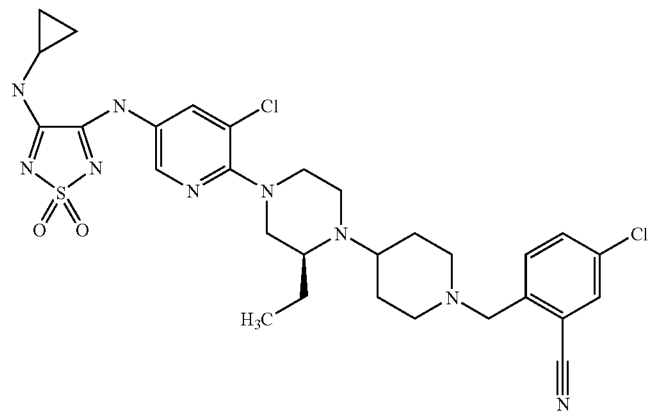 | B |
| 261 | 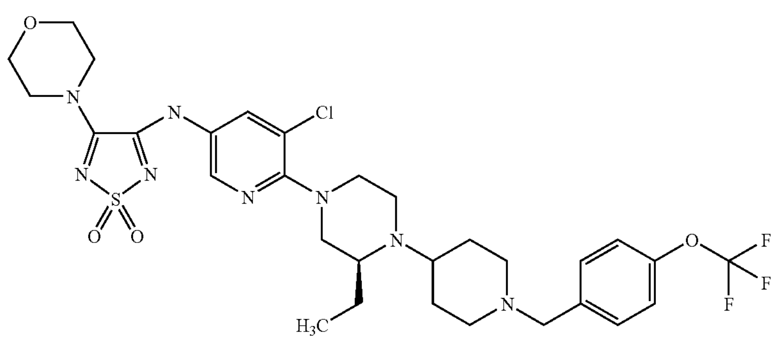 | B |
| 262 | 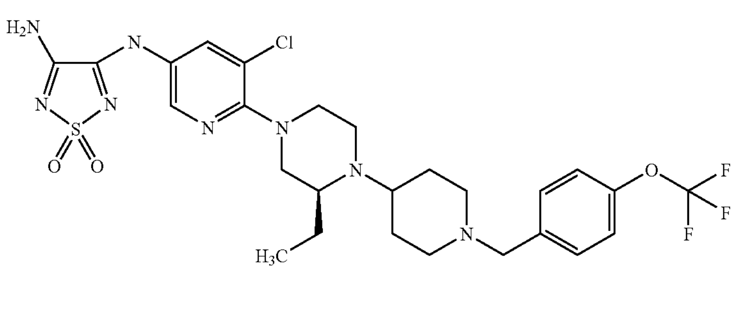 | B |

TABLE 1-continued

| Compound No. | STRUCTURE | IC$_{50}$ |
|---|---|---|
| 263 | 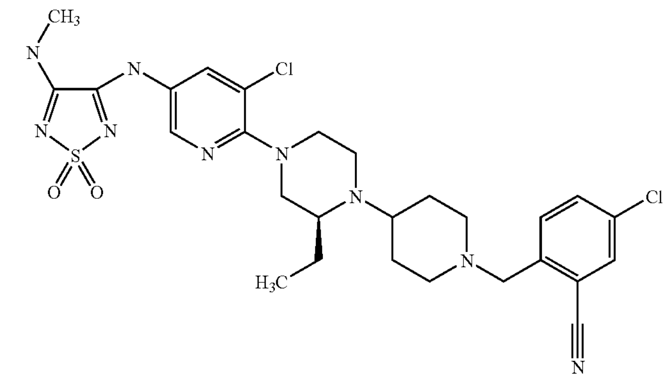 | B |
| 264 | 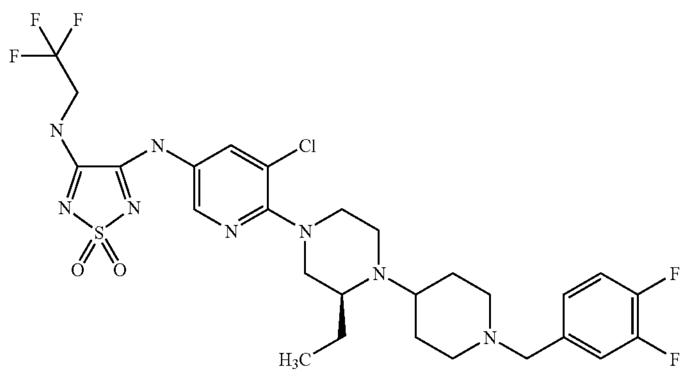 | C |
| 265 | 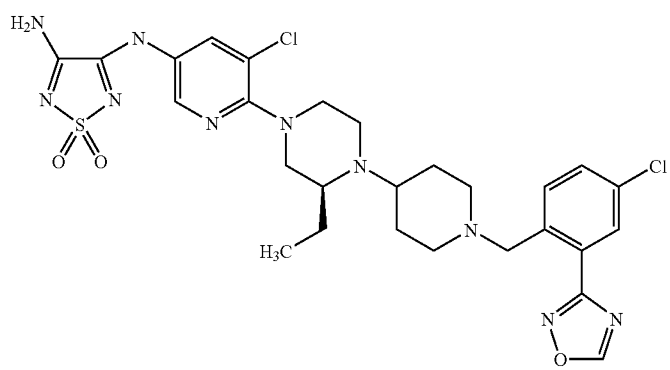 | C |
| 266 | 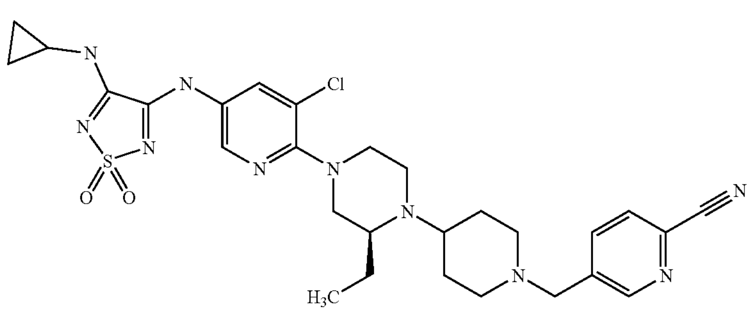 | C |

TABLE 1-continued

| Compound No. | STRUCTURE | IC$_{50}$ |
|---|---|---|
| 267 | 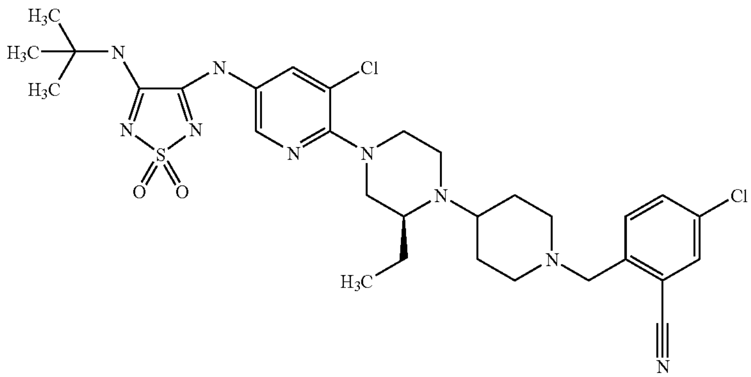 | C |
| 268 | 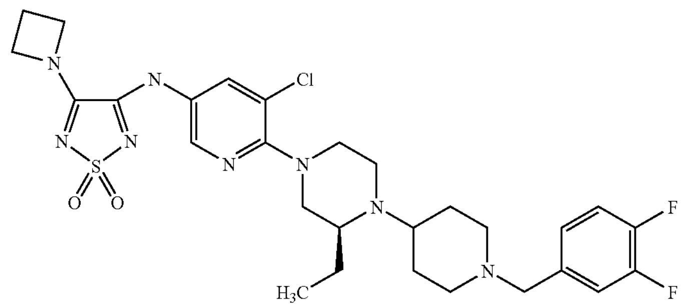 | C |
| 269 | 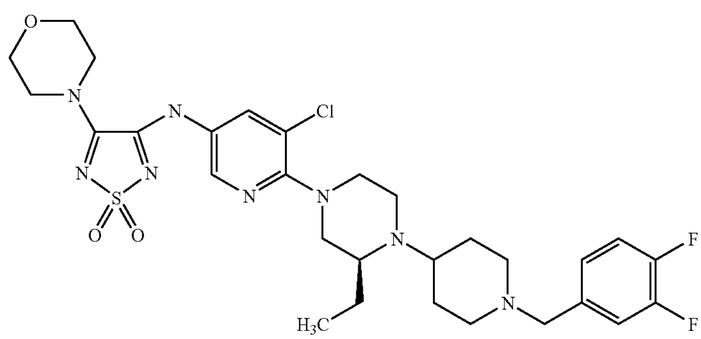 | C |
| 270 | 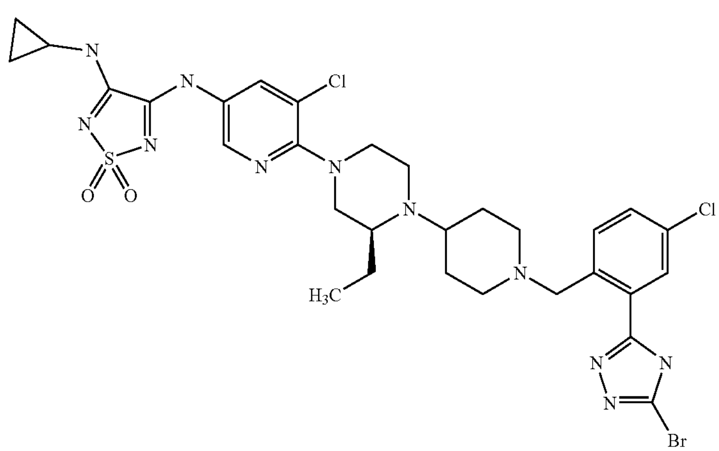 | C |

TABLE 1-continued

| Compound No. | STRUCTURE | IC$_{50}$ |
|---|---|---|
| 271 | 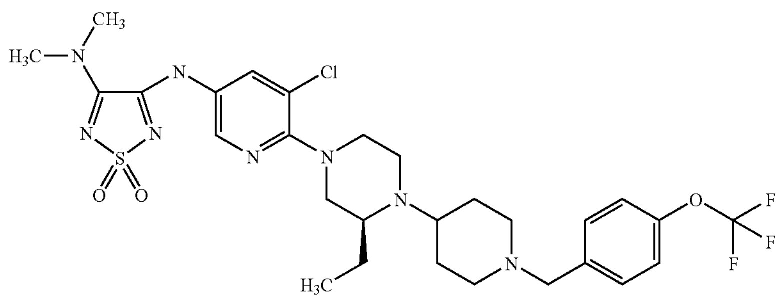 | C |
| 272 | 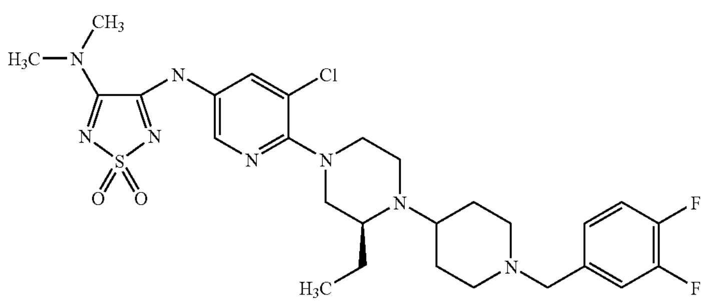 | C |
| 273 | 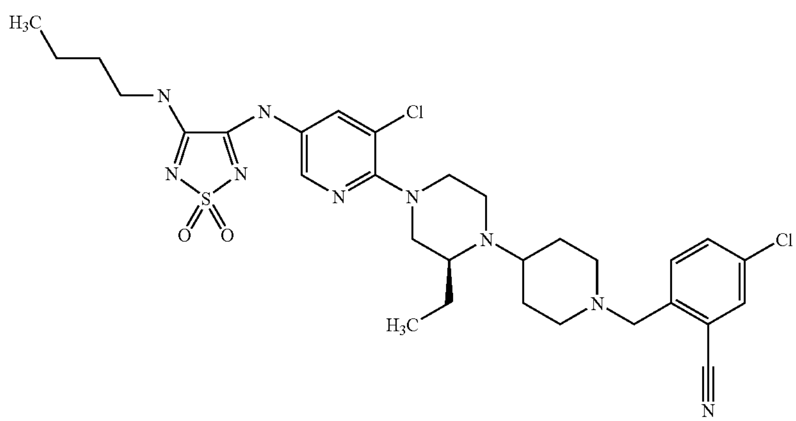 | C |
| 274 | 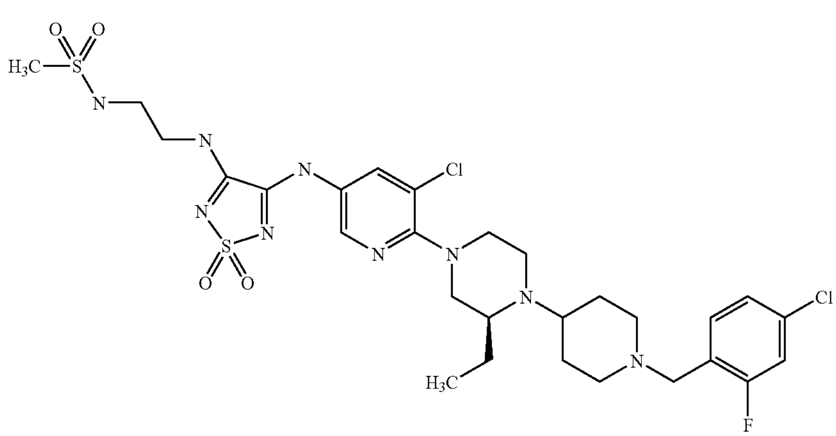 | C |

TABLE 1-continued

| Compound No. | STRUCTURE | IC$_{50}$ |
|---|---|---|
| 275 | 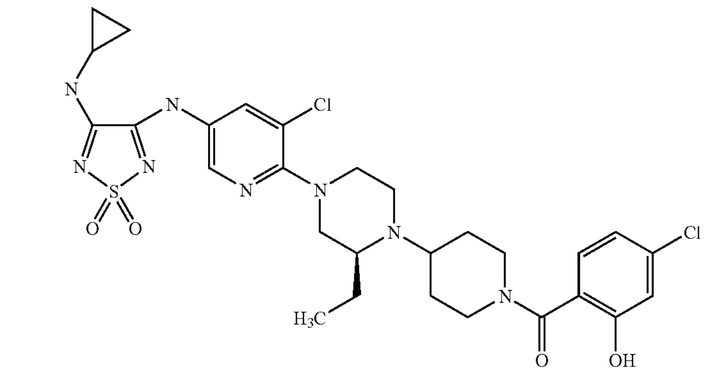 | C |
| 276 | 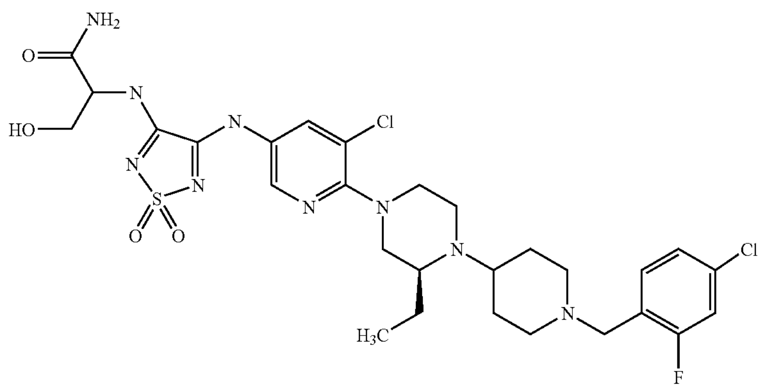 | C |
| 277 | 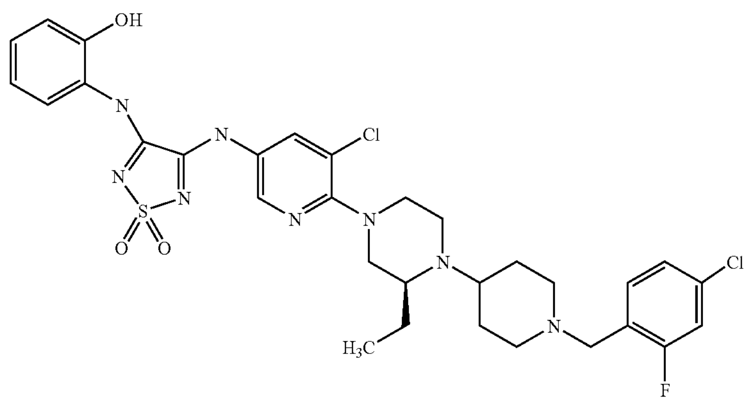 | C |
| 278 | 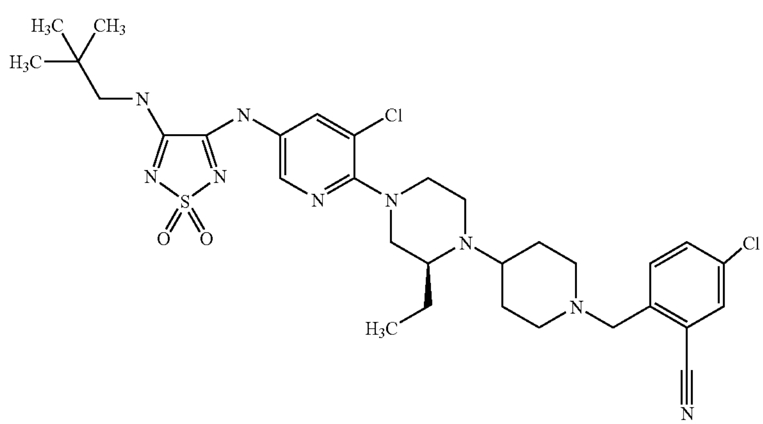 | C |

TABLE 1-continued
| Compound No. | STRUCTURE | $IC_{50}$ |
|---|---|---|
| 279 | 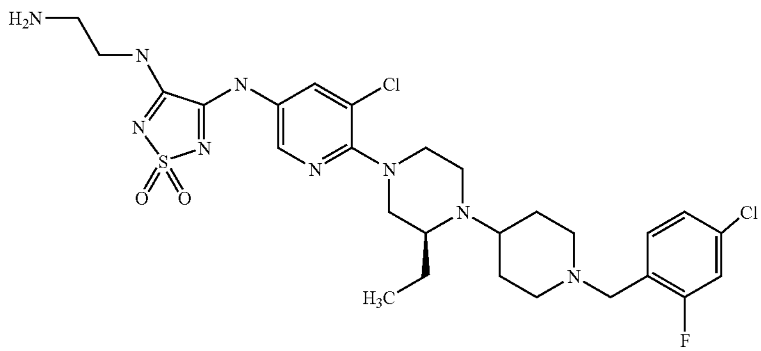 | C |
| 280 | 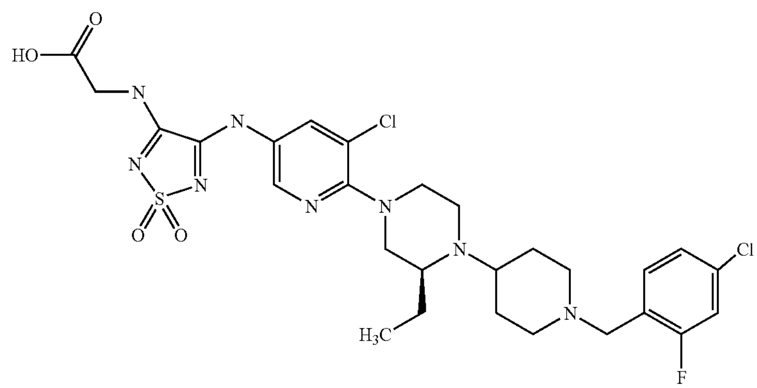 | C |
or a pharmaceutically acceptable salt, solvate or ester thereof.
For example, the compound according to Formula 1 can be selected from the group consisting of compounds of the formulae:
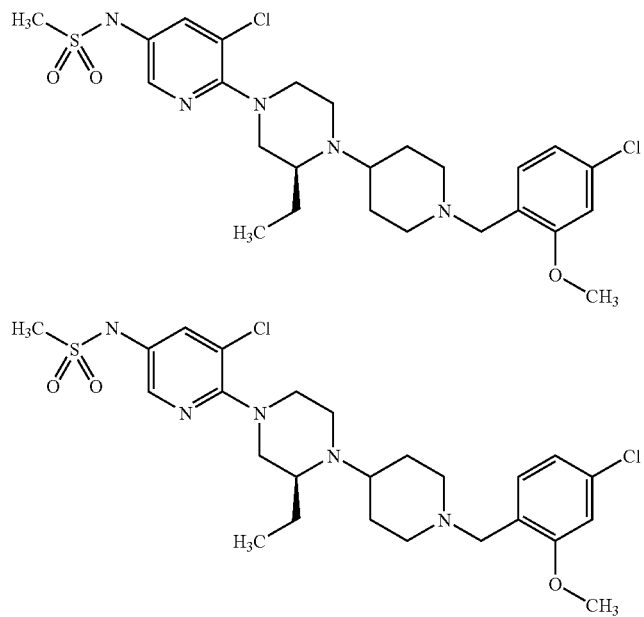

-continued
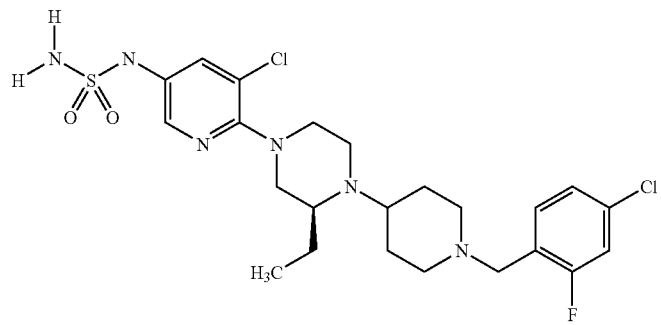
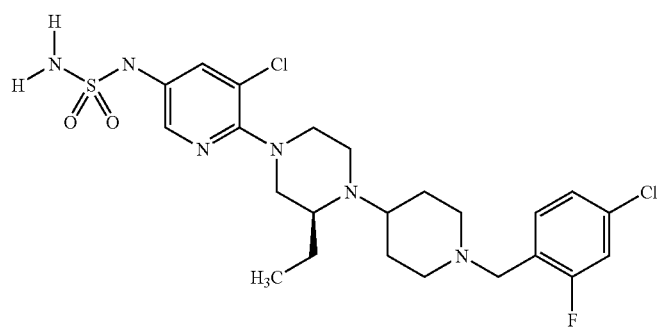
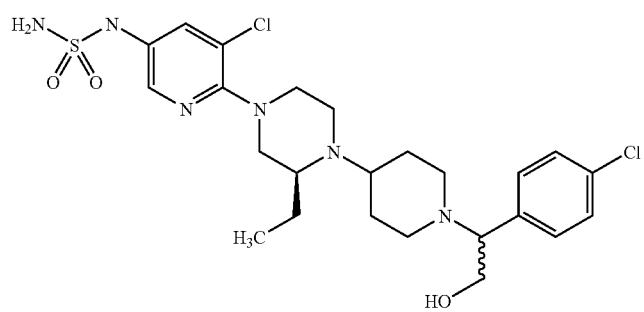
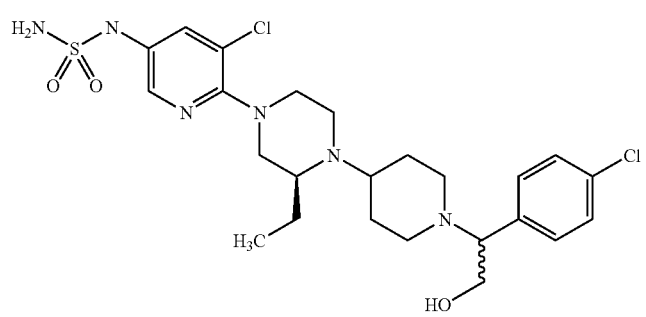
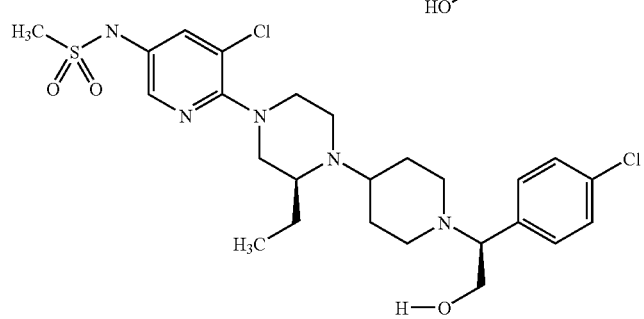

-continued
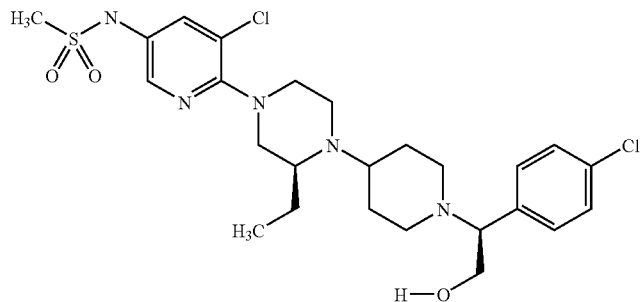
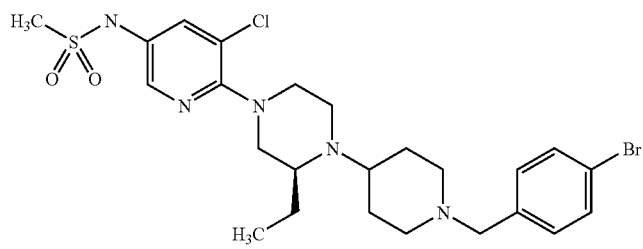
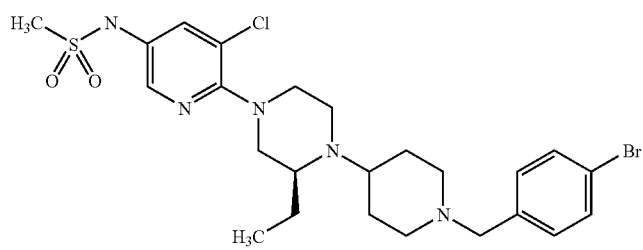
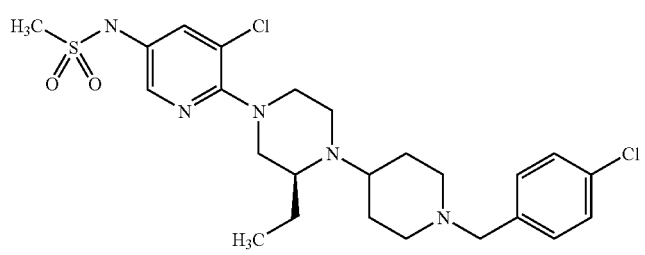
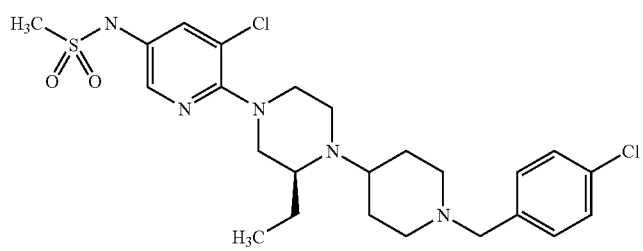
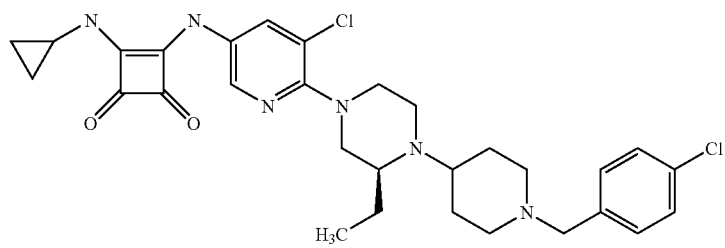

-continued
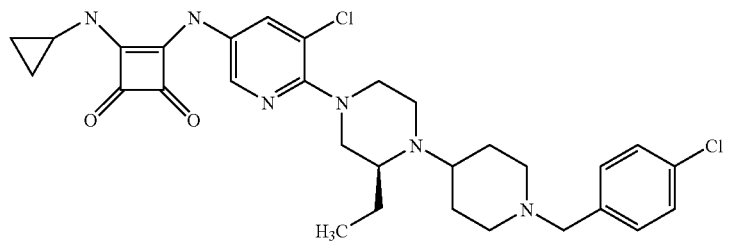
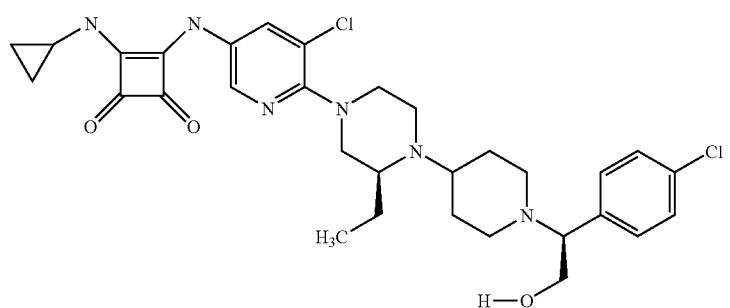
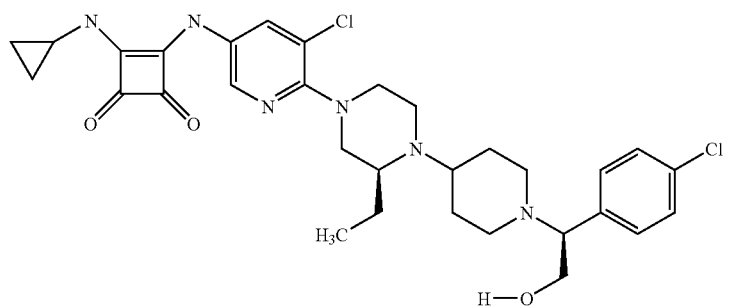
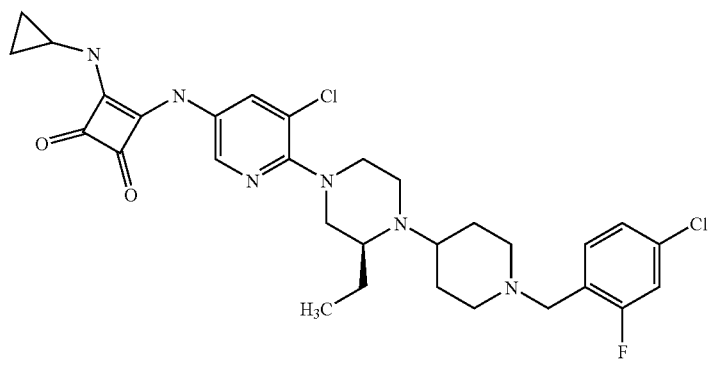
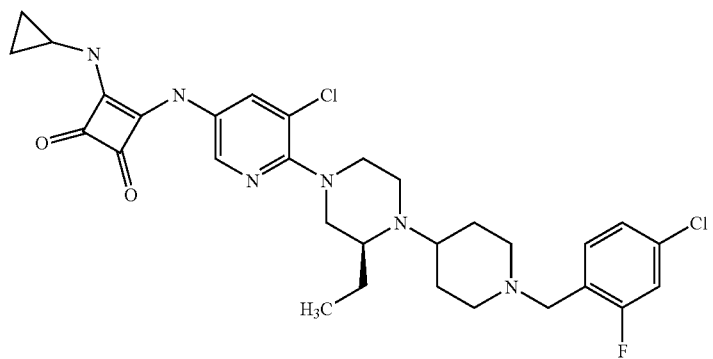

-continued
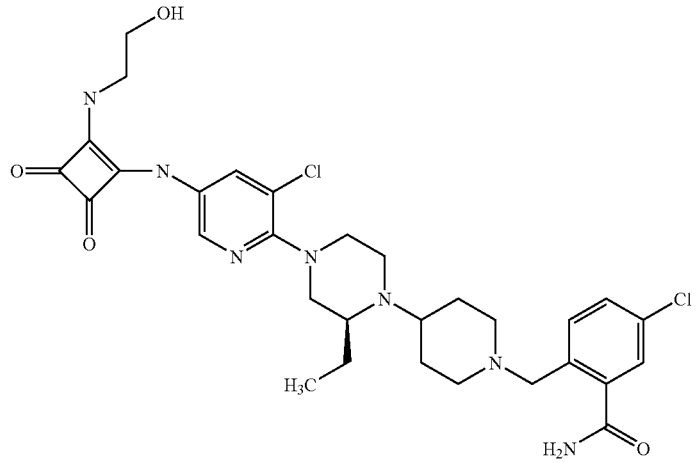
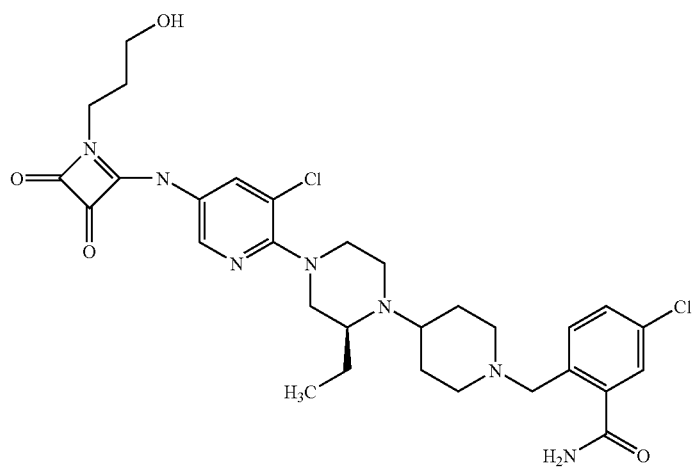
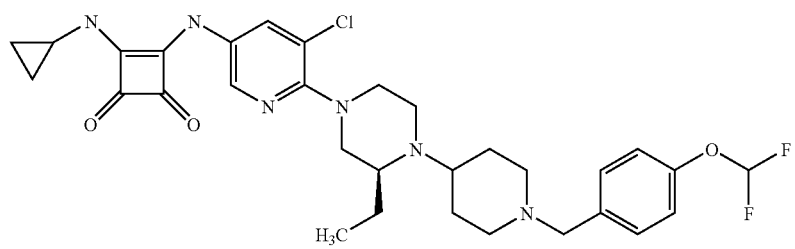
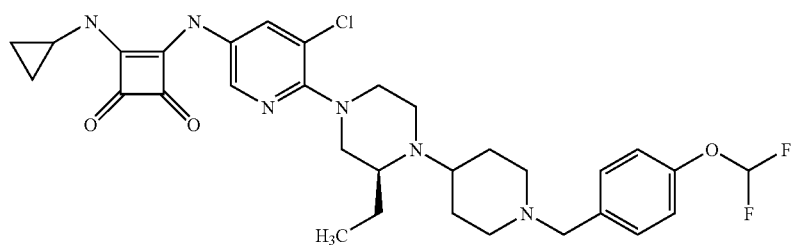

-continued
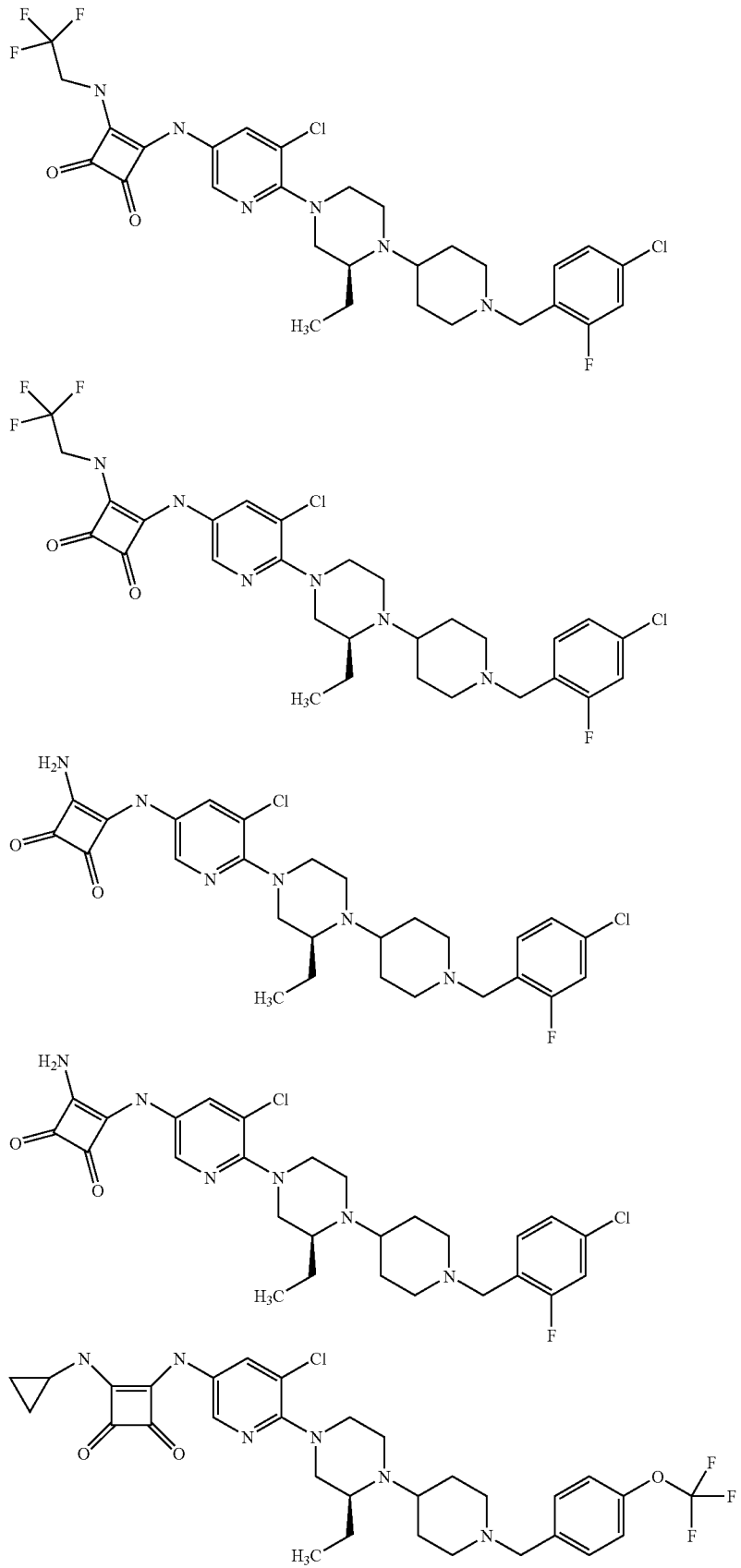

-continued
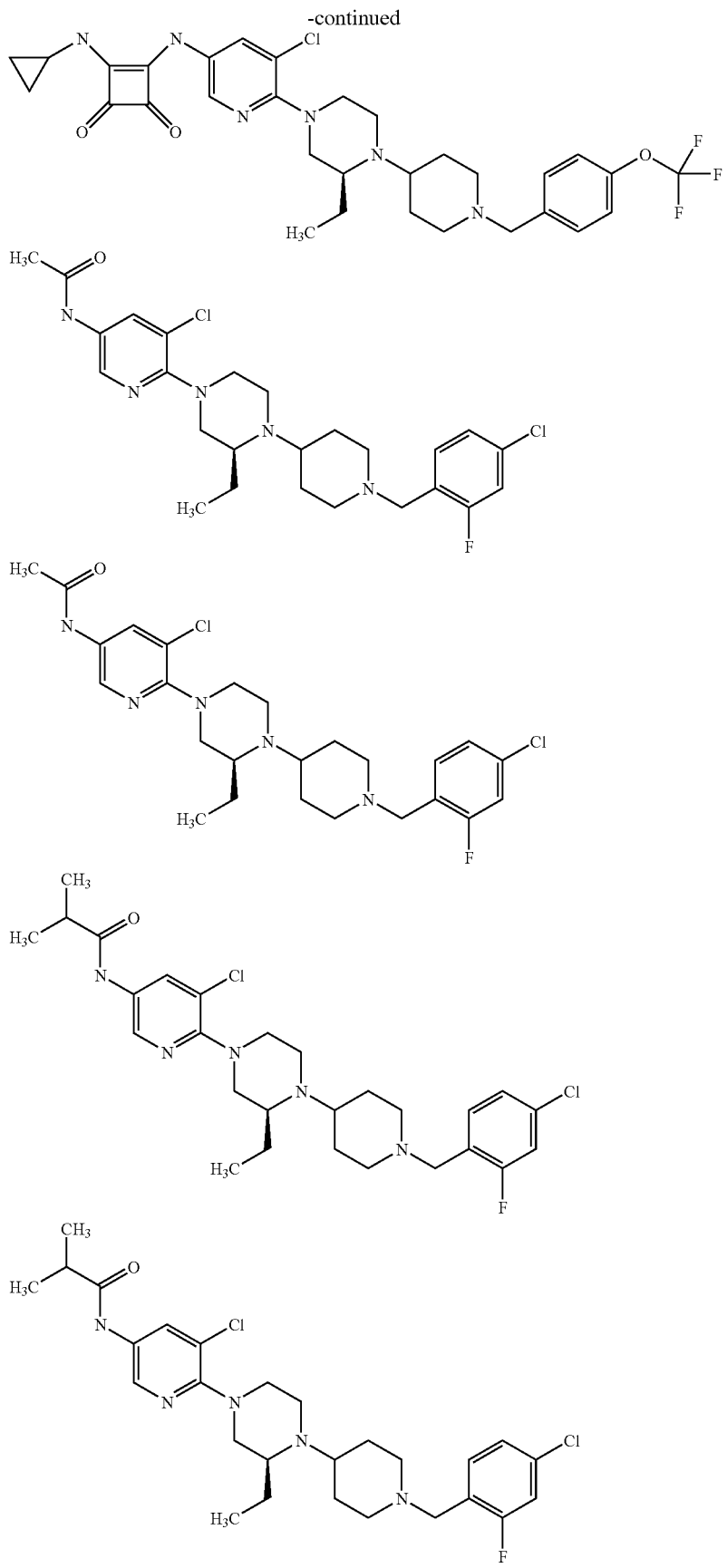

-continued
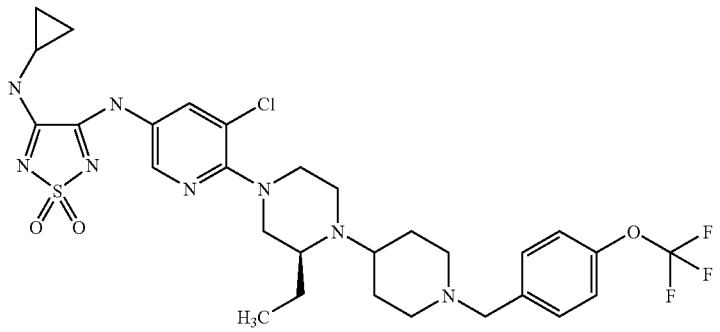
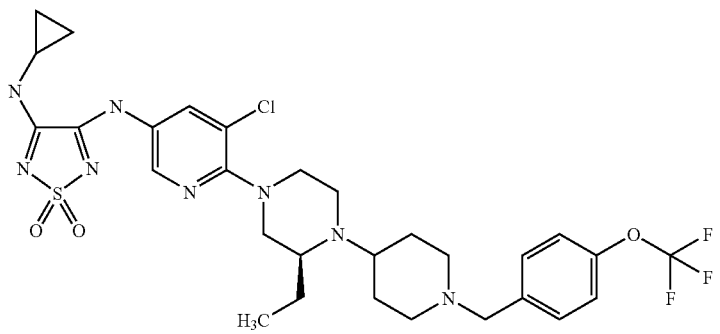
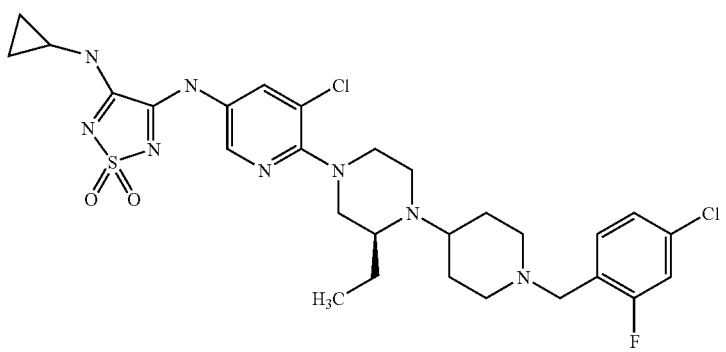
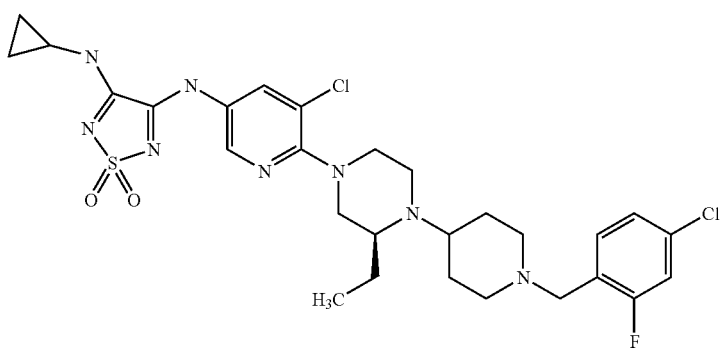
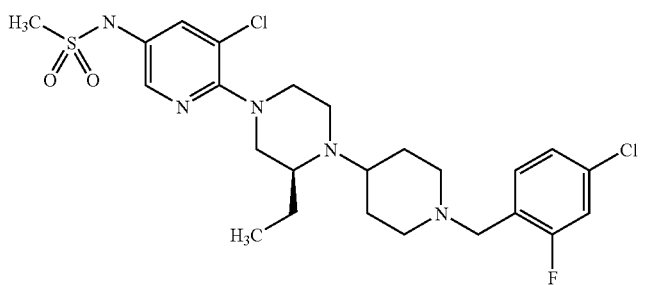

-continued
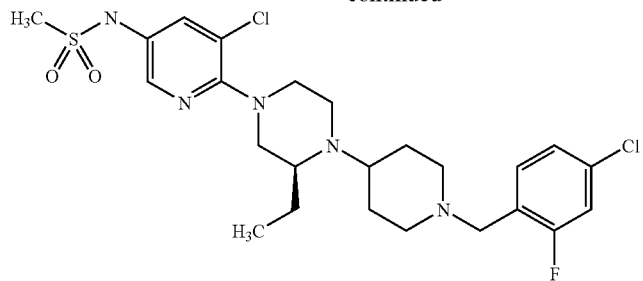
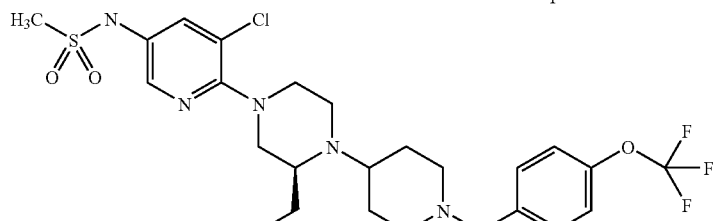
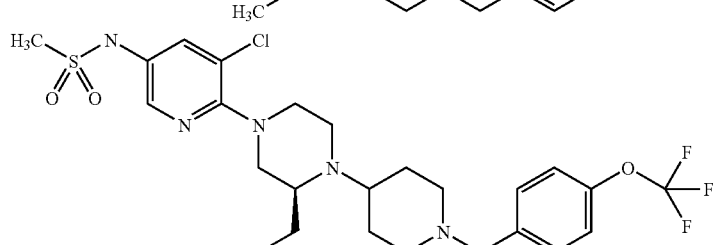
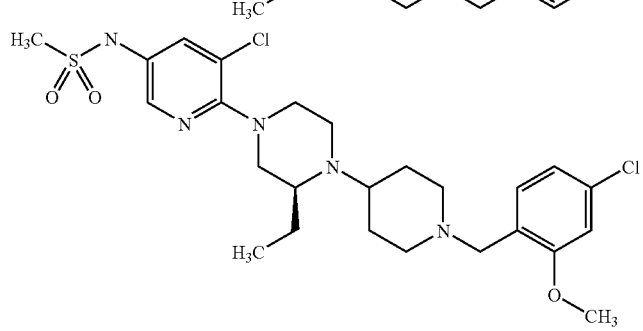
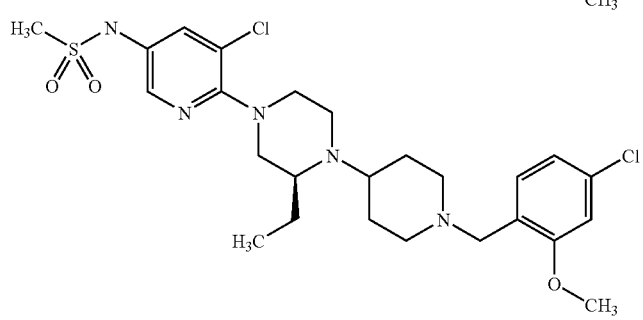
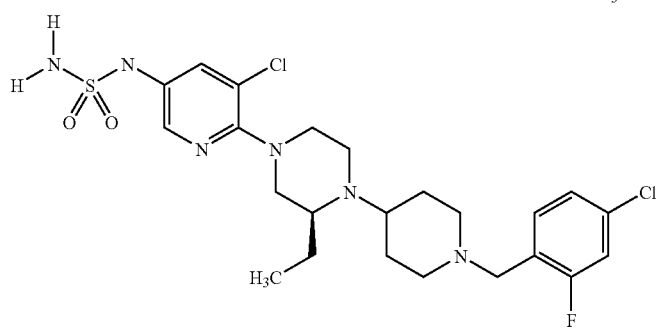

-continued
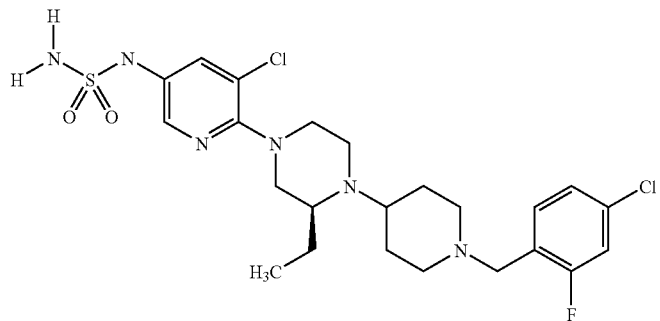
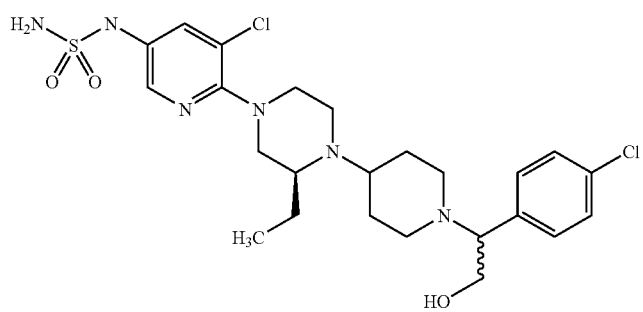
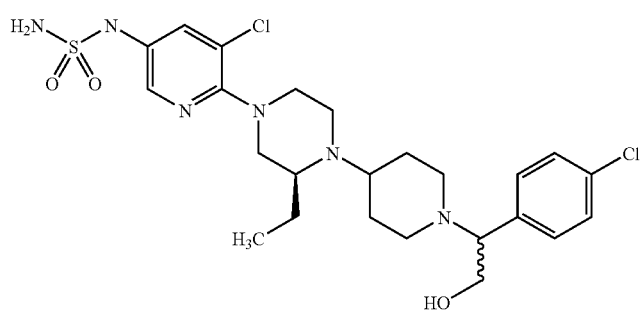
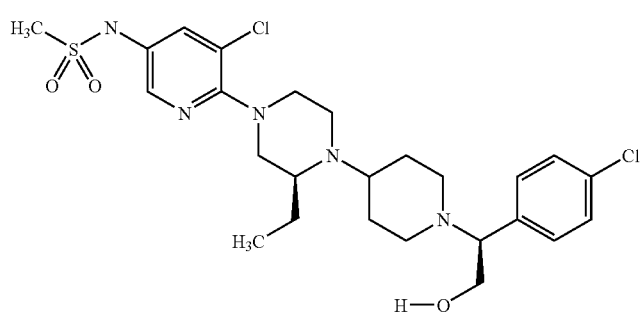
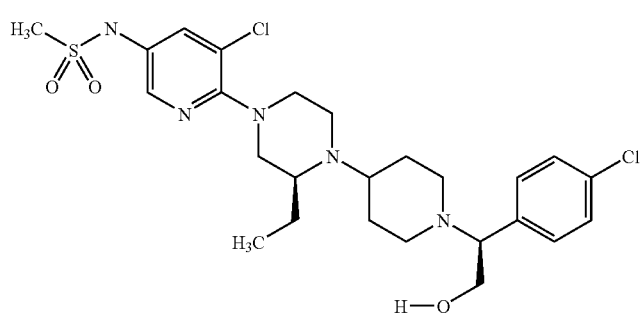

-continued
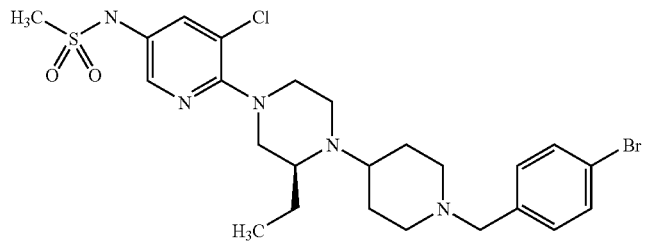
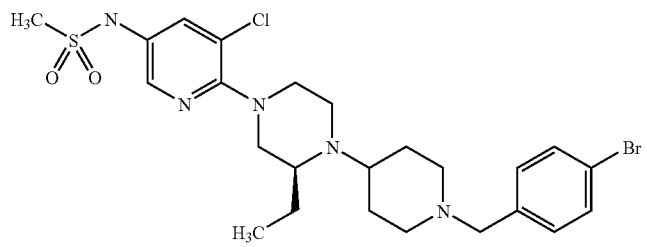
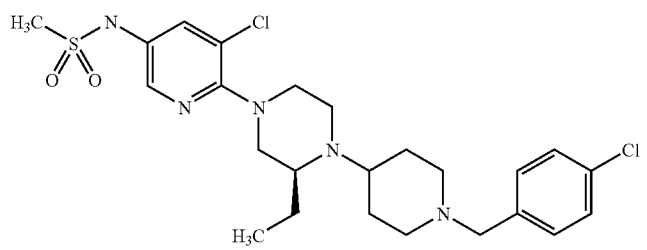
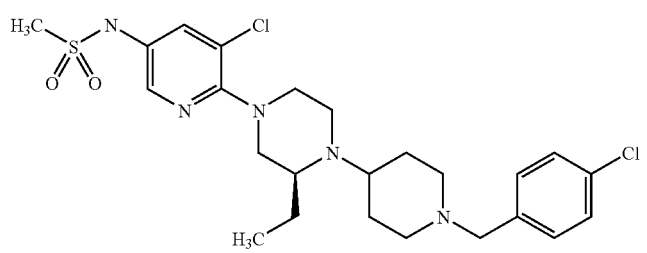
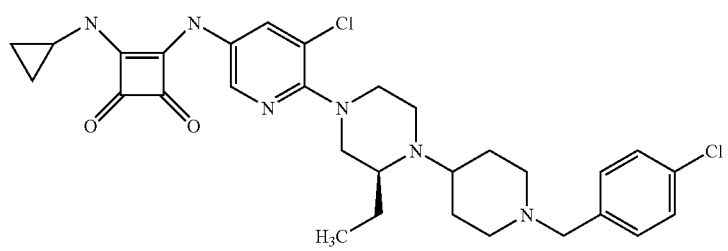
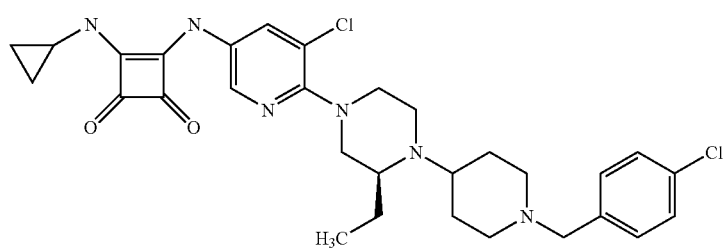

-continued
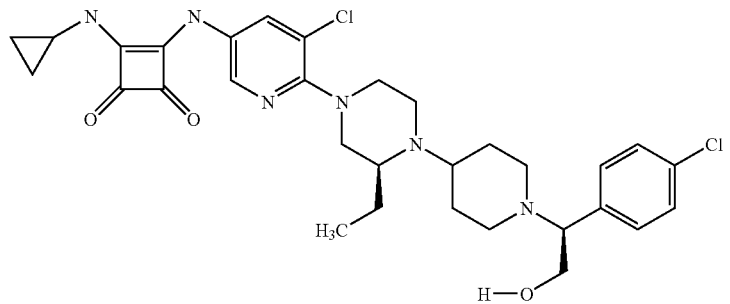
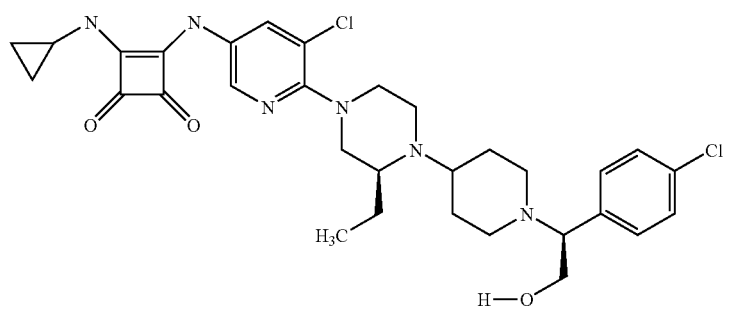
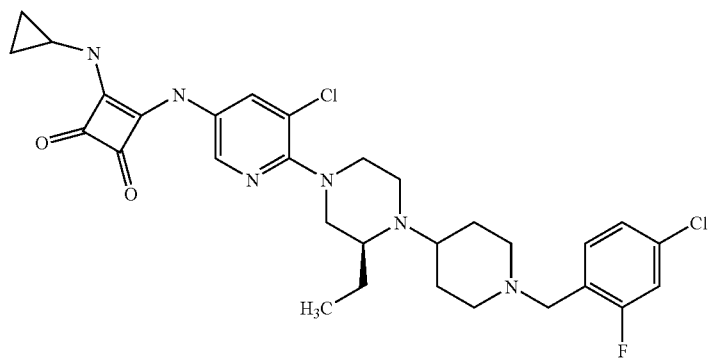
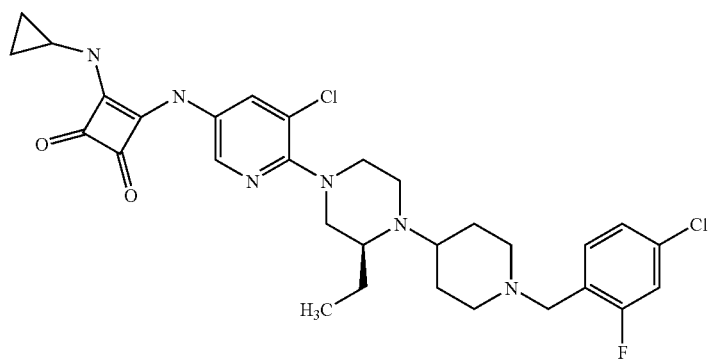

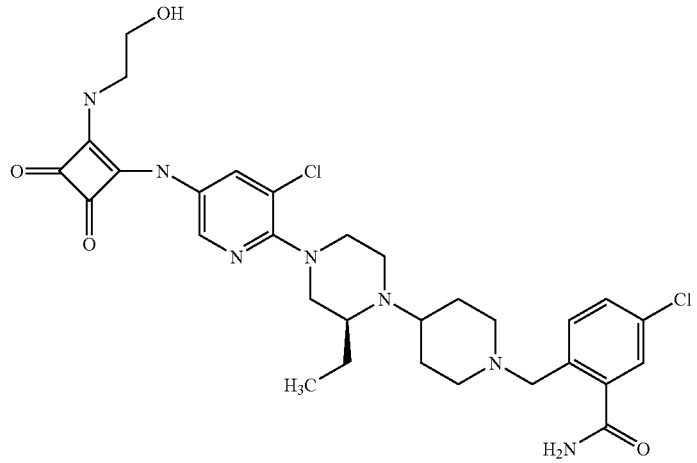
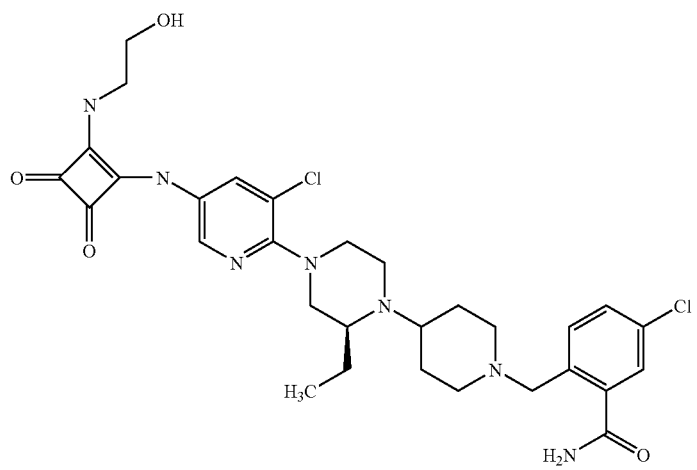
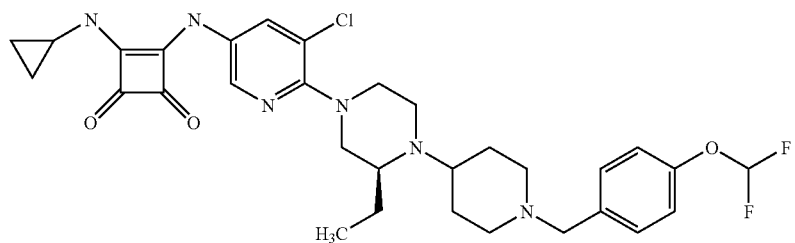
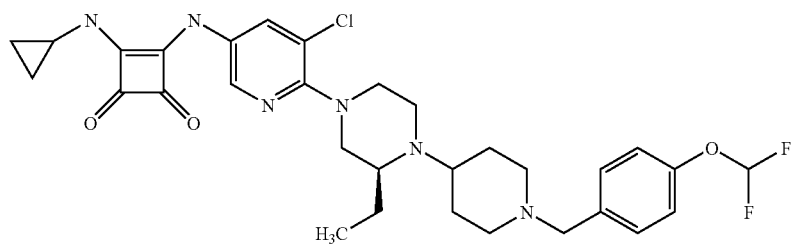

-continued
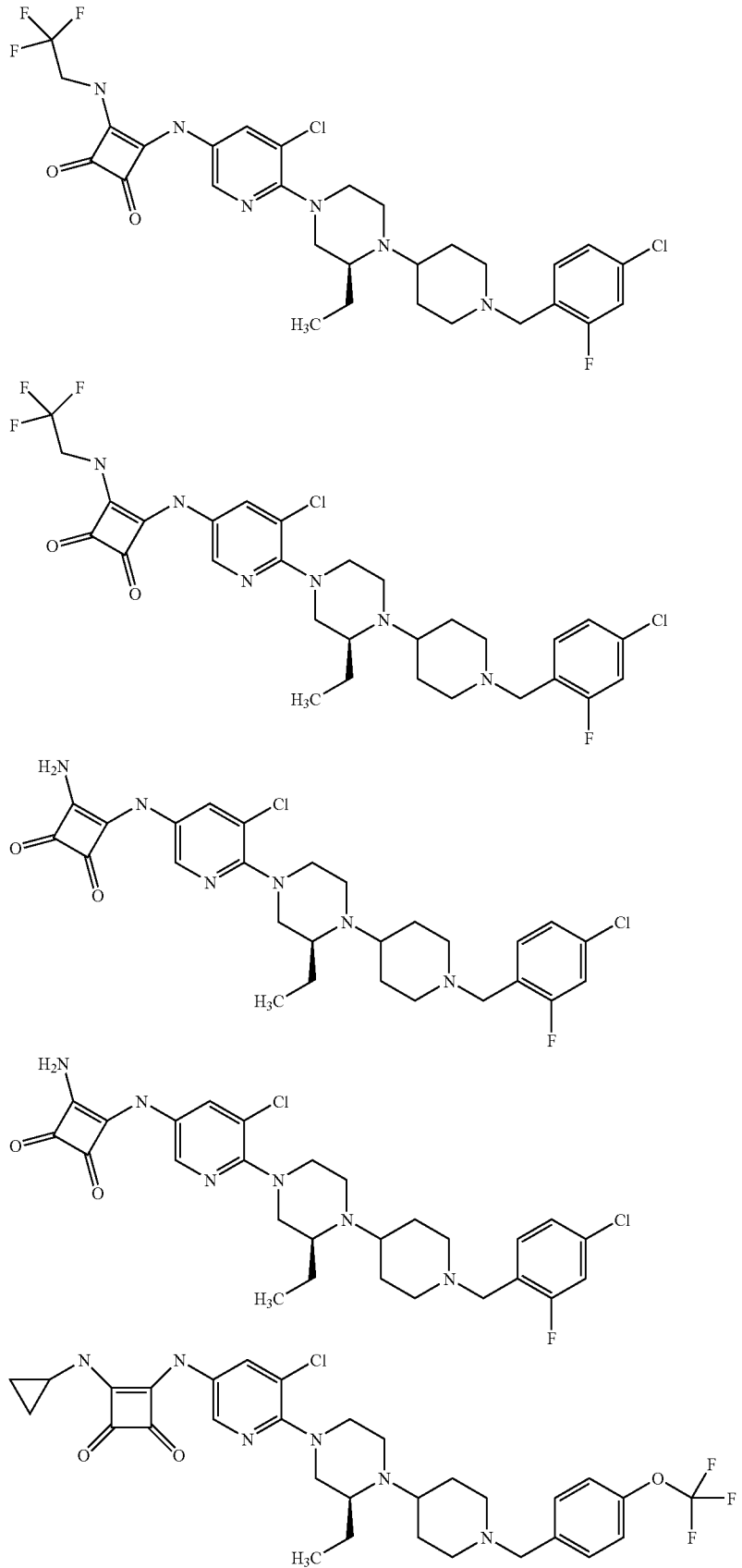

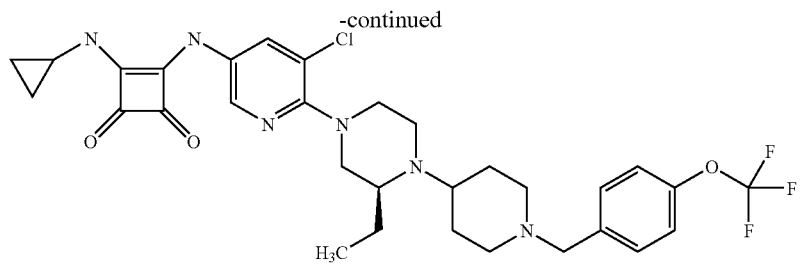
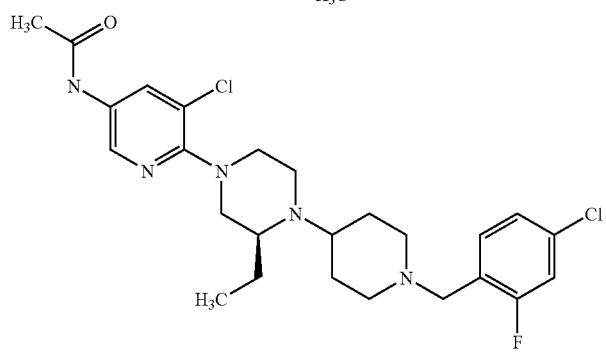
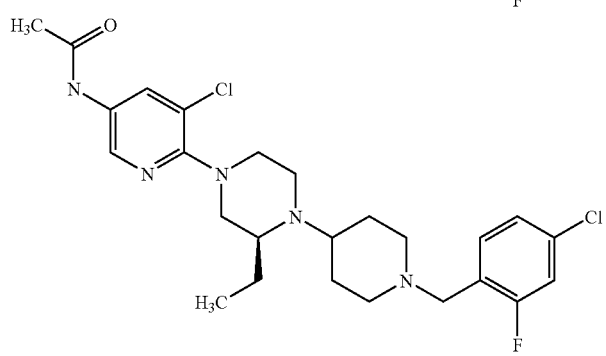
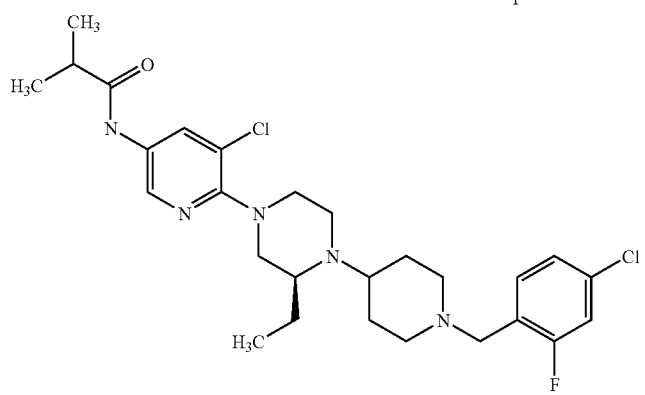
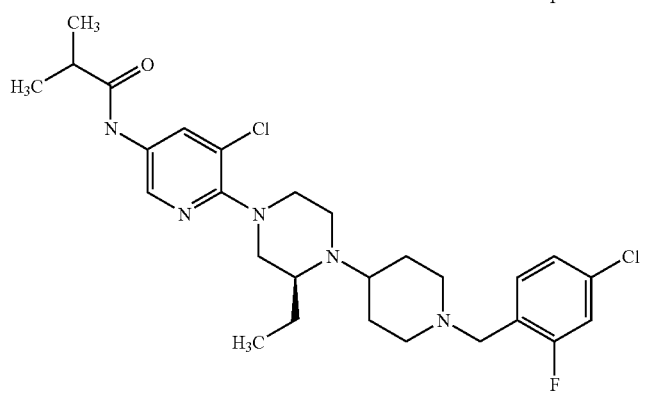

-continued
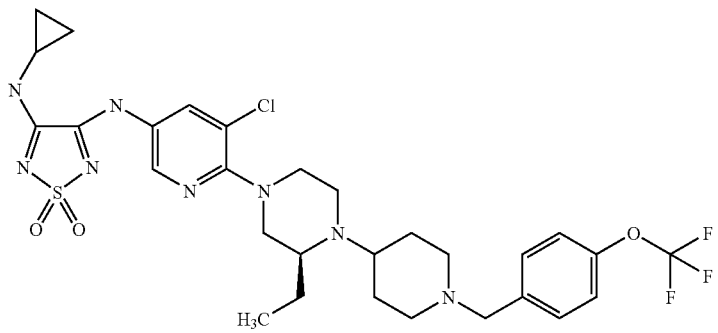
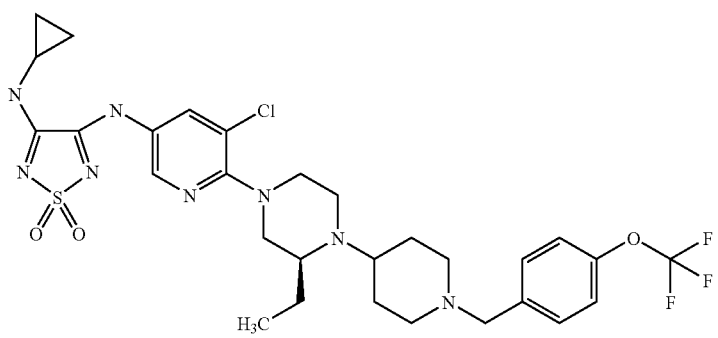
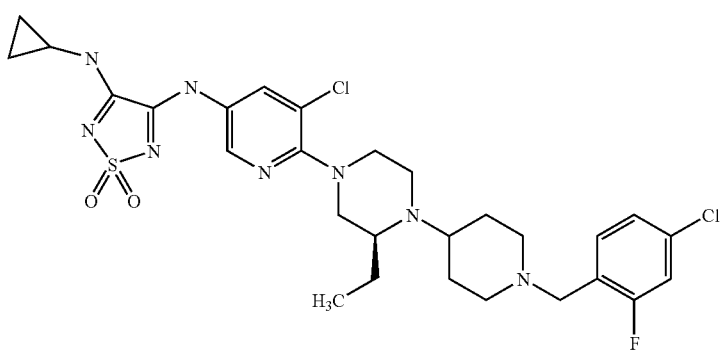
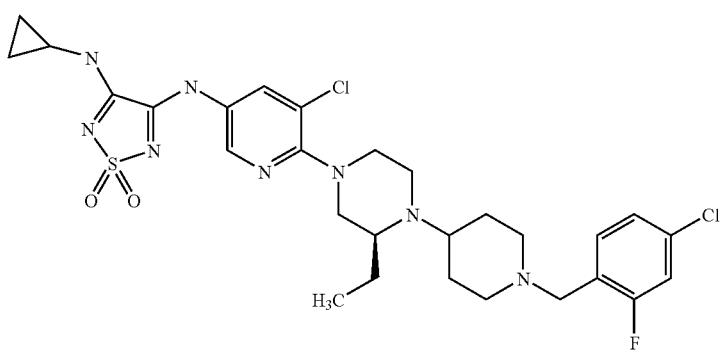
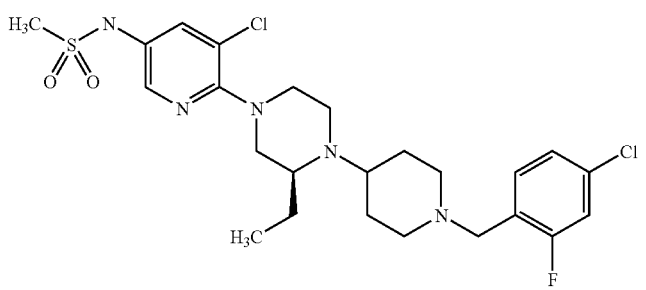

-continued
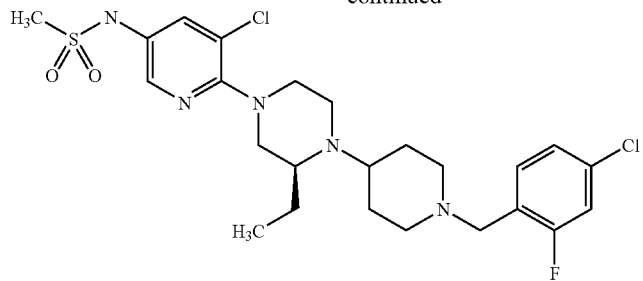
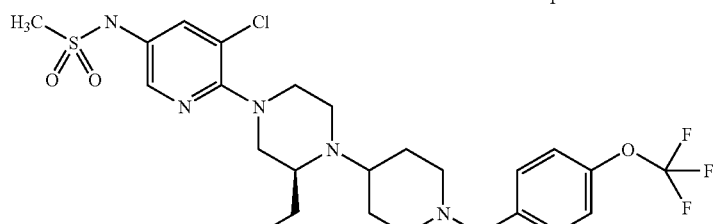
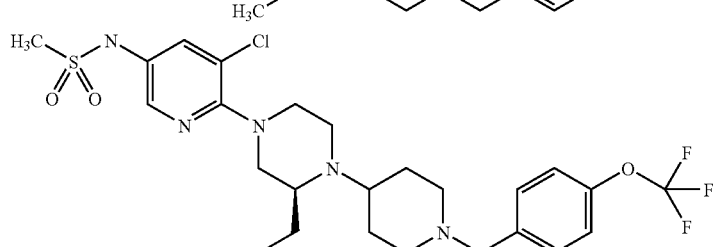
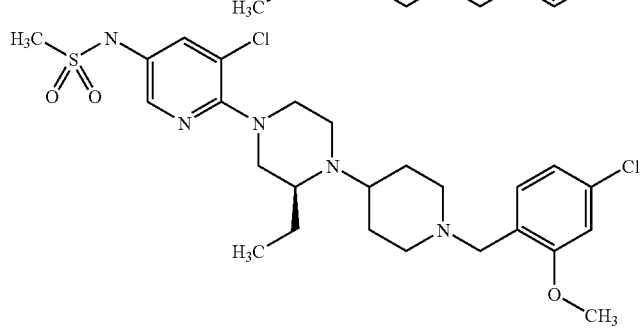
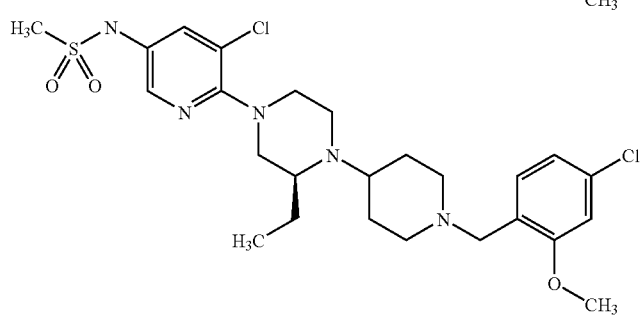
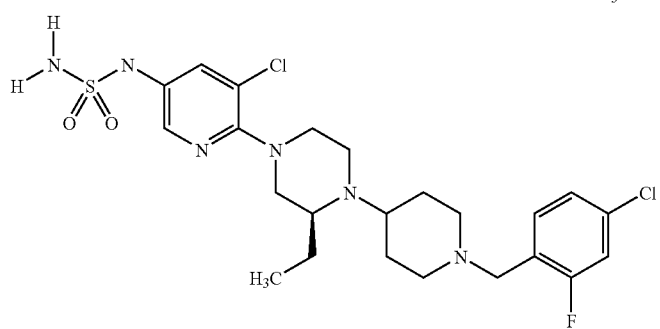

-continued
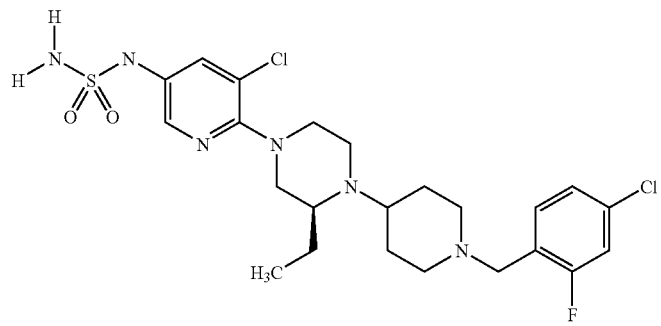
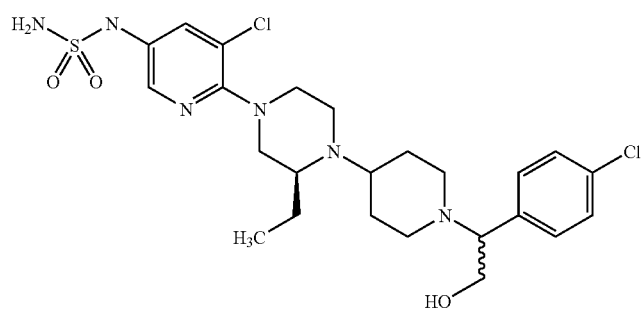
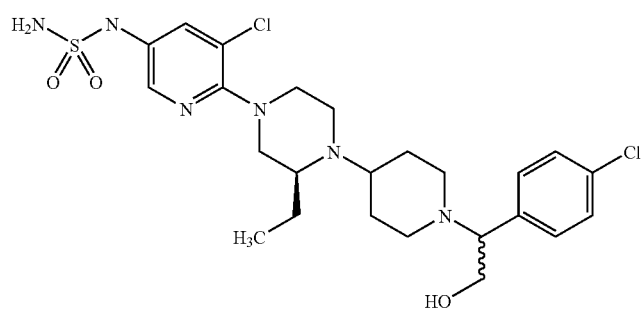
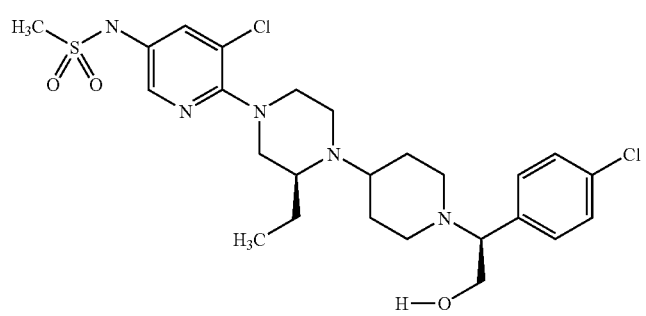
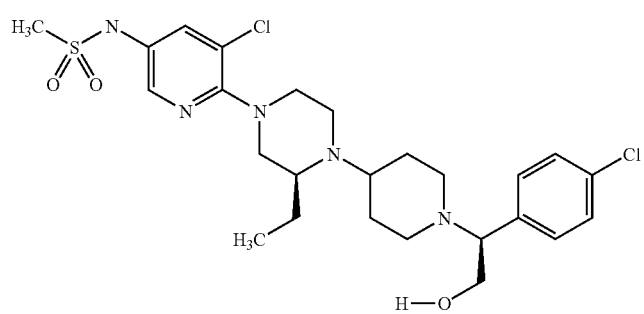

-continued
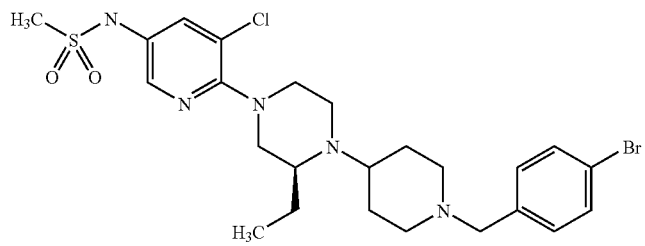
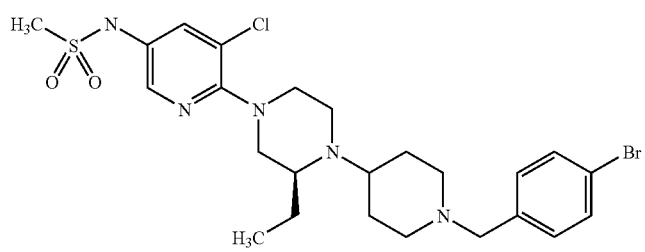
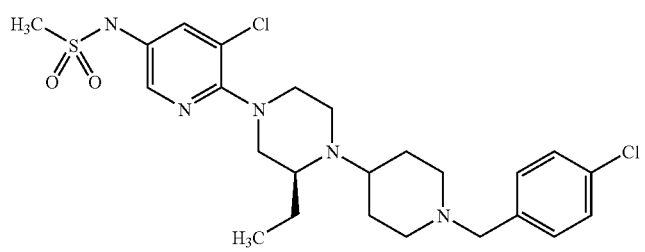
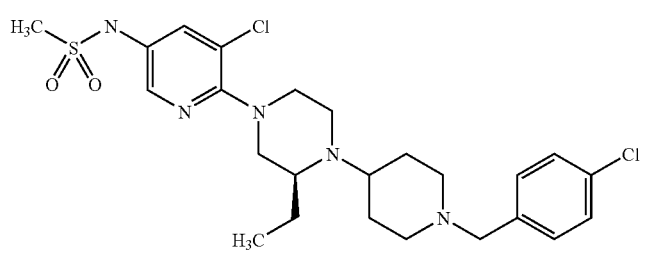
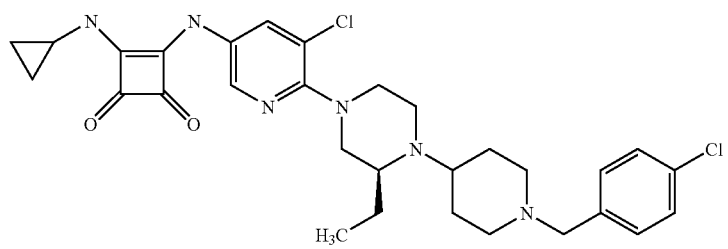
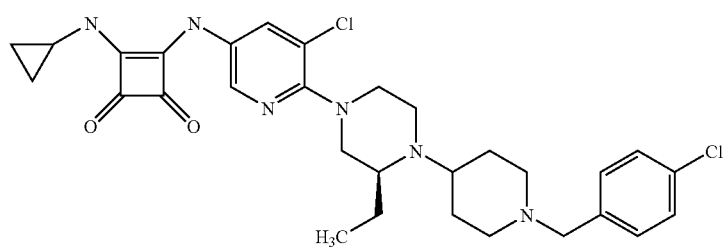

-continued
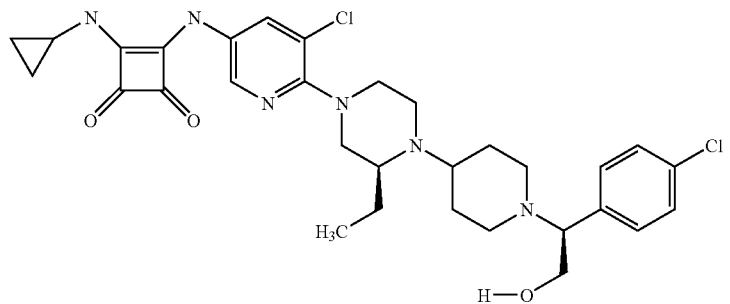
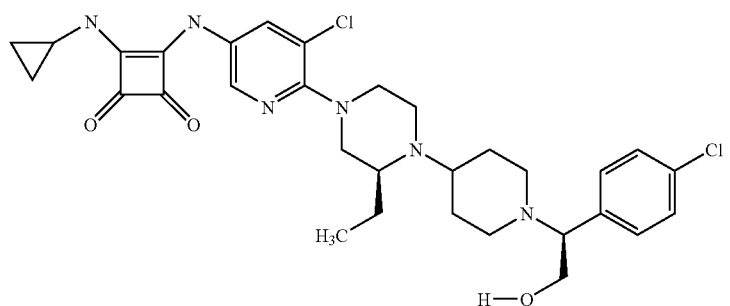
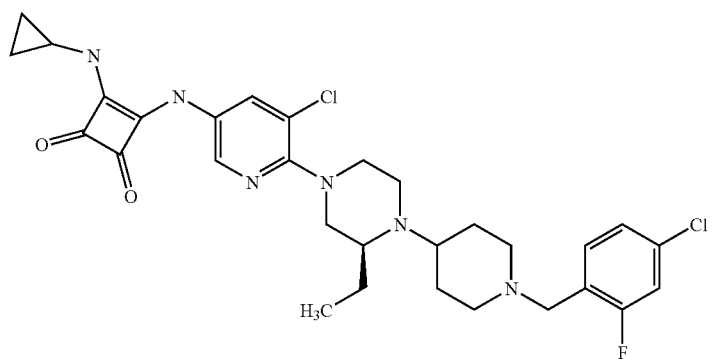
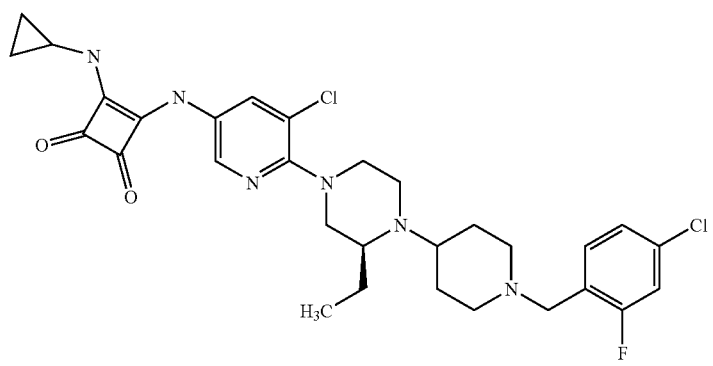

-continued
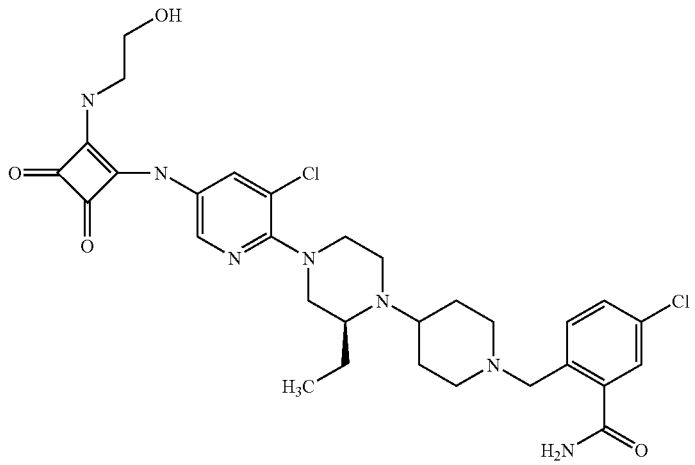
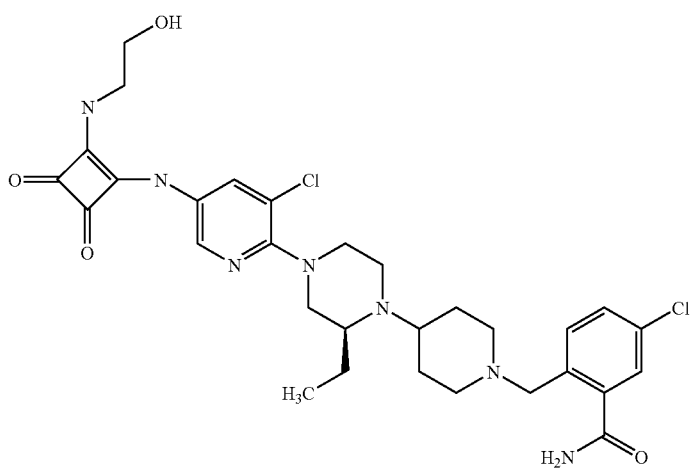
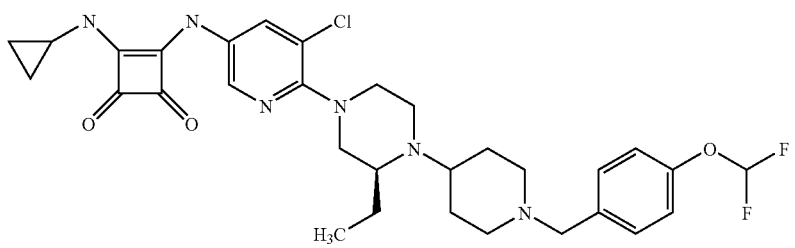
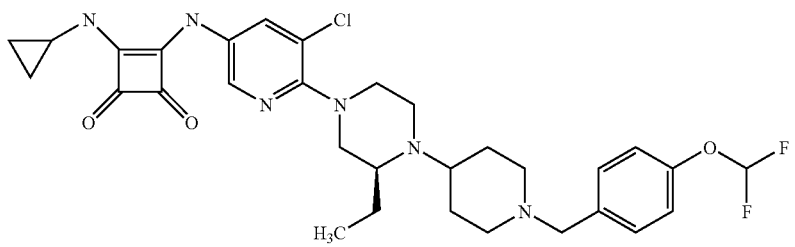

-continued
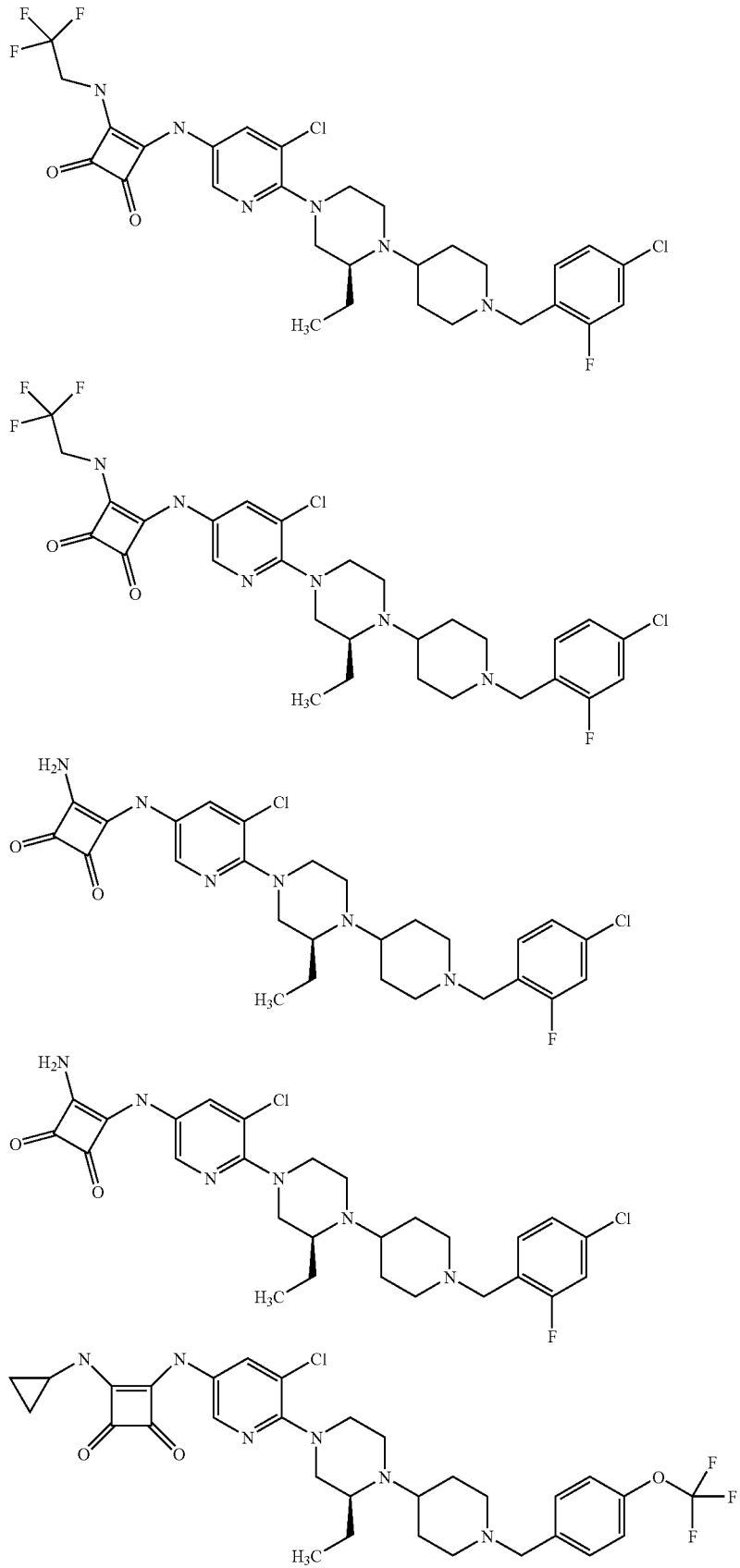

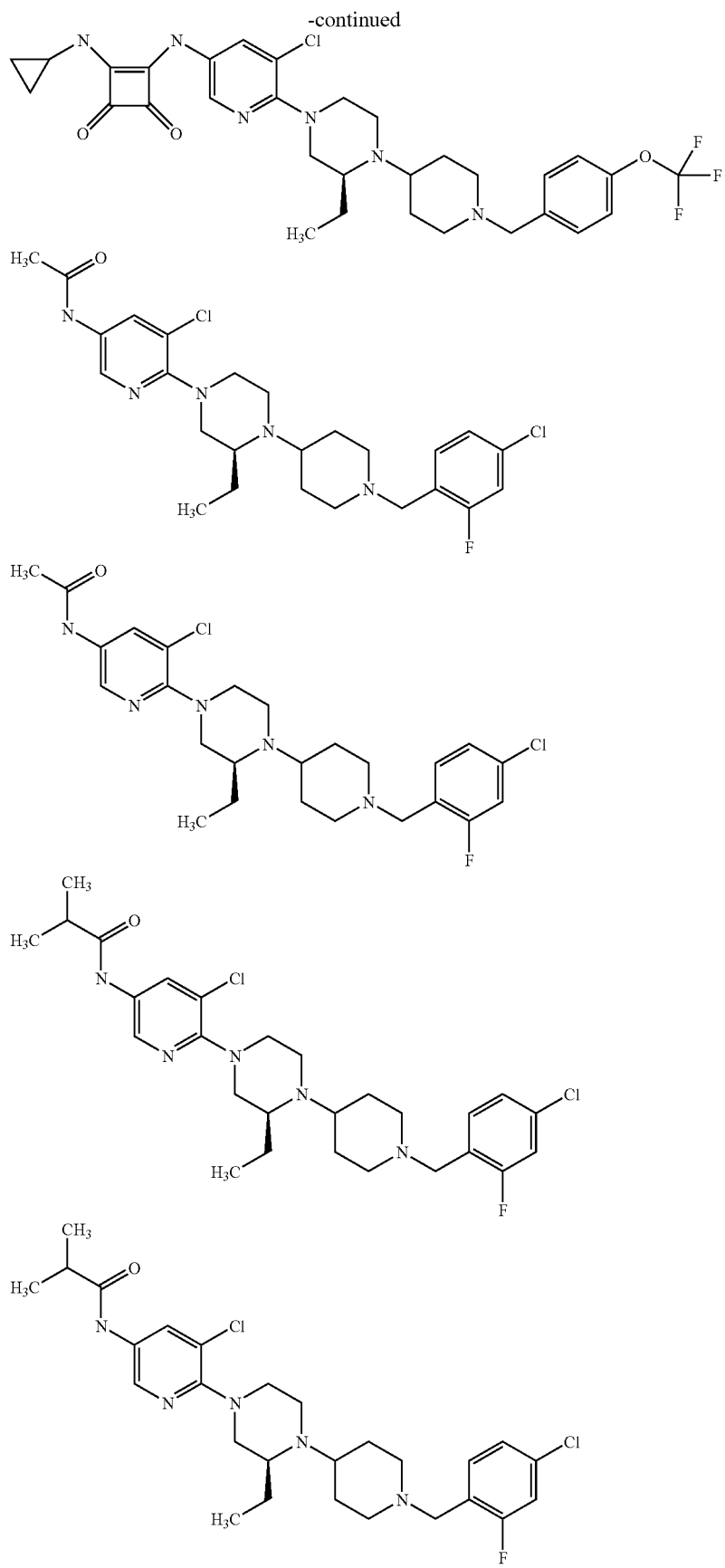

-continued
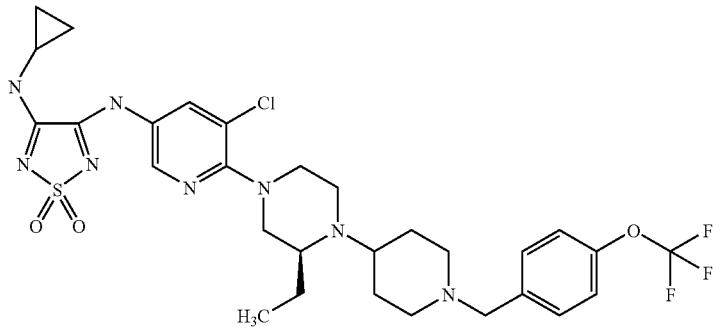
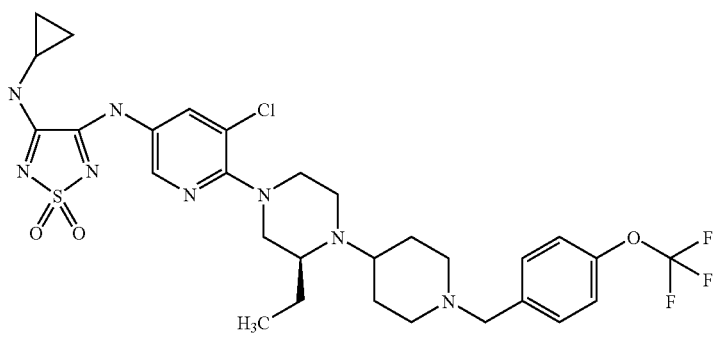
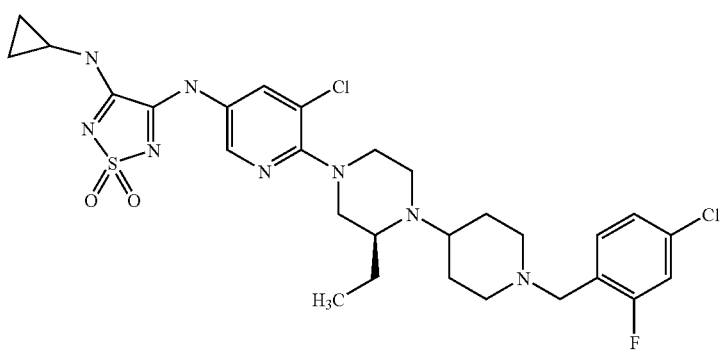
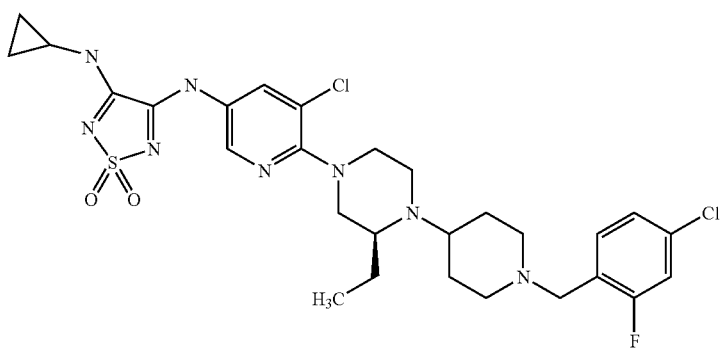
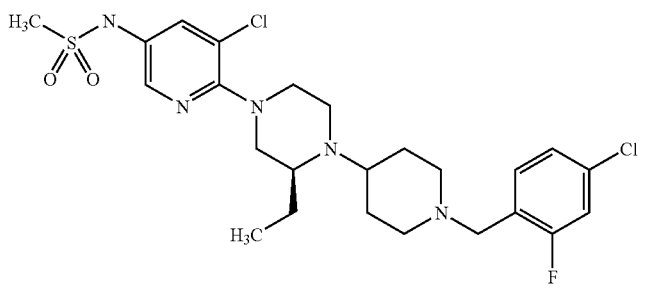

-continued
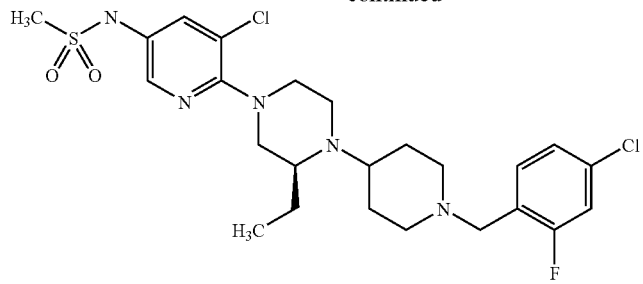
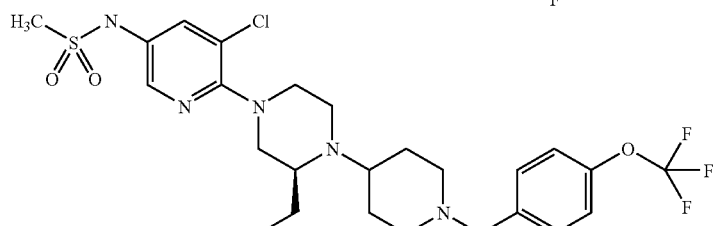
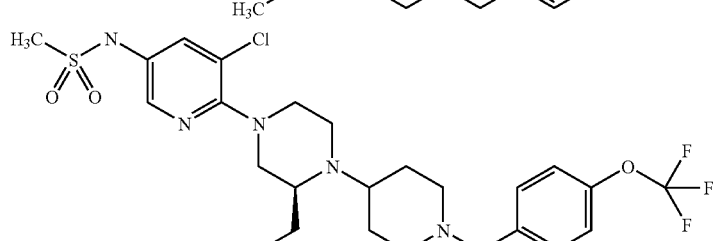
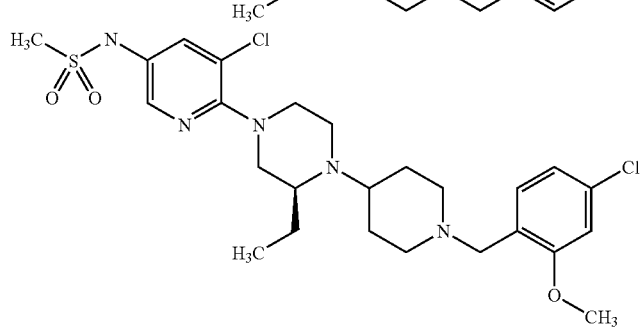
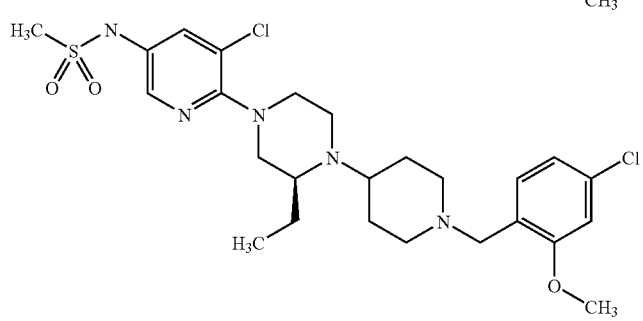
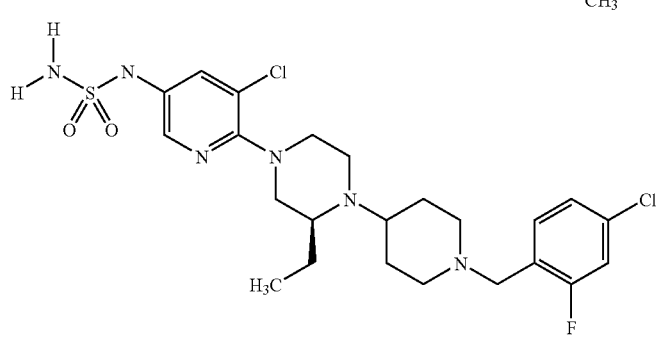

-continued
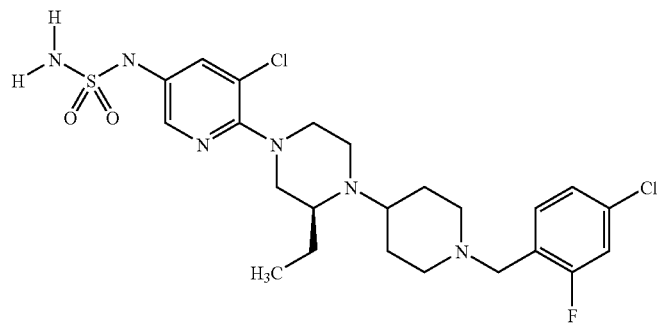
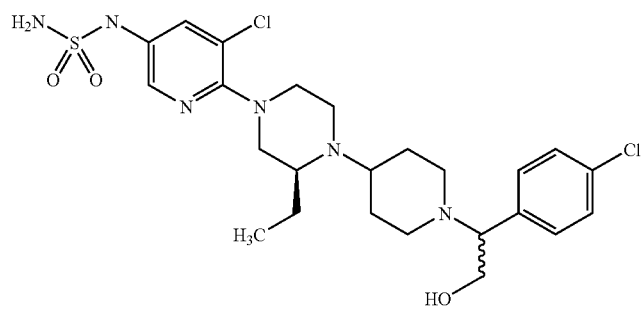
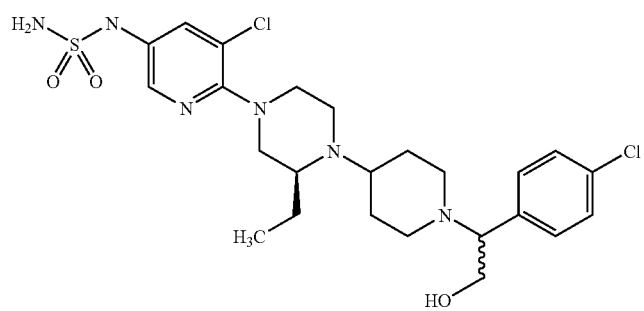
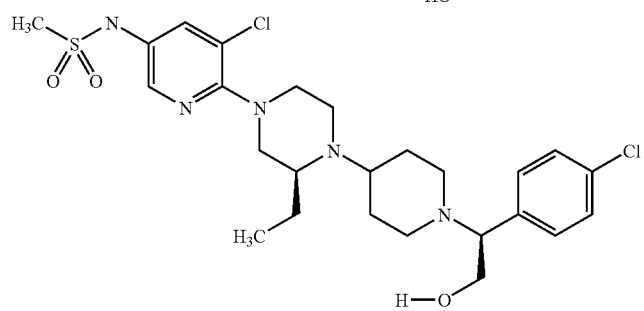
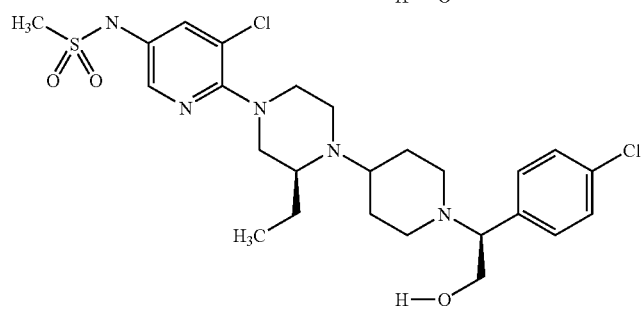

-continued
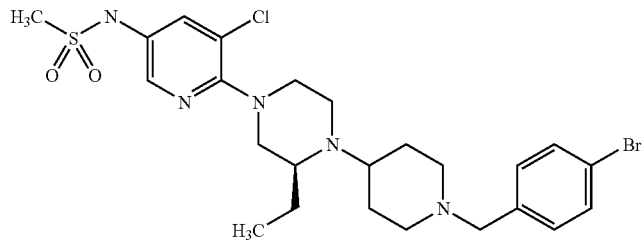
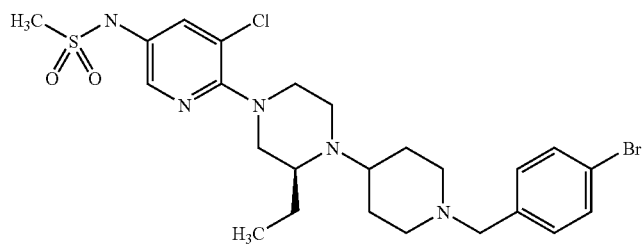
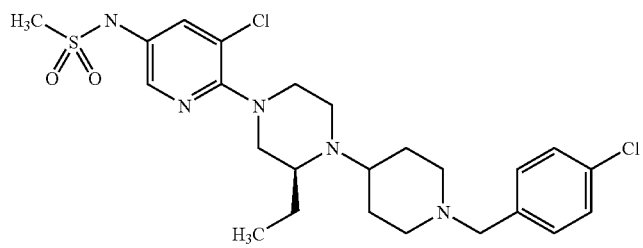
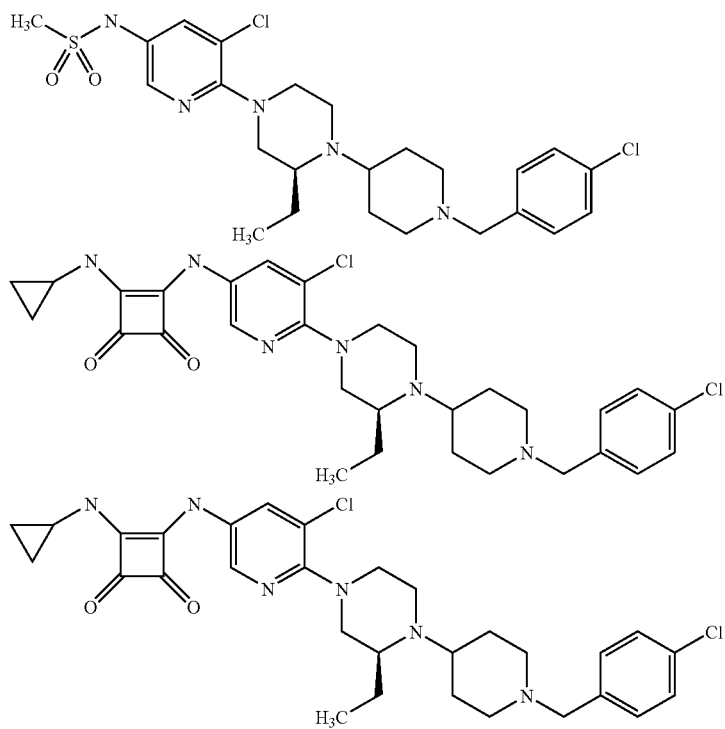

-continued
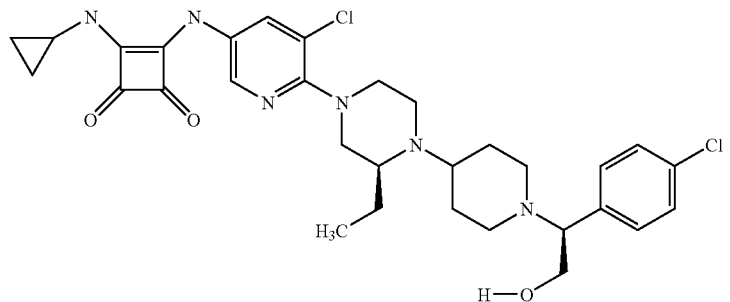
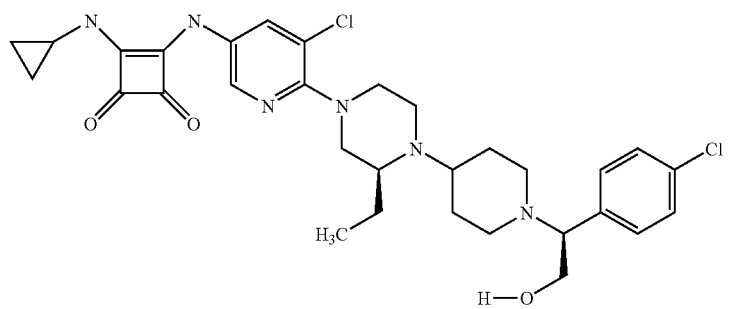
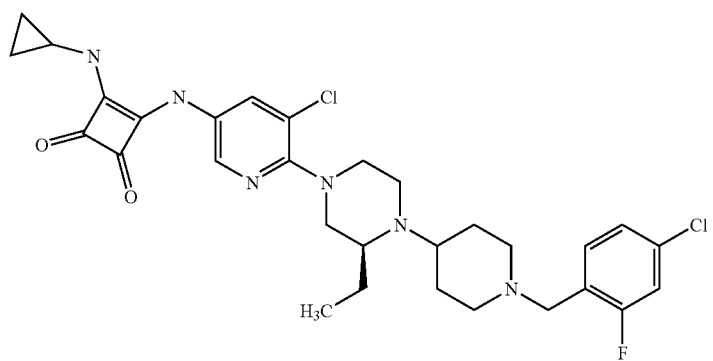
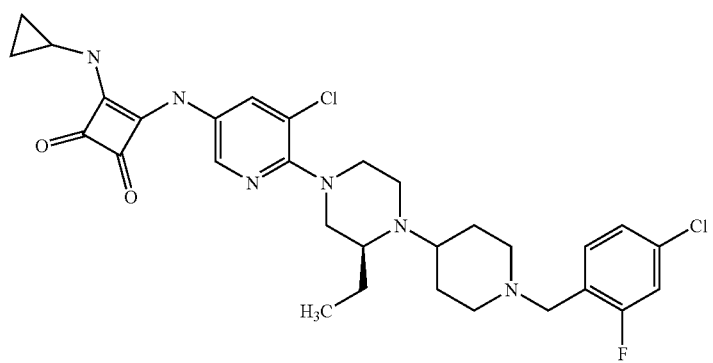

-continued
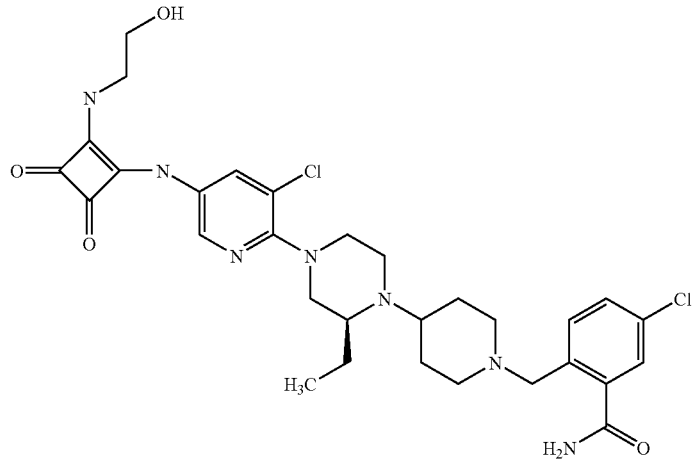
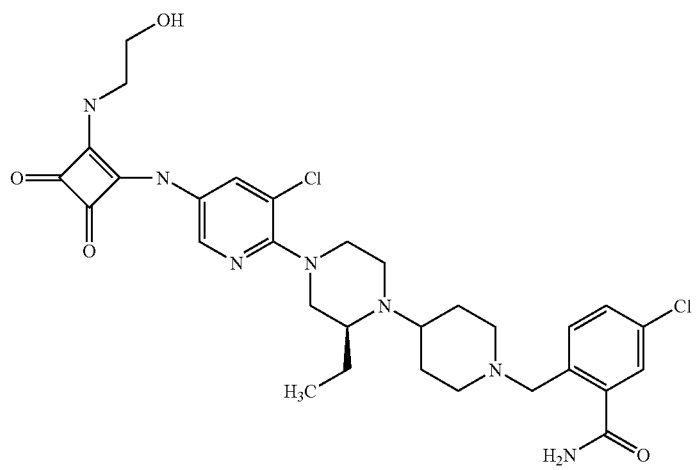
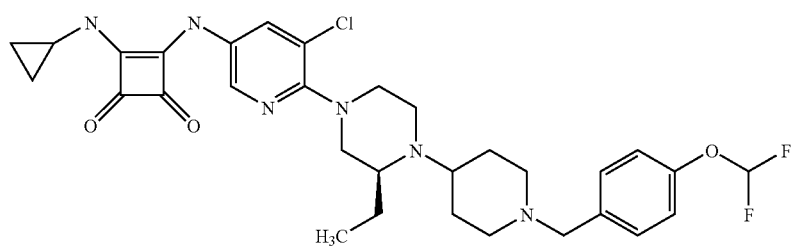
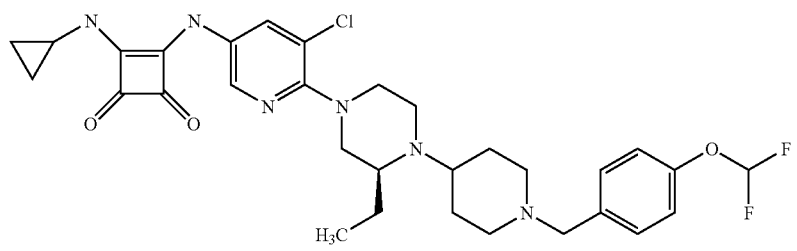

-continued
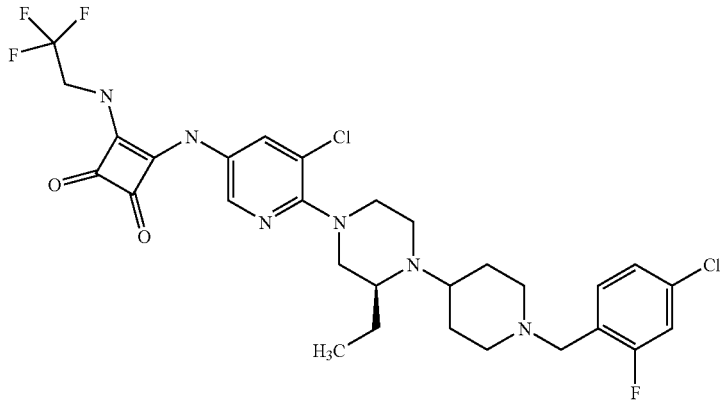
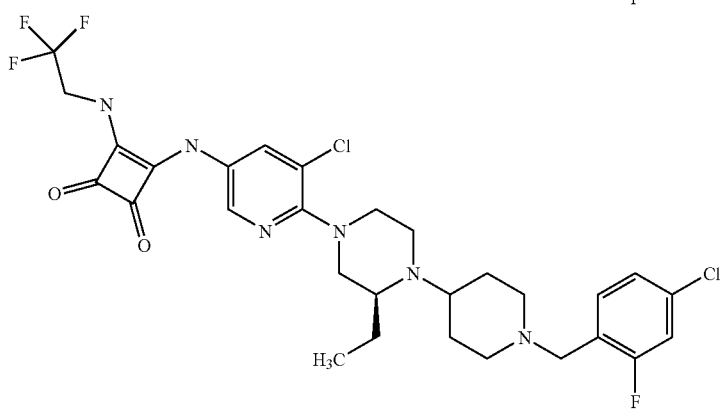
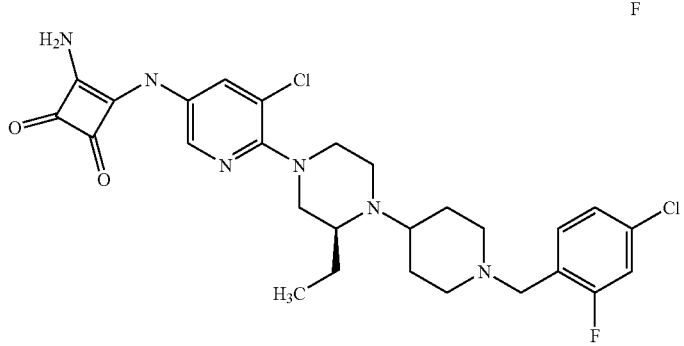
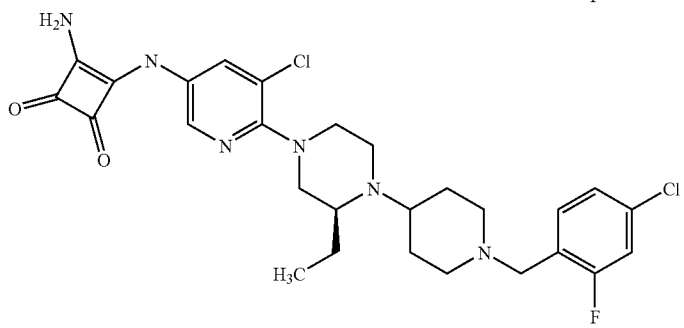
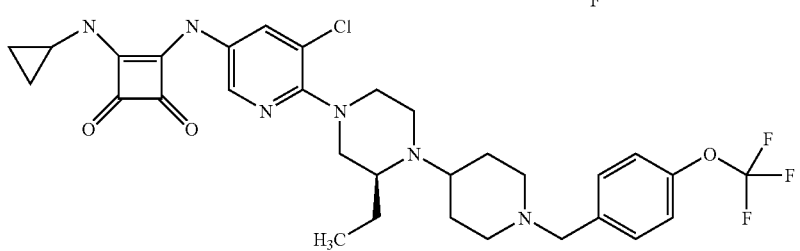

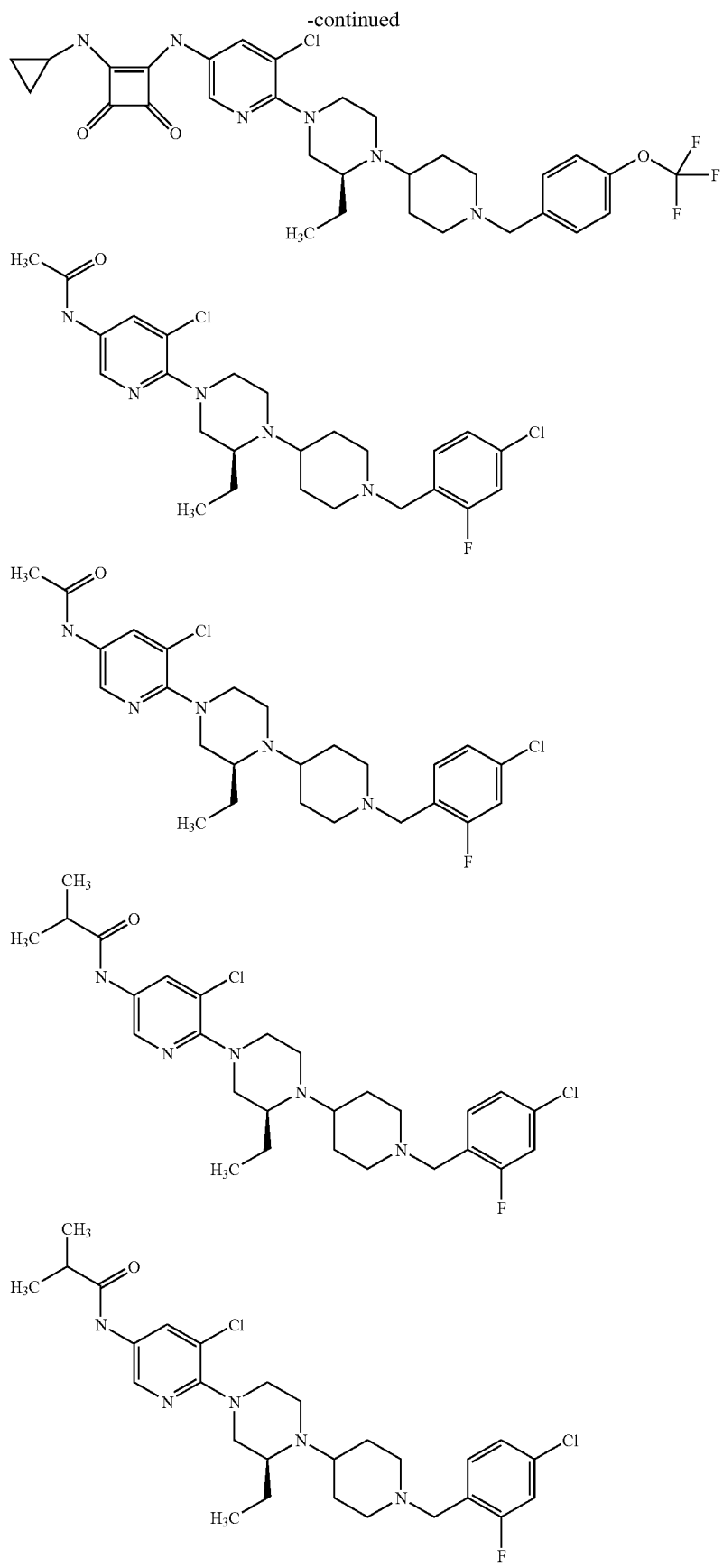

-continued
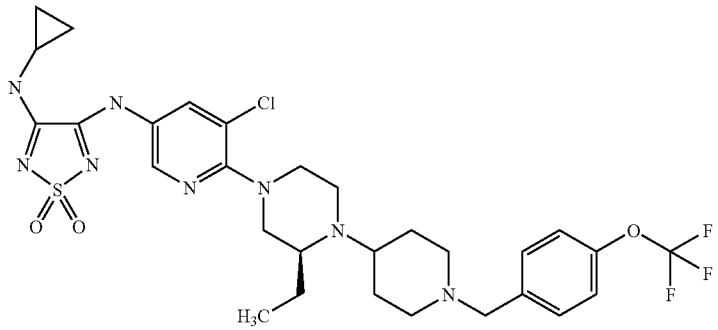
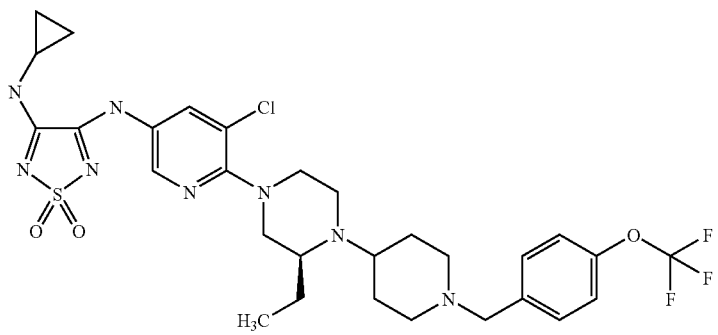
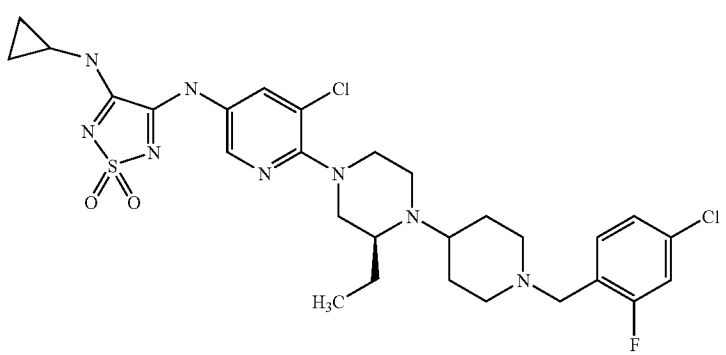
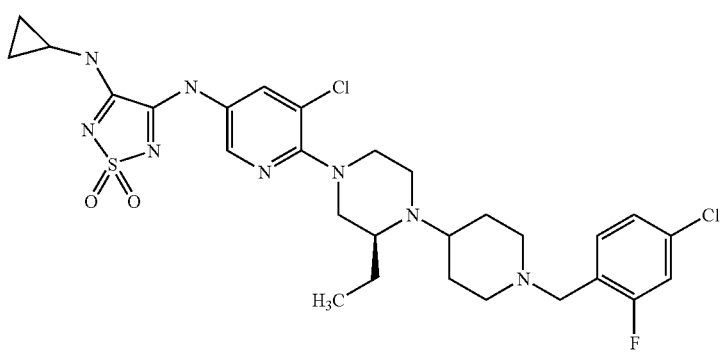
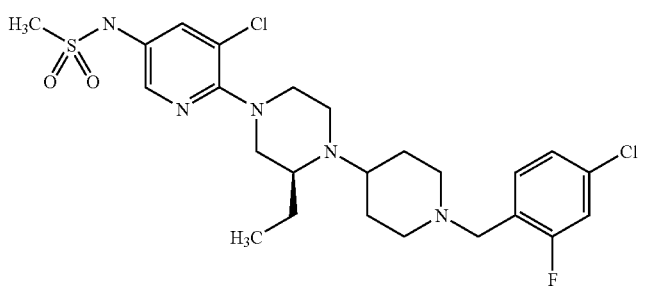

-continued
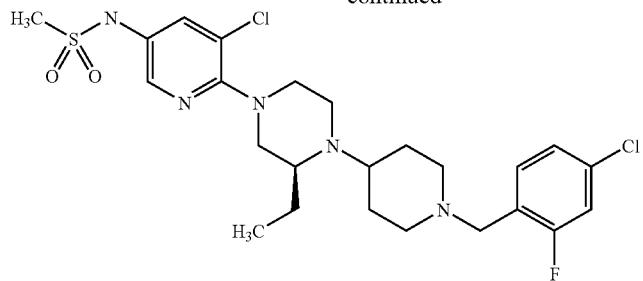
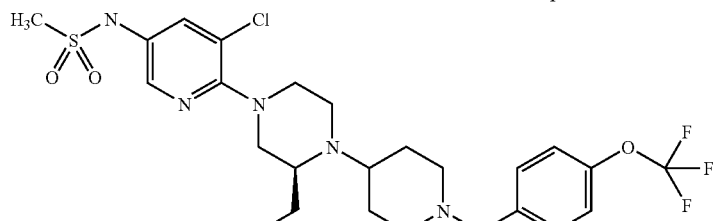
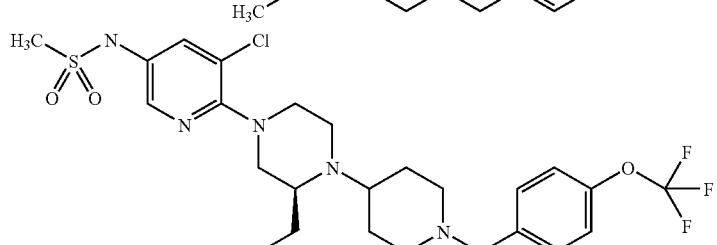
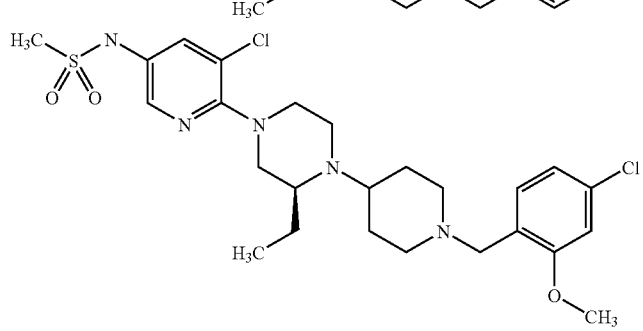
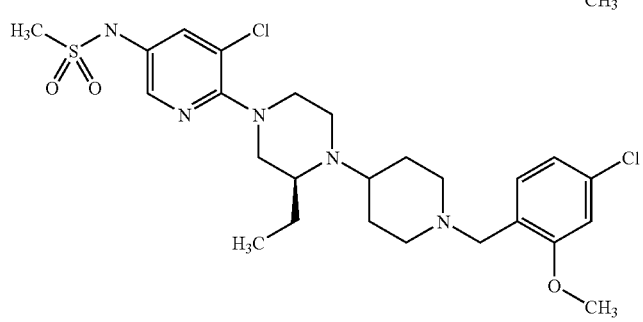
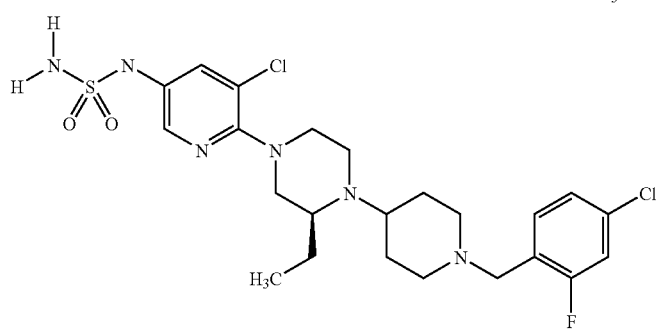

-continued
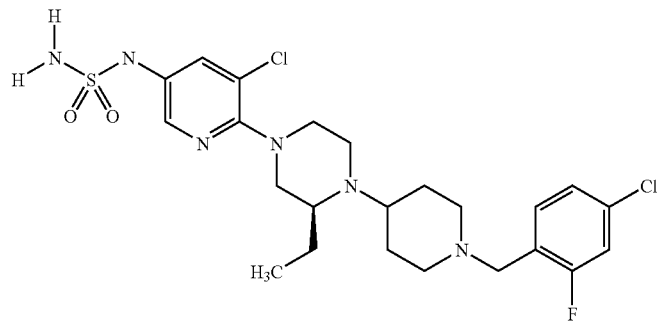
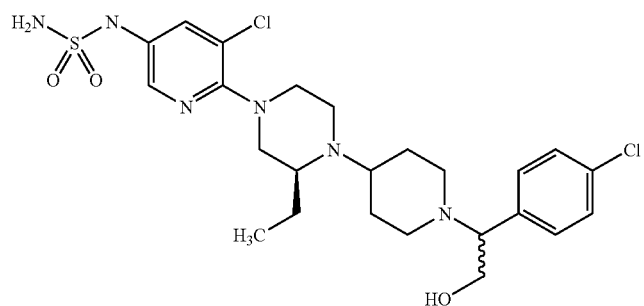
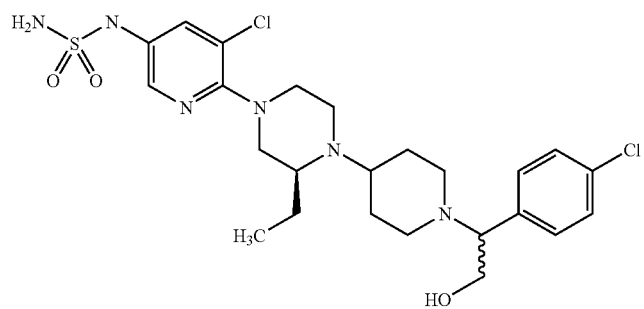
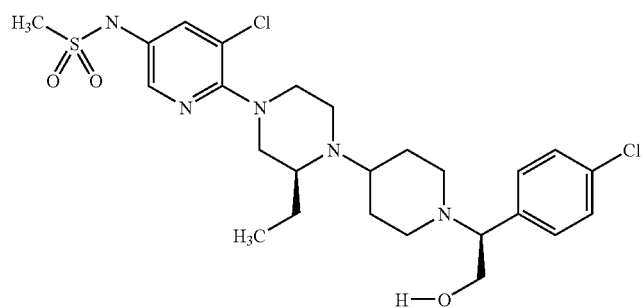
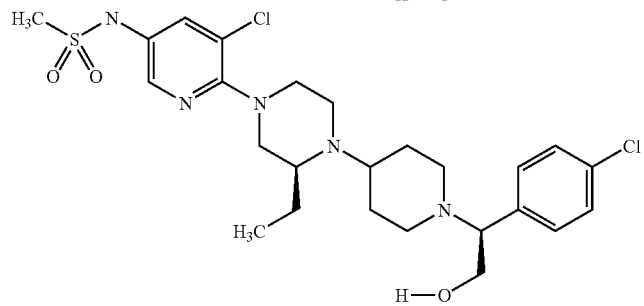

-continued
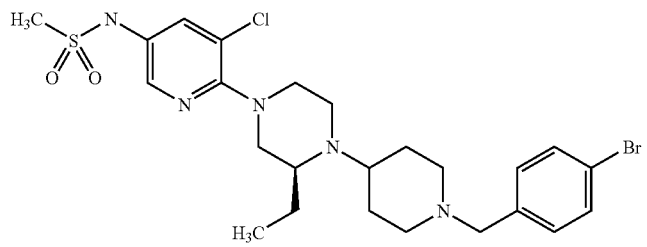
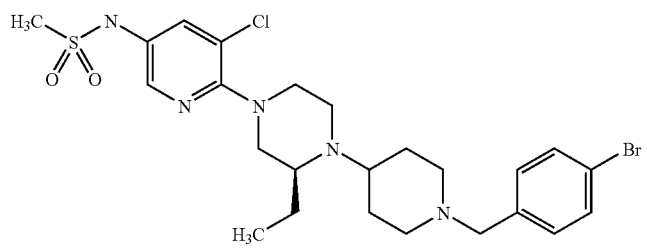
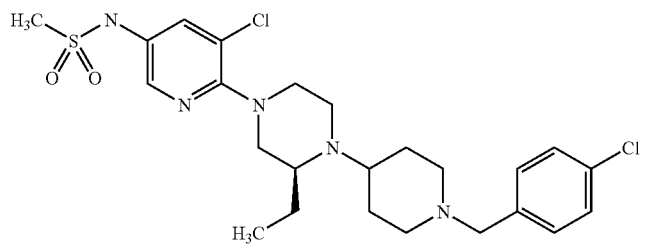
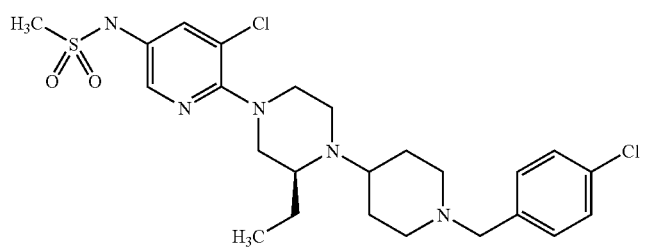
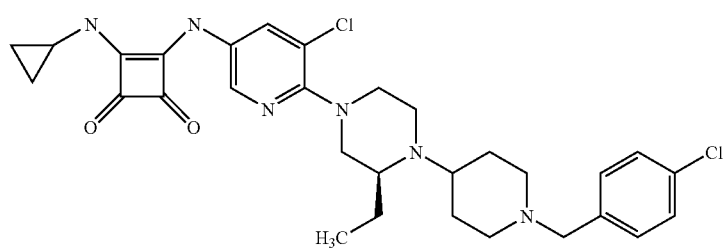
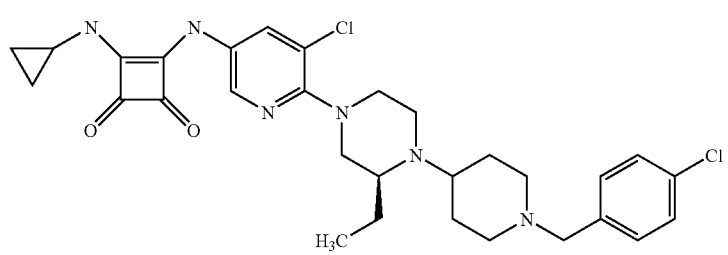

-continued
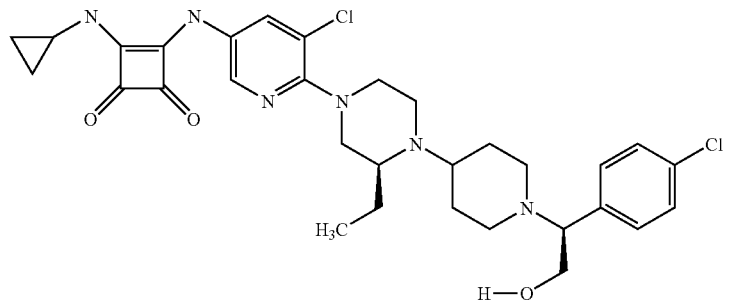
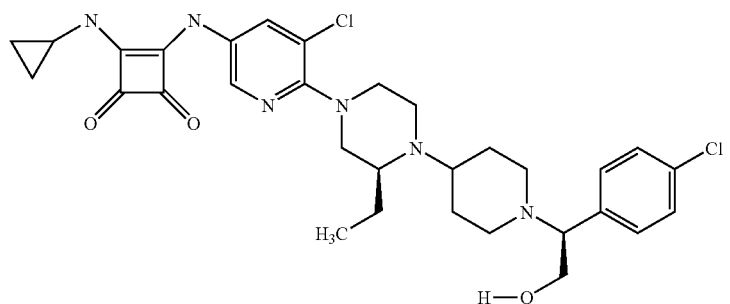
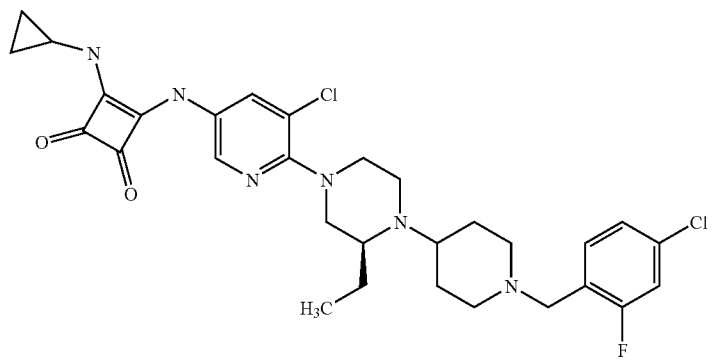
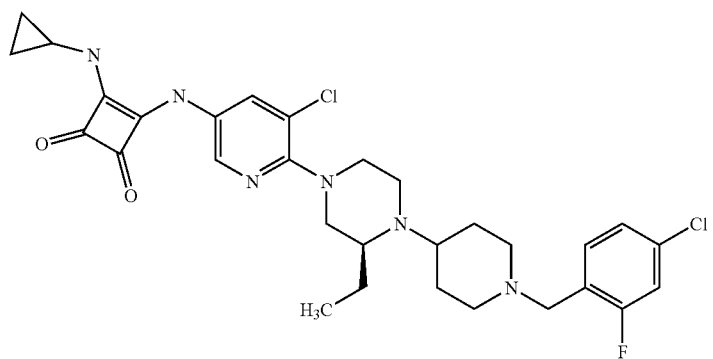

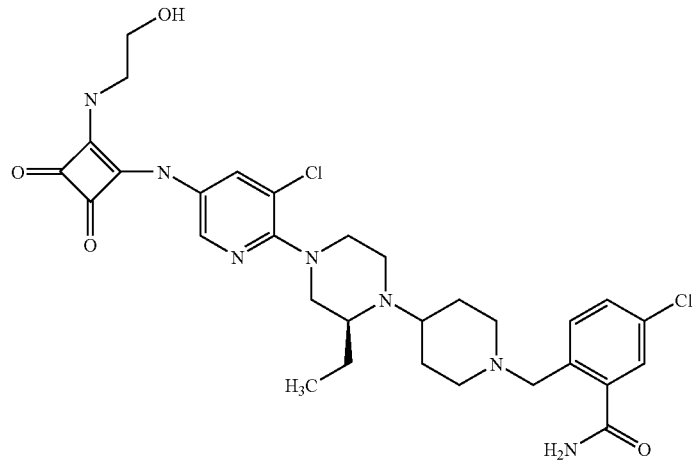
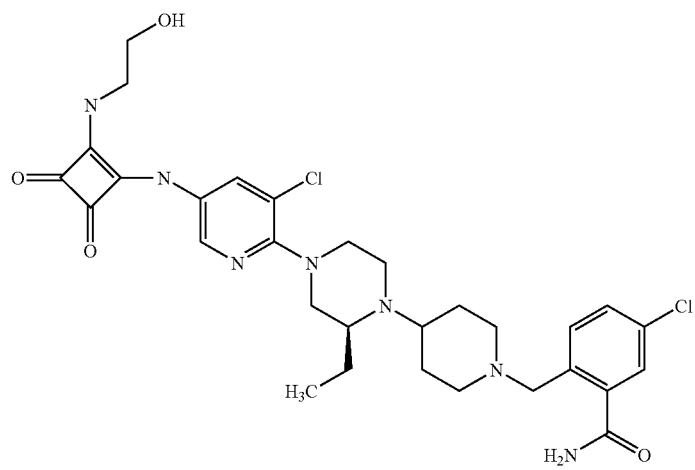
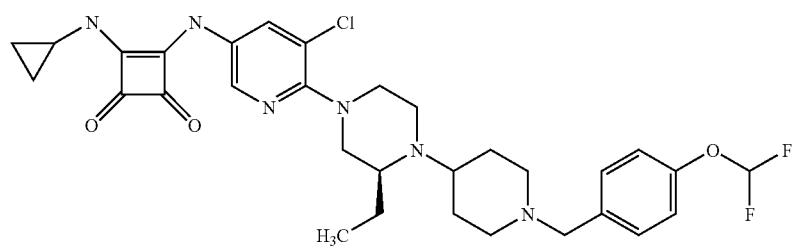
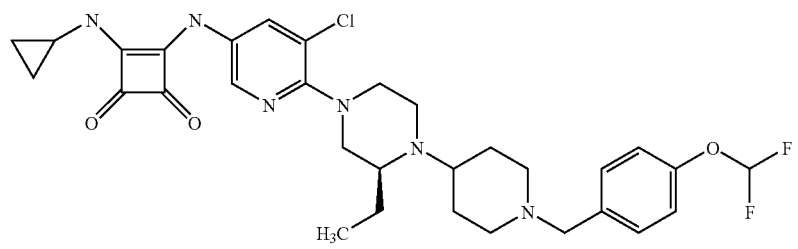

-continued
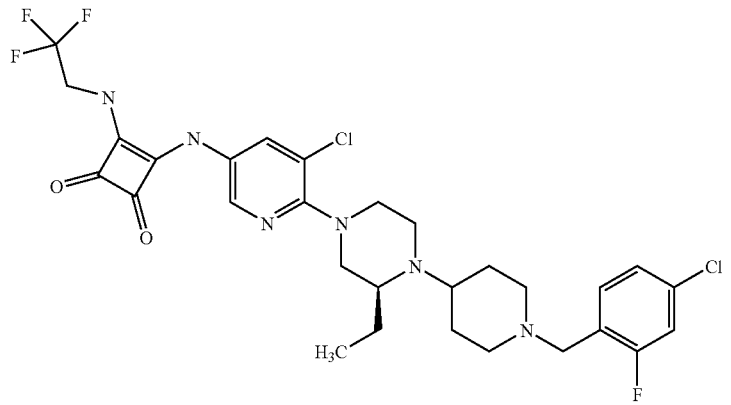
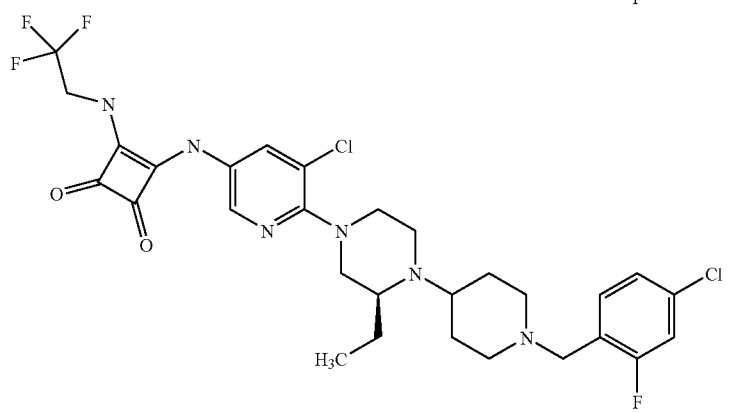
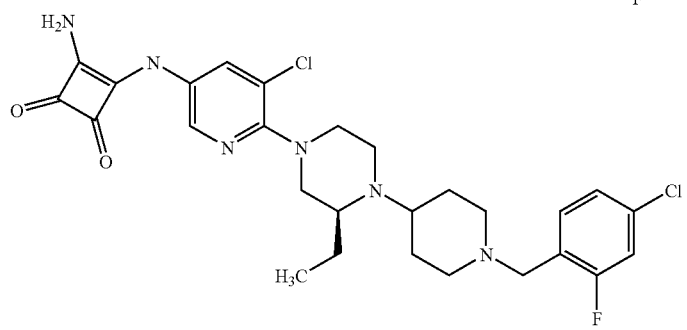
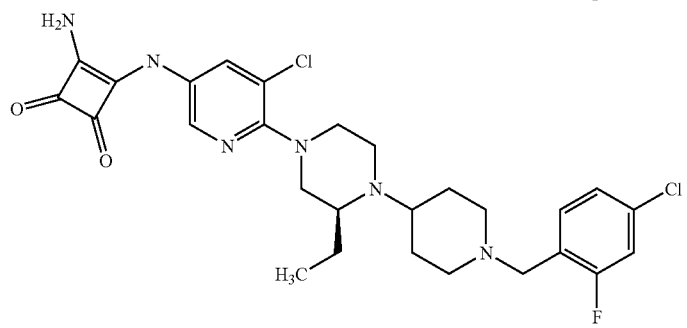
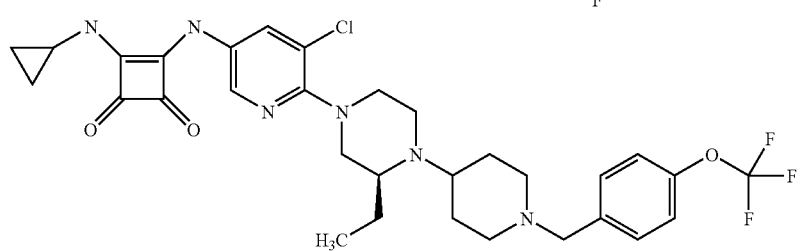

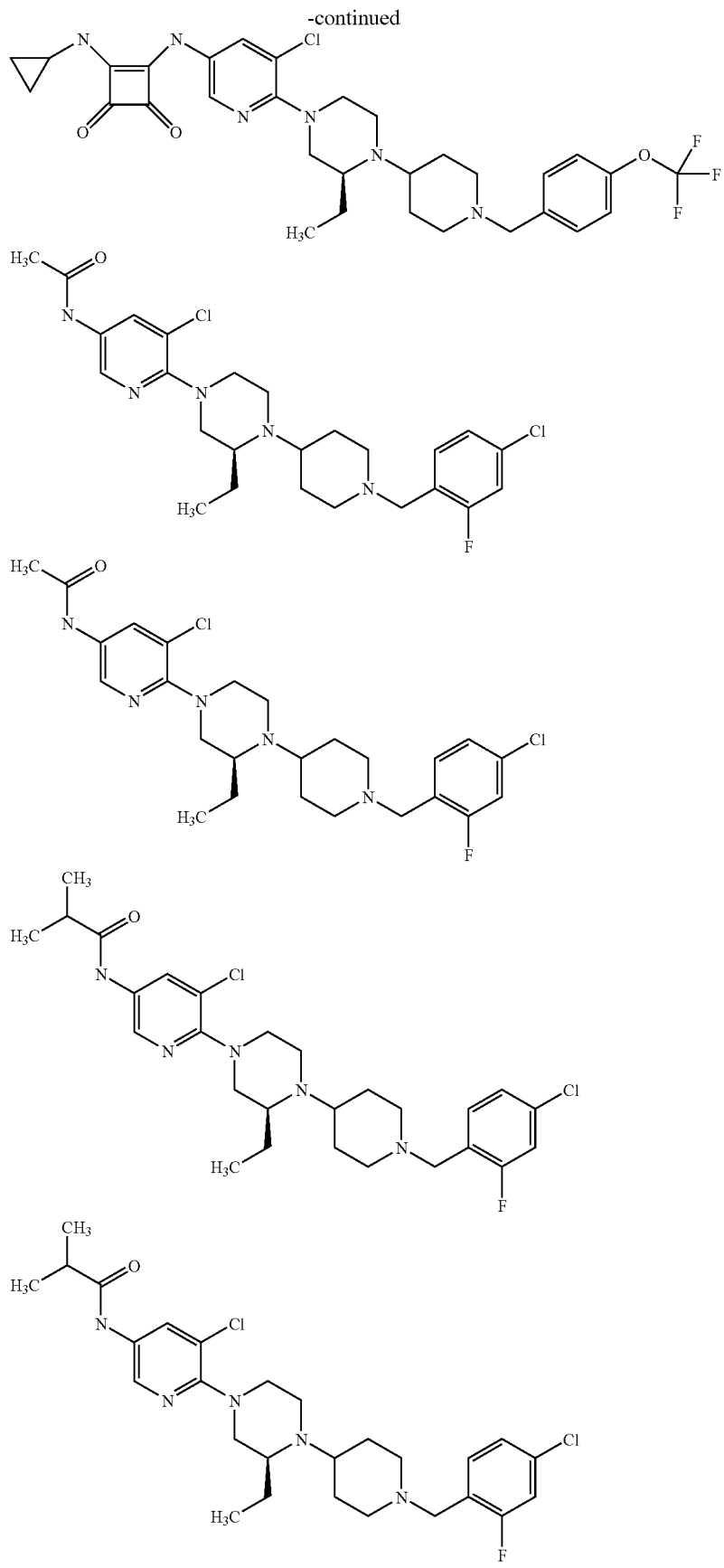

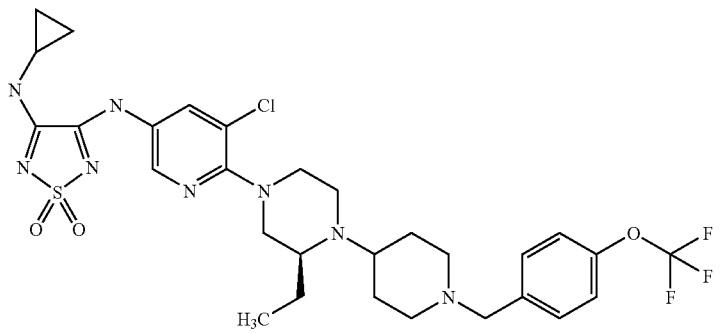
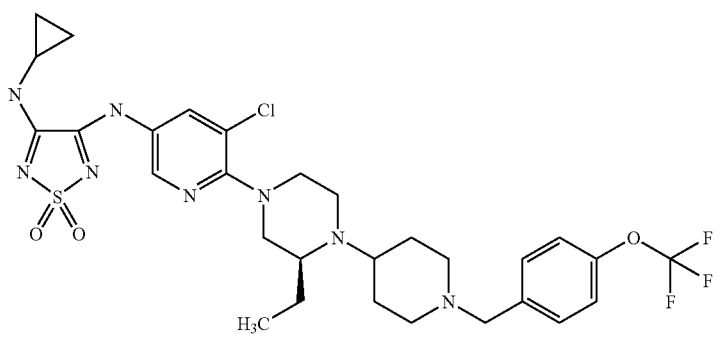
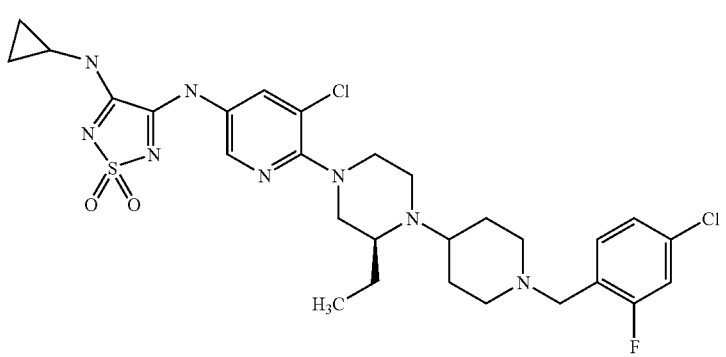
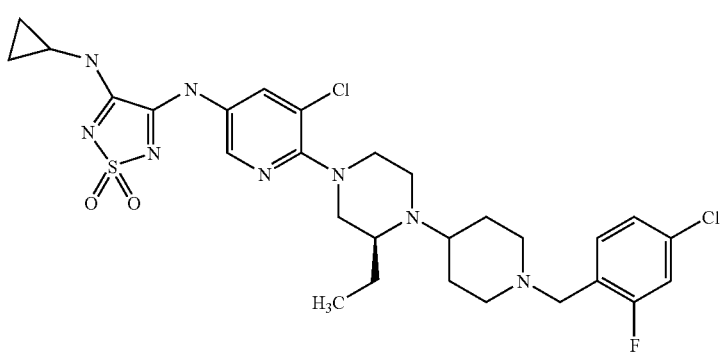
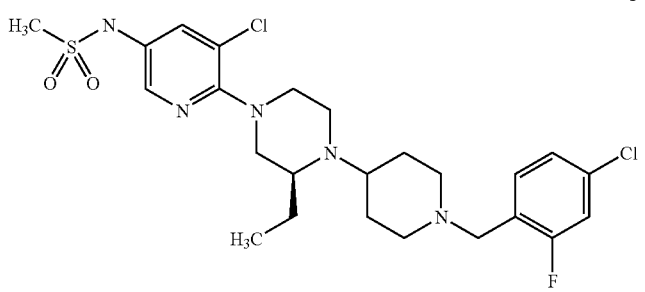

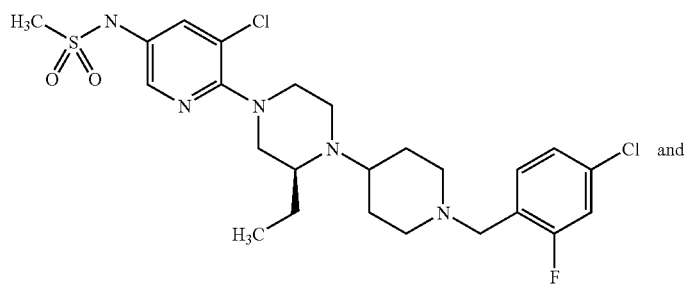
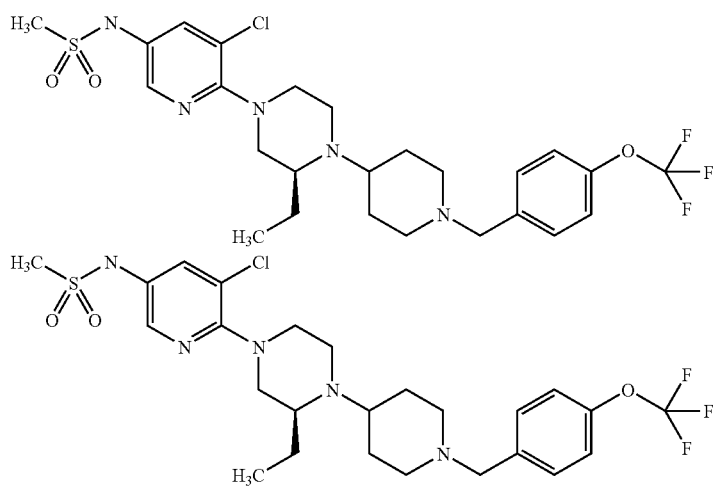
or pharmaceutically acceptable salts, solvates or esters thereof.
In yet another aspect, this invention discloses the following compounds:
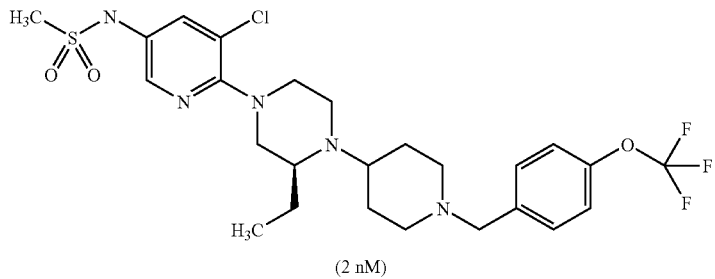
(2 nM)
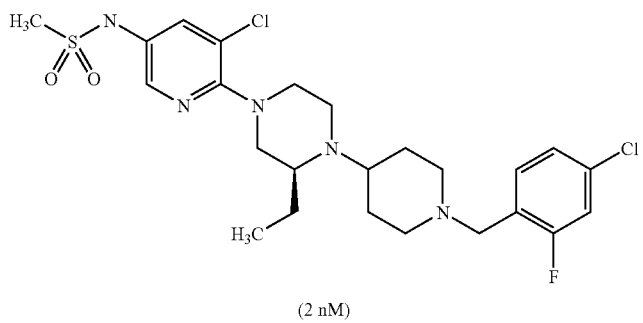
(2 nM)

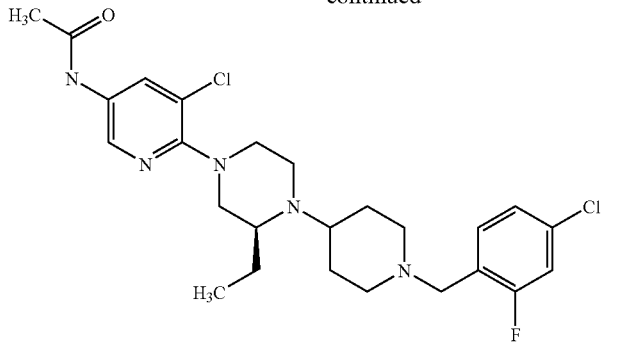

(1.2 nM)

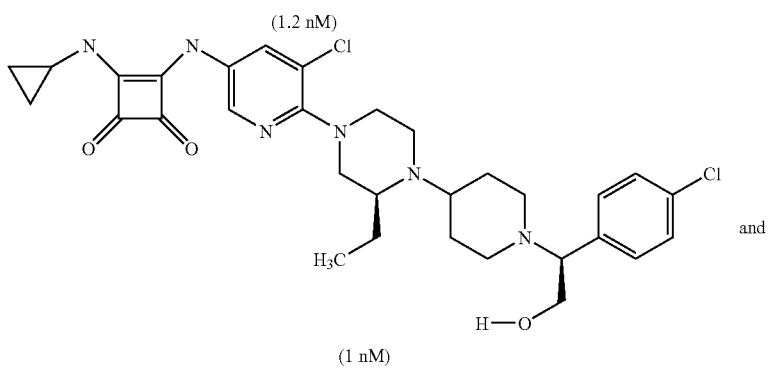

(1 nM) and

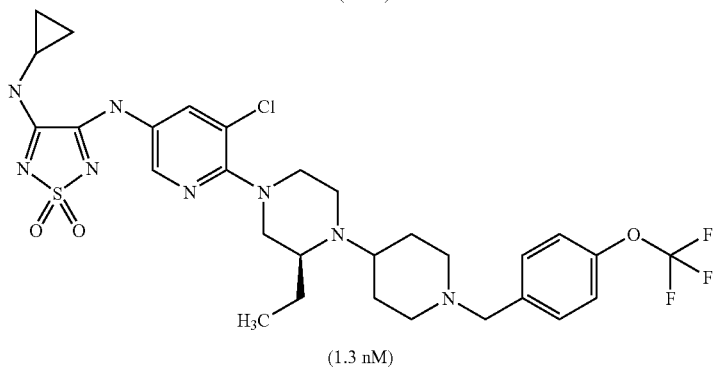

(1.3 nM)

or pharmaceutically acceptable salts, solvates or esters thereof. The human $IC_{50}$ values (in nM) for the above compounds have been set forth above underneath their chemical structures.

In yet another aspect, the compound according to Formula 1 is in purified form.

In another embodiment, this invention provides a pharmaceutical composition comprising at least one compound of Formula 1, or a pharmaceutically acceptable salt, solvate or ester thereof in combination with at least one pharmaceutically acceptable carrier.

In still another embodiment, the invention provides a pharmaceutical composition of Formula 1, further comprising at least one additional agent, drug, medicament, antibody and/or inhibitor for treating a CXCR3 chemokine receptor mediated disease.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for non-limiting illustration purposes, a compound of Formula III and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

In yet another embodiment, the present invention discloses methods for preparing pharmaceutical compositions comprising the inventive heterocyclic substituted piperazine compounds of Formula 1 as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. anti-inflammatory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Some useful terms are described below:

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution—refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

It will be apparent to those skilled in the art that many modifications, variations and alterations to the present disclosure, both to materials and methods, may be practiced. Such modifications, variations and alterations are intended to be within the spirit and scope of the present invention.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention. Certain compounds of the present invention may exist in multiple crystalline forms or amorphous forms. All physical forms of the current invention are contemplated.

Compounds of this invention which contain unnatural proportions of atomic isotopes (i.e. "radiolabeled compounds") whether their use is therapeutic, diagnostic or as a research reagent are contemplated under this invention.

Another embodiment of the invention discloses the use of the pharmaceutical compositions disclosed above for treatment of diseases of a CXCR3 chemokine receptor mediated disease in a patient in need of such treatment comprising administering to the patient a therapeutically effective amount of at least one compound according to Formula 1, or a pharmaceutically acceptable salt, solvate or ester thereof.

In another embodiment, the method is directed to administering to the patient (a) an effective amount of at least one compound according to Formula 1, or a pharmaceutically acceptable salt, solvate or ester thereof concurrently or sequentially with (b) at least one additional agent, drug, medicament, antibody and/or inhibitor for treating a CXCR3 chemokine receptor mediated disease, in combination with a pharmaceutically acceptable carrier.

In another embodiment, at least one compound of Formula 1 binds to a CXCR3 receptor.

The method can further comprise administering: (a) a therapeutically effective amount of at least one compound according to Formula 1, or a pharmaceutically acceptable salt, solvate or ester thereof concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives (such as cyclosporins and methotrexate); steroids (including corticosteroids such as glucorticoids); PDE IV inhibitors, anti-TNF-α compounds, TNF-α-convertase (TACE) inhibitors, MMP inhibitors, cytokine inhibitors, glucocorticoids, other chemokine inhibitors such as CCR2 and CCR5, CB2-selective inhibitors, p38 inhibitors, biological response modifiers; anti-inflammatory agents and therapeutics. The disease can be an inflammatory disease (e.g., psoriasis, inflammatory bowel disease) Another embodiment of this invention is directed to a method of inhibiting or blocking T-cell mediated chemotaxis in a patient in need of such treatment the method comprising administering to the patient a therapeutically effective amount of at least one compound according to Formula 1 or a pharmaceutically acceptable salt, solvate or ester thereof.

Another embodiment of this invention is directed to a method of treating inflammatory bowel disease (such Crohn's disease, ulcerative colitis) in a patient in need of such treatment comprising administering to the patient a therapeutically effective amount of at least one compound according to Formula 1, or a pharmaceutically acceptable salt, solvate or ester thereof.

Another embodiment of this invention is directed to a method of treating inflammatory bowel disease in a patient in need of such treatment comprising administering to the patient a therapeutically effective amount of: (a) at least one compound of Formula 1, or a pharmaceutically acceptable salt, solvate or ester thereof concurrently or sequentially with (b) at least one compound selected from the group consisting of: sulfasalazine, 5-aminosalicylic acid, sulfapyridine, anti-TNF compounds, anti-IL-12 compounds, corticosteroids, glucocorticoids, T-cell receptor directed therapies (such as anti-CD3 antibodies), immunosuppresives, methotrexate, azathioprine, and 6-mercaptopurines.

Another embodiment of this invention is directed to a method of treating or preventing graft rejection in a patient in need of such treatment comprising administering to the patient a therapeutically effective amount of at least one compound according to Formula 1, or a pharmaceutically acceptable salt, solvate or ester thereof.

Another embodiment of this invention is directed to a method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: cyclosporine A, FK-506, FTY720, beta-interferon, rapamycin, mycophenolate, prednisolone, azathioprine, cyclophosphamide and an antilymphocyte globulin.

Another embodiment of this invention is directed to a method of treating multiple sclerosis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: beta-interferon, glatiramer acetate, corticosteroids, glucocorticoids, methotrexate, azothioprine, mitoxantrone, VLA-4 inhibitors, FTY720, anti-IL-12 inhibitors, and CB2-selective inhibitors.

Another embodiment of this invention is directed to a method of treating multiple sclerosis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: methotrexate, cyclosporin, leflunomide, sulfasalazine, corticosteroids, β-methasone, β-interferon, glatiramer acetate, prednisone, etonercept, and infliximab.

Another embodiment of this invention is directed to a method of treating rheumatoid arthritis in a patient in need of such treatment the method comprising administering to the patient a therapeutically effective amount of: (a) at least one compound according to Formula 1, or a pharmaceutically acceptable salt, solvate or ester thereof concurrently or sequentially with (b) at least one compound selected from the group consisting of: non-steroidal anti-inflammatory agents, COX-2 inhibitors, COX-1 inhibitors, immunosuppressives, cyclosporine, methotrexate, steroids, PDE IV inhibitors, anti-TNF-α compounds, MMP inhibitors, corticosteroids, glucocorticoids, chemokine inhibitors, CB2-selective inhibitors, caspase (ICE) inhibitors and other classes of compounds indicated for the treatment of rheumatoid arthritis.

Another embodiment of this invention is directed to a method of treating psoriasis in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, steroids, corticosteroids, anti-TNF-α compounds, anti-IL compounds, anti-IL-23 compounds, vitamin A and D compounds and fumarates.

Another embodiment of this invention is directed to a method of treating ophthalmic inflammation (including, for e.g., uveitis, posterior segment intraocular inflammation, Sjogren's syndrome) or dry eye in a patient in need of such treatment the method comprising administering to the patient a therapeutically effective amount of: a) at least one compound according to Formula 1, or a pharmaceutically acceptable salt, solvate or ester thereof concurrently or sequentially with (b) at least one compound selected from the group consisting of: immunosuppressives, cyclosporins, methotrexate, FK506, steroids, corticosteroids, and anti-TNF-α compounds.

Another embodiment of this invention is directed to a method of treating a disease selected from the group consisting of: inflammatory disease, rheumatoid arthritis, multiple sclerosis, inflammatory bowel disease, graft rejection, psoriasis, fixed drug eruptions, cutaneous delayed-type hypersensitivity responses, ophthalmic inflammation (including e.g., uveitis, posterior segment intraocular inflammation, and Sjogren's syndrome), tuberculoid leprosy and cancer in a patient in need of such treatment, such method comprising administering to the patient an effective amount of at least one compound according to Formula 1, or a pharmaceutically acceptable salt, solvate or ester thereof.

Another embodiment of this invention is directed to a method of treating a disease selected from the group consisting of inflammatory disease, rheumatoid arthritis, multiple sclerosis, inflammatory bowel disease, graft rejection, psoriasis, fixed drug eruptions, cutaneous delayed-type hypersensitivity responses and tuberculoid leprosy, ophthalmic inflammation, type I diabetes, viral meningitis and cancer in a patient in need of such treatment, such method comprising administering to the patient an effective amount of (a) at least one compound according to Formula 1, or a pharmaceutically acceptable salt, solvate or ester thereof concurrently or sequentially with (b) at least one medicament selected from the group consisting of: disease modifying antirheumatic drugs; nonsteroidal antiinflammatory drugs; COX-2 selective inhibitors; COX-1 inhibitors; immunosuppressives; steroids; PDE IV inhibitors, anti-TNF-α compounds, MMP inhibitors, corticosteroids, glucocorticoids, chemokine inhibitors, CB2-selective inhibitors, biological response modifiers; anti-inflammatory agents and therapeutics.

Another embodiment of the invention discloses a method of making the inventive compounds disclosed above.

Unless otherwise stated, the following abbreviations have the stated meanings in the Examples below:
DBU=1,8-diazabicyclo[5.4.0]undec-7-ene
DBN=1,5-diazabicyclo[4.3.0]non-5-ene
EDCI=1-(3-dimethylaminopropyl)-3-ethylcarbodiimide
HATU=N-(Diethylamino)-1H-1,2,3-triazolo[4,5-b]pyridine-1-ylmethylene]-N-methylmet hanaminium Hexafluorophosphate N-oxide
HOBT=1-hydroxybenzotriazole
DCC=dicyclohexylcarbodiimide
Dibal-H=diisobutylaluminum hydride
DBPD=2-(Di-t-butylphosphino)biphenyl
DMF=Dimethylformamide
LAH=lithium aluminum hydride
$NaBH(OAc)_3$=sodium triacetoxyborohydride
$NaBH_4$=sodium borohydride
$NaBH_3CN$=sodium cyanoborohydride
LDA=lithium diisopropylamide
p-TsOH=p-toluenesulfonic acid
p-TsCl=p-toluenesulfonyl chloride
PPTS=pyridinium p-toluenesulfonate
m-CPBA=m-Chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Dissociation Constant for substrate/receptor complex
pA2=$-logEC_{50}$, as defined by J. Hey, Eur. J. Pharmacol., (1995), Vol. 294, 329-335.
Ci/mmol=Curie/mmol (a measure of specific activity)
Tr=Triphenylmethyl
Tris=Tris(hydroxymethyl)aminomethane

GENERAL SYNTHESIS

Compounds of the present invention can be prepared by a number of ways evident to one skilled in the art. Preferred methods include, but are not limited to, the general synthetic procedures described herein. One skilled in the art will recognize that one route will be optimal depending on the choice of appendage substituents. Additionally, one skilled in the art will recognize that in some cases the order of steps has to be controlled to avoid functional group incompatibilities. One skilled in the art will recognize that a more convergent route (i.e. non-linear or preassembly of certain portions of the molecule) is a more efficient method of assembly of the target compounds. One such method for the preparation of compounds of general Formula 1 where variables [$R^{17}$, $R^{18}$, $R^3$, $R^6$, $R^{10}$, $R^{11}$, $R^{12}$, $R^{20}$, Y, Z, Q, L, m, n, w and p] are as defined above, is shown in scheme 1. $Pr^2$ and $Pr^3$ are protecting groups exemplified below. Alternative methodology for introduction of an arylamine moiety is well known in the open literature.

The prepared compounds may be analyzed for their composition and purity as well as characterized by standard analytical techniques such as, for example, elemental analysis, NMR, mass spectroscopy, and IR spectroscopy.

condition). Suitable protecting groups for carboxylic acids include methyl, ethyl, isopropyl, or benzyl ester and the like. Suitable protecting groups for an amine ($Pr^2$ or $Pr^3$) include methyl, benzyl, ethoxyethyl, t-butoxycarbonyl, phthaloyl and the like. All protecting groups can be appended to and removed by literature methods known to those skilled in the art.

One skilled in the art will recognize that the synthesis of compounds of Formula 1 may require the construction of an amide bond. Methods include but are not limited to the use of a reactive carboxy derivative (e.g. acid halide, or ester at elevated temperatures) or the use of an acid with a coupling reagent (e.g. DECI, DCC) with an amine at 0° C. to 100° C.

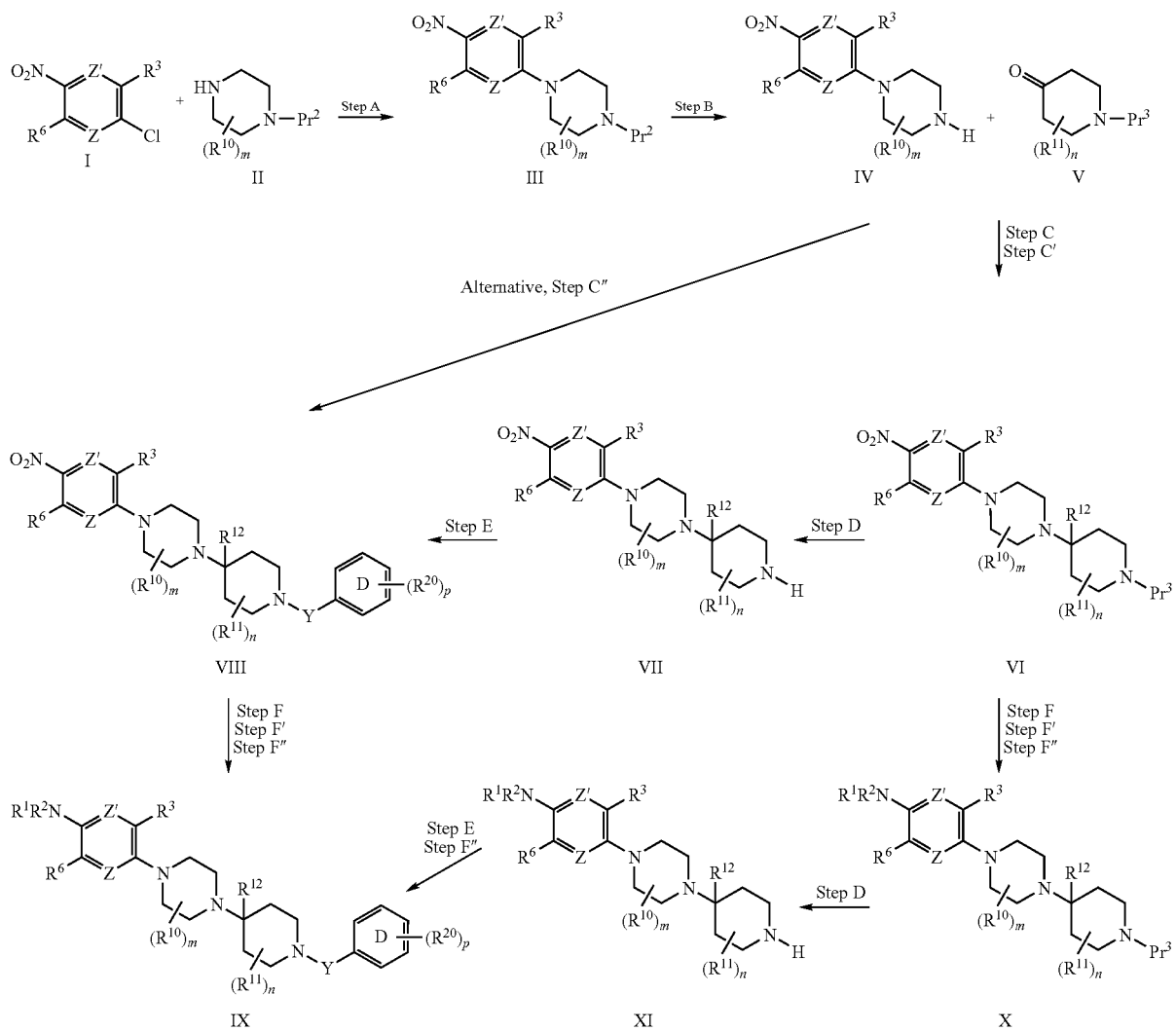

The starting material and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

One skilled in the art will recognize that the synthesis of compounds of Formula 1 may require the need for the protection of certain functional groups (i.e. derivatization for the purpose of chemical compatibility with a particular reaction Suitable solvents for the reaction are halogenated hydrocarbons, ethereal solvents, dimethylformamide and the like. The reaction may be conducted under pressure or in a sealed vessel.

One skilled in the art will recognize that the synthesis of compounds of Formula 1 may require the construction of an amine bond. One such method is but not limited to the reaction of a primary or secondary amine with a reactive carbonyl (e.g. aldehyde or ketone) under reductive amination conditions. Suitable reducing reagents of the intermediate imine are sodium borohydride, sodium triacetoxyborohydride and the like at 0° C. to 100° C. Suitable solvents for the reaction are halogenated hydrocarbons, ethereal solvents, dimethylformamide and the like. Another such method is, but not limited to, the reaction of a primary or secondary amine with a reactive alkylating agent such as an alkyl halide, benzyl halide, mesylate, tosylate or the like. Suitable solvents for the reaction are halogenated hydrocarbons, ethereal solvents, dimethylformamide and the like. The reaction may be conducted under pressure or in a sealed vessel at 0° C. to 100° C.

One skilled in the art will recognize that the synthesis of compounds of Formula 1 may require the reduction of a reducible functional group. Suitable reducing reagents include sodium borohydride, lithium aluminum hydride, diborane and the like at −20° C. to 100° C. Suitable solvents for the reaction are halogenated hydrocarbons, ethereal solvents, dimethylformamide and the like.

One skilled in the art will recognize that the synthesis of compounds of Formula 1 may require the oxidation of a functional group. Suitable oxidizing reagents include oxygen, hydrogen peroxide, m-chloroperoxybenzoic acid and the like at −20° C. to 100° C. Suitable solvents for the reaction are halogenated hydrocarbons, ethereal solvents, water and the like.

The starting materials and the intermediates of a reaction may be isolated and purified if desired using conventional techniques, including but not limited to filtration, distillation, crystallization, chromatography and the like. Such materials can be characterized using conventional means, including physical constants and spectral data.

General Description of Scheme 1

Step A

An appropriately substituted 2-halo-5-nitropyridine, 1-halo-4-nitrophenyl, or a suitable coupling analog of structure I is allowed to react with an optionally substituted or protected piperazine of structure II to afford a compound of general structure III. Preferably the reaction is carried out in a solvent such as dioxane in the presence of a base such as triethylamine, diisopropylethylamine, potassium carbonate or cesium carbonate. Optionally, catalysts such as palladium acetate may be added and the reaction heated to a temperature between 30° C. and 150° C.

Step B

If the product of step A is a protected piperazine of structure III, deprotection is required. When $Pr^2$ is an optionally substituted benzyl group, deprotection can be effected by reaction under a pressure of hydrogen gas in the presence of a suitable catalyst such as palladium. When $Pr^2$ is ethoxyethyl, deprotection can be effected by reaction with trimethylsilyl iodide. When $Pr^2$ is t-butoxycarbonyl, deprotection can be effected with a strong acid such as trifluoroacetic acid or hydrogen chloride.

Step C

A piperazine of structure IV is allowed to react with a ketone of structure V in the presence of a reducing agent to afford a compound of structure VI where $R^{12}$ is hydrogen. General conditions for the reductive amination reaction are described herein.

Step C'

A piperazine of structure IV is allowed to react with a ketone with structure V in the presence of a reducing agent to form a compound of structure VI where $R^{12}$ is a cyanide residue. Typical conditions are the reaction of an equimolar quantity of a piperazine of structure IV and a ketone of structure V in the presence of titanium isopropoxide in a halogenated solvent such as methylene chloride for 1-48 hours. Subsequent addition of a cyanide source such as dimethylaluminum cyanide affords a compound of structure VI where $R^{12}$ is a cyanide residue.

Step C"

A piperazine of structure IV is allowed to react with a ketone of structure V in the presence of a reducing reagent to afford a compound of structure VIII where $R^{12}$ is hydrogen. General conditions for the reductive amination reaction are described above.

Step D

A protected piperidine of structure VI or X is deprotected to provide the secondary amine of structure VII or XI, respectively. When $Pr^3$ is an optionally substituted benzyl group, deprotection can be effected by reaction under a pressure of hydrogen gas in the presence of a suitable catalyst such as palladium. When $Pr^2$ is ethoxyethyl, deprotection can be effected by reaction with trimethylsilyl iodide. When $Pr^2$ is t-butoxycarbonyl, deprotection can be effected with a strong acid such as trifluoroacetic acid or hydrogen chloride.

Step E

A secondary amine of structure VII or XI is either alkylated or acylated to provide compounds of structures VIII or IX, respectively. General methods for such alkylations and acylations are described above and are well known to those skilled in the art.

Step F

A nitro compound of structure VI or VIII is allowed to react with an appropriate reducing reagent such as tin(II) chloride in a solvent such as ethanol or ethyl acetate to afford the corresponding amine.

Step F'

A compound of structures VIII and VI can be functionalized by methods as alkylation, acylation, or sulfonylation to provide compounds of structures X or IX. General methods for such alkylations, acylations, and sulfonylations are described above and are well known to those skilled in the art.

Step F"

Optionally, functional group manipulation or multi-step elaboration of a compound of structure VI or XI may be done to provide additional related compounds of structures VI or XI, respectively.

PREPARATIVE EXAMPLES

The following Preparative Examples are intended to illustrate, but not to limit, the scope of the invention.

Preparative Example 1

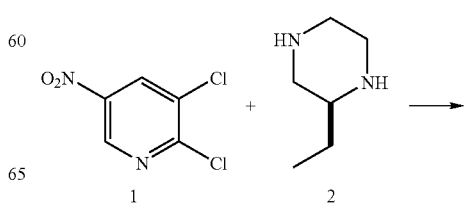

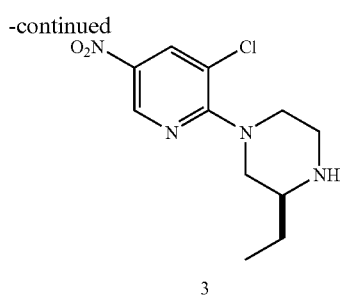

3

2,3-Dichloro-5-nitropyridine (1) was prepared from commercially available 2-hydroxy-5-nitropyridine (Aldrich) according to the procedure of Koch and Schnatterer, in *Synthesis* 1990, 499-501.

2(S)-Ethylpiperazine (2) was prepared from commercially available starting materials by analogy to the procedure of Kiely and Priebe, in *Org. Prep. Proc. Int.* 1990, 22, 761-768.

Solid 2,3-dichloro-5-nitropyridine (1, 20 g, 88 mmol) was finely ground and added portionwise over ~15 min to a stirred solution of 2(S)-ethylpiperazine (2, 11 g, 90%; 10 g, 8.8 mmol) and triethylamine (14 mL, 9.7 g, 96 mmol) in dichloromethane (400 mL). The reaction mixture was stirred at room temperature for 24 hours. The solvent was removed by rotary evaporation under reduced pressure and the resulting brown liquid was adsorbed onto ~75 g silica gel. Purification by silica gel chromatography [2.5% (7 M ammonia in methanol) in dichloromethane) gave piperazinylpiperidine 3 as a yellow-orange semi-solid (17 g, 72% yield). MS: [M+H]⁺=271.

Preparative Example 2

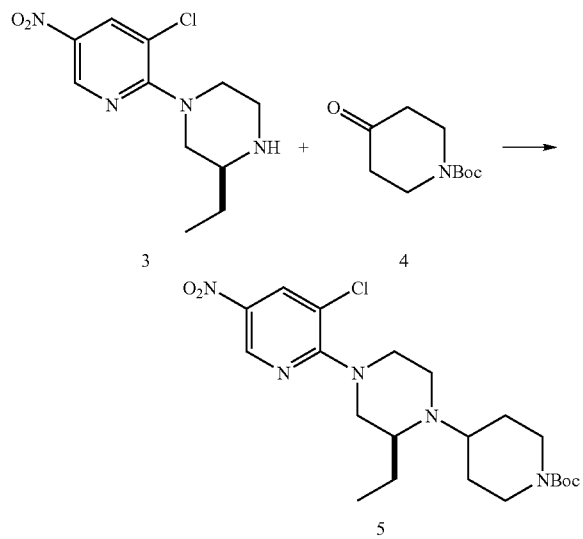

To a solution of the secondary amine 3 (12.2 g, 40.8 mmol) in dry 1,2-dichloroethane (100 mL) was added a solution of 1-(t-butoxycarbonyl)-4-piperidone (4, 12.2 g, 61.2 mmol) in dry 1,2-dichloroethane (40 mL). The orange solution was stirred at room temperature for 30 min, cooled to 0° C. with an external ice-water bath, and then heated at 70° C. for 18 hours. The reaction mixture was diluted with dichloromethane (100 mL) and washed successively with saturated aqueous NaHCO₃ (2×100 mL), water (1×100 mL), and brine (1×100 mL). The organic layer was dried over anhydrous magnesium sulfate, filtered, and concentrated under reduced pressure to yield a brown oil (30 g). Purification of the oil by silica gel chromatography (1.5% (7 M ammonia in methanol) in dichloromethane) gave 5 (16.2 g, 82% yield) as a yellow-brown solid. MS: [M+H]⁺=454.

Preparative Example 3

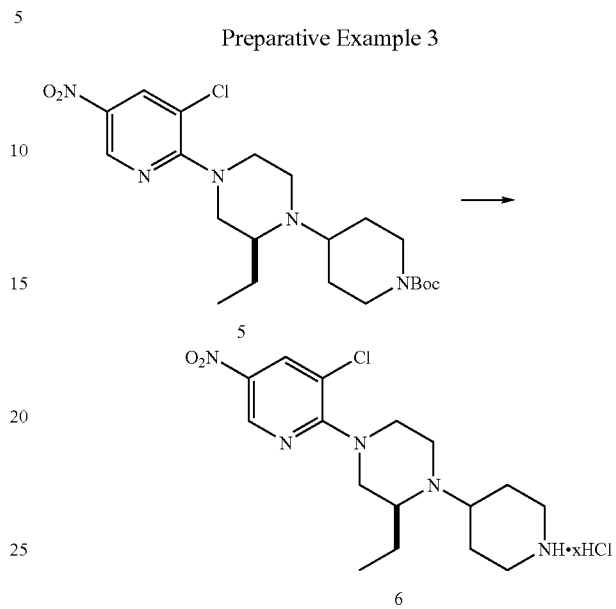

A solution of 5 (5.5 g, 12 mmol) and hydrogen chloride (15 mL, 4 M in dioxane; 61 mmol) in methanol (200 mL) was stirred at room temperature for 15 hours. The solvent was evaporated under reduced pressure to give 6 as a pale yellow solid (4.90 g, 95% yield, based on .2HCl salt). MS: [M+H]⁺=354.

Preparative Example 4

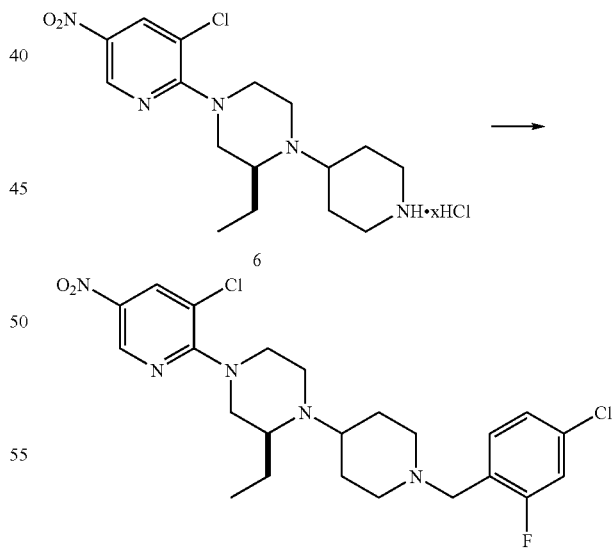

To a solution of 6 (315 mg, 0.74 mmol based on .2HCl salt) and triethylamine (493 μL, 360 mg, 3.6 mmol) in dry DMF (2 mL) was added a solution of 2-fluoro-4-chlorobenzyl bromide (168 μL, 219 mg, 0.98 mmol) in DMF (0.5 mL). The reaction mixture was stirred at room temperature for 18 hours, after which it was diluted with ethyl acetate (50 mL)

and washed with water (10 mL). The aqueous phase was extracted with ethyl acetate (2×10 mL). The combined organic phases were washed with brine (30 mL), dried over anhydrous magnesium sulfate, filtered and concentrated under reduced pressure to yield a light brown oil. Purification by silica gel chromatography (1→2% (7 M ammonia in methanol) in dichloromethane) gave 7 as a yellow oil (309 mg, 84% yield). MS: $[M+H]^+=496$.

Preparative Example 5

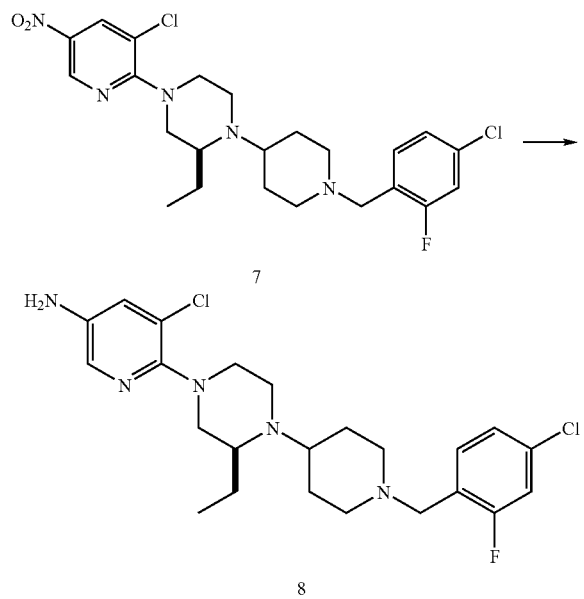

Solid, anhydrous tin(II) chloride (14 g, 74 mmol) was added portion wise to a solution of 7 (7.32 g, 15 mmol) in absolute ethanol (140 mL). The suspension was stirred at room temperature for 2 hours. Solvent was removed under reduced pressure to afford an orange-brown residue that was then partitioned between 0.4 M aqueous sodium hydroxide solution (500 mL) and dichloromethane (500 mL). The aqueous layer was extracted further with dichloromethane (4×100 mL). The combined extracts were washed with brine (~250 mL), dried over anhydrous magnesium sulfate, filtered, and concentrated under reduced pressure to give an orange solid. Purification of the solid by silica gel chromatography (5% (7 M ammonia in methanol) in dichloromethane) gave 8 as an orange-brown solid (4.1 g, 60% yield). MS: $[M+H]^+=466$.

Preparative Example 6

Preparation of Table 1 Compound No. 7

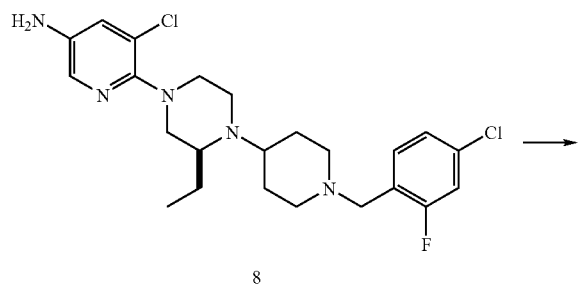

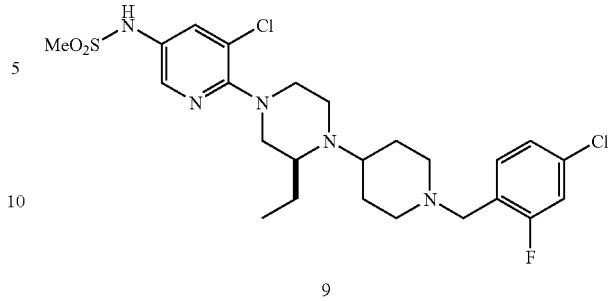

To an ice-cold solution of 8 (47 mg) in dichloromethane (500 μL) was added a solution of methanesulfonyl chloride (446 μL, 0.68 M in 1,2-dichloroethane), dropwise over 5 min. The reaction mixture was stirred at 0° C. for 1 hour and at room temperature for 18 hours. The reaction mixture was diluted with ethyl acetate (50 mL) and was washed with 1 N aqueous sodium hydroxide (25 mL), water (25 mL), and brine (25 mL). The organic layer was dried over anhydrous magnesium sulfate, filtered, and concentrated under reduced pressure. Purification of the resulting brown gum by preparative TLC (10% (7 M ammonia in methanol) in dichloromethane) gave 9 as a white solid (38 mg, 70% yield). MS: $[M+H]^+=544$.

Preparative Example 7

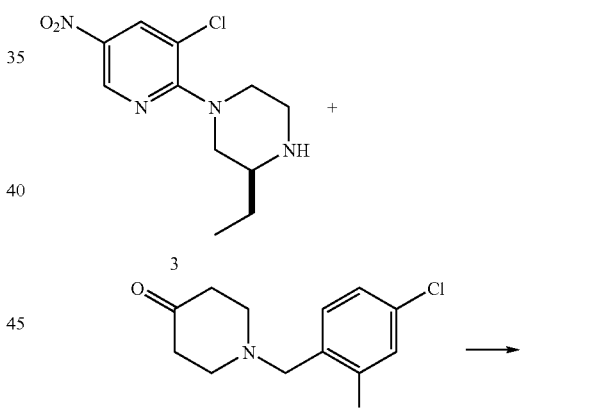

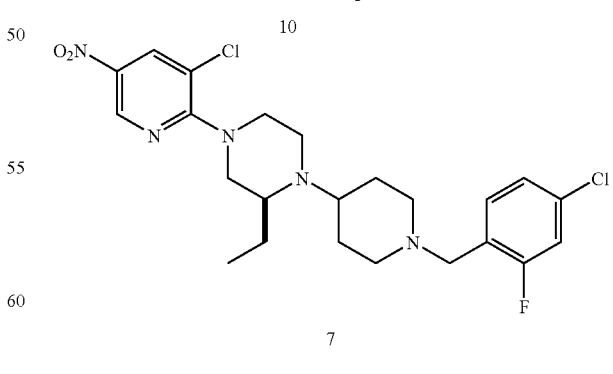

A solution of secondary amine 3 (5.04 g, 18.6 mmol) and ketone 10 (6.75 g, 27.9 mmol) in 1,2-dichloroethane (50 mL) was stirred at room temperature for 8 hours. The solution was cooled to 0° C. and sodium triacetoxyborohydride (7.89 g, 37.2 mmol) was added portion wise. The reaction mixture was stirred at 0° C. for 30 min, room temperature for 2 hours, and 70° C. for 15 hours. The mixture was allowed to cool to room temperature, and was then partitioned between dichloromethane (500 mL) and water (400 mL). The organic layer was removed, and the pH of the aqueous layer was adjusted to neutrality with 0.4 M aqueous sodium hydroxide. The neutralized aqueous solution was extracted with dichloromethane (4×250 mL). The combined organic solutions were washed with brine (500 mL), dried over anhydrous magnesium sulfate, filtered, and concentrated under reduced pressure to yield a red-brown oil. Purification by silica gel chromatography (3:1 ethyl acetate-dichloromethane, then 5% (7 M ammonia in methanol) in dichloromethane) gave 7 as a yellow-orange syrup (7.32 g, 78% yield). MS: $[M+H]^+=496$.

Preparative Example 8

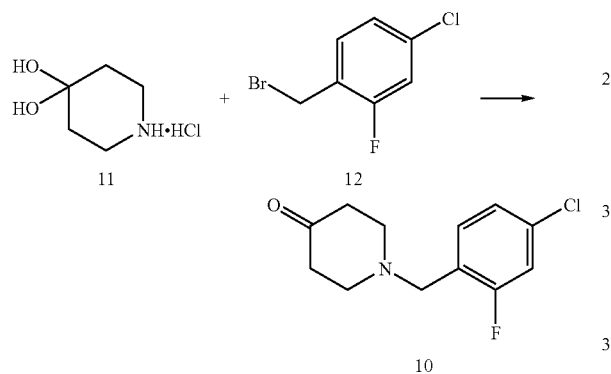

A mixture of piperidine hydrate hydrochloride (11, 13.7 g, 90 mmol) and potassium carbonate (31 g, 224 mmol) in DMF (100 mL) was stirred at room temperature for 30 min. Neat 2-fluoro-4-chlorobenzyl bromide (12, 20.0 g, 90 mmol) was added, and the reaction mixture was stirred for 2 days. Solids were then removed by filtration through a sintered glass funnel. The filtrate was partitioned between diethyl ether (100 mL) and water (100 mL). The aqueous layer was extracted with diethyl ether (50 mL). The combined organic phases were washed with water (50 mL), 10% aqueous sodium thiosulfate (50 mL), and brine (50 mL), then dried over anhydrous magnesium sulfate, filtered, and concentrated under reduced to afford 10 (20.9 g, 97% yield). MS: $[M+H]^+=242$.

Preparative Example 9

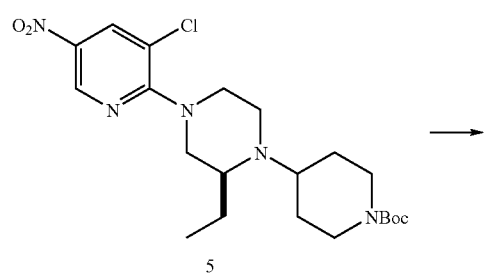

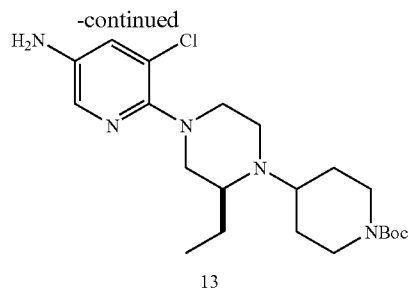

The nitro compound 5 (4.0 g, 8.8 mmol) was dissolved in absolute ethanol (60 mL). Anhydrous tin(II) chloride (8.4 g, 44 mmol) was added in small portions, and the reaction mixture was stirred at room temperature for 2 days. The reaction mixture was poured into ice-cold 10% aqueous sodium hydroxide solution (100 mL) and was then stirred for 30 min. The slurry was extracted with ethyl acetate (2×150 mL). The combined organic phases were washed successively with water (100 mL) and brine (100 mL), dried over anhydrous magnesium sulfate, filtered, and concentrated under reduced pressure to yield a light yellow solid. Purification by silica gel chromatography (5% (7 M ammonia in methanol) in dichloromethane) gave amine 13 as an off-white solid (1.65 g, 50% yield).

Preparative Example 10

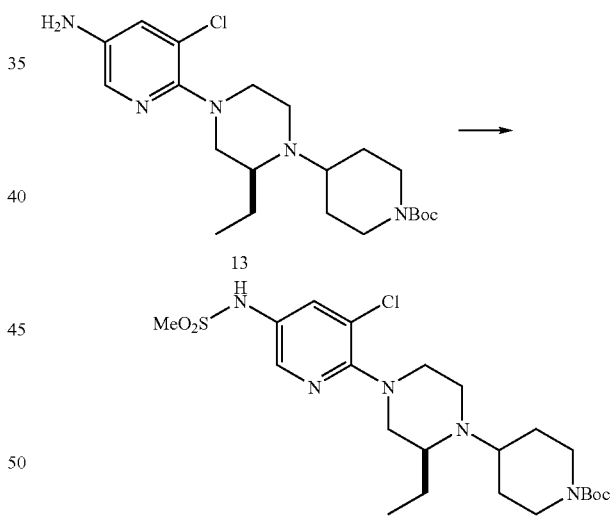

A solution of amine 13 (1.8 g, 4.3 mmol) and triethylamine (1 mL, 0.73 g, 7.2 mmol) in dry dichloromethane (50 mL) was cooled to 0° C. and methanesulfonyl chloride (0.7 mL, 1.0 g, 8.9 mmol) was added. The reaction mixture was stirred and allowed to warm to room temperature over 1 hour. The reaction mixture was diluted with dichloromethane (50 mL) and was washed successively with 1 N sodium bicarbonate solution (50 mL) and brine (50 mL). The organic layer was dried over anhydrous magnesium sulfate, filtered, and concentrated to yield 2.4 g of a brown solid.

The brown solid was dissolved in methanol (50 mL) and a solution of lithium hydroxide monohydrate (906 mg, 22 mmol) in water (20 mL) was added. The reaction solution was stirred overnight at room temperature. The volatile solvent was evaporated under reduced pressure to yield an off-white suspension. The suspension was extracted with ethyl acetate (2×100 mL) and the extracts were washed successively with 1 N aqueous sodium bicarbonate solution (50 mL) and brine (50 mL). The organic layer was dried over anhydrous magnesium sulfate, filtered, and concentrated under reduced pressure to yield a pale yellow solid, purification of which by silica gel chromatography (5% (7 M ammonia in methanol) in dichloromethane) gave 14 as a yellow solid (2.05 g, 96% yield). MS: $[M+H]^+=501$.

Preparative Example 11

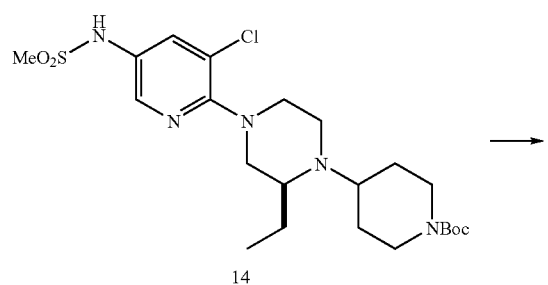

14

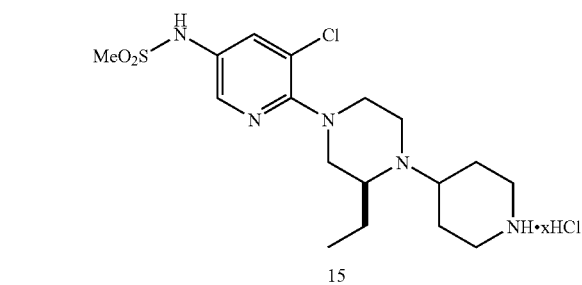

15

Carbamate 14 (2.3 g, 4.6 mmol) was dissolved in methanol (45 mL) and hydrogen chloride (10 mL, 4 N in dioxane, 40 mmol) was added. The solution was stirred for 3 hours at room temperature. The solvent was evaporated under reduced pressure to give amine salt 15 as a yellow solid (2.45 g). MS: $[M+H]^+=402$.

Preparative Example 12

Preparation of Table 1 Compound No. 10

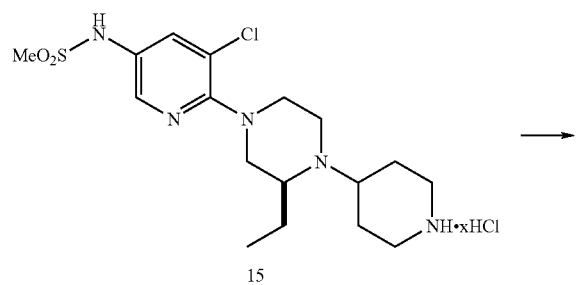

15

-continued

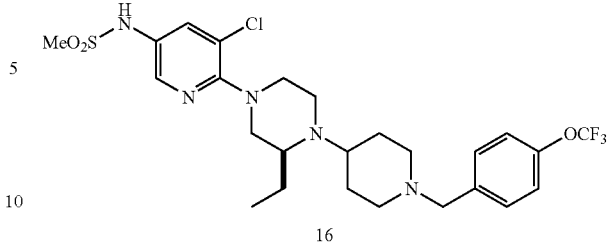

16

Amine salt 15 (102 mg, 0.200 mmol, based on .3HCl salt), diisopropylethylamine (1 mL, 740 mg, 5.7 mmol), and 4-(trifluoromethoxy)benzaldehyde (57 μL, 76 mg, 0.400 mmol) were dissolved in dichloromethane (5 mL) and the resulting solution was stirred at room temperature for 30 min. The solution was cooled to 0° C., and solid sodium triacetoxyborohydride (85 mg, 0.400 mmol) was added. The reaction was stirred at room temperature overnight. The reaction mixture was diluted with dichloromethane (50 mL) and washed with water (25 mL) and brine (25 mL). The organic layer was dried over anhydrous magnesium sulfate, filtered, and concentrated to give a brown oil. Purification of the crude product by silica gel chromatography (8% (7 M ammonia in methanol) in dichloromethane) gave 16 as a beige solid (89 mg, 77% yield). MS: $[M+H]^+=576$.

Preparative Example 13

Preparation of Table 1 Compound No. 53

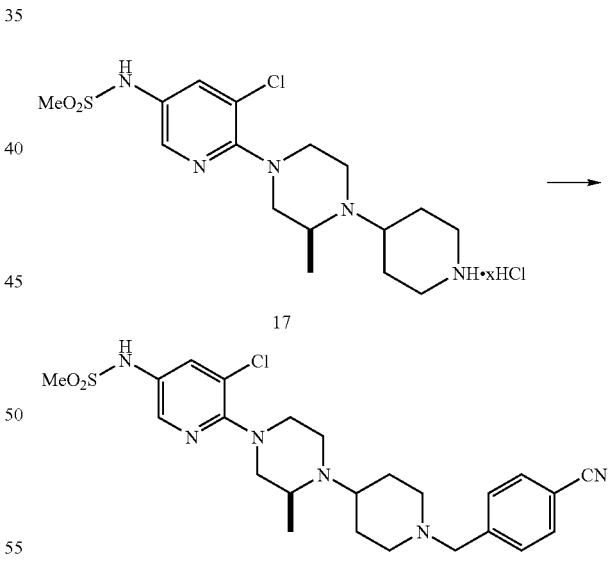

17

18

Amine salt 17 (92 mg, 0.200 mmol, based on .2HCl salt), diisopropylethylamine (1 mL, 740 mg, 5.7 mmol), and 4-cyanobenzyl bromide (78 mg, 0.40 mmol) were dissolved in N,N-dimethylacetamide (2 mL) and stirred at room temperature for 18 hours. The reaction mixture was diluted with ethyl acetate (50 mL) and washed with water (2×25 mL) and brine (25 mL). The organic layer was dried over anhydrous magnesium sulfate, filtered, and concentrated to give an orange-brown solid. Purification by silica gel chromatography (5% (7

M ammonia in methanol) in dichloromethane) gave 18 (88 mg, 88% yield). MS: [M+H]⁺=503.

Preparative Example 14

Preparation of Table 1 Compound No. 63

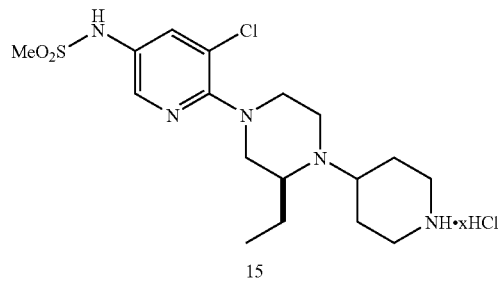

15

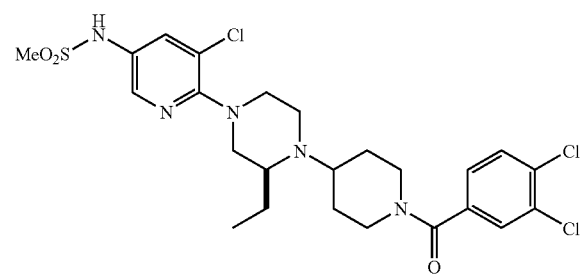

19

Amine salt 15 (50 mg, 98 mmol based on .3HCl salt) and triethylamine (57 µL, 42 mg, 410 mmol) were dissolved in dichloromethane (300 µL) and 3,4-dichlorobenzoyl chloride (23 mg, 110 mmol) was added. The reaction was allowed to proceed for 20 hours at room temperature. The solvent was evaporated under reduced pressure to afford a brown residue. Subsequent purification of the residue by preparative TLC (10% (7 M ammonia in methanol) in dichloromethane) gave amide 19 (28 mg, 57% yield). MS: [M+H]⁺=503.

Preparative Example 15

Preparation of Table 1 Compound No. 40

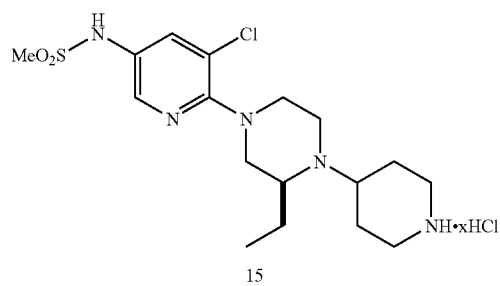

15

-continued

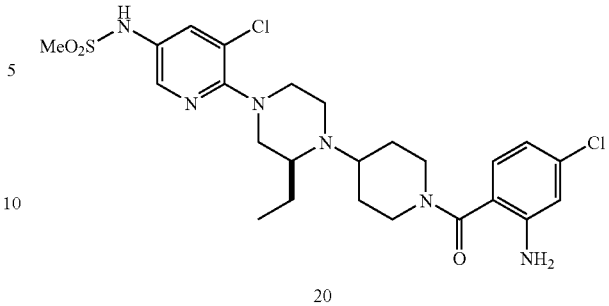

20

Amine salt 15 (50 mg, 98 mmol based on .3HCl salt) was suspended in DMF (1 mL) and diisopropylethylamine (90 µL, 68 mg, 0.50 mmol), 2-amino-4-chlorobenzoic acid (23 mg, 0.135 mmol), DECI (26 mg, 0.135 mmol), and HOBT (18 mg, 0.135 mmol) were added sequentially. The stirred reaction mixture was heated with stirring at 70° C. The reaction mixture was partitioned in ethyl acetate (40 mL) and water (10 mL). The aqueous layer was extracted further with ethyl acetate (2×30 mL) and the combined organic layers were then washed with brine (30 mL), dried over anhydrous magnesium sulfate, and concentrated under reduced pressure to give a brown oil. Purification by preparative TLC (10% (7 M ammonia in methanol) in dichloromethane) afforded the amide 20 (35 mg, 64% yield). MS: [M+H]⁺=555.

Preparative Example 16

Preparation of Table 1 Compound No. 57

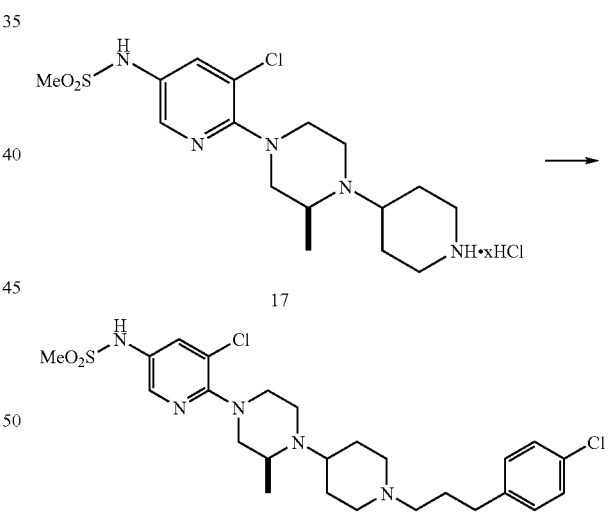

Amine salt 17 (39 mg, 0.078 mmol, based on .3HCl salt), cesium carbonate (65 mg, 0.200 mmol), and 1-chloro-3-(4-chlorophenyl)propane (18 mg, 0.094 mmol) were dissolved in N,N-dimethylacetamide (1 mL) and stirred at 90° C. for 18 hours. The reaction mixture was cooled to room temperature, diluted with ethyl acetate (50 mL) and washed with water (2×25 mL) and brine (25 mL). The organic layer was dried over anhydrous magnesium sulfate, filtered, and concentrated to give an orange-brown solid. Purification by HPLC (acetonitrile/water gradient) gave alkylated amine 21 (20 mg, 57% yield). MS: [M+H]⁺=540.

Preparative Example 17

Preparation of Table 1 Compound No. 2

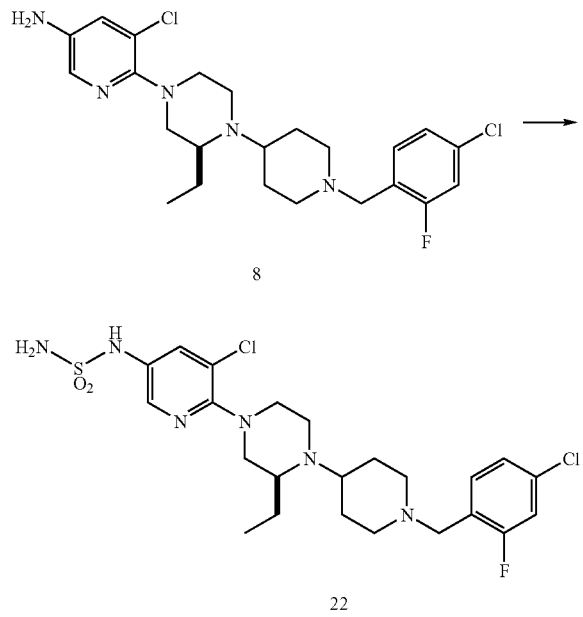

To a solution of ice-cold chlorosulfonyl isocyanate (31 µL, 50 mg, 0.35 mmol) in dry dichloromethane (0.900 mL) was added dropwise a solution of t-butanol (34 µL, 26 mg, 0.35 mmol) in dichloromethane (0.350 mL). The clear, colorless solution was stirred at 0° C. for 30 min, then was added dropwise by syringe to an ice-cold solution of amine 8 (110 mg, 0.236 mmol) and triethylamine (49 µL, 36 mg, 0.35 mmol) in dichloromethane (0.790 mL). The reaction mixture was stirred at 0° C. for 10 min and at room temperature for a further 20 hours. The solvent was then evaporated under reduced pressure to afford an off-white solid.

The solid was suspended in methanol (2 mL) and hydrogen chloride solution (0.5 mL, 4 M in dioxane, 2 mmol) was added. The clear solution was stirred at room temperature for 15 hours. The solvent was evaporated and the residue was partitioned between ethyl acetate (30 mL) and water (20 mL). The aqueous layer was neutralized with 1 N aqueous sodium hydroxide and extracted with ethyl acetate (2×50 mL). The combined organic phases were washed with brine (~30 mL), dried over anhydrous magnesium sulfate, filtered, and evaporated to give an off-white solid. Purification by preparative TLC (10% (7 M ammonia in methanol) in dichloromethane) gave sulfamide 22 as an off-white solid (54 mg, 42% yield). MS: [M+H]$^+$=545.

Preparative Example 18

Preparation of Table 1 Compound No. 73

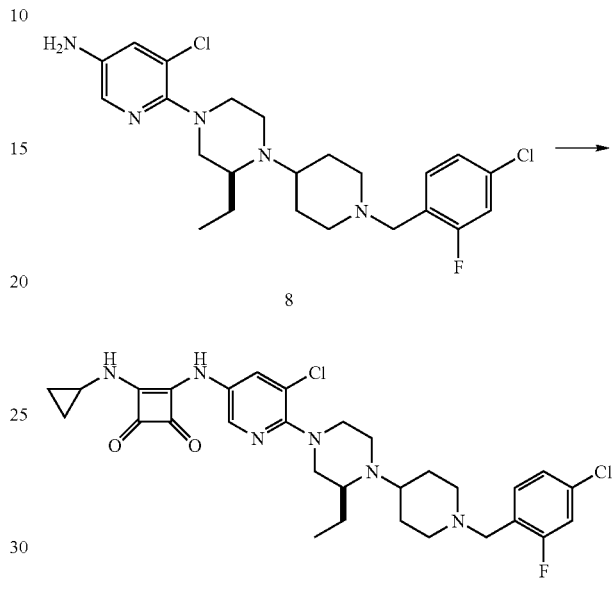

3,4-Diethoxycyclobutenedione (93 µL, 107 mg, 0.628 mmol, Aldrich) was added to a solution of amine 8 (266 mg, 0.571 mmol) in absolute ethanol (2.0 mL) and the reaction mixture was stirred at room temperature for 2 days.

Cyclopropylamine (60 µL, 49 mg, 0.856 mmol) was added to the reaction mixture described above in step F', and the reaction was allowed to proceed for 14 hours at room temperature. The solvent was allowed to evaporate under a stream of nitrogen to afford a brown residue. Purification of the residue by reverse-phase HPLC (0-100% acetonitrile-water gradient) gave the diaminocyclobutenedione 23 (203 mg, 59% yield). MS: [M+H]$^+$=601.

Preparative Example 19

Preparation of Table 1 Compound No. 235

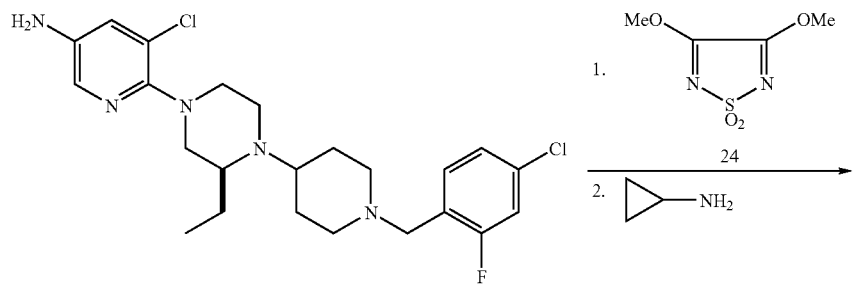

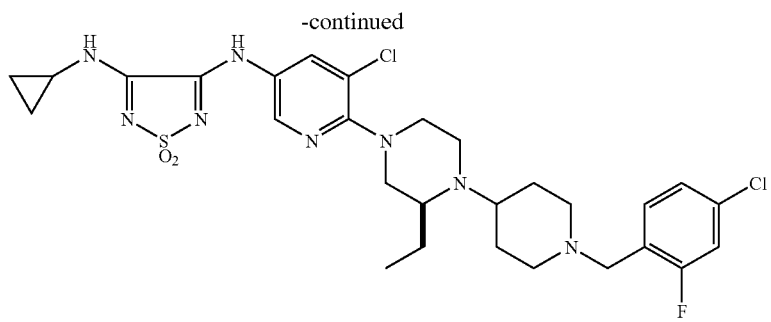

25

3,4-Dimethoxy-1,2,5-thiadiazole-1,1-dioxide (24) was prepared according to the method of Carmack et al., in *J. Org. Chem.* 1975, 40, 2743.

An admixture of amine 8 (32 mg, 0.067 mmol) and 24 (36 mg, 0.200 mmol) was dissolved in methanol (150 µL) and DMF (20 µL) was added. The reaction mixture was stirred at room temperature for 18 hours.

Cyclopropylamine (23 µL, 19 mg, 0.335 mmol) was added to the reaction mixture described above in step F', and the reaction was allowed to proceed for 2 days at room temperature. The solvent was allowed to evaporate under a stream of nitrogen to afford a brown residue. Purification of the residue by reverse-phase HPLC (0→100% acetonitrile-water gradient) gave 25 (18 mg, 43% yield). MS: [M+H]$^+$=637.

Preparative Example 20

Preparation of Table 1 Compound No. 177

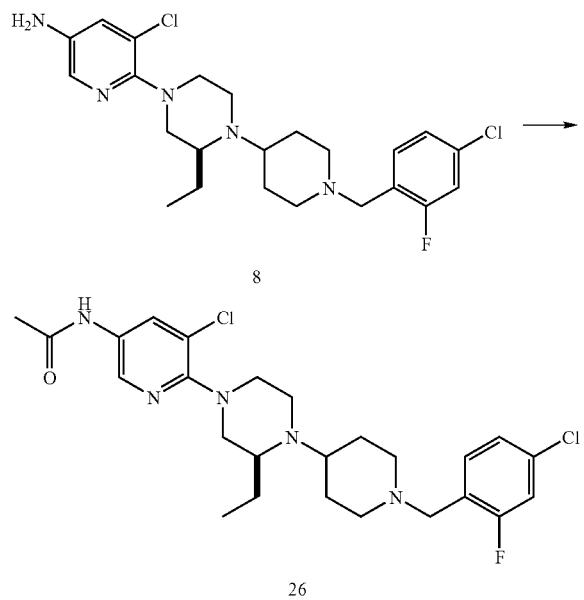

A solution of amine 8 (47 mg, 0.1 mmol) and triethylamine (15 µL, 11 mg, 0.1 mmol) in dry dichloromethane (3 mL) was cooled to 0° C. and acetyl chloride (7 µL, 8 mg, 0.1 mmol) was added. The reaction mixture was stirred at 0° C. for 1 hour and at room temperature overnight. The reaction mixture was diluted with dichloromethane (25 mL) and was washed successively with 1 N sodium bicarbonate solution (10 mL) and brine (10 mL). The organic layer was dried over anhydrous magnesium sulfate, filtered, and concentrated under reduced pressure. Purification of the crude product by silica gel chromatography (5% (7 M ammonia in methanol) in dichloromethane)-gave amide 26 as a white solid (40 mg, 78% yield). MS: [M+H]$^+$=508.

Preparative Example 21

Preparation of Table 1 Compound No. 178

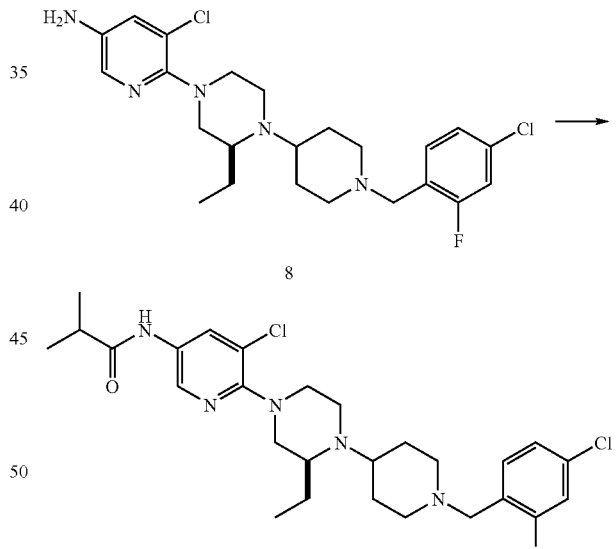

A solution of amine 8 (47 mg, 0.1 mmol) and triethylamine (15 µL, 11 mg, 0.1 mmol) in dry dichloromethane (3 mL) was cooled to 0° C. and isobutyryl chloride (11 µL, 11 mg, 0.1 mmol) was added. The reaction mixture was stirred at 0° C. for 1 hour and at room temperature overnight. The reaction mixture was diluted with dichloromethane (25 mL) and was washed successively with 1 N sodium bicarbonate solution (10 mL) and brine (10 mL). The organic layer was dried over anhydrous magnesium sulfate, filtered, and concentrated under reduced pressure. Purification of the crude product by silica gel chromatography (5% (7 M ammonia in methanol) in dichloromethane) gave amide 27 as a white solid (41 mg, 77% yield). MS: [M+H]$^+$=536.

Preparative Example 22

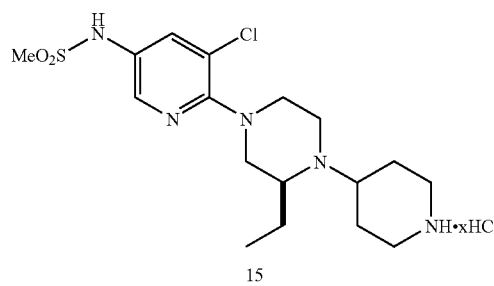

15

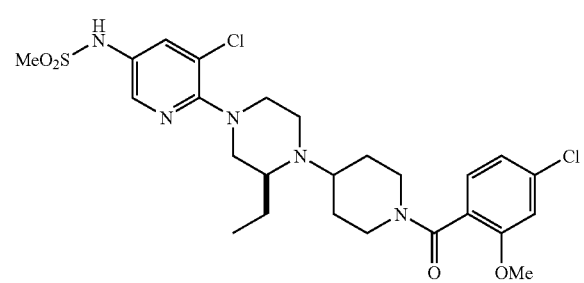

28

Amine salt 15 (204 mg, 400 mmol based on .3HCl salt) was suspended in DMF (4 mL) and diisopropylethylamine (0.5 mL, 372 mg, 2.9 mmol), 2-methoxy-4-chlorobenzoic acid (112 mg, 0.600 mmol), DECI (115 mg, 0.599 mmol), and HOBT (81 mg, 0.600 mmol) were added successively. The reaction mixture was heated with stirring at 70° C. The reaction mixture was partitioned in ethyl acetate (100 mL) and water (50 mL). The aqueous layer was extracted further with ethyl acetate (2×25 mL), and the combined organic layers were then washed with brine (50 mL), dried over anhydrous magnesium sulfate, and concentrated under reduced pressure to give a brown oil. Purification by preparative TLC (5% (7 M ammonia in methanol) in dichloromethane) afforded amide 28 (180 mg, 64% yield). MS: [M+H]$^+$=570.

Preparative Example 23

Preparation of Table 1 Compound No. 1

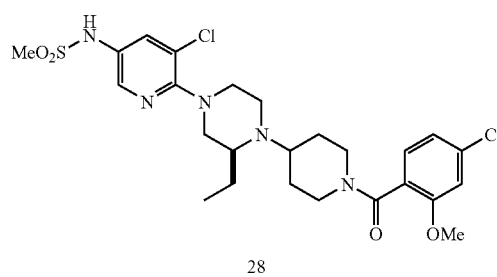

28

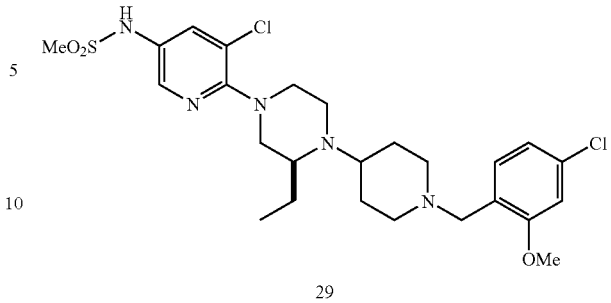

29

Borane-methyl sulfide complex (320 μL, 10 M in THF, 3.2 mmol) was added to a solution of amide 28 (180 mg, 0.32 mmol) in THF (4 mL). The solution was stirred at reflux for 4 hours, cooled to room temperature, and diluted with ethyl acetate (50 mL). The organic solution was washed sequentially with 1 N aqueous hydrochloric acid, 1 N aqueous sodium hydroxide, water, and brine. The organic layer was dried over anhydrous magnesium sulfate, filtered, and concentrated under reduced pressure. Purification by silica gel chromatography (5% (7 M ammonia in methanol) in dichloromethane) gave substituted benzylamine 29 (130 mg, 74% yield). MS: [M+H]$^+$=556.

Preparative Example 24

Preparation of Table 1 Compound No. 6

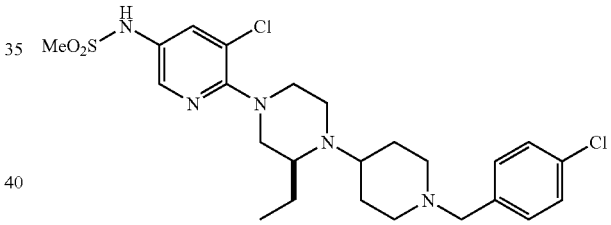

Compound 30 was prepared by the same method shown for Preparative Examples 4 through 6, using 4-chlorobenzyl chloride in place of 2-fluoro-4-chlorobenzyl bromide. MS: [M+H]$^+$=526.

Preparative Example 25

Preparation of Table 1 Compound No. 5

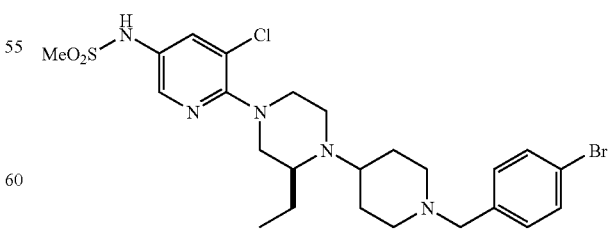

Compound 31 was prepared by the same method shown for Preparative Example 12, using 4-bromobenzaldehyde in place of 4-(trifluoromethoxy)benzaldehyde. MS: [M+H]$^+$=570.

Preparative Example 26

Preparation of Methyl 2-chloro-2-(4-chlorophenyl)acetate (32)

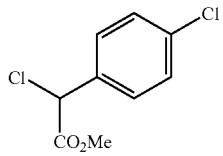

32

Neat thionyl chloride (66 mL, 108 g, 0.911 mol) was added to solid p-chloromandelic acid (20 g, 0.107 mol, Aldrich) and the mixture was stirred at 70° C. for 19 hours. The majority of the volatile components was removed by evaporation under reduced pressure, and residual thionyl chloride was removed by co-evaporation with toluene (2×200 mL). The remaining pale yellow liquid was cooled to 0° C. and methanol (100 mL) was added slowly. The resulting solution was stirred at room temperature for 8 hours. The solvent was evaporated under reduced pressure to give a pale yellow crude product. Purification of the crude product by silica gel chromatography (19:1 hexanes-ether) gave ester 32 (15.5 g, 67% yield).

Preparative Example 27

Preparation of Table 1 Compound No. 39

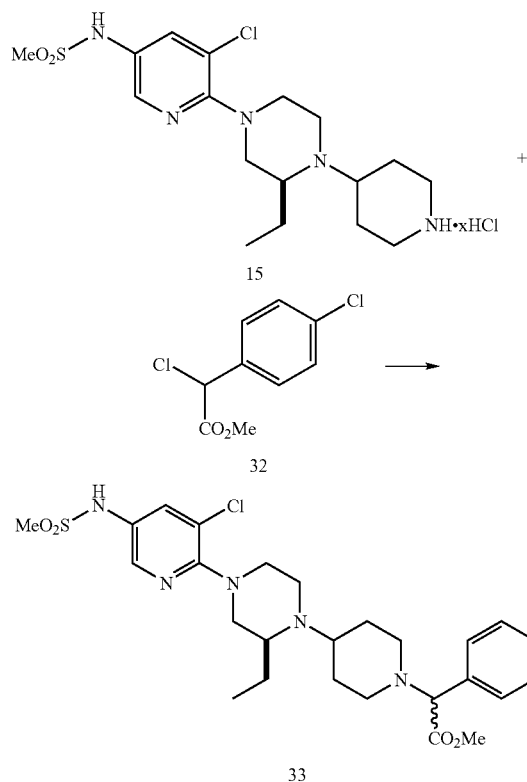

Compound 33 was prepared by the same method shown for Preparative Example 13, using Compound 32 in place of 4-cyanobenzyl bromide. Optionally, the stereoisomers of 33 may be separated by HPLC. MS: [M+H]$^+$=584.

Preparative Example 28

Preparation of Table 1 Compound No. 11

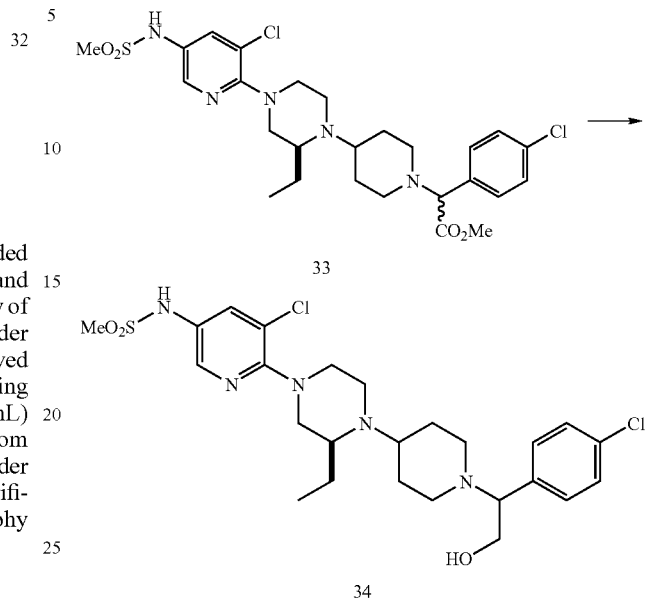

Lithium borohydride (308 μL, 2.0 M in THF; 0.616 mmol) was added to a solution of ester 33 (180 mg) in THF (1.5 mL) at 0° C. The reaction mixture was stirred at 0° C. for 30 min and at room temperature for 24 hours. An additional portion of lithium borohydride (600 μL, 2.0 M in THF; 1.2 mmol) and THF (2 mL) was added and the reaction was allowed to proceed for a further 14 hours. The reaction mixture was diluted with ethyl acetate (50 mL) and water (~10 mL) was cautiously added. 1 N aqueous hydrochloric acid was added dropwise until effervescence was no longer observed. The aqueous layer was adjusted to pH 7 with 0.5 M aqueous sodium hydroxide and then extracted further with ethyl acetate (3×25 mL). The combined organic layers were washed with brine (~30 mL), dried over anhydrous magnesium sulfate, filtered, and concentrated under reduced pressure. The crude product was purified by silica gel chromatography (10% (7 M ammonia in methanol) in dichloromethane) to give alcohol 34 as a white solid (140 mg, 82% yield). Optionally, the stereoisomers of 34 may be separated by HPLC. MS: [M+H]$^+$=556.

Preparative Example 29

Preparation of Amine Salt 35

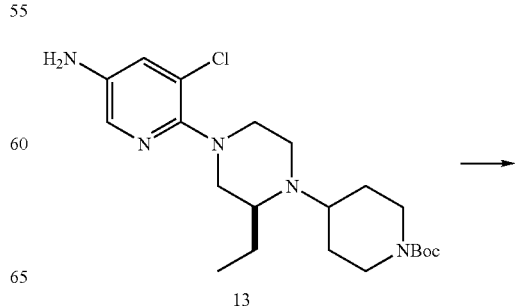

13

-continued

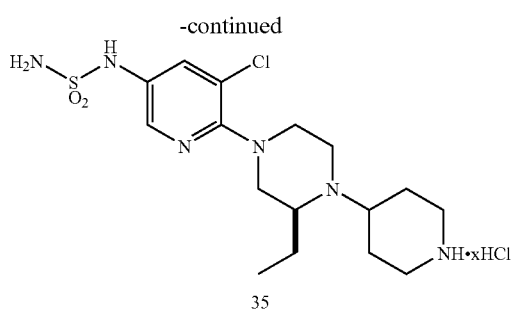

35

To a solution of ice-cold chlorosulfonyl isocyanate (92 µL, 150 mg, 1.06 mmol) in dry dichloromethane (2.6 mL) was added dropwise a solution of t-butanol (101 µL, 79 mg, 1.06 mmol) in dichloromethane (1 mL). The clear, colorless solution was stirred at 0° C. for 30 min, then was added dropwise by syringe over 10 min to an ice-cold solution of amine 13 (225 mg, 0.53 mmol) and triethylamine (147 µL, 107 mg, 1.06 mmol) in dichloromethane (1.8 mL). The reaction mixture was stirred at 0° C. for 30 min and at room temperature for a further 18 hours. The solvent was then evaporated under reduced pressure to afford a brown solid.

The solid was suspended in methanol (3 mL) and hydrogen chloride solution (1.5 mL, 4 M in dioxane, 6 mmol) was added. The solution was stirred at room temperature for 18 hours. The solvent was evaporated to give 35 (205 mg, 75% yield), which was used without further purification. MS: $[M+H]^+=403$.

Preparative Example 30

Preparation of Table 1 Compound No. 3

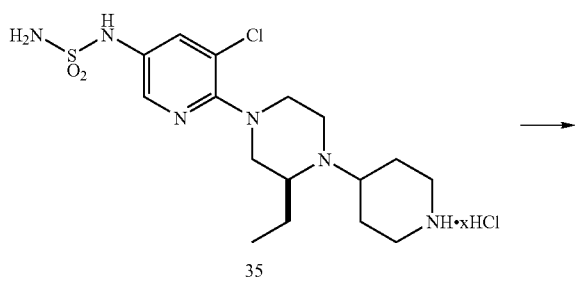

35

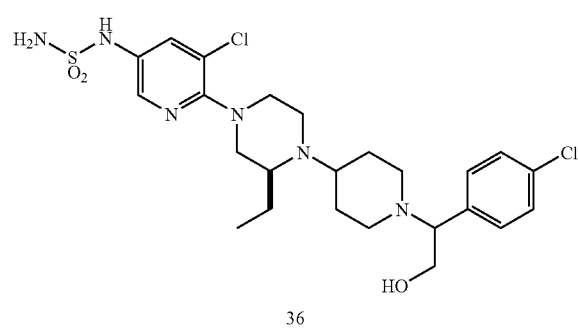

36

Amine salt 35 was converted to 36 according to methods outlined for Preparative Examples 27 and 28. MS: $[M+H]^+=557$ Preparative Example 31

Preparation of Table 1 Compound No. 37

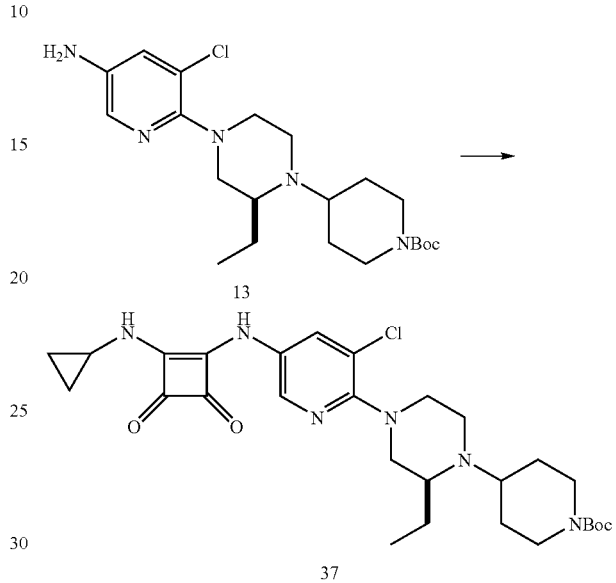

3,4-Diethoxycyclobutenedione (340 µL, 390 mg, 2.30 mmol, Aldrich) was added to a solution of amine 13 (750 mg, 1.77 mmol) in absolute ethanol (12 mL) and the reaction mixture was stirred at room temperature for 2 days.

Step F'''.

Cyclopropylamine (240 µL, 200 mg, 3.5 mmol) was added to the reaction mixture, which was stirred for 14 hours at room temperature. The solvent was removed under reduced pressure afford a brown residue. Purification of the residue by silica gel chromatography (5% (7 M ammonia in methanol) in dichloromethane) gave 37 (541 mg, 55% yield). MS: $[M+H]^+=559$.

Preparative Example 32

Preparation of Table 1 Compound No. 70

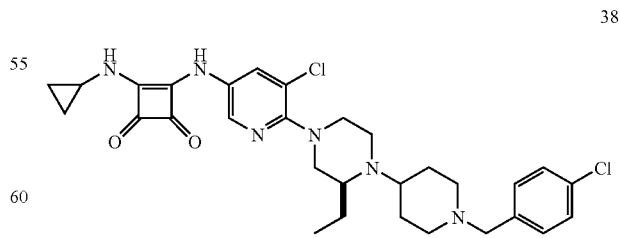

38

Compound 38 was prepared from carbamate 37 by sequential application of methods illustrated for Preparative Examples 11 and 13, substituting 4-chlorobenzyl chloride for 4-cyanobenzyl bromide. MS: $[M+H]^+=583$.

Preparative Example 33

Preparation of Table 1 Compound No. 77

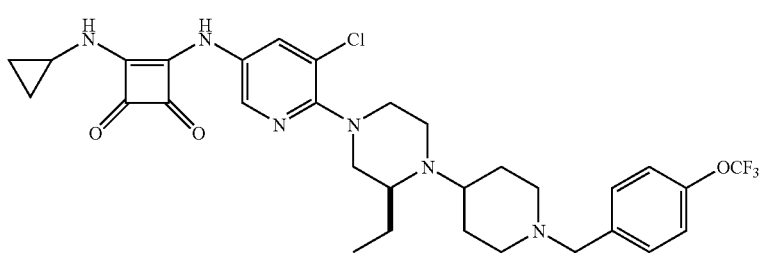

39

Compound 39 was prepared from carbamate 37 by sequential application of methods illustrated for Preparative Examples 11 and 13, substituting 4-(trifluoromethoxy)benzyl bromide for 4-cyanobenzyl bromide.
MS: [M+H]$^+$=633.

Preparative Example 34

Preparation of Table 1 Compound No. 74

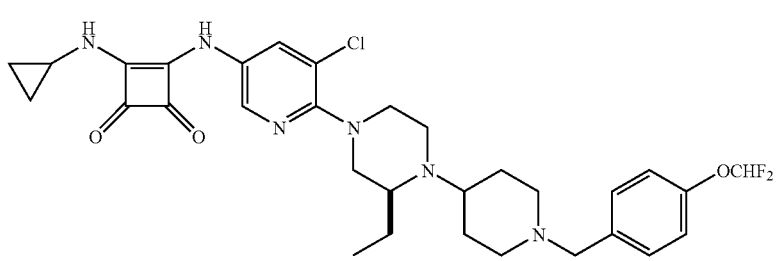

40

Compound 40 was prepared from carbamate 37 by sequential application of methods illustrated for Preparative Examples 11 and 13, substituting 4-(difluoromethoxy)benzyl bromide for 4-cyanobenzyl bromide. MS: [M+H]$^+$=615.

Preparative Example 35

Preparation of Table 1 Compound No. 42

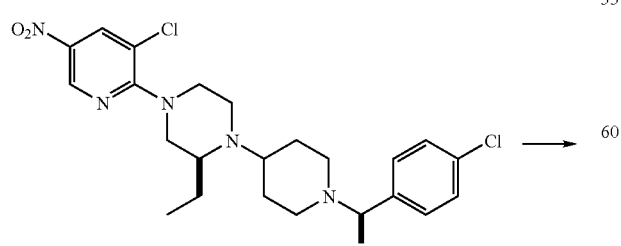

41

-continued

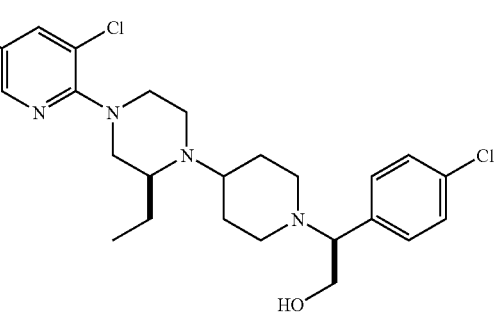

42

Ester 41 was prepared from amine salt 6 according to the method for Preparative Example 4, substituting Compound 32 for 2-fluoro-4-chlorobenzyl bromide. MS: [M+H]$^+$=536.

Lithium borohydride (2 mL, 2.0 M in THF, 4 mmol) was added to a solution of ester 41 (205 mg, 0.382 mmol) in dry THF (1 mL) at 0° C. The reaction was allowed to proceed for 0° C. for 30 min and at room temperature for 24 hours. Water (20 mL) and ethyl acetate (20 mL) were added and the mixture was stirred for 30 min. The aqueous layer was extracted with ethyl acetate (3×20 mL). The combined organic phases were washed with brine (50 mL), dried over anhydrous magnesium sulfate, filtered, and concentrated under reduced pressure. Purification of the crude product by silica gel chromatography (10% (7 M ammonia in methanol) in dichloromethane) gave alcohol 42 (94 mg, 50% yield). MS: [M+H]$^+$=478.

Preparative Example 36

Preparation of Table 1 Compound No. 71

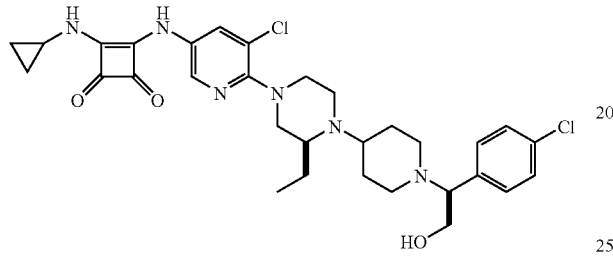
43

Compound 43 was prepared from amine 42 by the method outlined for Preparative Example 18. MS: [M+H]$^+$=613.

Preparative Example 37

Preparation of Table 1 Compound No. 76

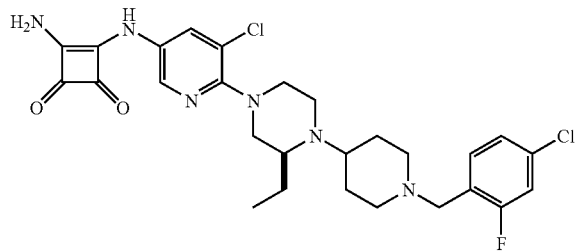
44

Compound 44 was prepared from amine 8 by the method outlined for Preparative Example 18, substituting ammonium hydroxide for cyclopropylamine. MS: [M+H]$^+$=561.

Preparative Example 38

Preparation of Table 1 Compound No. 75

Compound 45 was prepared from amine 8 by the method outlined for Preparative Example 18, substituting 2,2,2-trifluoroethylamine for cyclopropylamine. MS: [M+H]$^+$=643.

Preparative Example 39

Preparation of Bromide 47

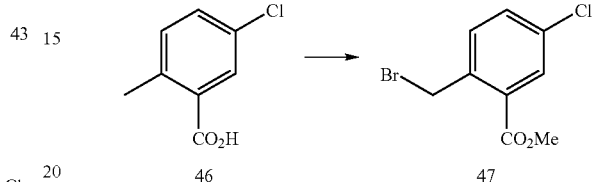
46    47

5-Chloro-2-methylbenzoic acid (46, 5.0 g, 29.3 mmol) was suspended in dichloromethane (30 mL) and thionyl chloride (3.2 mL, 5.2 g, 44 mmol) was added. The solution was stirred at room temperature for 1 hour. Methanol was added and the reaction was allowed to proceed for a further 16 hours. The volatile components were evaporated under reduced pressure. The resulting residue was taken up again in methanol (30 mL) and pyridine (5 mL) was added. The solution was stirred at room temperature for 2 days. The solvent was evaporated under reduced pressure. The residue was dissolved in dichloromethane and washed with water. The organic phase was dried over anhydrous magnesium sulfate, filtered, and concentrated to afford methyl 5-chloro-2-methylbenzoate (5.3 g, 96% yield) that was used in the following step without further purification.

N-Bromosuccinimide (5.3 g, 30 mmol) and benzoyl peroxide (343 mg, 1.4 mmol) were added sequentially to a solution of methyl 5-chloro-2-methylbenzoate (5.2 g, 28 mmol) in carbon tetrachloride (180 mL). The reaction mixture was stirred at 70° C. for 24 hours, then allowed to cool to room temperature, and was washed with saturated aqueous sodium bisulfite solution. The aqueous layer was extracted with dichloromethane. The combined organic layers were dried over anhydrous magnesium sulfate, filtered, and concentrated under reduced pressure to afford bromide 47 (6.4 g, 50% purity, remainder starting material).

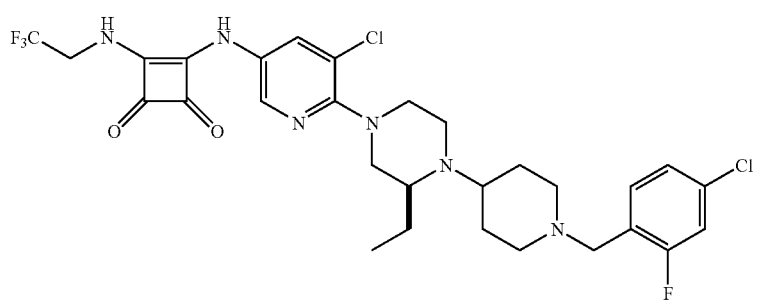
45

Preparative Example 40

Preparation of Table 1 Compound No. 72

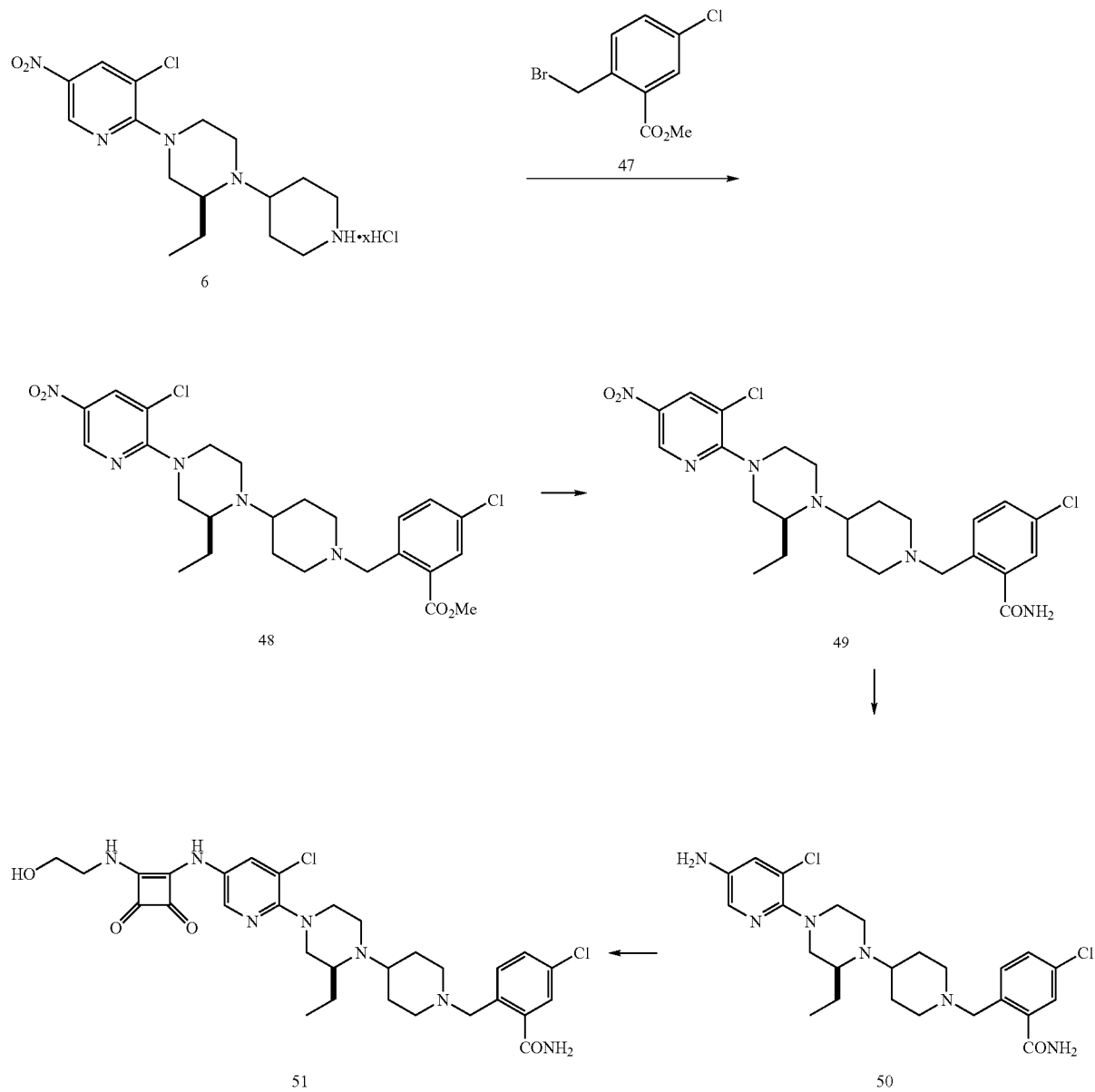

To a solution of amine salt 6 (250 mg, 0.54 mmol based on .3HCl salt) and diisopropylethylamine (500 µL, 371 mg, 2.9 mmol) in dry dichloromethane (2 mL) was added bromide 47 (262 mg, 50% purity, 131 mg, 0.5 mmol). The reaction mixture was stirred at room temperature for 18 hours. Evaporation of the solvent under reduced pressure gave a brown oil that was purified by silica gel chromatography (2% (7 M ammonia in methanol) in dichloromethane) to give 48 as a yellow oil (257 mg, 89% yield). MS: [M+H]$^+$=536.

Ester 48 (252 mg, 0.471 mmol) was dissolved in ammonia solution (4 mL, 7 M in methanol, 28 mmol, Acros Organics) and the solution was heated overnight at 70° C. in a pressure vessel. The reaction mixture was cooled to room temperature and the solvent was evaporated under reduced pressure. The residue was taken up again in ammonia solution (4 mL, 7 M in methanol, 28 mmol, Acros Organics) and the solution was heated at 70° C. for a further 3 days. The reaction mixture was cooled to room temperature and the solvent was evaporated under reduced pressure to give amide 49 (245 mg, 100% yield). MS: [M+H]$^+$=521.

Amide 49 was converted to 51 by sequential application of methods outlined in Preparative Examples 9 and 18, substituting ethanolamine for cyclopropylamine in the last step. MS: [M+H]$^+$=630.

Preparative Example 41

Preparation of Table 1 Compound No. 234

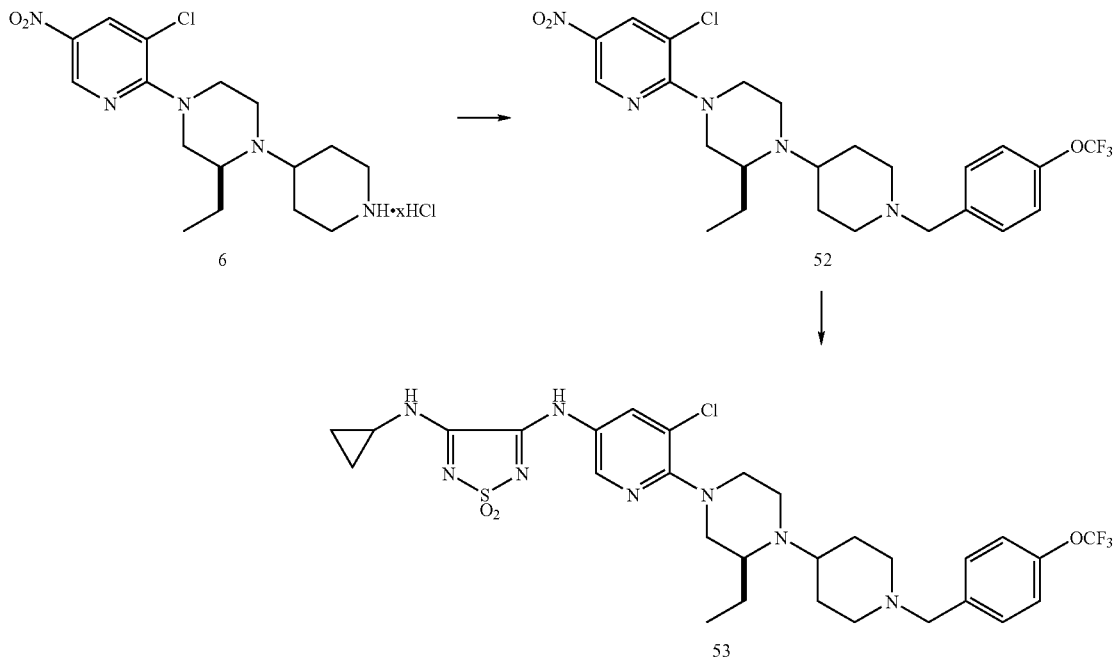

Amine salt 6 was converted into 52 according to the method presented in Preparative Example 4, using 4-(trifluoromethoxy)benzyl bromide in place of 2-fluoro-4-chlorobenzyl bromide. Nitro compound 52 was transformed into 53 by sequential application of methods presented in Preparative Examples 5 and 19. MS: $[M+H]^+=669$.

Preparative Example 42

Preparation of Table 1 Compound No. 36

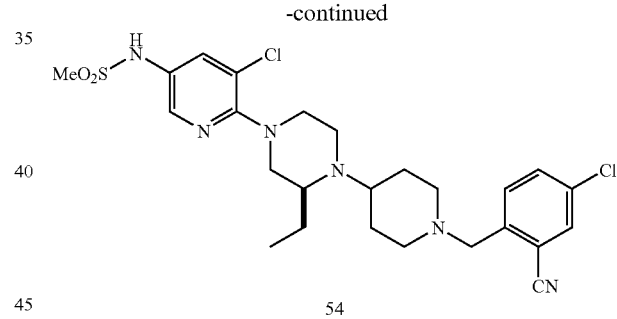

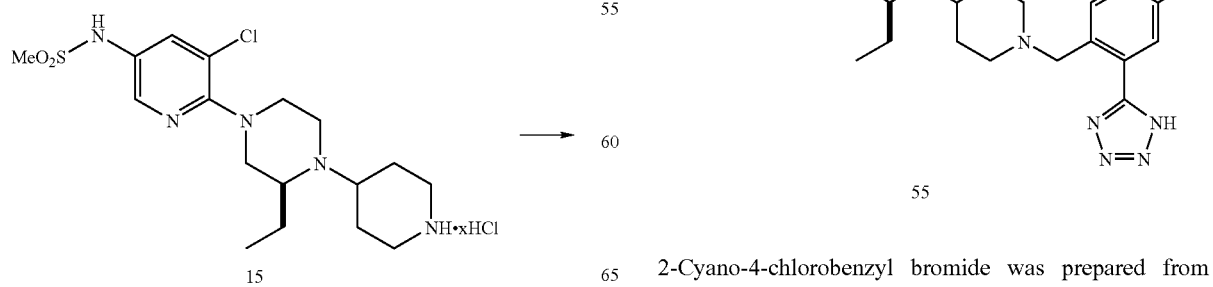

2-Cyano-4-chlorobenzyl bromide was prepared from 5-chloro-2-methylbenzonitrile (Matrix Scientific) by the method given in Preparative Example 39.

Amine salt 15 was converted to 54 by the method given in Preparative Example 13, substituting 2-cyano-4-chlorobenzyl bromide for 4-cyanobenzyl bromide.

The nitrile 54 (102 mg, 0.185 mmol) was then dissolved in DMF (1.8 mL) and triethylamine hydrochloride (77 mg, 0.560 mmol) and sodium azide (84 mg, 1.3 mmol) were added sequentially. The reaction mixture was stirred at 80° C. for 18 hours. A second portion of sodium azide (84 mg, 1.3 mmol) was added and the reaction mixture was stirred for a further 2 days at 80° C. and 2 days at room temperature. The reaction mixture was diluted with dichloromethane (100 mL), and the solvents were evaporated under reduced pressure. Residual DMF was removed by co-evaporation with toluene (2×50 mL). The residue was purified by preparative TLC (20% methanol-dichloromethane) to provide 55 (28 mg). MS: [M+H]$^+$=594.

Preparative Example 43

Preparation of Table 1 Compound No. 9

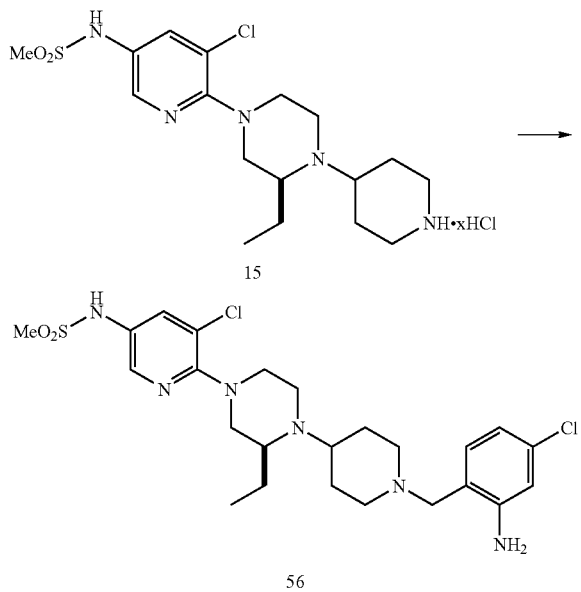

Amine salt 15 was converted to 56 first by application of the method shown in Preparative Example 12, substituting 4-chloro-2-nitrobenzaldehyde (Aldrich) for 4-(trifluoromethoxy)benzaldehyde, and then by following the reduction procedure shown in Preparative Example 35. MS: [M+H]$^+$=541.

Preparative Example 44

Preparation of Table 1 Compound No. 14

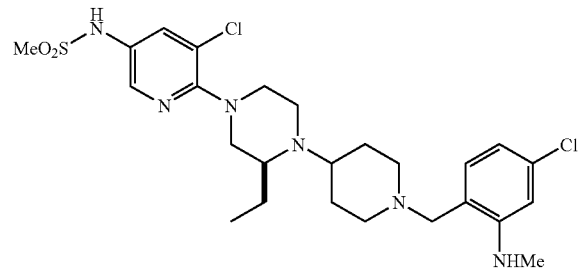

Compound 57 was prepared from amine 56 using the method shown for Preparative Example 12, substituting paraformaldehyde for 4-(trifluoromethoxy)benzaldehyde and omitting diisopropylethylamine. MS: [M+H]$^+$=555.

Preparative Example 45

Lithium 2-amino-6-chloronicotinate (58)

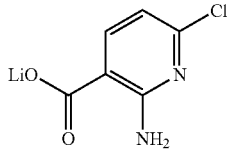

A solution of 2,5-dichloronicotinic acid (20.2 g, 0.105 mol, Aldrich) in methanol (500 mL) was cooled to 0° C. and neat thionyl chloride (38 mL, 63 g, 0.525 mol) was added over ~30 min. The reaction mixture was stirred at 0° C. for 1 hour. The cooling bath was removed, the reaction temperature was allowed to warm to room temperature, and the reaction was allowed to stir for an additional 2 days at room temperature. The solvent was removed under reduced pressure to give an off-white residue. The residue was dissolved in ether (~500 mL) and the resulting solution was washed successively with saturated aqueous sodium bicarbonate solution (~300 mL), water (~300 mL), and brine (~300 mL). The organic layer was separated, dried over anhydrous magnesium sulfate, and filtered. Removal of the solvent under reduced pressure yielded methyl 2,5-dichloronicotinate (21.0 g, 97% yield) as a white solid.

Performed in duplicate on identical scales in two pressure vessels, methyl 2,5-dichloronicotinate (4.5 g, 22 mmol) was dissolved in ammonia solution (250 mL, 0.5 M in 1,4-dioxane; 0.125 mol). The pressure vessels were sealed and heated at (85±5)° C. for 9 days. The two reaction mixtures were allowed to cool to room temperature, then combined and concentrated under reduced pressure to yield a white solid. Dissolution of the solid in 1:1 acetone-methanol (~500 mL), followed by adsorption onto silica gel (25 g) and then purification by flash column chromatography (25:10:1 hexanes-dichloromethane-ether), gave methyl 2-amino-5-chloronicotinate (6.08 g, 75% yield).

A solution of LiOH.H$_2$O (1.38 g, 33 mmol) in water (33 mL) was added in one portion to a suspension of methyl 2-amino-5-chloronicotinate (6.08 g, 27 mmol) in methanol (110 mL). The reaction mixture was stirred at 70° C. for 24 hours, and gradually became homogeneous. The solvents were removed under reduced pressure, and after the resulting white solid was dried under vacuum (<1 mmHg) to constant weight, lithium 2-amino-5-chloronicotinate (58) was obtained (5.51 g, 95% yield).

Preparative Example 46

Preparation of Table 1 Compound No. 31

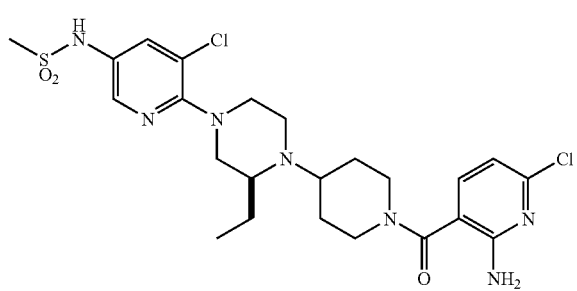

The amide 59 was prepared from amine salt 15 following the method for Preparative Example 15, substituting the carboxylate salt 58 for 2-amino-4-chlorobenzoic acid. MS: [M+H]$^+$=556.

Preparative Example 47

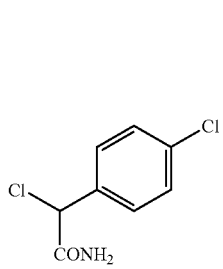

60

Neat thionyl chloride (50 mL, 81 g, 0.69 mol) was added to solid p-chloromandelic acid (9.3 g, 0.050 mol, Aldrich) and the mixture was stirred at 70° C. for 19 hours. The majority of the volatile components was removed by evaporation under reduced pressure, and residual thionyl chloride was removed by co-evaporation with toluene (2×200 mL). The remaining pale yellow liquid was cooled to 0° C. and ammonia solution (50 mL, 0.5 M in dioxane, 25 mmol) was added slowly. The resulting solution was stirred at room temperature for 2 days. The solvent was evaporated under reduced pressure to give a pale yellow residue. Crystallization from dichloromethane-hexanes gave amide 60 (10.0 g, 98% yield).

Preparative Example 48

Preparation of Table 1 Compound No. 31

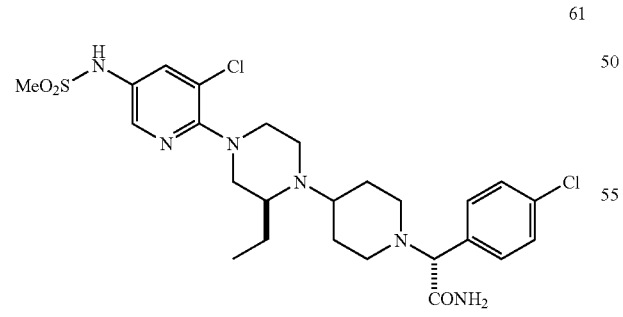

61

Compound 61 was prepared from amine salt 15 by the method shown in Preparative Example 13, substituting the chloro-amide 60 for 4-cyanobenzyl bromide. MS: [M+H]$^+$=569.

Preparative Example 49

Preparation of Table 1 Compound No. 52

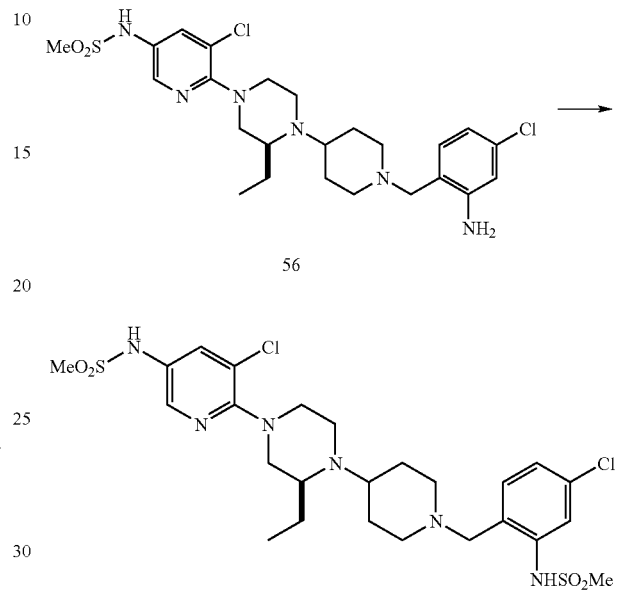

The sulfonamide 62 was prepared from amine 56 following the procedure for Preparative Example 10. MS: [M+H]$^+$=619.

Preparative Example 50

Preparation of Table 1 Compound No. 54

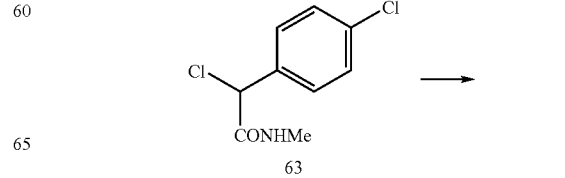

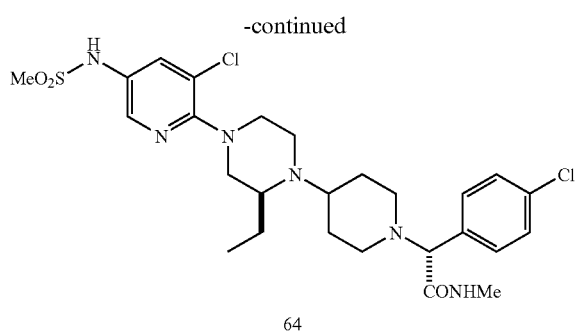

64

Chloro-amide 63 was prepared from p-chloromandelic acid (Aldrich) via the method given for Preparative Example 47, substituting methylamine for ammonia.

Compound 64 was prepared from amine salt 15 following the procedure given in Preparative Example 13, substituting the chloro-amide 63 for 4-cyanobenzyl bromide. MS: [M+H]$^+$=583.

Preparative Example 51

Preparation of Table 1 Compound No. 84

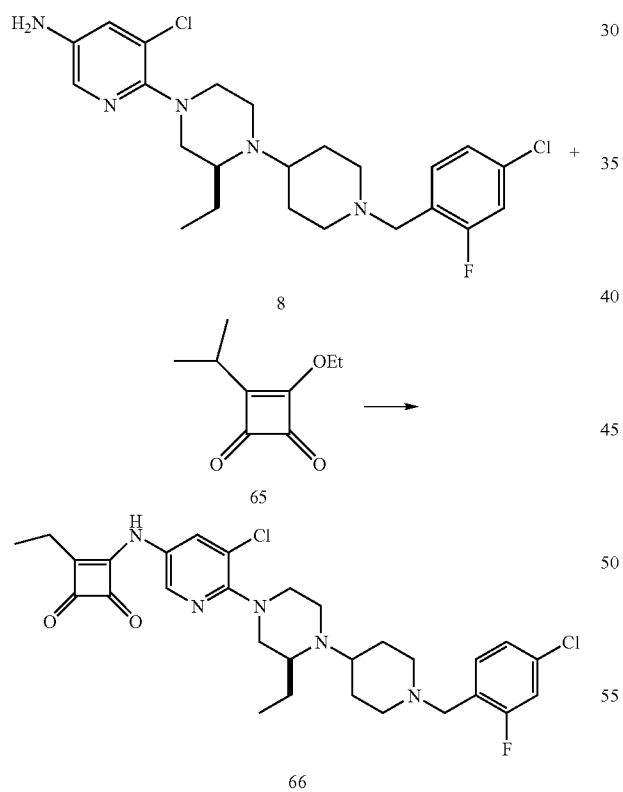

2-Ethoxy-3-isopropylcyclobutene-1,2-dione (65) was prepared from 2,3-diethoxycyclobutene-1,2-dione (Aldrich) using the procedure of Moore et al., given in *J. Org. Chem.* 1996, 61, 6009-6012.

Solid 8 (48 mg, 0.10 mmol) was added to a solution of 65 (52 mg, 0.31 mmol) in absolute ethanol (0.2 mL). The resulting solution was stirred at room temperature for 2 days. The solvent was evaporated under reduced pressure and the residue was purified by reverse-phase HPLC (0→100% acetonitrile-water gradient) to give 66 (32 mg, 53% yield). MS: [M+H]$^+$=588.

Preparative Example 52

Preparation of Table 1 Compound No. 148

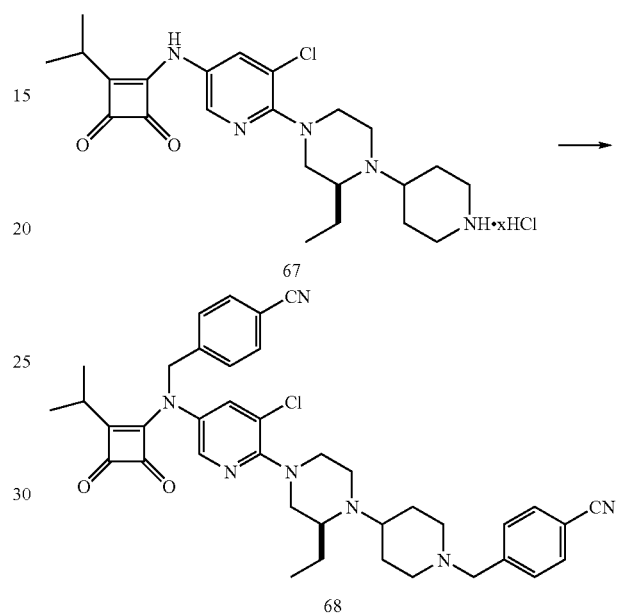

Compound 67 was prepared from amine 13, first by reaction with 65 according to the method given in Preparative Example 51 and then by following the method given in Preparative Example 11.

Amine salt 67 (40 mg, 0.077 mmol, based on .2HCl salt) and triethylamine (62 µL, 45 mg, 0.45 mmol) were dissolved in DMF (0.250 mL). p-Cyanobenzyl bromide (21 mg, 0.11 mmol) was added and the reaction mixture was stirred at room temperature for 20 hours. The reaction mixture was filtered and purified directly by reverse-phase HPLC (0→100% acetonitrile-water gradient) to give 68 (10 mg, 19% yield). MS: [M+H]$^+$=676.

Preparative Example 53

Preparation of Table 1 Compound No. 189

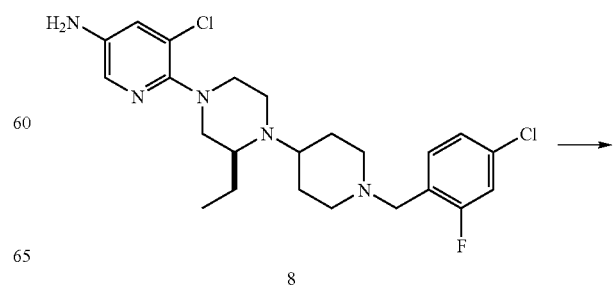

-continued

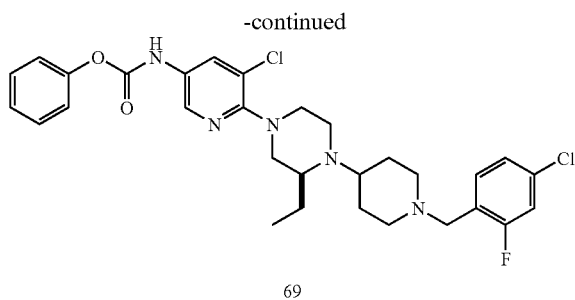

69

Phenyl chloroformate (90 mL, 111 mg, 0.71 mmol) was added dropwise over 5 min to an ice-cold solution of amine 8 (300 mg, 0.644 mmol) in 3:1 dichloromethane-pyridine (4 mL). The reaction mixture was allowed to warm to room temperature over 10 min, then stirred for a further 18 hours at room temperature. Solvent was removed under reduced pressure. The residue was purified by silica gel chromatography (2→5% (7 M ammonia in methanol) in dichloromethane) to give 69 (280 mg, 74% yield). MS: $[M+H]^+=586$.

Preparative Example 54

Preparation of Table 1 Compound No. 188

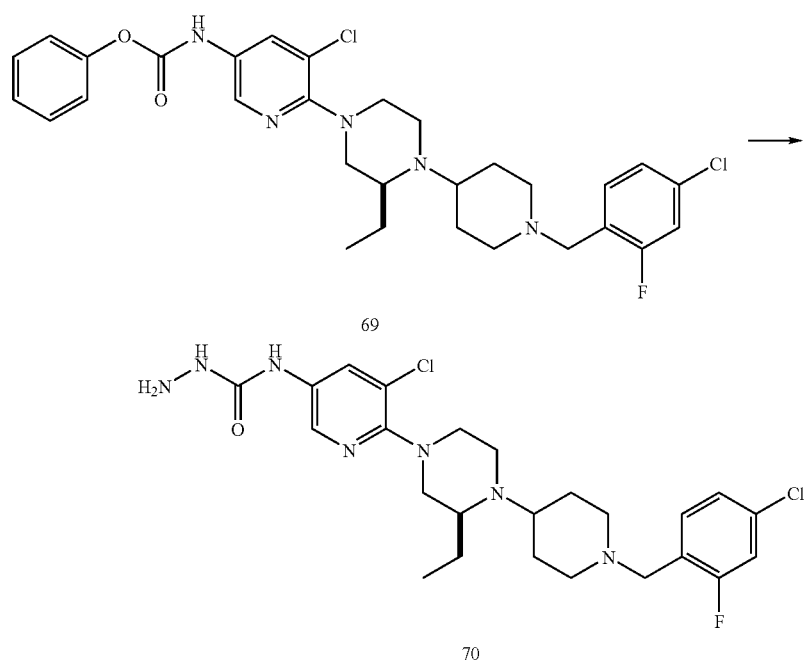

Carbamate 69 and anhydrous hydrazine (75 µL, 77 mg, 2.4 mmol) were dissolved in 1,4-dioxane (1 mL) and heated at reflux for 3 hours, then cooled to room temperature and partitioned between ethyl acetate (50 mL) and water (20 mL). The organic layer was washed with brine (50 mL), dried over anhydrous magnesium sulfate, filtered, and concentrated to give semicarbazide 70 (62 mg, 50% yield). MS: $[M+H]^+=524$.

Preparative Example 55

Preparation of Table 1 Compound No. 179

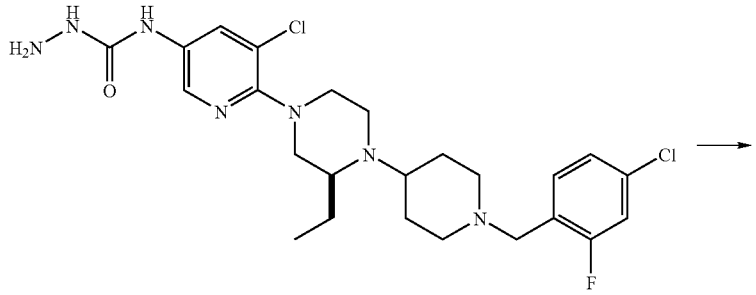

70

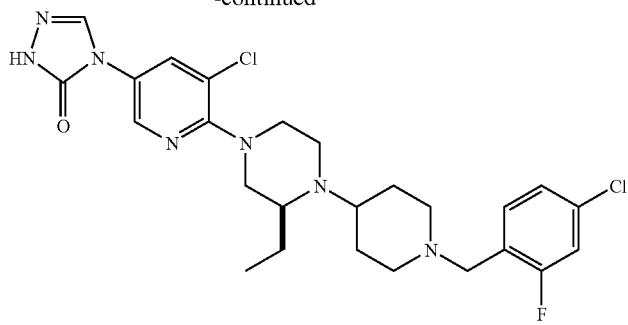

71

Formamidine acetate (62 mg, 0.60 mmol) was added to a solution of semicarbazide 70 (62 mg, 0.12 mmol) in DMF (0.250 mL) and the reaction mixture was stirred at 130° C. for 18 hours. The reaction mixture was cooled to room temperature, diluted with dichloromethane (20 mL), and washed with brine (5 mL). The organic layer was dried over anhydrous magnesium sulfate, filtered, and concentrated under reduced pressure to give a brown residue. Purification by preparative TLC (10% (7 M ammonia in methanol) in dichloromethane) gave triazolone 71 (23 mg, 37% yield). MS: [M+H]$^+$=534.

Preparative Example 56

Preparation of Table 1 Compound No. 185

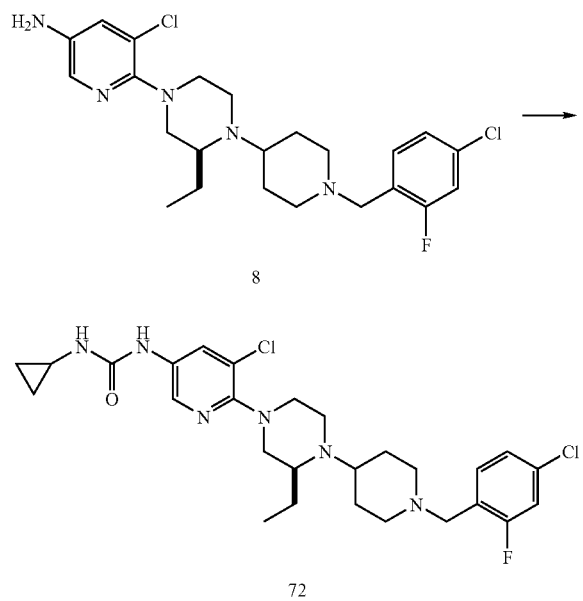

1,17-Carbonyldiimidazole (49 mg, 0.30 mmol, Aldrich) was added to a solution of amine 8 (47 mg, 0.10 mmol) in THF (1 mL). The solution was stirred overnight at room temperature. Excess cyclopropylamine (25 μL, 21 mg, 0.36 mmol) was added and the reaction was allowed to proceed for a further 5 hours. The reaction mixture was diluted with ethyl acetate (25 mL) and washed sequentially with water (10 mL) and brine (10 mL). The organic layer was dried over anhydrous magnesium sulfate, filtered, and concentrated under reduced pressure to yield a yellow-orange oil. Purification by preparative TLC (5% (7 M ammonia in methanol) in dichloromethane) gave urea 72 (27 mg, 50% yield). MS: [M+H]$^+$=549.

Preparative Example 57

Preparation of Table 1 Compound No. 204

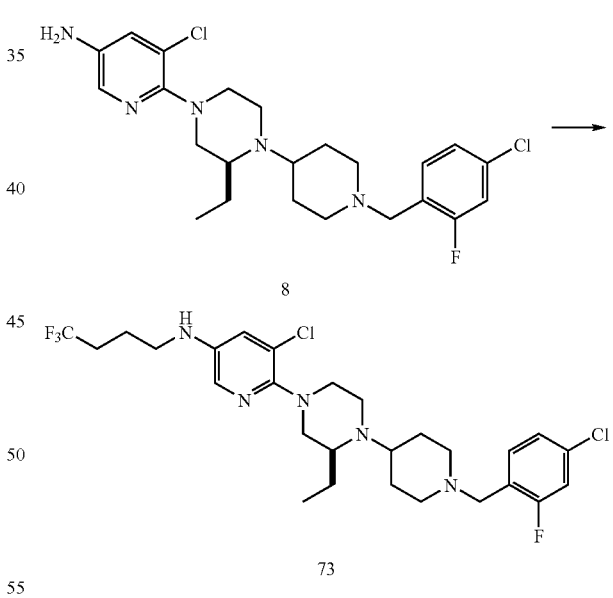

Sodium hydride (5 mg, 60% dispersion in oil, 2.8 mg, 0.12 mmol) was added to a solution of 8 (40 mg, 0.09 mmol) in dry DMF (350 μL). The reaction was allowed to proceed at room temperature for 4 days. The reaction mixture was diluted with ethyl acetate (50 mL) and washed sequentially with water (10 mL) and brine (10 mL). The organic layer was dried over anhydrous magnesium sulfate, filtered, and concentrated under reduced pressure. Preparative TLC separation (10% (7 M ammonia in methanol) in dichloromethane) gave alkylated amine 73 (6 mg, 12% yield). MS: [M+H]$^+$=558.

Preparative Example 58

Preparation of Table 1 Compound No. 205

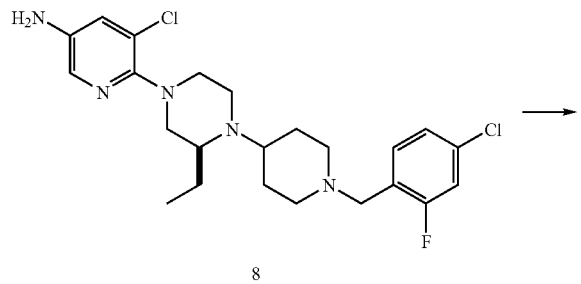

8

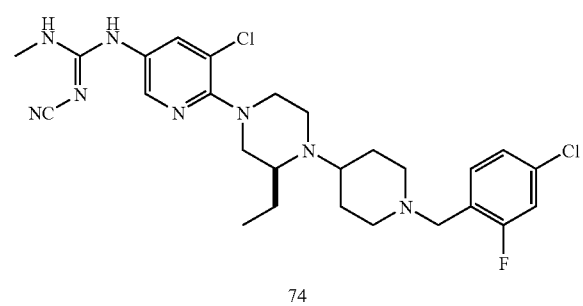

74

Diphenyl cyanocarbonimidate (25 mg, 0.10 mmol, Aldrich) was added to a solution of 8 (40 mg, 0.09 mmol) and triethylamine (14 μL, 10 mg, 0.10 mmol) in 1,2-dichloroethane (100 μL). The reaction mixture was stirred at room temperature for 27 hours. Excess methylamine (400 μL, 2.0 M in THF, 0.8 mmol) was added and the solution was stirred at room temperature for 24 hours. Evaporation of the solvent under reduced pressure followed by purification by preparative TLC (10% (7 M ammonia in methanol) in dichloromethane) gave 74 (30 mg, 64% yield). MS: [M+H]$^+$=547.

Preparative Example 59

Preparation of Table 1 Compound No. 210

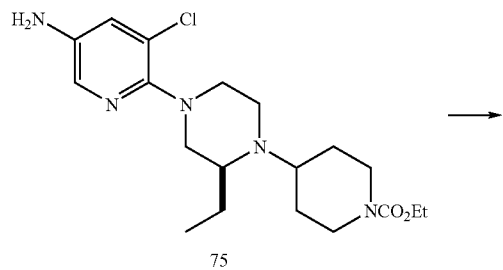

75

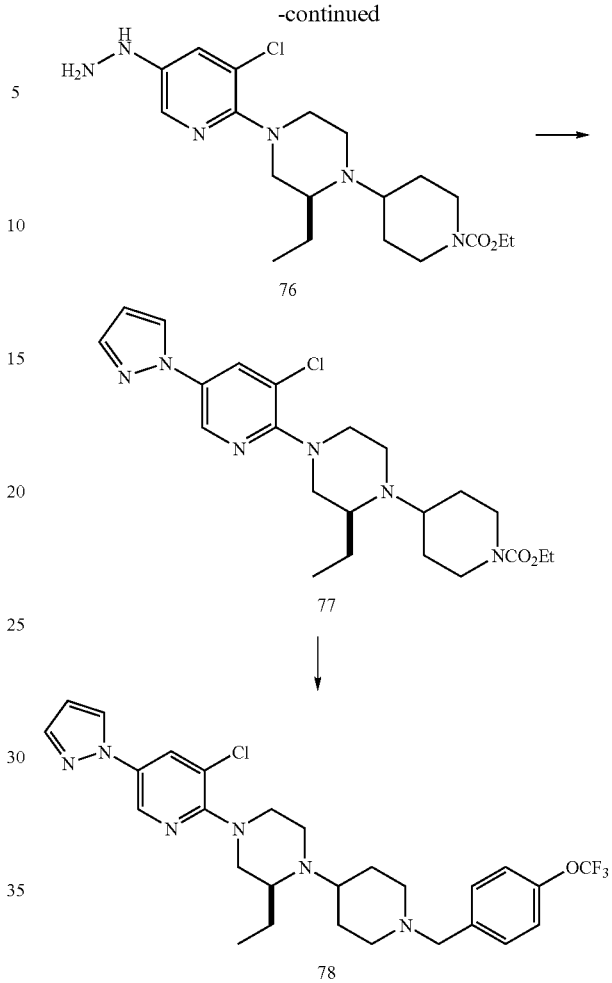

Amine 75 was prepared from the combination of 3 and 1-carbethoxy-4-piperidone (Aldrich) according to the method shown in Preparative Example 2, followed by application of the procedure of Preparative Example 9.

Amine 75 (1.10 g, 2.8 mmol) was dissolved in concentrated hydrochloric acid (10 mL) and the solution was cooled to −10° C. Sodium nitrite (211 mg, 3.1 mmol), dissolved in water (1 mL) was added dropwise into the reaction mixture. Tin(II) chloride (2.6 g, 13 mmol) was dissolved in concentrated hydrochloric acid (5 mL), cooled to −10° C., and added dropwise to the reaction mixture. The solution was allowed to warm to room temperature and was stirred for a further 30 min. The reaction mixture was cooled to 0° C. and 20% aqueous sodium hydroxide solution (20 mL) was added cautiously. The aqueous solution was extracted with ethyl acetate (100 mL), the organic layer washed with brine (50 mL), dried over anhydrous sodium sulfate, filtered, and concentrated. Silica gel chromatography (5% (7 M ammonia in methanol) in dichloromethane) gave 76 (310 mg). MS: [M+H]$^+$=411.

Hydrazine 76 (310 mg, 0.76 mmol) was dissolved in 1:1 ethanol/water (6 mL). Concentrated hydrochloric acid (0.1 mL) and 1,1,3,3-tetraethoxypropane (0.220 mL, 200 mg, 0.91 mmol) were added. The mixture was heated at reflux overnight, then cooled to room temperature, diluted with ethyl acetate (50 mL), and washed sequentially with saturated aqueous sodium bicarbonate solution (3×25 mL), water (25 mL) and brine (25 mL). The organic layer was dried over anhydrous sodium sulfate, filtered, and concentrated to give 77. The carbamate 77 was dissolved in 1,2-dichloroethane (1 mL) and iodotrimethylsilane (0.64 mL, 896 mg, 4.5 mmol) was added. The solution was stirred at 70° C. overnight, then cooled to room temperature and diluted with methanol (1 mL). Solvent was removed under reduced pressure to give a brown oil. Sequential application of methods given in Preparative Examples 11 and 12 gave 78 (50 mg, 33% yield from 75). MS: [M+H]$^+$=549.

Preparative Example 60

Preparation of Table 1 Compound No. 211

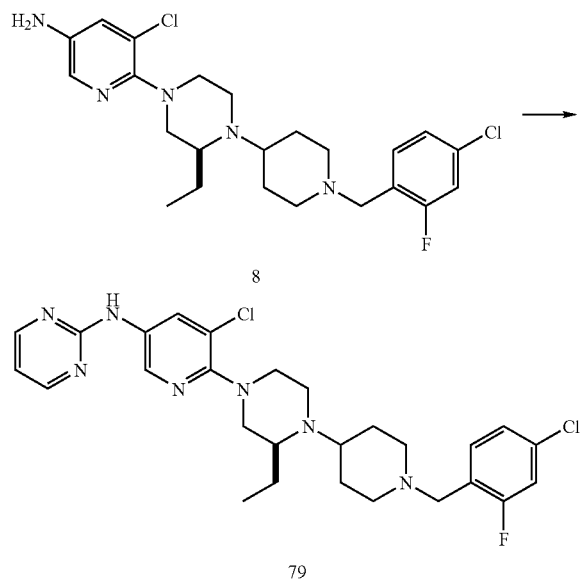

2-Chloropyrimidine (35 mg, 0.30 mmol), palladium acetate (45 mg, 0.30 mmol), 2-(di-t-butylphosphino)biphenyl (60 mg, 0.20 mmol, Strem Chemicals), and cesium carbonate (100 mg, 0.30 mmol) and amine 8 (47 mg, 0.10 mmol) were added sequentially into 1,4-dioxane (1.0 mL). The mixture was heated at 110° C. overnight, cooled to room temperature, and applied directly to a silica gel column. Elution with 2% (7 M ammonia in methanol) in dichloromethane gave 79 (10 mg, 18% yield). MS: [M+H]$^+$=544.

Preparative Example 61

Preparation of Table 1 Compound No. 221

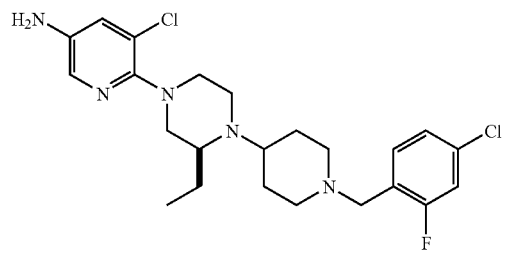

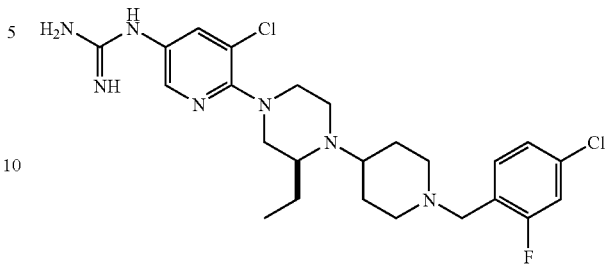

1,3-Bis(t-butoxycarbonyl)-2-methyl-2-thiopseudourea (30 mg, 0.10 mmol, Aldrich), mercury(II) chloride (27 mg, 0.10 mmol), and triethylamine (300 µL, 216 mg, 2.1 mmol) were added sequentially to a solution of 8 (47 mg, 0.10 mmol) in DMF (1 mL). The reaction was stirred overnight at room temperature. The reaction mixture was diluted with ethyl acetate (50 mL) and washed sequentially with water (25 mL) and brine (25 mL). The organic layer was dried over anhydrous sodium sulfate, filtered, and concentrated to give a brown oil. The oil was dissolved in ethyl acetate (1 mL) and hydrogen chloride (1.0 mL, 4 M solution in 1,4-dioxane, 4 mmol) was added. The solution was stirred at room temperature for 18 hours. The solvent was evaporated and the residue was purified by reverse-phase HPLC to give 80 (38 mg, 75% yield). MS: [M+H]$^+$=508.

Preparative Example 62

Preparation of Table 1 Compound No. 222

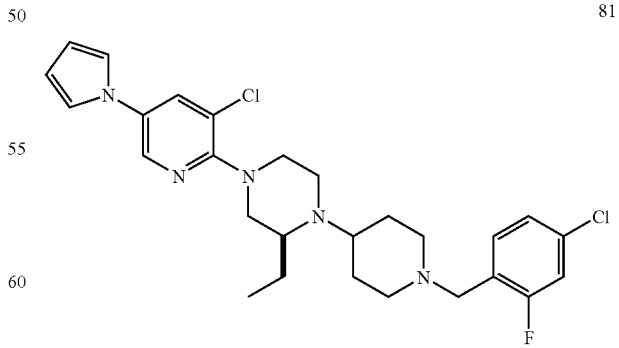

Compound 81 was prepared from amine 8 by the procedure of Josey, in *Org. Synth., Collective Vol.* 5, p. 716. MS: [M+H]$^+$=516.

Preparative Example 63

Preparation of Table 1 Compound No. 213

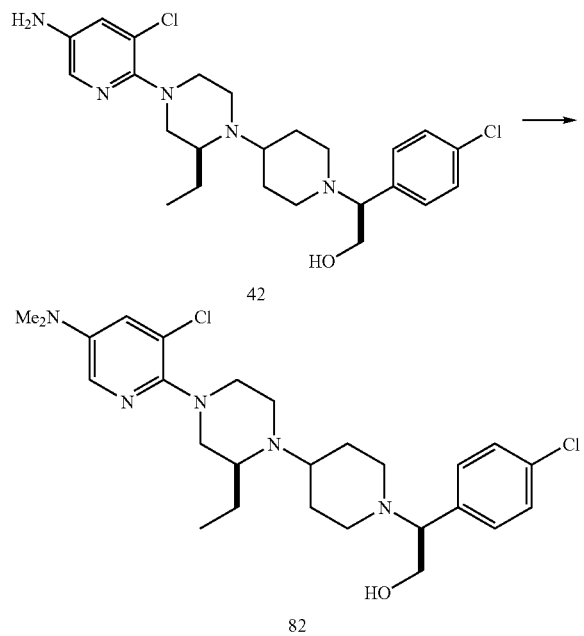

The amine 42 (100 mg, 0.210 mmol) was dissolved in dichloromethane (2 mL). Excess paraformaldehyde (63 mg) was added and the mixture was stirred at room temperature for 1 hour. Sodium triacetoxyborohydride (443 mg, 2.09 mmol) was then added and the reaction was stirred overnight at room temperature. Work-up was carried out as described in Preparative Example 7 to afford 82 (28 mg, 26% yield). MS: $[M+H]^+=506$.

Preparative Example 64

Preparation of Intermediates 84 and 85

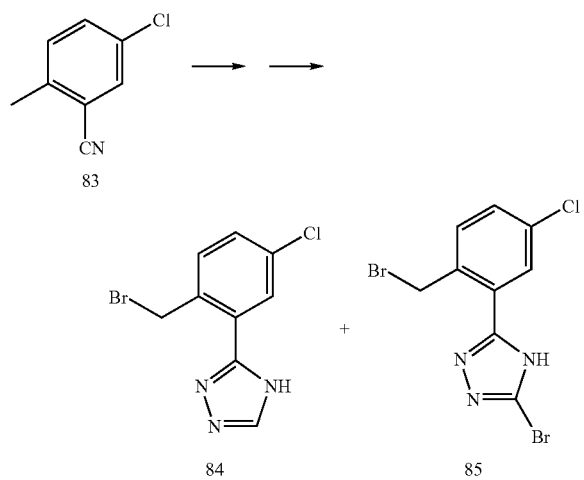

5-Chloro-2-methylbenzonitrile (83) was converted to 2-cyano-4-chlorobenzyl bromide by the method given in Preparative Example 39. A mixture of 2-cyano-4-chlorobenzyl bromide and sodium methoxide (13.2 mL, 0.5 M in MeOH, 6.6 mmol) in methanol (6 mL) was stirred for 2 hours at 25° C. To this was added formyl hydrazide (409 mg, 6.75 mmol) in methanol at 25° C. The reaction mixture was stirred at the temperature for 1 hour and then at reflux for 4 days. The reaction mixture was cooled, poured into water, and neutralized by addition of 1 N HCl solution. The organic layers were extracted with ethyl acetate and the combined organic solutions were washed with brine, dried over anhydrous sodium sulfate, and concentrated under reduced pressure. The residual material was purified by $SiO_2$ column chromatography. Then, a mixture of the purified material (206 mg, 1.06 mmol), N-bromosuccinimide (567 mg, 3.19 mmol) and benzoyl peroxide (7.7 mg, 0.03 mmol) in carbon tetrachloride (15 mL) was stirred under nitrogen for 15 minutes at 25° C. The reaction mixture was heated to reflux for 3 hours. The reaction mixture was cooled and the precipitate was filtered. The filtrate was concentrated under reduced pressure and the residue was purified by preparative TLC (3% MeOH in $CH_2Cl_2$) to afford 84 (64 mg, 22%) and 85 (72 mg, 20%). MS (84): M+H=272, MS (85): M+H=350.

Preparative Example 65

Preparation of Table 1 Compound No. 215

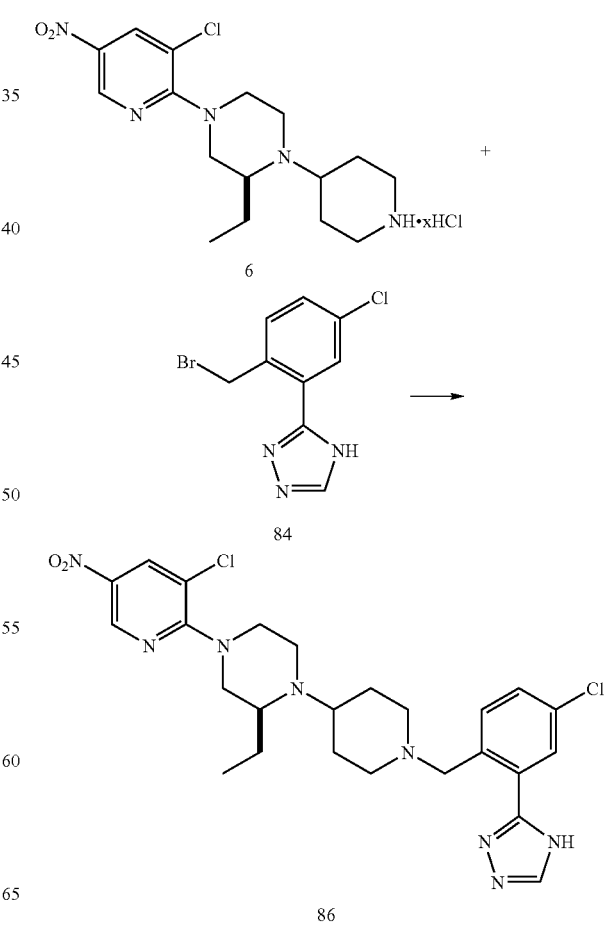

Amine salt 6 was combined with 84 according to the method given in Preparative Example 13 to afford 86.

Preparative Example 66

Preparation of Table 1 Compound No. 230

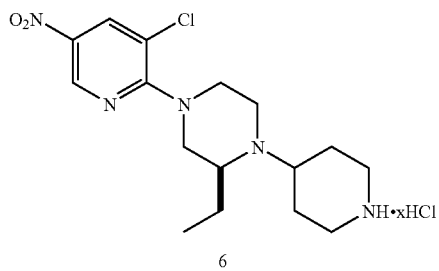

6

+

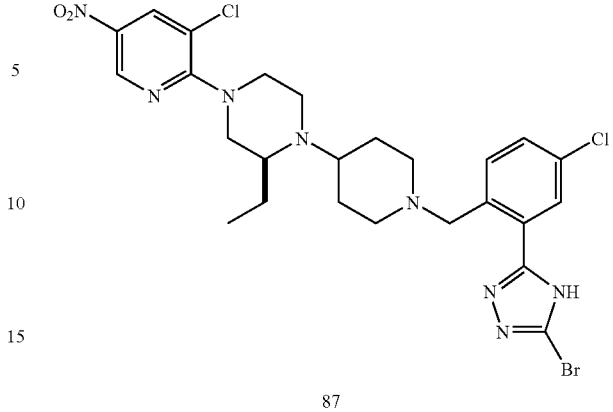

87

Amine salt 6 was combined with 85 according to the method given in Preparative Example 13 to afford 87.

Preparative Example 67

Preparation of Table 1 Compound No. 236

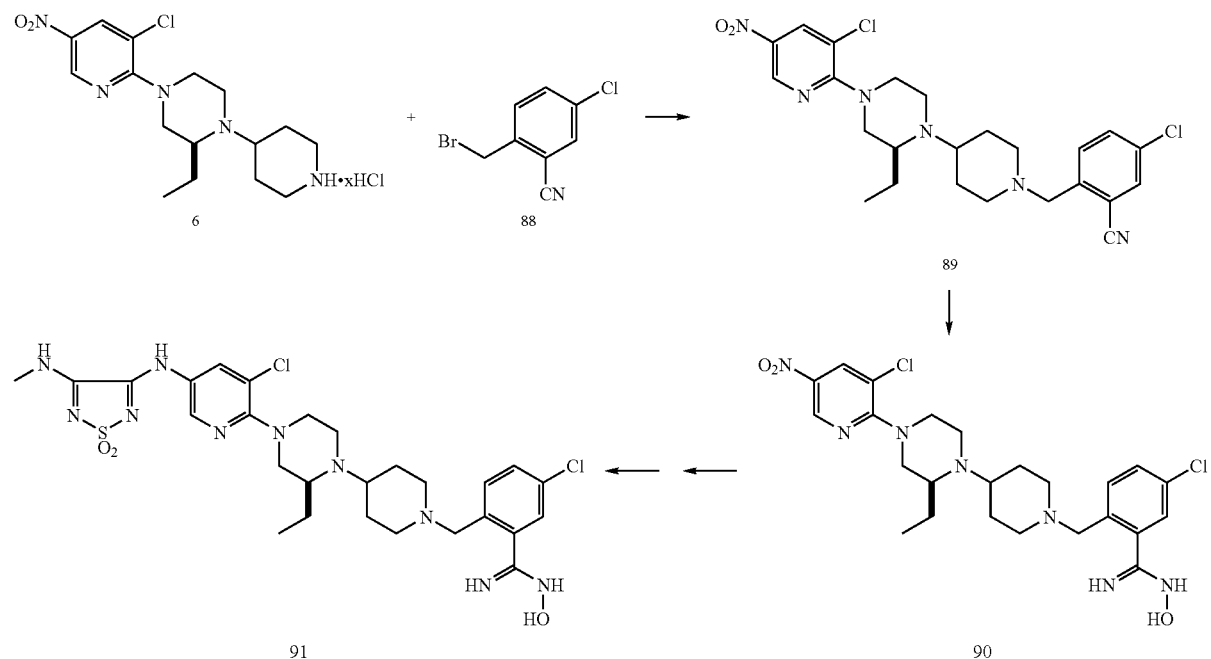

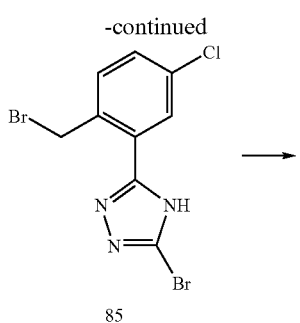

85

Bromide 88, prepared from 5-chloro-2-methylbenzonitrile (Matrix Scientific) was combined with amine salt 6 according to the method of Preparative Example 13 to give 89. Nitrile 89 (377 mg, 0.75 mmol) was then dissolved in absolute ethanol (3 mL). Hydroxylamine hydrochloride (150 mg, 1.5 mmol) and diisopropylethylamine (261 μL, 194 mg, 1.5 mmol) were added. The reaction mixture was stirred at reflux for 16 hours. The reaction mixture was cooled to room temperature, neutralized with saturated sodium bicarbonate solution, and extracted with ethyl acetate. The organic solution was washed with brine, dried over anhydrous sodium sulfate, filtered, and concentrated to give 90 as a yellow solid. Purification by silica gel chromatography (8% (7 M ammonia in methanol) in dichloromethane) gave 90 (167 mg, 42% yield). MS: [M+H]$^+$=536.

The nitro compound 90 was converted to 91 following procedures given in Preparative Examples 5 and 19, substituting methylamine for cyclopropylamine in the final step. MS: [M+H]$^+$=651.

Preparative Example 68

Preparation of Table 1 Compound No. 249

Compound 90 (500 mg, 0.900 mmol) was dissolved in triethyl orthoformate (3 mL) and pyridinium p-toluenesulfonate (250 mg) was added. The mixture was stirred at 70° C. overnight, then cooled to room temperature, diluted with dichloromethane, and washed with brine. The organic solution was dried over anhydrous sodium sulfate, filtered, and evaporated under reduced pressure to give 92. The nitro compound 92 was converted to 93 following procedures given in Preparative Examples 5 and 19. MS: [M+H]$^+$=687.

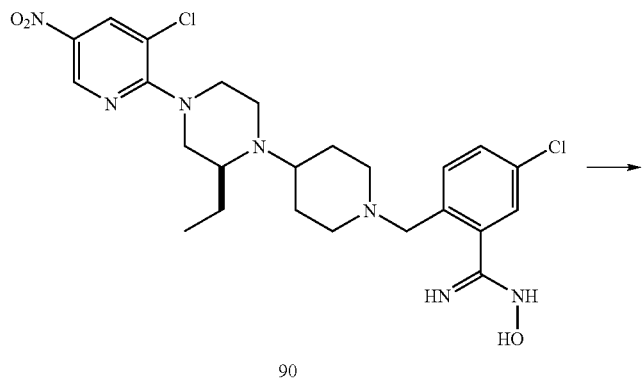
90

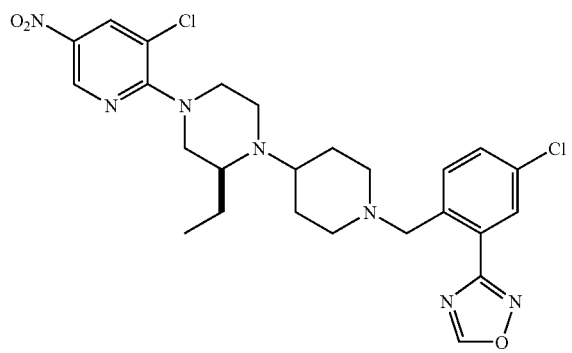
92

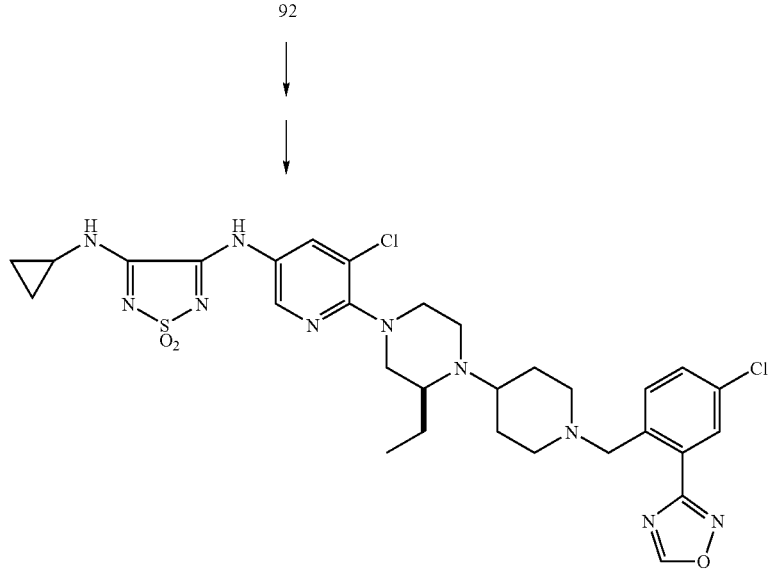
93

Preparative Example 69

Preparation of Table 1 Compound No. 229

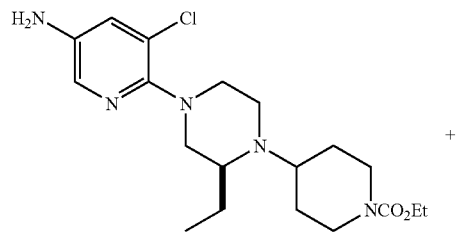

75

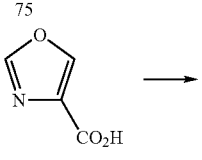

94

→

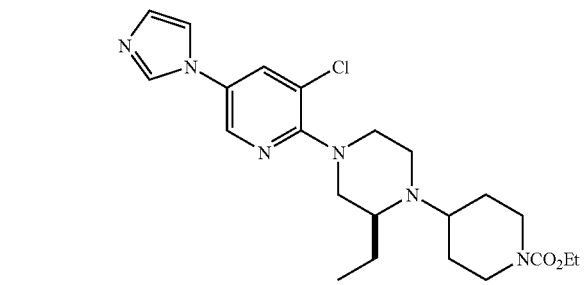

95

↓
↓

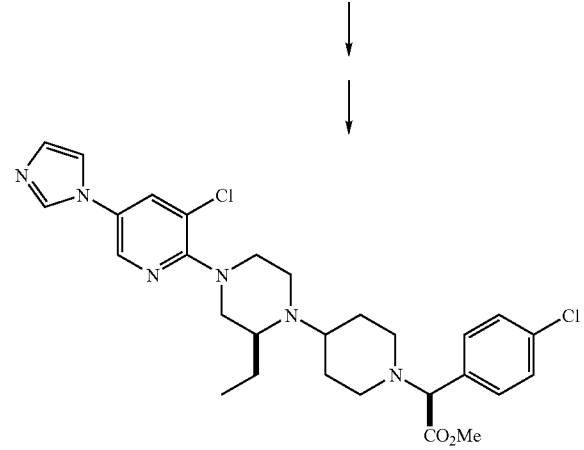

96

Compound 75 was prepared from the combination of 3 with 1-carbethoxy-4-piperidone (Aldrich) according to the method given in Preparative Example 2, followed by application of the procedure given in Preparative Example 9.

Oxazole-4-carboxylic acid (94) was prepared according to the procedure of Schöllkopf et al. in *Liebigs Ann. Chem.* 1979, 1370-1387.

The combination of 75 and 94 to give 95 was carried out by the procedure of Cornforth and Cornforth in *J. Chem. Soc.* 1947, 96-102. Compound 95 was converted to 96 by sequential application of methods given in Preparative Examples 59, 11, and 13, but substituting chloro-ester 32 for 4-cyanobenzyl bromide in the final step. MS: $[M+H]^+=557$.

Preparative Example 70

Preparation of Table 1 Compound No. 10

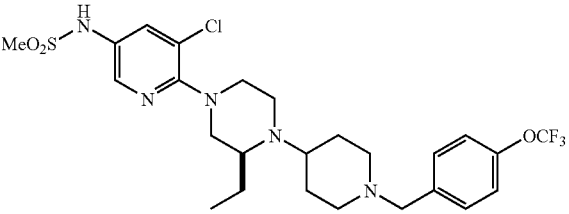

97

Compound 97 was prepared by the same method shown for Preparative Examples 4 through 6, using 4-(trifluoromethoxy)benzyl bromide in place of 2-fluoro-4-chlorobenzyl bromide. MS: $[M+H]^+=576$.

Preparative Example 71

Preparation of Table 1 Compound No. 109

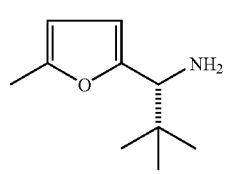

98

-continued

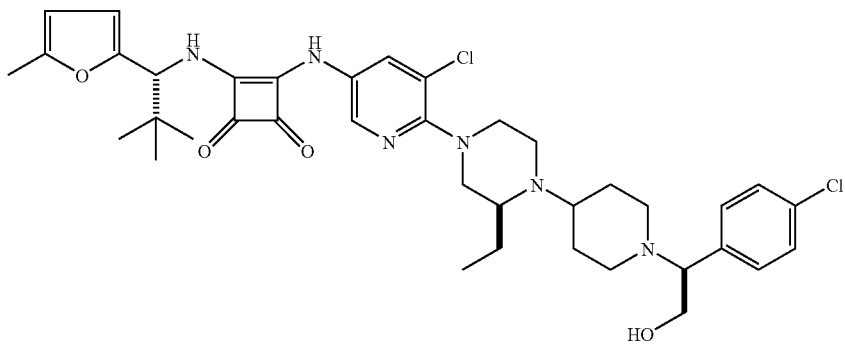

99

Amine 98 was prepared according to the method of Taveras et al. in WO 03/080053 and WO 04/011418.

Compound 99 was prepared from amine 42 by the method outlined for Preparative Example 18, but using amine 98 in place of cyclopropylamine in the final step. MS: [M+H]$^+$=723.

Preparative Example 72

Preparation of Table 1 Compound No. 207

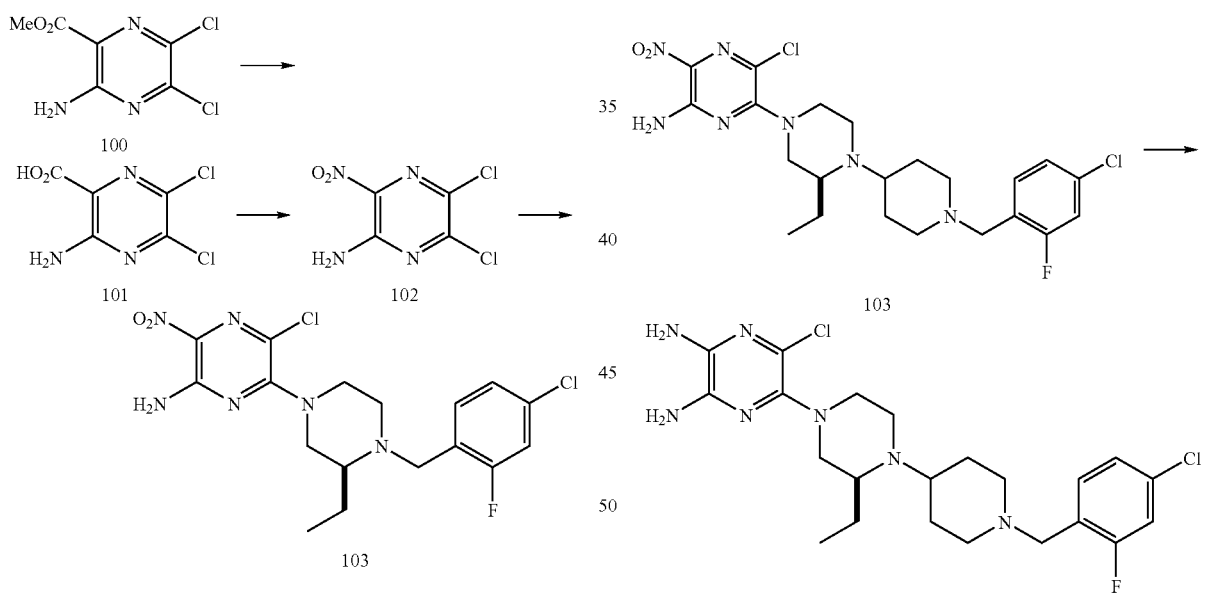

A suspension of 100 (3.6 g, 16 mmol, Aldrich) and sodium hydroxide (1.6 g, 39 mmol) in water (30 mL) was heated at reflux for 15 min. The solution was filtered, allowed to cool to room temperature, and was acidified with 1 N hydrochloric acid. The precipitated solid 101 (1.2 g, 36% yield) was collected by filtration, air-dried, and dried further under vacuum.

A solution of 101 (1.1 g, 5.3 mmol) in concentrated sulfuric acid (9 mL) was cooled to 0° C. and a 1:1 (v/v) nitric acid-sulfuric acid mixture (680 μL) was added. The reaction mixture was stirred at room temperature for 3 hours, then poured into ice (~150 mL). The precipitated solid was collected by filtration and then dissolved in ethyl acetate. The organic solution was neutralized with saturated aqueous sodium carbonate solution, dried over anhydrous sodium sulfate, filtered, and concentrated under reduced pressure to give 102 (619 mg, 56% yield).

The nitro compound was then converted to 103 by sequential application of procedures given in Preparative Examples 1 and 7. MS: [M+H]$^+$=496.

Preparative Example 73

Preparation of Table 1 Compound No. 219

A solution of 103 (60 mg, 0.12 mmol) in 4:1 ethanol-water (8 mL) was treated with calcium chloride dehydrate (80 mg, 0.54 mmol) and iron powder (200 mg, 3.6 mmol) at room temperature. The resulting suspension was stirred at reflux for 2 hours, cooled to room temperature, and diluted with methanol. The solids were removed by filtration and the filtrate was concentrated under reduced pressure to give a brown gum. Purification by silica gel chromatography (10% (7 M ammonia in methanol) in dichloromethane) gave 104 (45 mg, 78% yield). MS: [M+H]$^+$=482.

Biological Examples

The inventive compounds can readily be evaluated to determine activity at the CXCR3 receptors by known methods, such as, for example, development of a human CXCR3 (N-delta 4) Binding Assay.

Cloning and Expression of Human CXCR3 (N-delta 4):

The DNA encoding human CXCR3 was cloned by PCR using human genomic DNA (Promega, Madison, Wis.) as a template. The PCR primers were designed based on the published sequence of human orphan receptor GPR9 (1) with incorporated restriction sites, a Kozak consensus sequence, CD8 leader and Flag tag. The PCR product was subcloned into the mammalian expression vector pME18Sneo, a derivative of the SR-alpha expression vector (designated as pME18Sneo-hCXCR3 (N-delta 4).

IL-3-dependent mouse pro-B cells Ba/F3 were transfected by electroporation in 0.4 ml Dulbecco's PBS containing $4 \times 10^6$ cells with 20 µg of pME18Sneo-hCXCR3 (N-delta 4) plasmid DNA. Cells were pulsed at 400 Volts, 100 OHMs, 960 µFd. The transfected cells were under selection with 1 mg/ml G418 (Life Technologies, Gaithersburg, Md.). G418-resistant Ba/F3 clones were screened for CXCR3 expression by specific binding of $[^{125}I]$ IP-10 (NEN Life Science Products, Boston, Mass.).

Preparation of Ba/F3-hCXCR3 (N-delta 4) Membranes:

Ba/F3 cells expressing human CXCR3 (N-delta 4) were pelleted and resuspended in the lysis buffer containing 10 mM HEPES, pH 7.5 and Complete® protease inhibitors (1 tablet per 100 ml) (Boehringer Mannheim, Indianapolis, Ind.) at a cell density of $20 \times 10^6$ cells per ml. After 5 minute incubation on ice, cells were transferred to 4639 cell disruption bomb (Parr Instrument, Moline, Ill.) and applied with 1,500 psi of nitrogen for 30 minutes on ice. Large cellular debris was removed by centrifugation at 1,000×g. Cell membrane in the supernatant was sedimented at 100,000×g. The membrane was resuspended in the lysis buffer supplemented with 10% sucrose and stored at −80° C. Total protein concentration of the membrane was determined by BCA method from Pierce (Rockford, Ill.).

Human CXCR3 (N-Delta 4) Scintillation Proximity Assay (SPA):

For each assay point, 2 µg of membrane was preincubated for 1 hr with 300 µg wheat germ agglutinin (WGA) coated SPA beads (Amersham, Arlington Heights, Ill.) in the binding buffer (50 mM HEPES, 1 mM $CaCl_2$, 5 mM $MgCl_2$, 125 mM NaCl, 0.002% $NaN_3$, 1.0% BSA) at room temperature. The beads were spun down, washed once, resuspended in the binding buffer and transferred to a 96-well Isoplate (Wallac, Gaithersburg, Md.). 25 pM of $[^{125}I]$ IP-10 with tested compounds in a series of titration were added to start the reaction. After 3 hr reaction at room temperature, the amount of $[^{125}I]$ IP-10 bound to the SPA beads was determined with a Wallac 1450 Microbeta counter.

The Ki ratings for the various compounds of the present invention are given in the afore-mentioned Table 1. From these ratings and value ranges, it would be apparent to the skilled artisan that the compounds of the invention have excellent utility as CXCR3 receptor antagonists.

While the present invention has been describe in conjunction with the specific embodiments set forth above, many alternatives, modifications and variations thereof will be apparent to those of ordinary skill in the art. All such alternatives, medications and variations are intended to fall within the spirit and scope of the present invention.

What is claimed is:
1. A compound having the general structure shown in Formula 1:

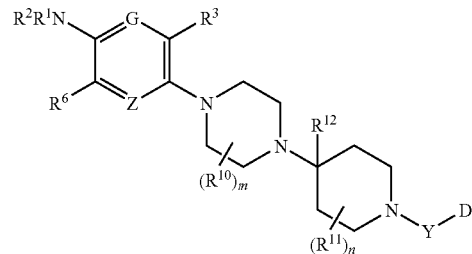

Formula 1 or a pharmaceutically acceptable salt, thereof wherein:
Z is N, or NO;
G is N, $C(R^4)$, or NO;
$R^1$ and $R^2$ are independently absent or present, and if present each is independently selected from the group consisting of H, alkyl, alkoxy, alkenyl, carbonyl, cycloalkyl, cycloalkenyl, alkylaryl, arylalkyl, aryl, amino, alkylamino, amidinyl, carboxamido, cyano, hydroxyl, urea, —N═CH, ═NCN, —$(CH_2)_q$OH, —$(CH_2)_q OR^{31}$, —$(CH_2)_q NH_2$, —$(CH_2)_q NHR^{31}$, —$(CH_2)_q N(R^{31})_2$, —$(CH_2)_q C(═O)NHR^{31}$, —$(CH_2)_q SO_2R^{31}$, —$(CH_2)_q NHSO_2R^{31}$, —$(CH_2)_q SO_2NHR^{31}$, —C(═S)N(H)alkyl, —N(H)—S(O)$_2$-alkyl, —N(H)C(═O)N(H)-alkyl, —S(O)$_2$alkyl, —S(O)$_2NH_2$, —S(O)$_2$N(H)alkyl, —S(O)$_2$N(alkyl)$_2$, —S(O)$_2$aryl, —S(O)$_2$heteroaryl, —S(O)$_2$heterocyclyl, —C(═S)N(H)cycloalkyl, —C(═O)N(H)NH$_2$, —C(═O)alkyl, —C(═O)heteroaryl, —C(═O)heterocyclyl, -heteroaryl, heterocyclyl, and heterocyclenyl; or alternatively the N taken together with the $R^1$ and $R^2$ forms a heterocycyl, heteroaryl or —N═C(NH$_2$)$_2$;
$R^3$, $R^4$, $R^6$ and $R^{29}$ moieties can be the same or different, each being independently selected from the group consisting of H, alkyl, alkylaryl, aralkyl, —CN, $CF_3$, haloalkyl, cycloalkyl, halogen, hydroxyalkyl, —N═CH—$(R^{31})$, —C(═O)N($R^{30}$)$_2$, —N($R^{30}$)$_2$, —$OR^{30}$, —$SO_2(R^{31})$, —N($R^{30}$)C(═O)N($R^{30}$)$_2$ and —N($R^{30}$)C(═O)$R^{31}$;
the $R^{10}$ moieties can be the same or different, each being independently selected from the group consisting of H, alkyl, cycloalkyl, aryl, heteroaryl, heterocyclenyl, heterocyclyl, alkylaryl, arylalkyl, —CO$_2$H, hydroxyalkyl, —C(═O)N($R^{30}$)$_2$, —$(CH_2)_q$OH, —$(CH_2)_q OR^{31}$, —$(CH_2)_q NHR^{31}$, —$(CH_2)_q N(R^{31})_2$, —$OR^{30}$, halogen, ═O, and —C(═O)$R^{31}$;
the $R^{11}$ moieties can be the same or different, each being independently selected from the group consisting of H, alkyl, cycloalkyl, aryl, heteroaryl, heterocyclyl, heterocyclenyl, alkylaryl, arylalkyl, hydroxyalkyl, carboxamide, $CO_2H$, —$(CH_2)_q$OH, —$(CH_2)_q OR^{31}$, —$(CH_2)_q NHR^{31}$, —$(CH_2)_q N(R^{31})_2$, —$OR^{30}$, halogen, ═O, and —C(═O)$R^{31}$;
the $R^{12}$ moieties can be the same or different, each being independently selected from the group consisting of H, alkyl, —CN, —C(═O)N($R^{30}$)$_2$, —$(CH_2)_q$OH, —$(CH_2)_q OR^{31}$, —$(CH_2)_q NHR^{31}$, —$(CH_2)_q N(R^{31})_2$, and —S(O$_2$)$R^{31}$;
D is a five to nine membered cycloalkyl, cycloalkenyl, aryl, heteroaryl, heterocyclenyl or heterocyclyl ring having 0-4 heteroatoms independently selected from O, S or N, wherein ring D is unsubstituted or optionally substituted with 1-5 independently selected $R^{20}$ moieties;

the $R^{20}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —$(CH_2)_qOH$, —$(CH_2)_qOR^{31}$, —$(CH_2)_qNH_2$, —$(CH_2)_qNHR^{31}$, —$(CH_2)_qN(R^{31})_2$, —$(CH_2)_qC(=O)NHR^{31}$, —$(CH_2)_qSO_2R^{31}$, —$(CH_2)_qNHSO_2R^{31}$, —$(CH_2)_qSO_2NHR^{31}$, -alkynylC$(R^{31})_2OR^{31}$, —$C(=O)R^{30}$, —$C(=O)N(R^{30})_2$, —$C(=NR^{30})NHR^{30}$, —$C(=NOH)N(R^{30})_2$, —$C(=NOR^{31})N(R^{30})_2$, —$C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})SO_2(R^{31})$, —$N(R^{30})C(=O)N(R^{30})_2$, —$N(R^{30})SO_2(R^{31})$, —$N(R^{30})S(O)_2N(R^{30})_2$, —$OR^{30}$, —$OC(=O)N(R^{30})_2$, —$SR^{30}$, —$SO_2N(R^{30})_2$, —$SO_2(R^{31})$, —$OSO_2(R^{31})$ and -OSi$(R^{30})_3$; or alternatively two $R^{20}$ moieties are linked together to form a five or six membered aryl, cycloalkyl, heterocyclyl, heterocyclenyl, or heteroaryl ring wherein said five or six membered aryl, cycloalkyl, heterocyclyl, heterocyclenyl, or heteroaryl ring is fused to ring D and the fused ring is optionally substituted with 0-4 $R^{21}$ moieties;

the $R^{21}$ moieties can be the same or different, each being independently selected from the group consisting of H, alkyl, alkenyl, alkylaryl, alkynyl, alkoxy, alkylamino, alkylthiocarboxy, alkylheteroaryl, alkylthio, alkylsulfinyl, alkylsulfonyl, alkoxycarbonyl, aminoalkyl, amidinyl, aralkyl, aralkenyl, aralkoxy, aralkoxycarbonyl, aralkylthio, aryl, aroyl, aryloxy, carboxamido, cyano, cycloalkyl, cycloalkenyl, formyl, guanidinyl, halogen, haloalkyl, heteroalkyl, heteroaryl, heterocyclyl, heterocyclenyl, hydroxyalkyl, hydroxamate, nitro, trifluoromethoxy, —$(CH_2)_qOH$, —$(CH_2)_qOR^{31}$, —$(CH_2)_qNH_2$, —$(CH_2)_qNHR^{31}$, —$(CH_2)_qN(R^{31})_2$, —$(CH_2)_qC(=O)NHR^{31}$, —$(CH_2)_qSO_2R^{31}$, —$(CH_2)_qNSO_2R^{31}$, —$(CH_2)_qSO_2NHR^{31}$, -alkynylC$(R^{31})_2OR^{31}$, —$C(=O)R^{30}$, —$C(=O)N(R^{30})_2$, —$C(=NR^{30})NHR^{30}$, —$C(=NOH)N(R^{30})_2$, —$C(=NOR^{31})N(R^{30})_2$, —$C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R^{30})_2$, —$N(R^{30})C(=O)N(R^{30})SO_2(R^{31})$, —$N(R^{30})C(=O)N(R^{30})_2$, —$N(R^{30})SO_2(R^{31})$, —$N(R^{30})S(O)_2N(R^{30})_2$, —$OR^{30}$, —$OC(=O)N(R^{30})_2$, —$SR^{30}$, —$SO_2N(R^{30})_2$, —$SO_2(R^{31})$, —$OSO_2(R^{31})$, and —$OSi(R^{30})_3$;

Y is selected from the group consisting of —$(CR^{13}R^{13})_r$—, —$CHR^{13}C(=O)$—, —$(CHR^{13})_rO$—, —$(CHR^{13})_rN(R^{30})$—, —$C(=O)$—, —$C(=NR^{30})$—, —$C(=N—OR^{30})$—, —$CH(C(=O)NHR^{30})$—, —$C(H)(heteroaryl)$—, —$C(R^{13}R^{13})_rC(R^{13})=C(R^{13})$—, —$(CHR^{13})_rC(=O)$— and —$(CHR^{13})_rN(H)C(=O)$—;

the $R^{13}$ moieties can be the same or different, each being independently selected from the group consisting of H, alkyl, alkylaryl, cycloalkyl, alkoxy, aryl, heteroaryl, heterocyclenyl, heterocyclyl, spiroalkyl, —CN, —$CO_2H$, —$C(=O)R^{30}$, —$C(=O)N(R^{30})_2$, —$(CHR^{30})_qOH$, —$(CHR^{30})_qOR^{31}$, —$(CHR^{30})_qNH_2$, —$(CH R^{30})_q$NHR$^{31}$, —$(CH_2)_qC(=O)NHR^{31}$, —$(CH_2)_qSO_2R^{31}$, —$(CH_2)_qNSO_2R^{31}$, —$(CH_2)_qSO_2NHR^{31}$, —$NH_2$, —$N(R^{30})_2$, —$N(R^{30})C(=O)N(R^{30})_2$, —$N(R^{30})SO_2(R^{31})$, —OH, —$OR^{30}$, —$SO_2N(R^{30})_2$, and —$SO_2(R^{31})$;

the $R^{30}$ moieties can be the same or different, each being independently selected from the group consisting of H, alkyl, alkylaryl, aryl, aralkyl, cycloalkyl, CN, —$(CH_2)_qOH$, —$(CH_2)_qOalkyl$, —$(CH_2)_qOalkylaryl$, —$(CH_2)_qOaryl$, —$(CH_2)_qOaralkyl$, —$(CH_2)_qOcycloalkyl$, —$(CH_2)_qNH_2$, —$(CH_2)_qNHalkyl$, —$(CH_2)_qN(alkyl)_2$, —$(CH_2)_qNHalkylaryl$, —$(CH_2)_qNHaryl$, —$(CH_2)_qNHaralkyl$, —$(CH_2)_qNHcycloalkyl$, —$(CH_2)_qC(=O)NHalkyl$, —$(CH_2)_qC(=O)N(alkyl)_2$, —$(CH_2)_qC(=O)NHalkylaryl$, —$(CH_2)_qC(=O)Nharyl$, —$(CH_2)_qC(=O)NHaralkyl$, —$(CH_2)_qC(=O)NHcycloalkyl$, —$(CH_2)_qSO_2alkyl$, —$(CH_2)_qSO_2alkylaryl$, —$(CH_2)_qSO_2aryl$, —$(CH_2)_qSO_2aralkyl$, —$(CH_2)_qSO_2cycloalkyl$, —$(CH_2)_qNSO_2alkyl$, —$(CH_2)_qNSO_2alkylaryl$, —$(CH_2)_qNSO_2aryl$, —$(CH_2)_qNSO_2aralkyl$, —$(CH_2)_qNSO_2cycloalkyl$, —$(CH_2)_qSO_2NHalkyl$, —$(CH_2)_qSO_2Nhalkylaryl$, —$(CH_2)_qSO_2NHaryl$, —$(CH_2)_qSO_2NHaralkyl$, —$(CH_2)_qSO_2NHcycloalkyl$, heterocyclenyl, heterocyclyl, and heteroaryl;

the $R^{31}$ moieties can be the same or different, each being independently selected from the group consisting of alkyl, alkylaryl, aryl, aralkyl, cycloalkyl, —$(CH_2)_qOH$, —$(CH_2)_qOalkyl$, —$(CH_2)_qOalkylaryl$, —$(CH_2)_qOaryl$, —$(CH_2)_qOaralkyl$, —$(CH_2)_qOcycloalkyl$, —$(CH_2)_qNH_2$, —$(CH_2)_qNHalkyl$, —$(CH_2)_qN(alkyl)_2$, —$(CH_2)_qNHalkylaryl$, —$(CH_2)_qNHaryl$, —$(CH_2)_qNHaralkyl$, —$(CH_2)_qNHcycloalkyl$, —$(CH_2)_qC(=O)NHalkyl$, —$(CH_2)_qC(=O)N(alkyl)_2$, —$(CH_2)_qC(=O)NHalkylaryl$, —$(CH_2)_qC(=O)NHaryl$, —$(CH_2)_qC(=O)NHaralkyl$, —$(CH_2)_qC(=O)Nhcycloalkyl$, —$(CH_2)_qSO_2alkyl$, —$(CH_2)_qSO_2alkylaryl$, —$(CH_2)_qSO_2aryl$, —$(CH_2)_qSO_2aralkyl$, —$(CH_2)_qSO_2cycloalkyl$, —$(CH_2)_qNSO_2alkyl$, —$(CH_2)_qNSO_2alkylaryl$, —$(CH_2)_qNSO_2aryl$, —$(CH_2)_qNSO_2aralkyl$, —$(CH_2)_qNSO_2cycloalkyl$, —$(CH_2)_qSO_2NHalkyl$, —$(CH_2)_qSO_2Nhalkylaryl$, —$(CH_2)_qSO_2NHaryl$, —$(CH_2)_qSO_2NHaralkyl$, —$(CH_2)_qSO_2NHcycloalkyl$, heterocyclenyl, heterocyclyl, and heteroaryl;

m is 0 to 4;

n is 0 to 4;

each q can be the same or different, each being independently selected from 1 to 5; and r is 1 to 4;

with the proviso that there are no two adjacent double bonds in any ring, and that when a nitrogen is substituted by two alkyl groups, said two alkyl groups may be optionally joined to each other to form a ring.

2. The compound according to claim 1, wherein $R^1$ and $R^2$ are independently absent or present, and if present each is independently selected from the group consisting of H, alkyl, aryl, amino, alkoxy, halogen, hydroxy, cycloalkyl, cycloalkenyl, arylalkyl, amidinyl, carboxamido, heteroaryl, heterocyclyl, heterocyclenyl, urea, —$S(O)_2alkyl$, —$S(O)_2N(H)alkyl$, —$S(O)_2heteroaryl$, —$S(O)_2heterocyclyl$, —$C(=O)$heteroaryl, —$C(=O)$heterocyclyl, —$S(O)_2N(alkyl)_2$, and —$C(=S)N(H)cycloalkyl$.

3. The compound according to claim 1, wherein $R^1$ and $R^2$ are independently absent or present, and if present each is independently selected from the group consisting of H, alkylaryl, aryl, heteroaryl, —$(CH_2)_qCF3$, $(CH_2)_qOH$, —$(CH_2)_qOR^{31}$, —$(CH_2)_qNH_2$, —$(CH_2)_qNH R^{31}$, —$(CH_2)_qN(R^{31})_2$, —$(CH_2)_qC(=O)NH R^{31}$, —$(CH_2)_qSO_2R^{31}$, —$(CH_2)_q$ NHSO$_2$R$^{31}$, —(CH$_2$)$_q$SO$_2$NHR$^{31}$, —(CH$_2$)$_q$amidinyl, cyclopropyl, cyclopropylhydroxyl, cyclobutyl, cyclobutylhydroxy, cyclopentyl, and cyclopentylhydroxy; and q is an integer from 1 to 5.

4. The compound according to claim 1, wherein R$^1$ and R$^2$ are independently absent or present, and if present each is independently selected from the group consisting of H, —CH$_3$, fluorophenylmethylene, trifluoromethylphenylmethylene, indanyl, cyanophenylmethylene, difluorophenylmethylene, bromophenylmethylene, chlorophenylmethylene, —CH$_2$CH$_2$Ophenyl, cyclopentyl, bromochlorophenylmethylene fluorochlorophenylmethylene, dichlorophenylmethylene, phenylmethylene, —(CH$_2$)$_3$phenyl, —CH$_2$CF3, methoxylphenylmethylene, —CH(CH$_3$)$_2$, —C$_2$H$_5$, —CH$_2$-cyclopropyl, —(CH$_2$)$_2$CH$_3$, cyclohexylmethylene, cyclohexyl, —CH$_2$CH$_2$SO$_2$CH$_3$, —CH$_2$—CH$_2$—NH$_2$, —CH$_2$CH$_2$CH$_3$, cyclopropyl, isoxazolyl, —CH$_2$CH$_2$OH, —CH$_2$CH$_2$Ophenyl, —CH$_2$CH$_2$CH$_3$, —NH$_2$, —(CH$_2$)$_2$NH$_2$, pyrazolyl, 5-methyl-isoxazolyl, —CH$_2$CH(OCH$_2$CH$_3$)$_2$, —OCH$_3$, —NHC(=O)NH$_2$, chloropyridyl, pyridylmethylene, —C(=O)NHcyclopropyl, —C(=O)N(H)C$_2$H$_5$. —C(=O)N(H)CH$_2$CF$_3$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, —C(=O)N(H)CH(CH$_3$)$_2$, thiazolyl, —C(=O)N(CH$_3$)$_2$, —S(O)$_2$CH$_2$CF$_3$, cyclopropyl, —S(O)$_2$CF$_3$, —CH$_2$CH(OCH$_2$CH$_3$)$_2$,

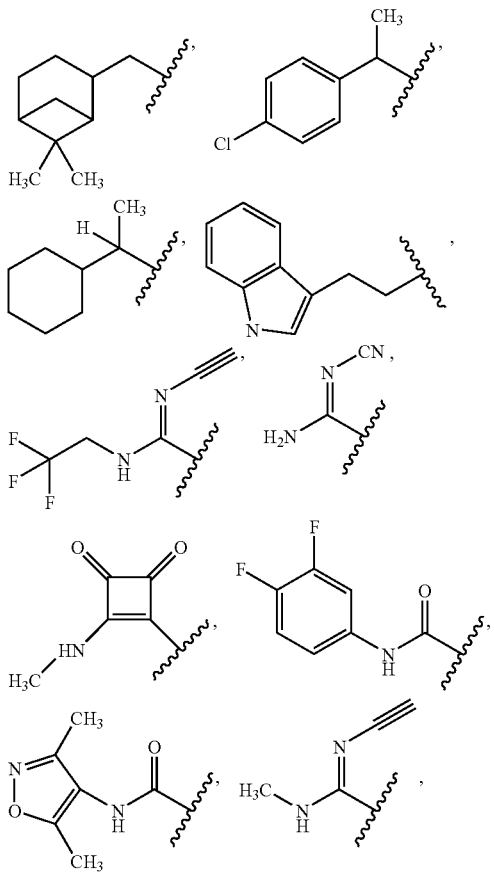

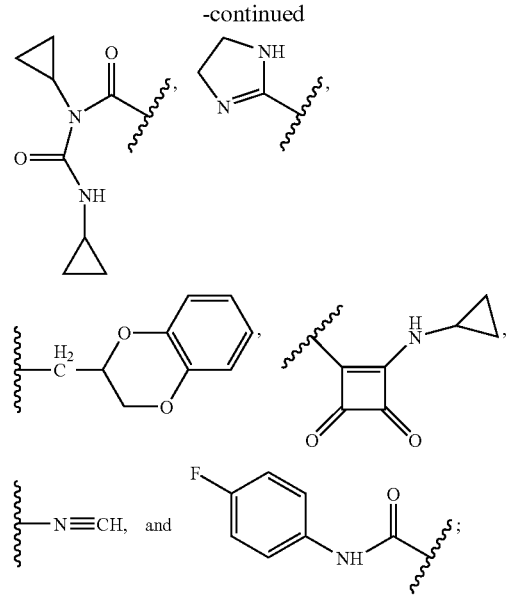

or when X is N, the N taken together with the R$^1$ and R$^2$ to which X is shown attached, forms a —N-cyclopropyl, —N-cyclobutyl, —N-cyclohexyl or

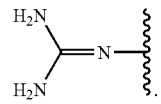

5. The compound according to claim 1, wherein R$^1$ and R$^2$ are independently absent or present, and if present each is independently selected from the group consisting of H, —CH$_3$, —C$_2$H$_5$, difluorophenylmethylene, cyclopropyl, dichlorophenylmethylene, —CH(CH$_3$)$_2$, cyclohexylmethylene, cyclohexyl, isoxazolyl, difluorophenvi, —CH$_2$CH$_2$OH, —CH$_2$, —CH$_2$—N(CH$_3$))$_2$, —C(=O)N(H)cyclopropyl, —C(=O)N(H)C$_2$H$_5$, —C(=O)N(H)CH$_2$CF3, —C(=O)N(H)CH(CH$_3$)$_2$, —C(=O)N(H)C(CH$_3$)$_3$, —C(=S)N(H)cyclopropyl, —C(=O)NH$_2$, —C(=O)N(H)CH$_3$, —S(O)$_2$CH$_3$, —S(O)$_2$N(CH$_3$)$_2$, —S(O)$_2$CH$_2$CH$_3$, —C(=O)CH$_3$, —S(O)$_2$(CH$_2$)$_2$CH$_3$, —C(=O)N(H)cyclohexyl, —C(=NH)NH$_2$, —C(=O)N(H)NH$_2$, thiazolyl,

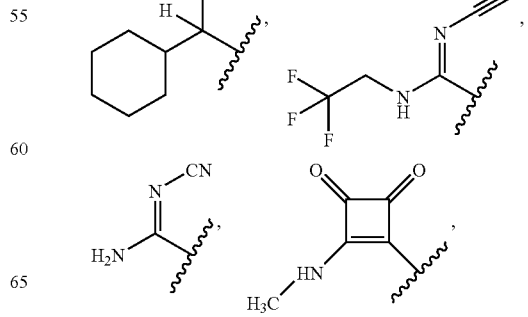

-continued

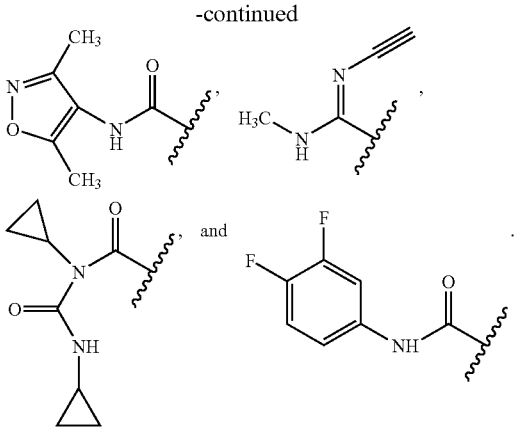

6. The compound according to claim 1, wherein Z is N.

7. The compound according to claim 1, wherein G is N or C($R^4$).

8. The compound according to claim 7, wherein G is N.

9. The compound according to claim 7, wherein G is C($R^4$).

10. The compound according to claim 7, wherein G is C(H), C(alkyl), C(halogen), C($CF_3$) or C(N($R^{30}$)$_2$).

11. The compound according to claim 1, wherein G and Z are N.

12. The compound according to claim 1, wherein G is C($R^4$) and Z is N.

13. The compound according to claim 1, wherein $R^3$ is selected from the group consisting of H, alkyl, haloalkyl, hydroxyalkyl, halogen, —N($R^{30}$)$_2$, —$OR^{30}$ and —$CF_3$.

14. The compound according to claim 13, wherein $R^3$ is selected from the group consisting of H, —$CH_3$, —$CH_2CH_3$, cyclopropyl, —F, —Cl, $OCH_3$, $OCF_3$ and $CF_3$.

15. The compound according to claim 1, wherein Z is N and $R^4$ is selected from the group consisting of H, alkyl, hydroxyalkyl, halogen, $OR^{30}$, or $CF_3$.

16. The compound according to claim 1, wherein $R^6$ is selected from the group consisting of H, alkyl, halogen, hydroxyalkyl, —CN, —N($R^{30}$)$_2$, —$OR^{30}$, —N=CH-alkyl, and —$NR^{30}$C(=O)alkyl.

17. The compound according to claim 16, wherein $R^6$ is selected from the group consisting of H, —$NH_2$, —$CH_3$, —CN and —F.

18. The compound according to claim 1, wherein $R^{10}$ is selected from the group consisting of H, alkyl, aralkyl, hydroxyalkyl, and carbonyl.

19. The compound according to claim 18, wherein $R^{10}$ is selected from the group consisting of —$CH_3$, —$CH_2CH_3$ and —$CH_2CH_2CH_3$, and m is 0-2.

20. The compound according to claim 1, wherein $R^{11}$ is selected from the group consisting of H, alkyl, hydroxyalkyl and carbonyl.

21. The compound according to claim 20, wherein $R^{11}$ is H or —$CH_3$.

22. The compound according to claim 1, wherein $R^{12}$ is selected from the group consisting of H, CN, —C(=O)N($R^{30}$)$_2$ and alkyl.

23. The compound according to claim 22, wherein $R^{12}$ is selected from the group consisting of H, —$CH_3$, CN and —$CH_2CH_3$.

24. The compound according to claim 1, wherein the ring atoms of ring D are independently C or N and substituted by independently selected 0-4 $R^{20}$ moieties.

25. The compound according to claim 1, wherein ring D is a 5 to 6 membered aryl, heteroaryl, heterocyclenyl, or heterocyclyl ring and substituted by independently selected 0-4 $R^{20}$ moieties.

26. The compound according to claim 1, wherein the $R^{20}$ moieties can be the same or different, each being independently selected from the group consisting of H, alkyl, alkylaryl, alkynyl, alkoxy, alkylamino, alkylheteroaryl, alkylsulfinyl, alkoxycarbonyl, aminoalkyl, amidinyl, aralkyl, araikoxy, aryl, aryloxy, cyano, cycloalkyl, cycloalkenyl, halogen, haloalkyl, heteroalkyl, heteroaryl, heterocyclyl, hydroxyalkyl, trifluoromethyl, trifluoromethoxy, —(CH$_2$)$_q$$OR^{31}$, —(CH$_2$)$_q$$NHR^{31}$, —(CH$_2$)$_q$C(=O)$NHR^{31}$, —(CH$_2$)$_q$$SO_2R^{31}$, —(CH$_2$)$_q$$NSO_2R^{31}$, —(CH$_2$)$_q$$SO_2NHR^{31}$, -alkynylC($R^{31}$)$_2$$OR^{31}$, —C(=O)$R^{30}$, —C(=O)N($R^{30}$)$_2$, —C(=O)$OR^{30}$, —N($R^{30}$)$_2$, —N($R^{30}$)C(=O)$R^{31}$, —NHC(=O)N($R^{30}$)$_2$, —N($R^{30}$)C(=O)$OR^{30}$, —N($R^{30}$)C(=NCN)N($R^{30}$)$_2$, —N($R^{30}$)C(=O)N($R^{30}$)$_2$, —N($R^{30}$)$SO_2(R^{31})$, —N($R^{30}$)$SO_2$N($R^{30}$)$_2$, —$OR^{30}$, —OC(=O)N($R^{30}$)$_2$, —$SR^{30}$, —$SO_2$N($R^{30}$)$_2$, —$SO_2(R^{31})$, —$OSO_2(R^{31})$, and —OSi($R^{30}$)$_3$.

27. The compound according to claim 1, wherein the $R^{20}$ moieties can be the same or different, each being independently selected from the group consisting of H, alkyl, amino, halogen, CN, $CH_3$, CF3, $OCF_3$, —(CH$_2$)$_q$$OR^{31}$, —(CH$_2$)$_q$$NHR^{31}$, —(CH$_2$)$_q$C(=O)$NHR^{31}$, —(CH$_2$)$_q$$SO_2R^{31}$, —(CH$_2$)$_q$$NSO_2R^{31}$, —(CH$_2$)$_q$$SO_2NHR^{31}$, -alkynylC($R^{31}$)$_2$$OR^{31}$, —C(=O)$R^{30}$, —C(=O)$OR^{30}$, —N($R^{30}$)$_2$, —N($R^{30}$)C(=O)$R^{31}$, —NHC(=O)N($R^{30}$)$_2$, —N($R^{30}$)C(=O)$OR^{31}$, —N($R^{30}$)C(=NCN)N($R^{30}$)$_2$, —N($R^{30}$)C(=O)N($R^{30}$)$_2$, —$OR^{30}$, —OC(=O)N($R^{30}$)$_2$, and —$OSO_2(R^{31})$.

28. The compound according to claim 1, wherein two $R^{20}$ moieties are linked together to form a five or six membered aryl, cycloalkyl, heterocyclenyl, heterocyclyl or heteroaryl ring wherein said five or six membered aryl, cycloalkyl, heterocyclenyl, heterocyclyl, and heteroaryl ring is fused to ring D and the fused ring is optionally substituted with 0 to 4 $R^{21}$ moieties.

29. The compound according to claim 1, wherein the $R^{20}$ moieties can be the same or different, each being independently selected from the group consisting of H, —CN, —$CH_3$, —$CF_3$, —$CH_2OH$, —$CO_2H$, —$CO_2CH_3$, —$NH_2$, —$NHCH_3$, —$OCF_3$, —OH, F, Cl, Br, —C(=NOH)$NH_2$, —$OCH_2CH_2S(O_2)CH_3$, —C(=O)$NH_2$,

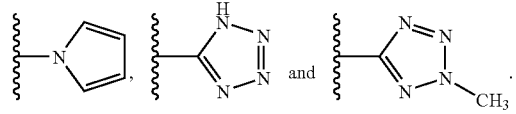

30. The compound according to claim 1, wherein Y is selected from the group consisting of: —(CHR$^{13}$)$_r$—, —(CR$^{13}$R$^{13}$)$_r$—, —C(=O)— and —CHR$^{13}$C(=O)—.

31. The compound according to claim 1, wherein Y is selected from the group consisting of: —$CH_2$—, —CH(CH$_3$)—, —CH(CH$_2$OH)—, —O(=O)— and —CH(CO$_2$alkyl)—.

32. The compound according to claim 1, wherein m is 0-3.

33. The compound according to claim 1, wherein n is 0-2.

34. The compound according to claim 1, wherein q is 1, 2 or 3.

35. The compound according to claim 1, wherein r is 1 or 2.

36. The compound according to claim 1, wherein Z is N, G is N or C($R^4$);

$R^1$ and $R^2$ are independently absent or present, and if present each is independently selected from the group consisting of H, alkylaryl, aryl, heteroaryl, —$(CH_2)_q$ $CF_3$, —$(CH_2)_q OH$, —$(CH_2)_q OR^{31}$, $(CH_2)_q NH_2$, —$(CH_2)_q NHR^{31}$, —$(CH_2)_q N(R^{31})_2$, —$(CH_2)_q C(=O)NHR^{31}$, —$(CH_2)_q SO_2 R^{31}$, —$(CH_2)_q NHSO_2 R^{31}$, —$(CH_2)_q SO_2 NHR^{31}$, —$(CH_2)_q$amidinyl, cyclopropyl, cyclopropylhydroxyl, cyclobutyl, cyclobutylhydroxy, cyclopentyl, and cyclopentylhydroxy;

$R^3$ is selected from the group consisting of H, alkyl, haloalkyl, hydroxyalkyl, halogen, —$N(R^{30})_2$, —$OR^{30}$ and —$CF_3$;

$R^4$ is selected from the group consisting of H, alkyl, haloalkyl, hydroxyalkyl, halogen, —$N(R^{30})_2$, —$OR^{30}$ and —$CF_3$;

$R^6$ is selected from the group consisting of H, alkyl, halogen, hydroxyalkyl, —CN, —$N(R^{30})_2$, —$OR^{30}$, —N=OH-alkyl, and —$NR^{30}C(=O)$alky;

$R^{10}$ is selected from the group consisting of H, alkyl, aralkyl, hydroxyalkyl, and carbonyl;

$R^{11}$ is selected from the group consisting of H, alkyl, hydroxyalkyl, and carbonyl;

$R^{12}$ is selected from the group consisting of H, CN, —$C(=O)N(R^{30})_2$ and alkyl;

ring D is a 5 to 6 membered aryl, heteroaryl, heterocyclenyl, or heterocyclyl ring and substituted by 0-4 $R^{20}$ moieties;

the $R^{20}$ moieties can be the same or different, each being independently selected from the group consisting of H, alkyl, amino, halogen, CN, $CH_3$, $CF_3$, $OCF_3$, —$(CH_2)_q OR^{31}$, —$(CH2)_q NHR^{31}$, —$(CH_2)_q C(=O)NHR^{31}$, $(CH_2)_q SO_2 R^{31}$, —$(CH_2)_q NSO_2 R^{31}$, —$(CH_2)_q SO_2 NHR^{31}$, -alkynyl$C(R^{31})_2 OR^{31}$, —$C(=O)R^{30}$, $C(=O)OR^{30}$, —$N(R^{30})_2$, —$N(R^{30})C(=O)R^{31}$, —$NHC(=O)N(R^{30})_2$, —$N(R^{30})C(=O)OR^{31}$, —$N(R^{30})C(=NCN)N(R)_2$, —$N(R^{30})C(=O)N(R^{30})_2$, —$OR^{30}$, —$OC(=O)N(R^{30})_2$,

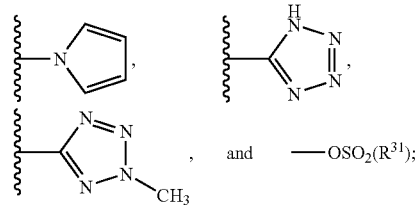

and —$OSO_2(R^{31})$;

Y is selected from the group consisting of: —$CH_2$—, —$CH(CH_3)$—, —$CH(CH_2 OH)$—, —$C(=O)$— and —$CH(CO_2 alkyl)$—;

m is 0-2;
n is 0-2;
q is 1 or 2; and
r is 1 or 2.

37. A compound selected from the group consisting of:

| Compound No. | STRUCTURE |
|---|---|
| 1 | 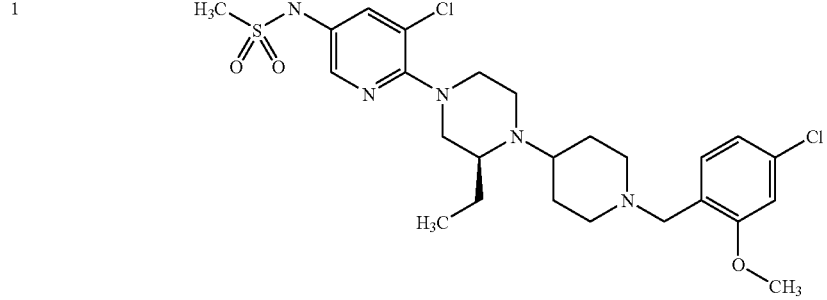 |
| 2 | 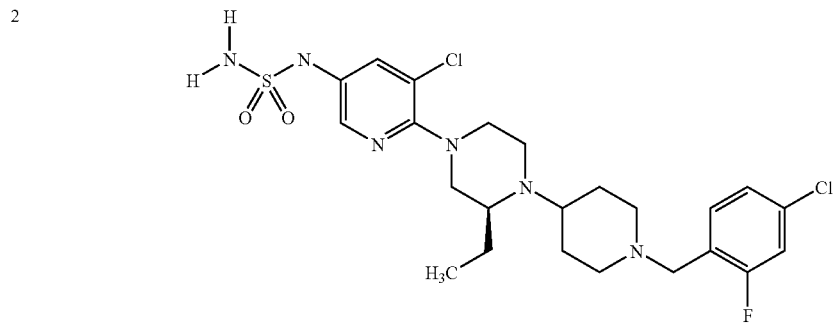 |

-continued
| Compound No. | STRUCTURE |
|---|---|
| 3 | 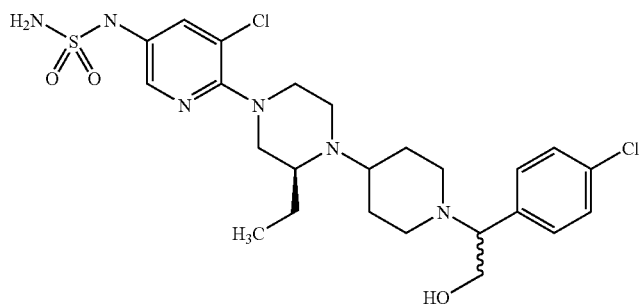 |
| 4 | 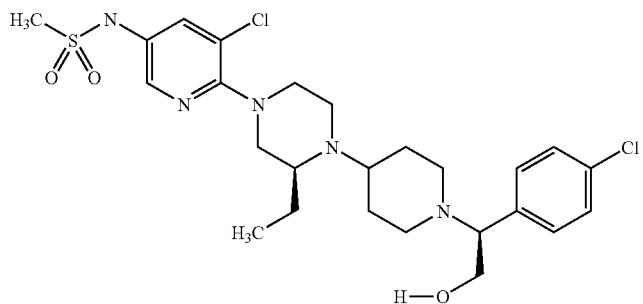 |
| 5 | 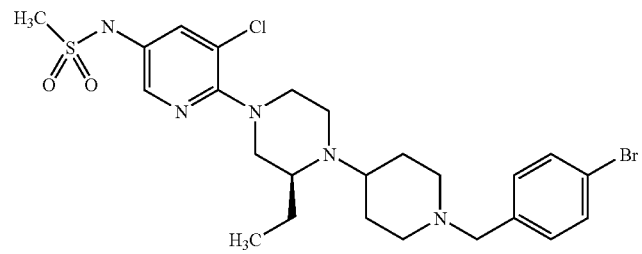 |
| 6 | 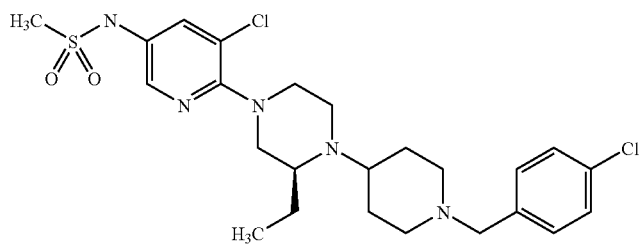 |
| 7 | 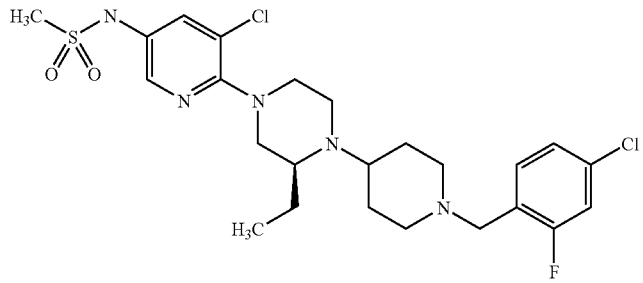 |

-continued
| Compound No. | STRUCTURE |
|---|---|
| 8 | 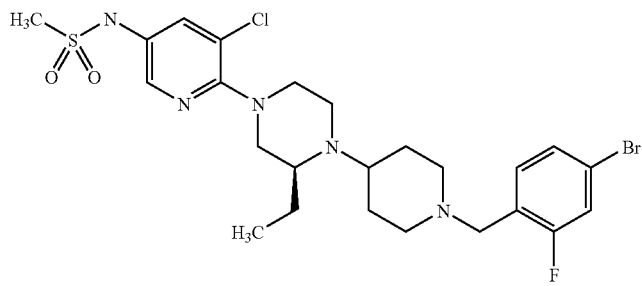 |
| 9 | 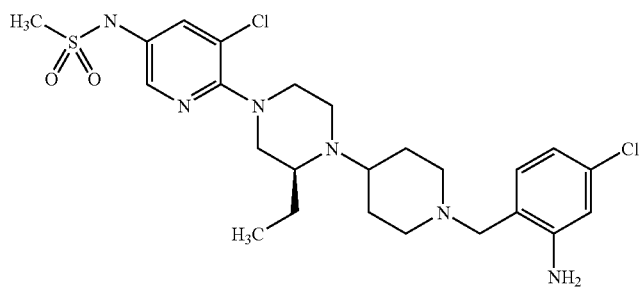 |
| 10 | 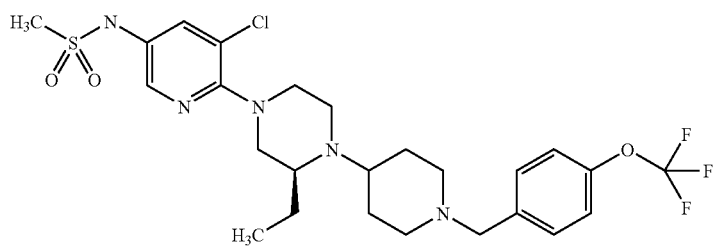 |
| 11 | 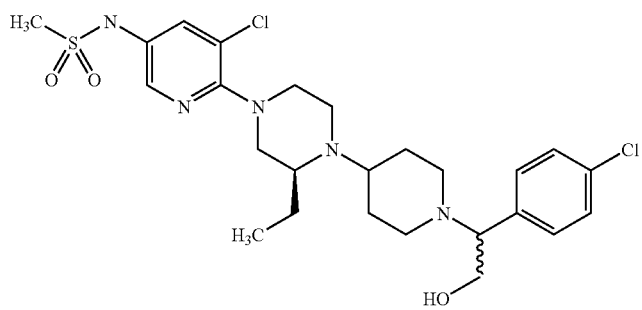 |
| 12 | 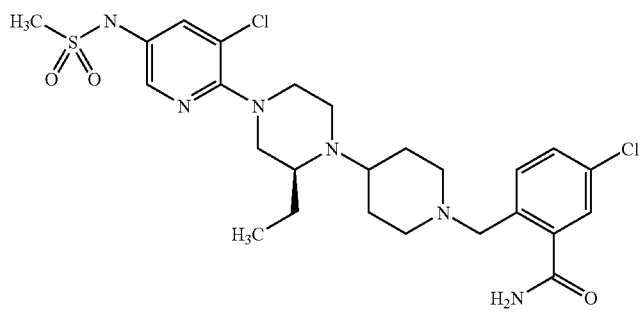 |

-continued
| Compound No. | STRUCTURE |
|---|---|
| 13 | 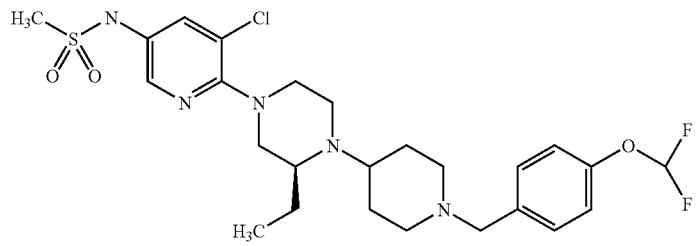 |
| 14 | 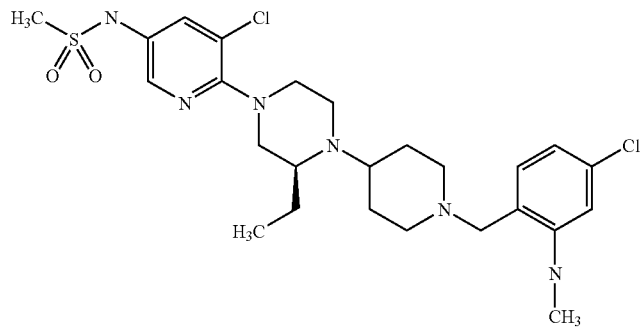 |
| 15 | 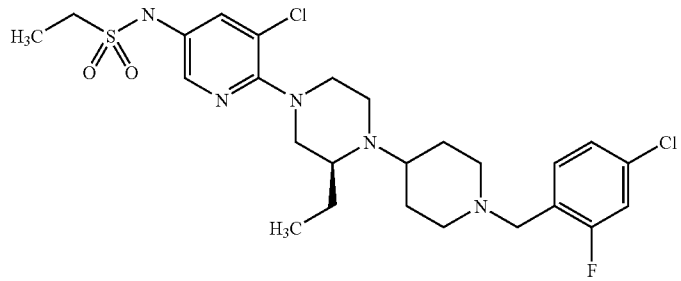 |
| 16 | 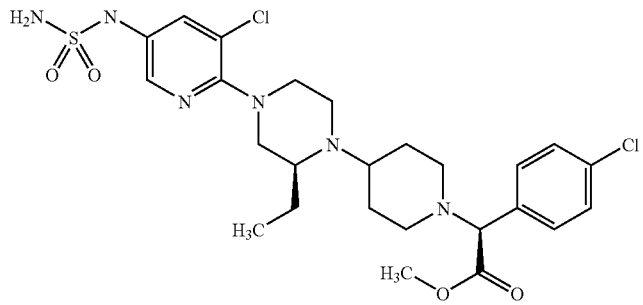 |
| 17 | 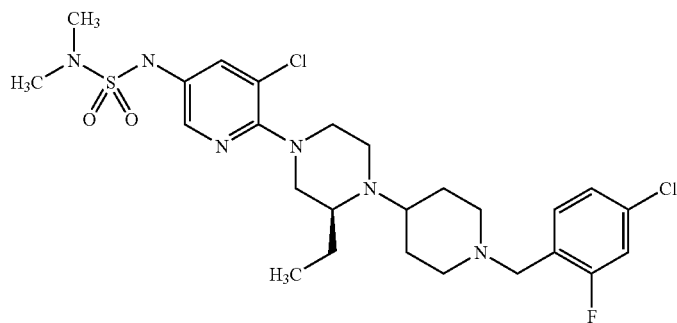 |

-continued
| Compound No. | STRUCTURE |
|---|---|
| 18 | 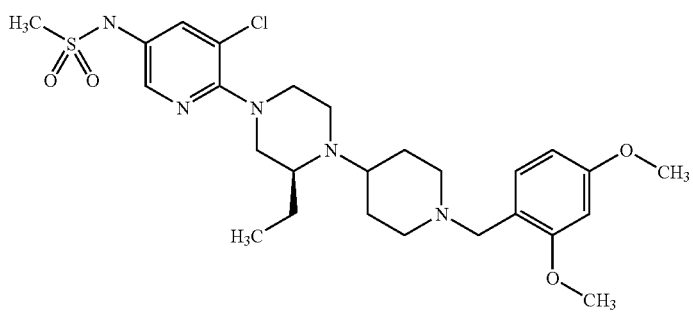 |
| 19 | 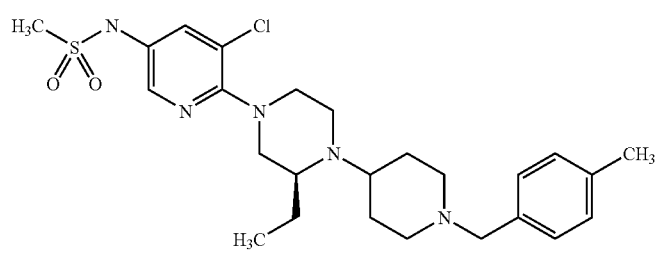 |
| 20 | 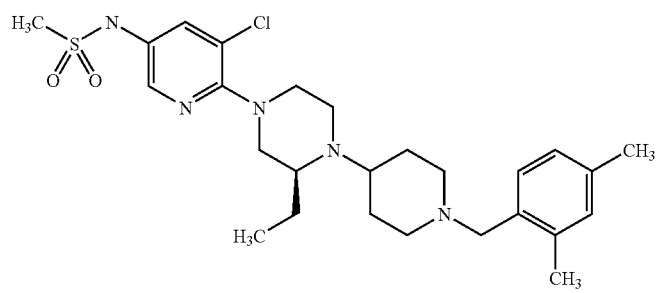 |
| 21 | 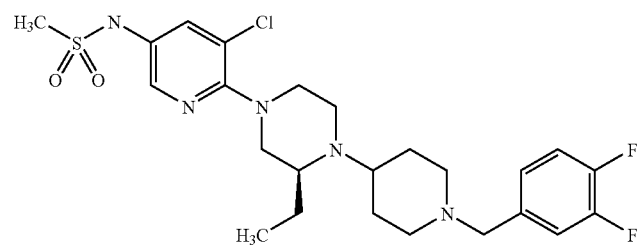 |
| 22 | 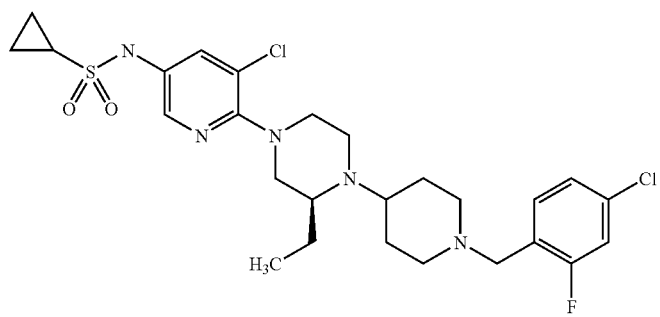 |

-continued
| Compound No. | STRUCTURE |
|---|---|
| 23 | 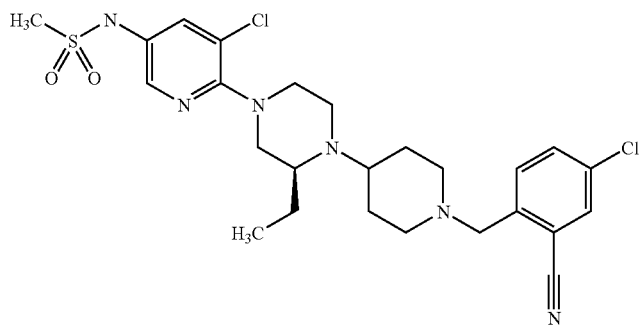 |
| 24 | 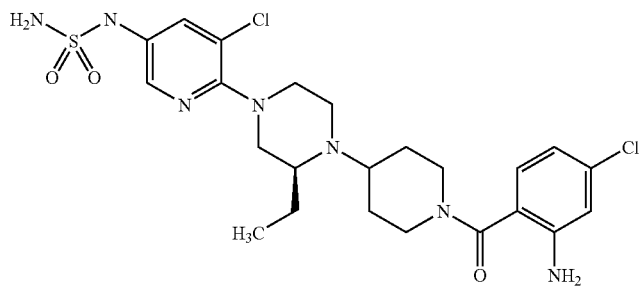 |
| 25 | 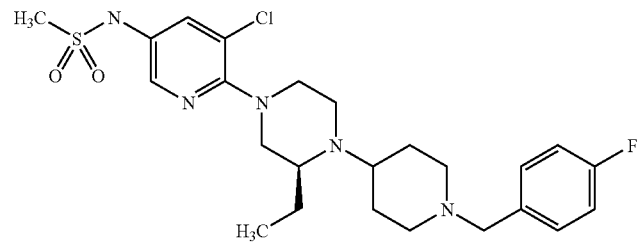 |
| 26 | 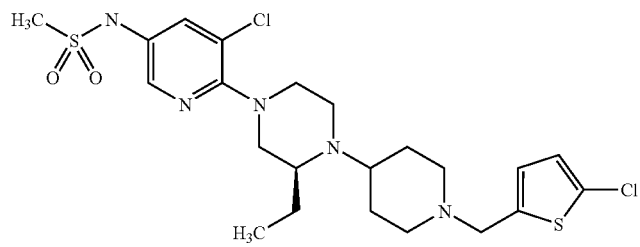 |
| 27 | 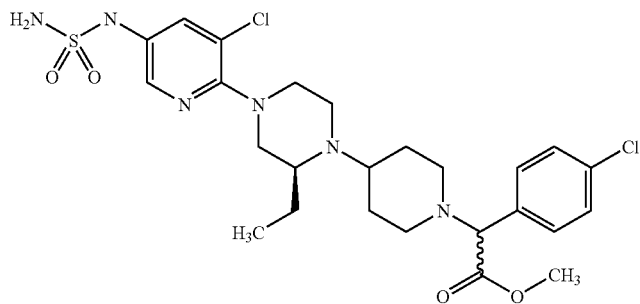 |

-continued
| Compound No. | STRUCTURE |
|---|---|
| 28 | 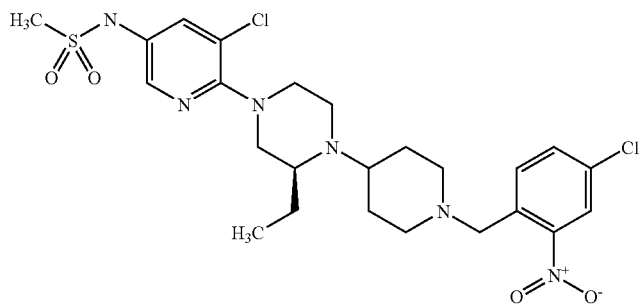 |
| 29 | 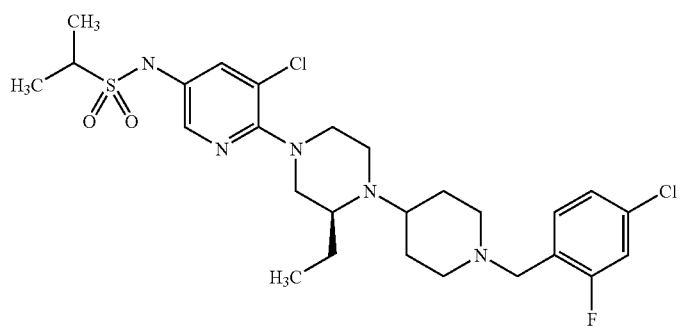 |
| 30 | 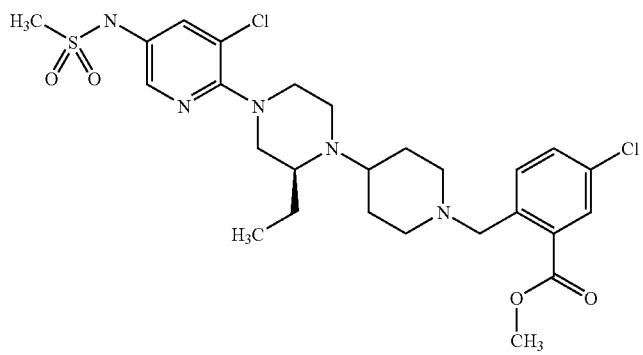 |
| 31 | 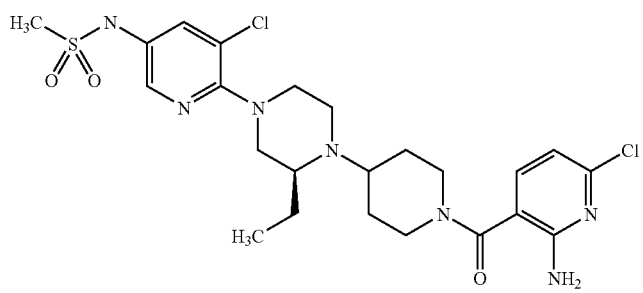 |
| 32 | 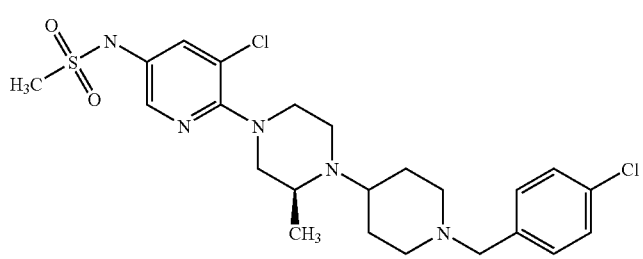 |

| Compound No. | STRUCTURE |
|---|---|
| 33 | 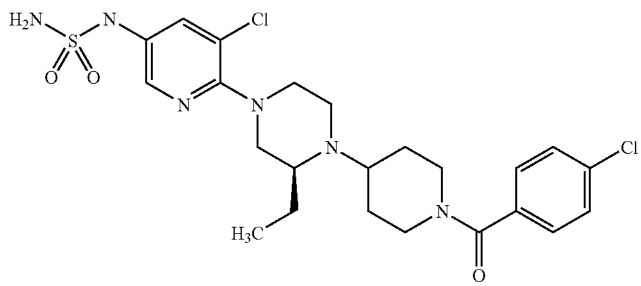 |
| 34 | 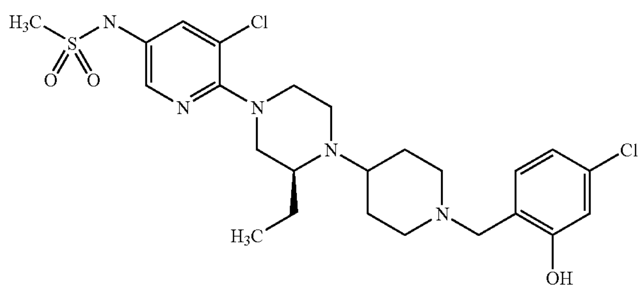 |
| 35 | 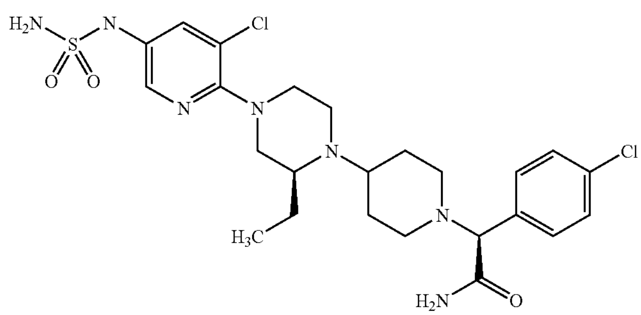 |
| 36 | 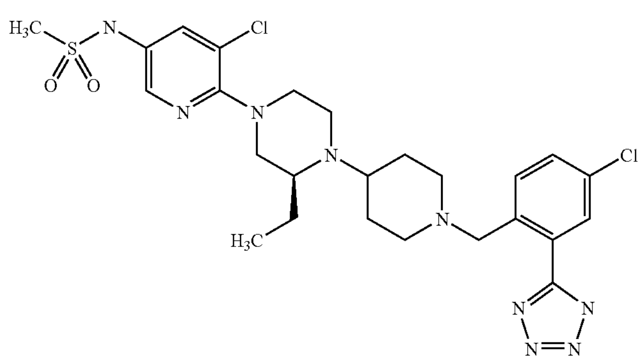 |
| 37 | 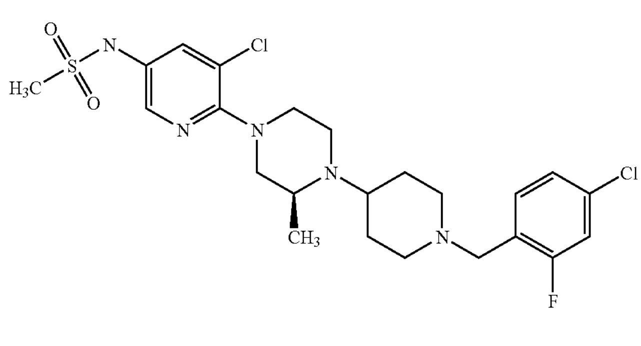 |

-continued
| Compound No. | STRUCTURE |
|---|---|
| 38 | 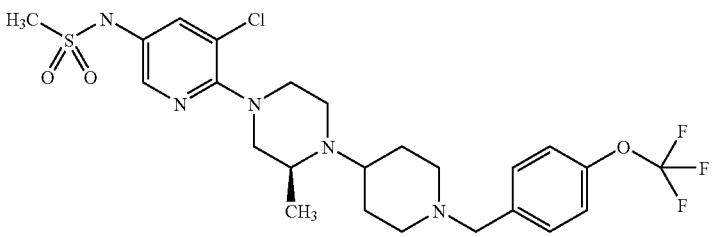 |
| 39 | 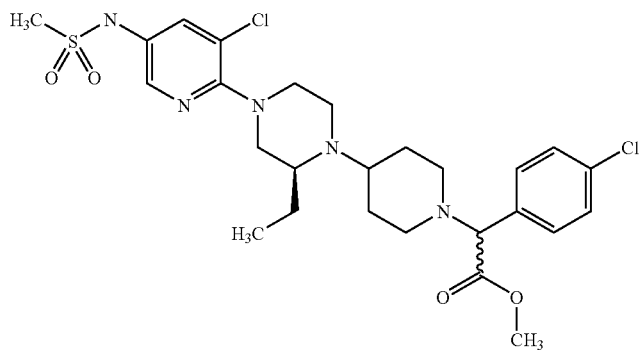 |
| 40 | 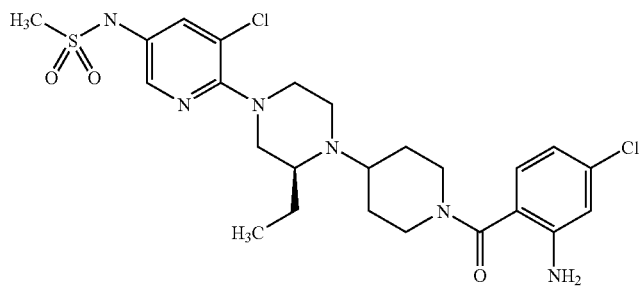 |
| 41 | 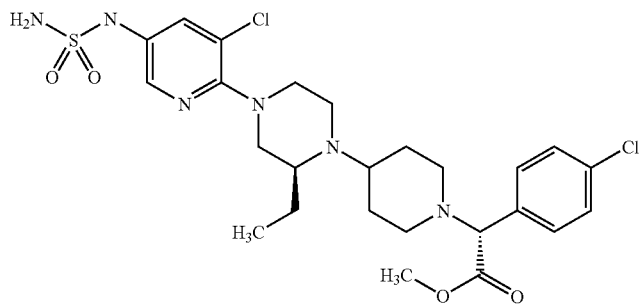 |
| 42 | 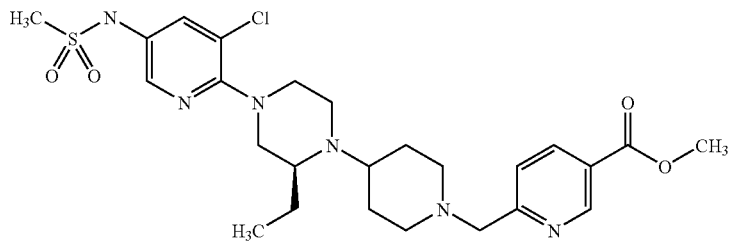 |

-continued
| Compound No. | STRUCTURE |
|---|---|
| 43 | 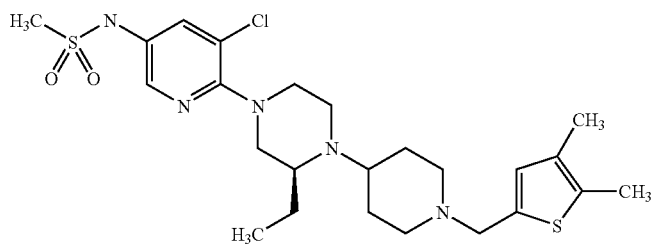 |
| 44 | 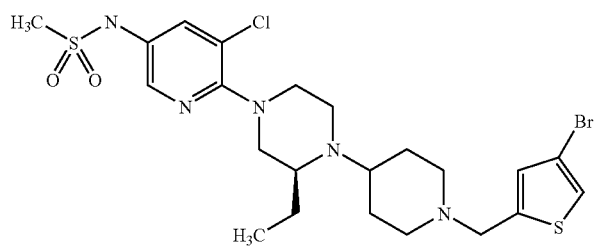 |
| 45 | 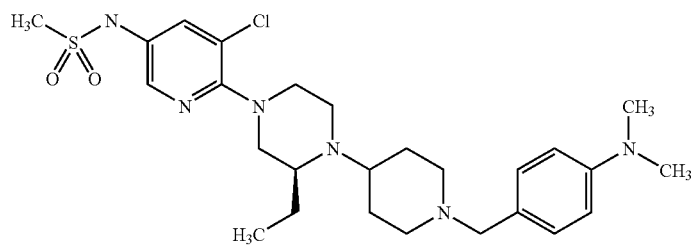 |
| 46 | 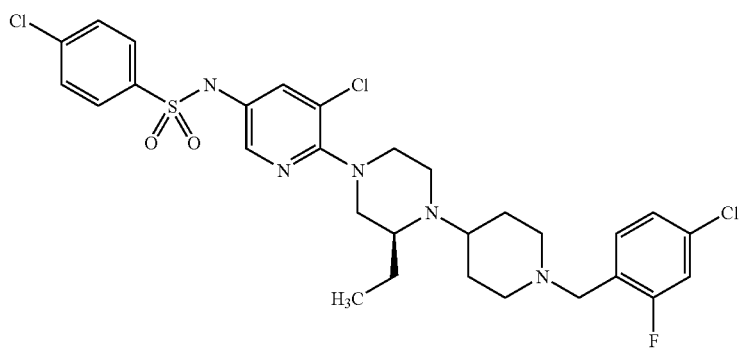 |
| 47 | 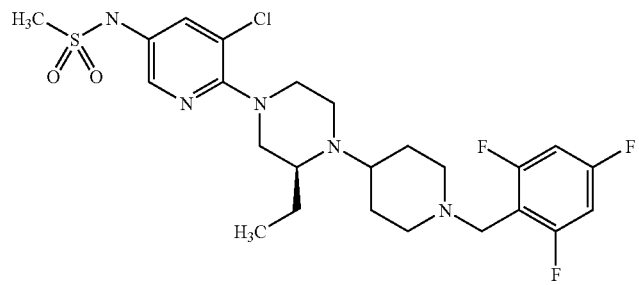 |

-continued
| Compound No. | STRUCTURE |
|---|---|
| 48 | 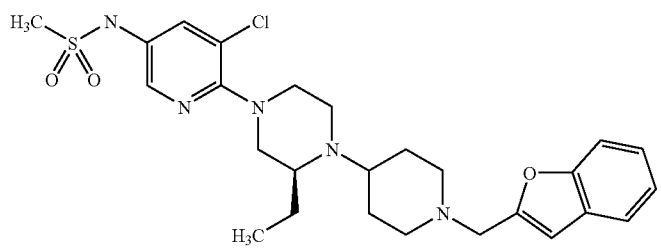 |
| 49 | 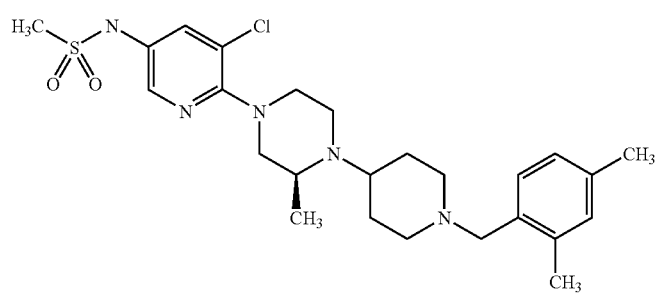 |
| 50 | 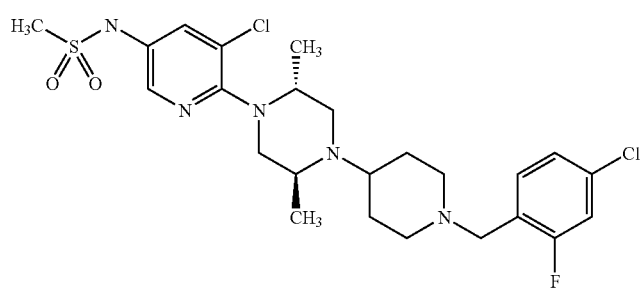 |
| 51 | 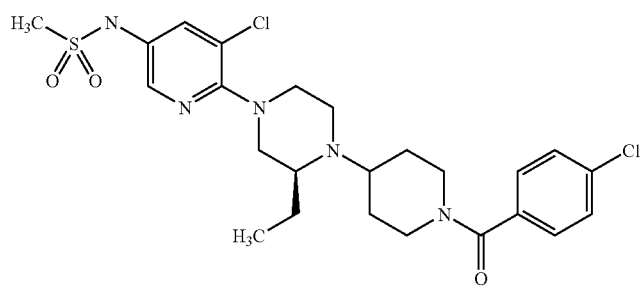 |
| 52 | 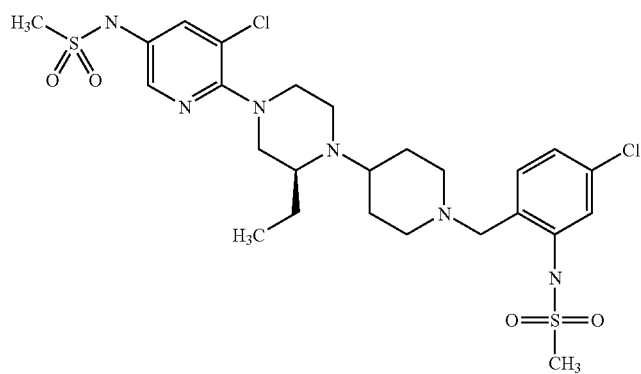 |

| Compound No. | STRUCTURE |
|---|---|
| 53 | 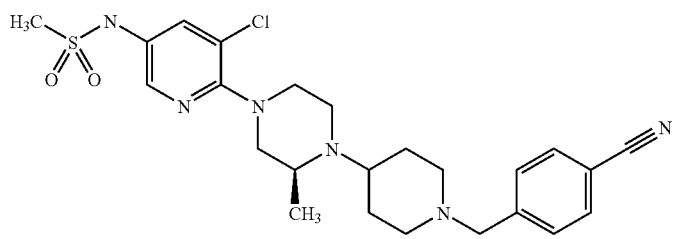 |
| 54 | 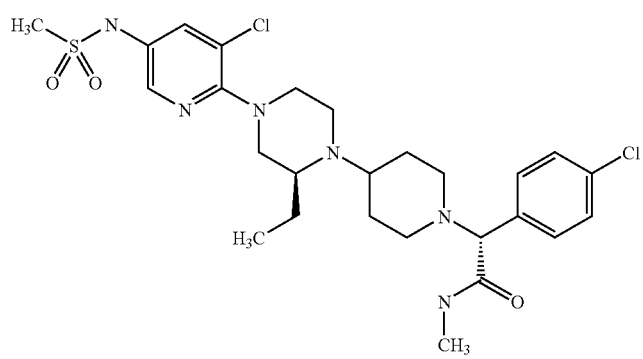 |
| 55 | 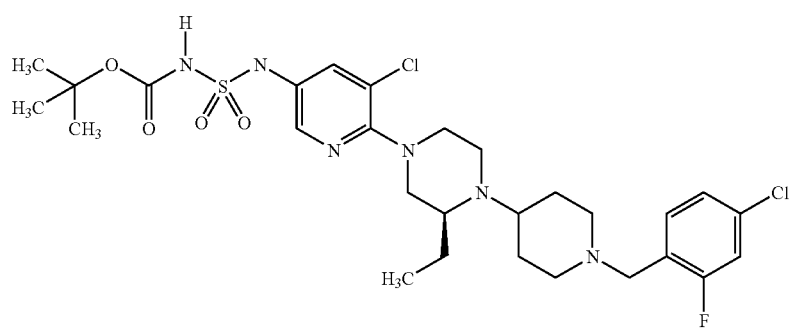 |
| 56 | 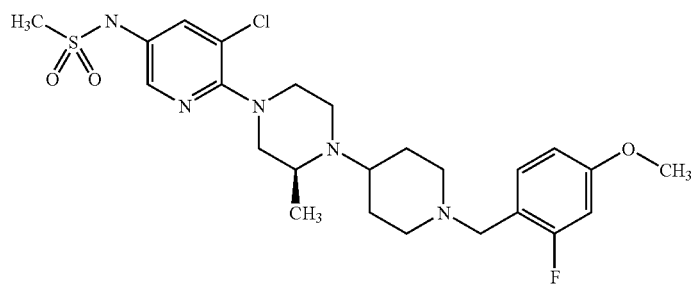 |
| 57 | 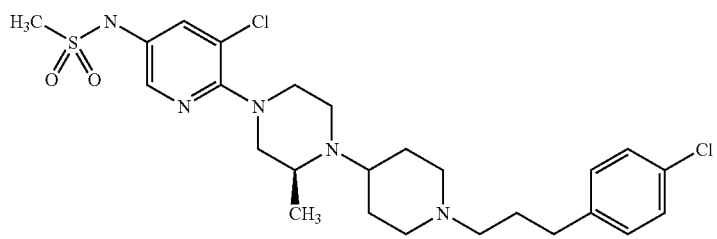 |

-continued
| Compound No. | STRUCTURE |
|---|---|
| 58 | 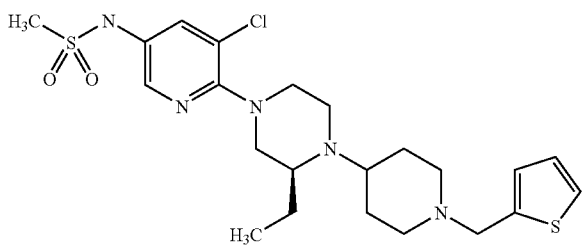 |
| 59 | 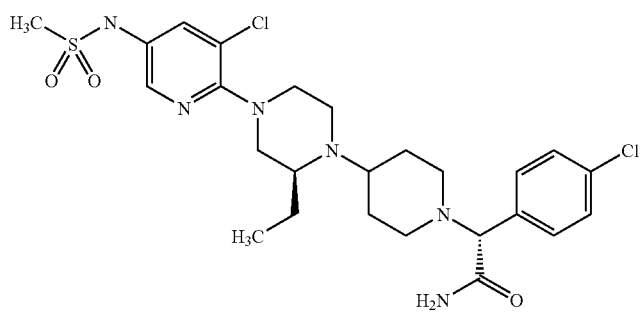 |
| 60 | 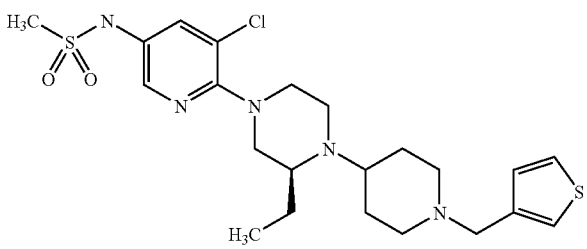 |
| 61 | 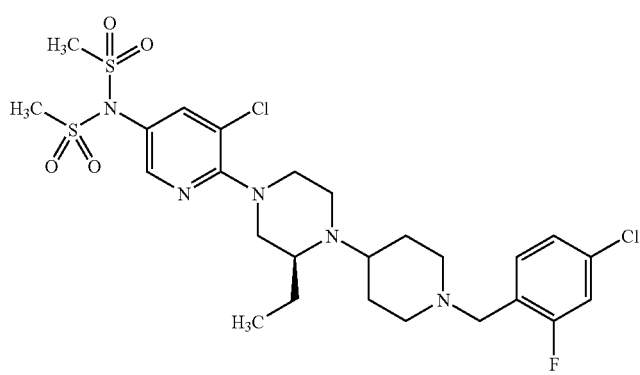 |
| 62 | 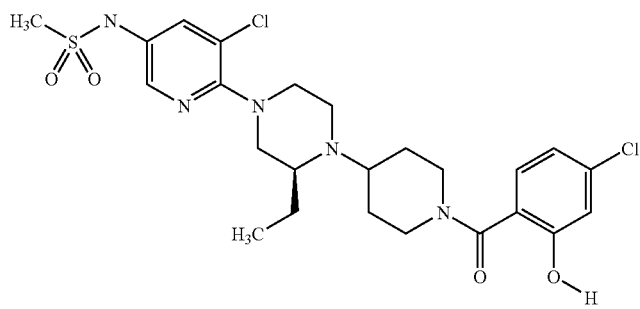 |

-continued
| Compound No. | STRUCTURE |
|---|---|
| 63 | 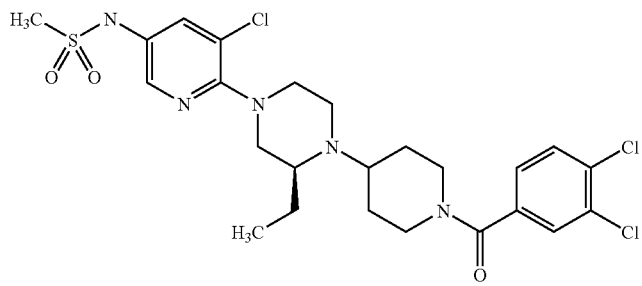 |
| 64 | 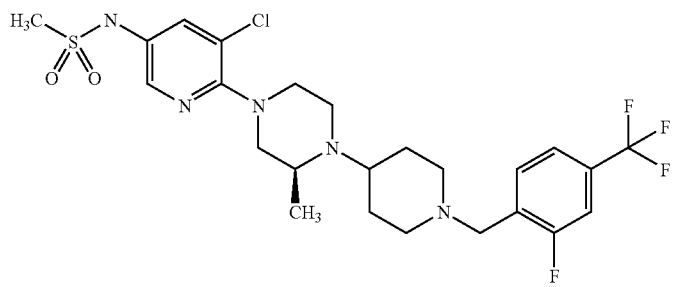 |
| 65 | 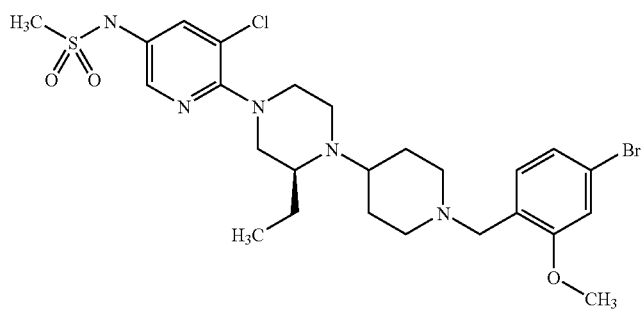 |
| 66 | 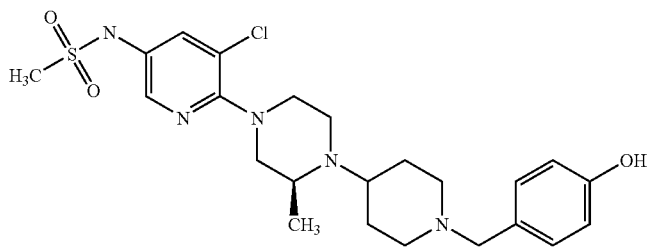 |
| 67 | 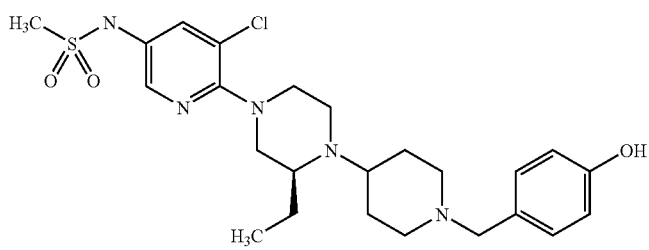 |

-continued

| Compound No. | STRUCTURE |
|---|---|
| 68 | 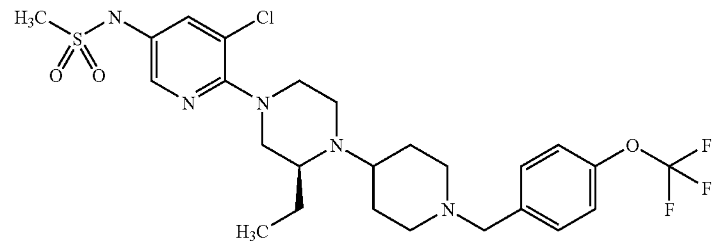 |
| 69 | 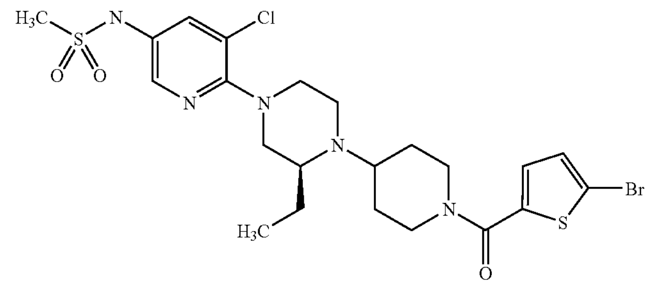 |
| 70 | 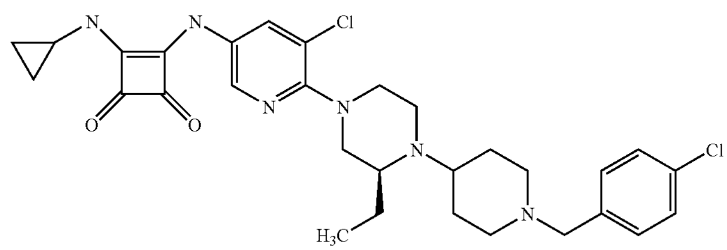 |
| 71 | 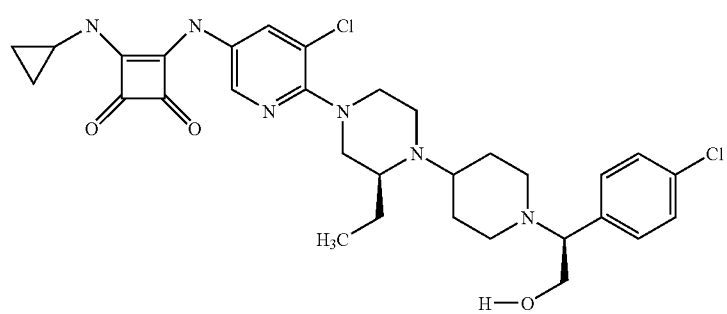 |
| 72 | 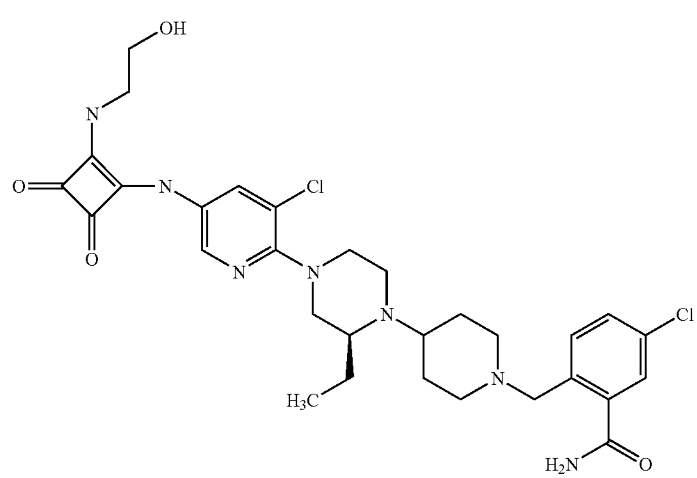 |

-continued
| Compound No. | STRUCTURE |
|---|---|
| 73 | 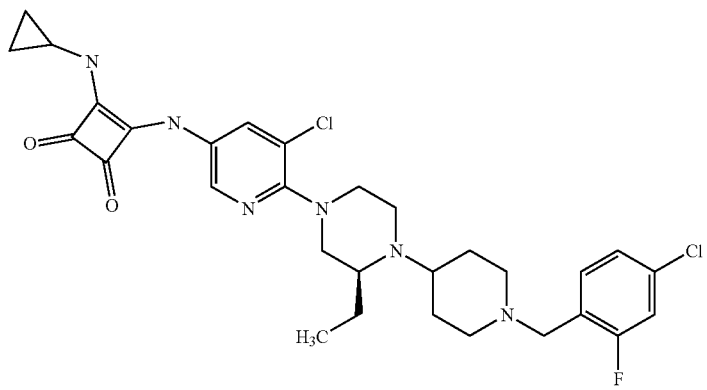 |
| 74 | 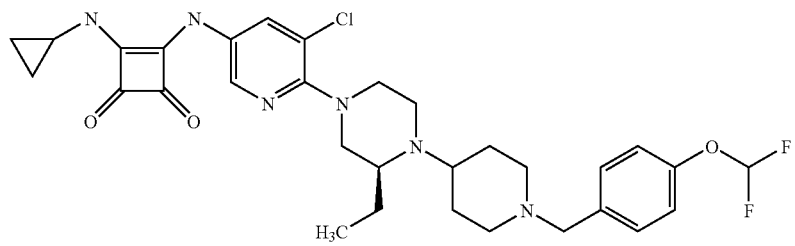 |
| 75 | 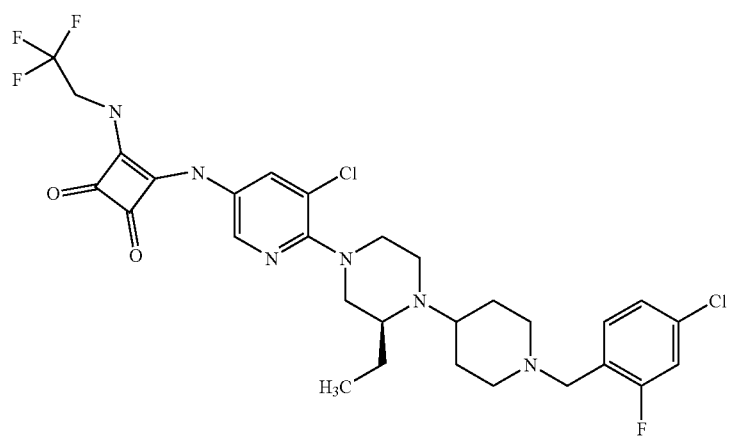 |
| 76 | 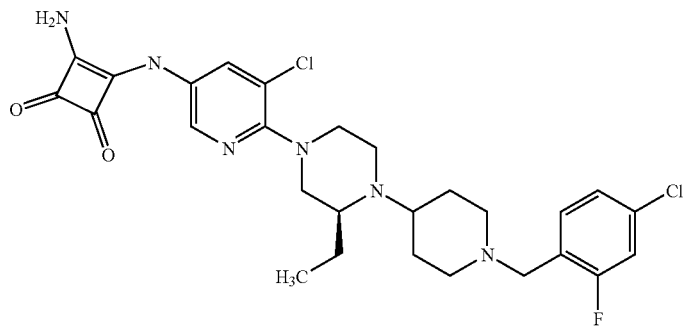 |

-continued
| Compound No. | STRUCTURE |
|---|---|
| 77 | 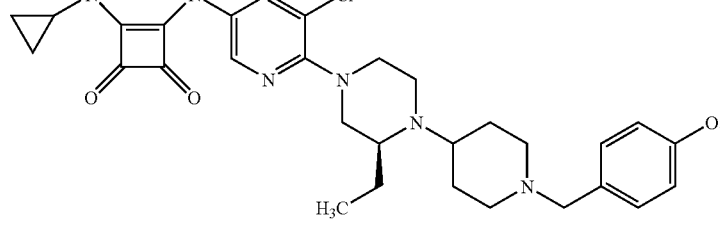 |
| 78 | 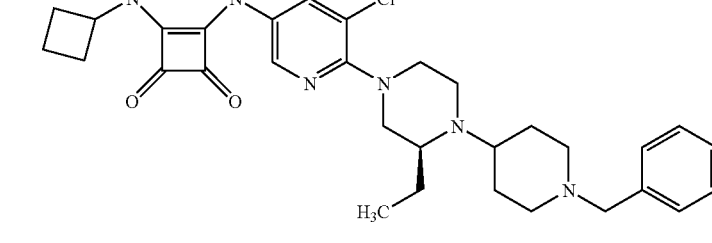 |
| 79 | 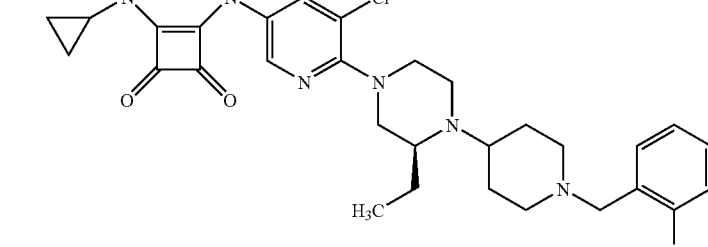 |
| 80 | 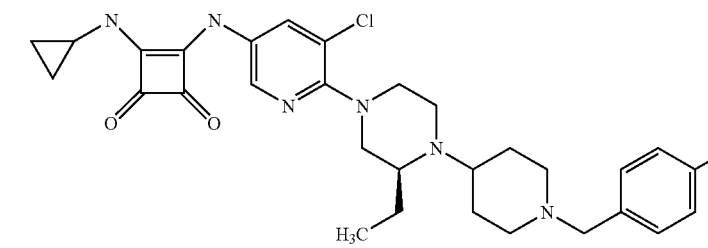 |
| 81 | 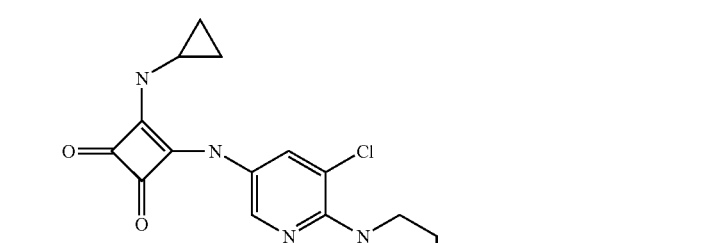 |

-continued
| Compound No. | STRUCTURE |
|---|---|
| 83 | 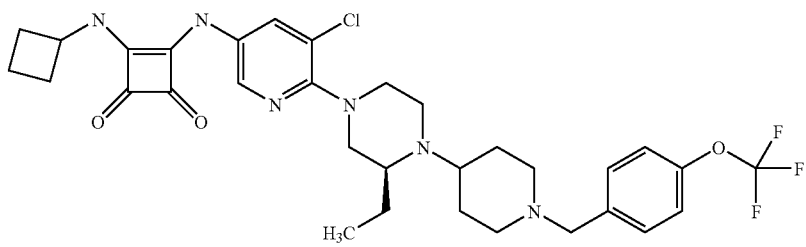 |
| 84 | 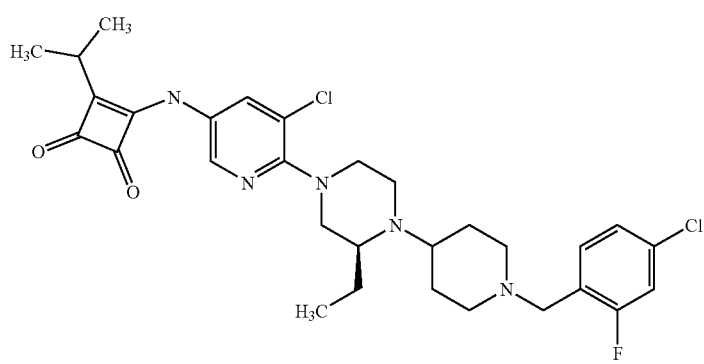 |
| 85 | 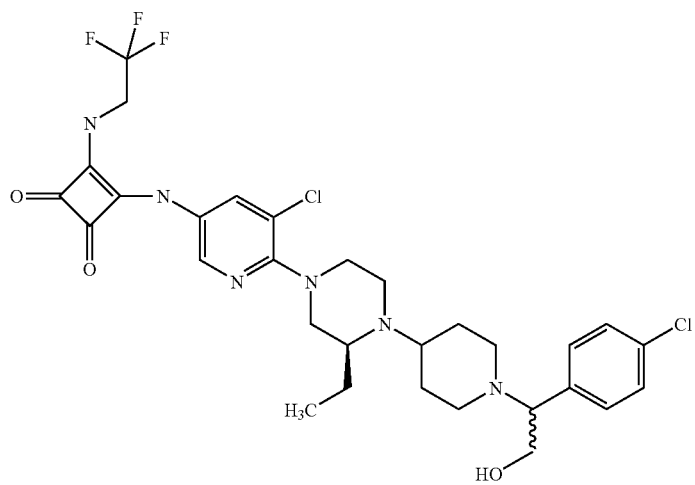 |
| 86 | 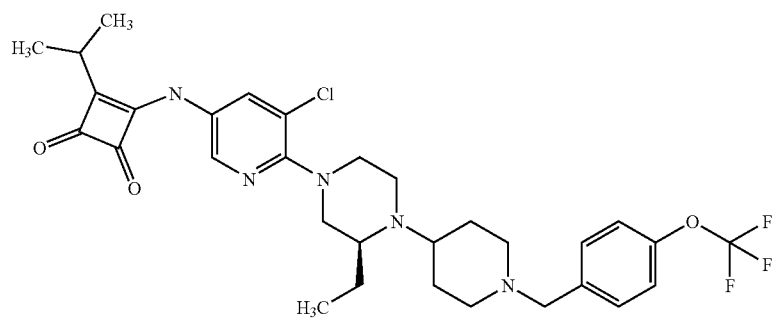 |

| Compound No. | STRUCTURE |
|---|---|
| 87 | 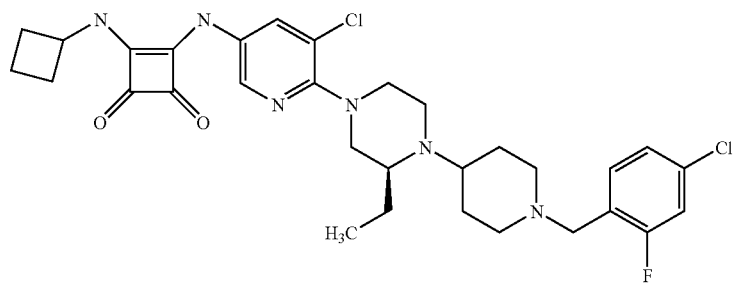 |
| 88 | 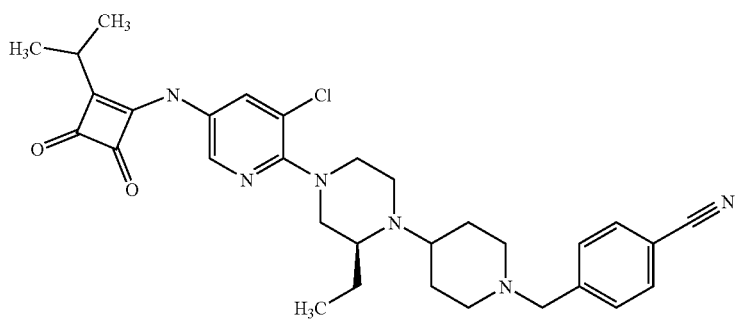 |
| 89 | 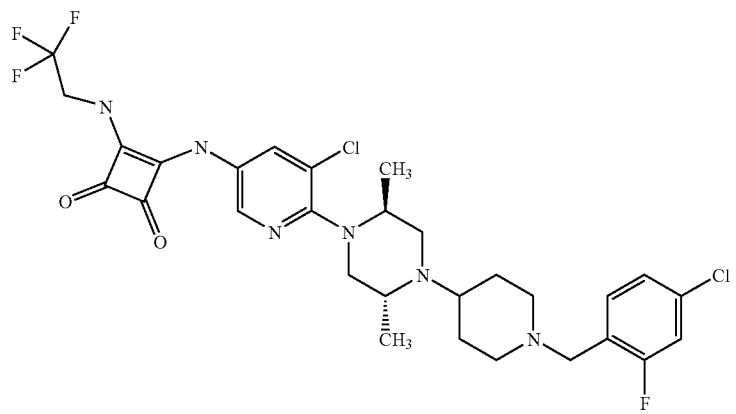 |
| 90 | 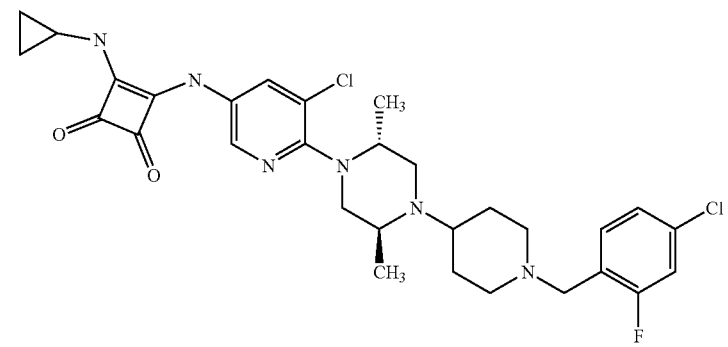 |

| Compound No. | STRUCTURE |
|---|---|
| 91 | 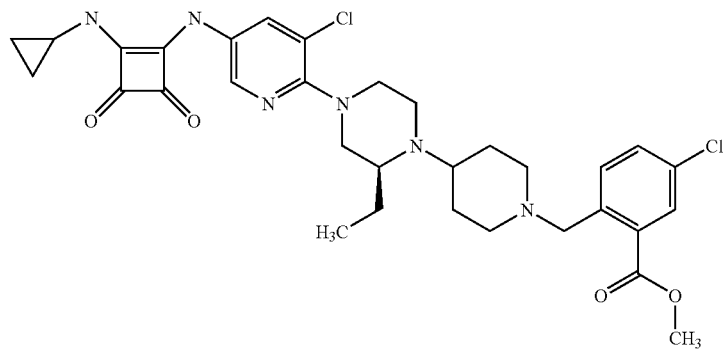 |
| 92 | 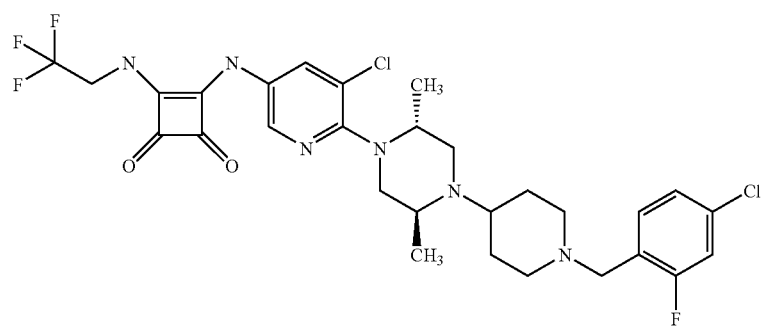 |
| 93 | 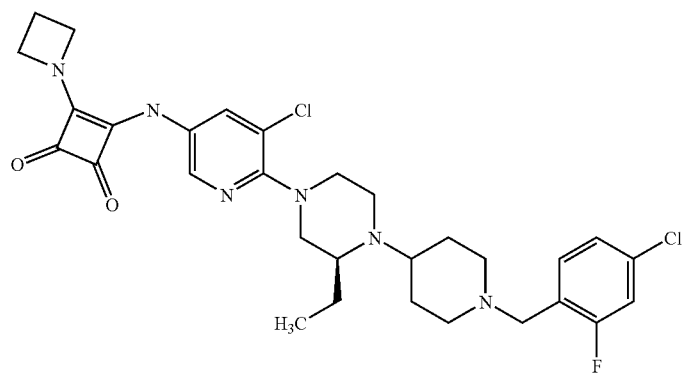 |
| 94 | 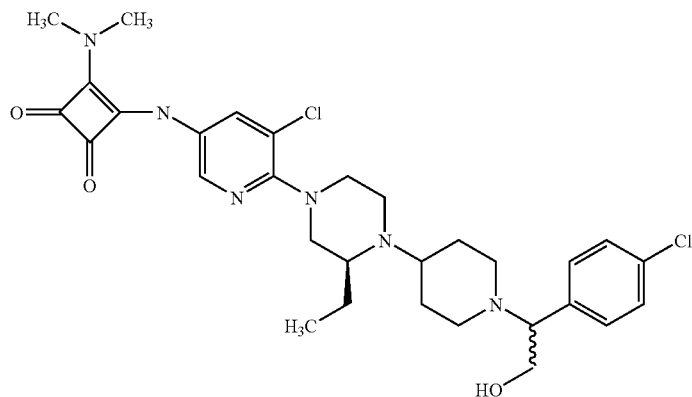 |

| Compound No. | STRUCTURE |
|---|---|
| 95 | 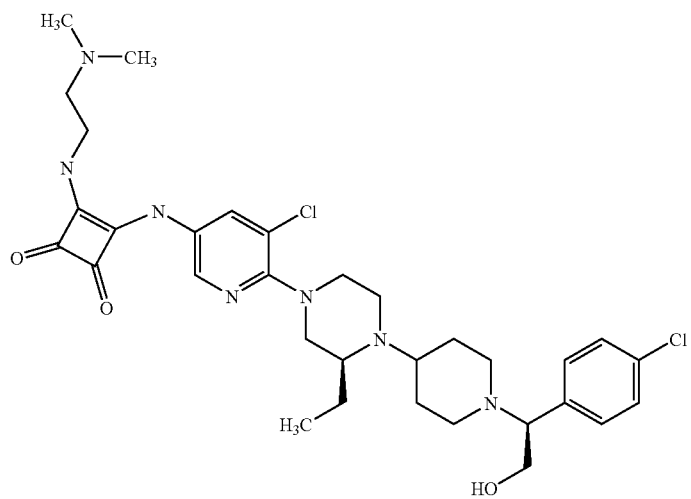 |
| 96 | 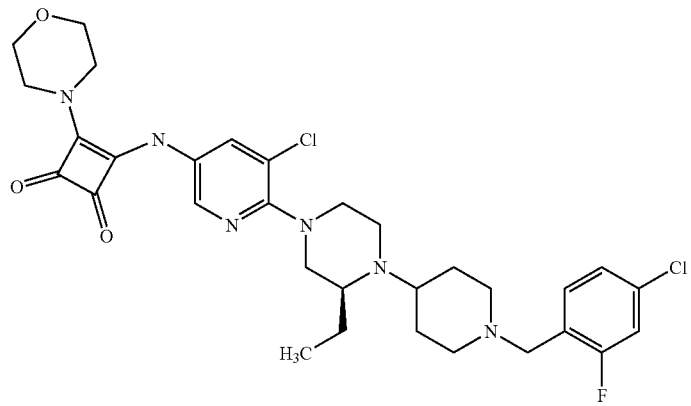 |
| 97 | 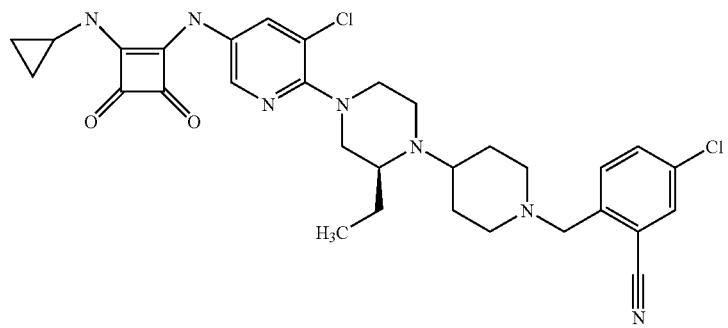 |

| Compound No. | STRUCTURE |
|---|---|
| 98 | 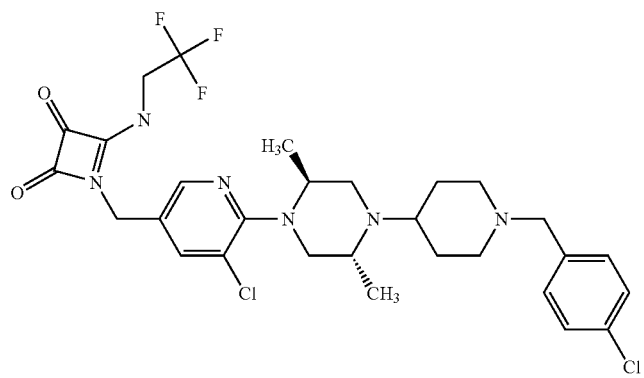 |
| 99 | 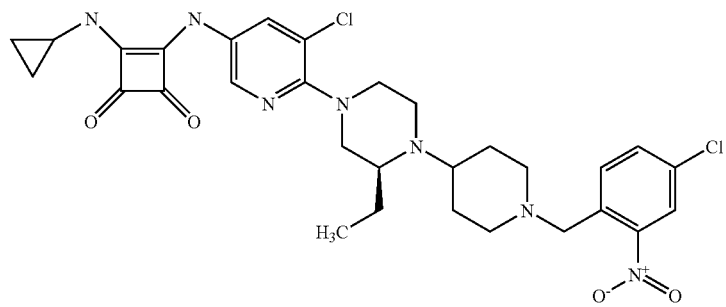 |
| 100 | 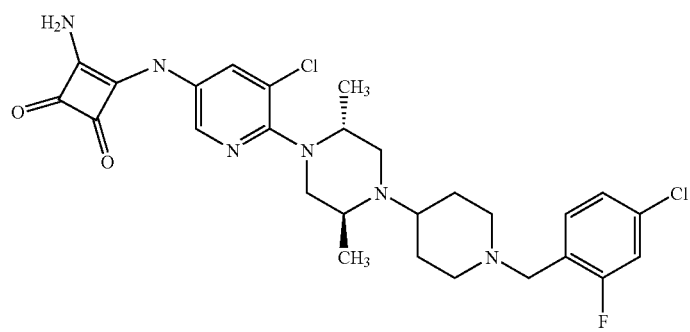 |
| 101 | 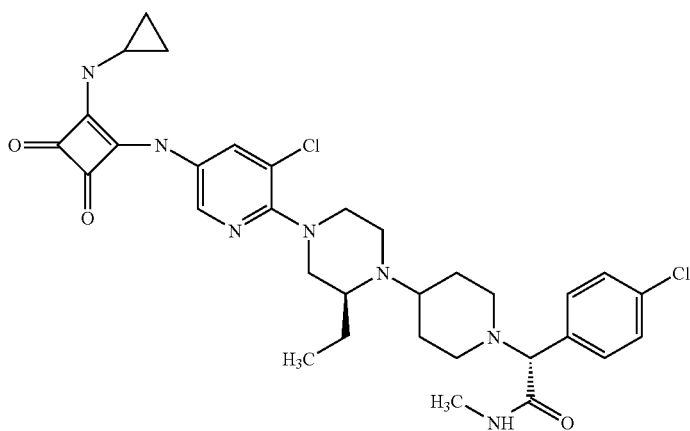 |

-continued
| Compound No. | STRUCTURE |
|---|---|
| 102 | 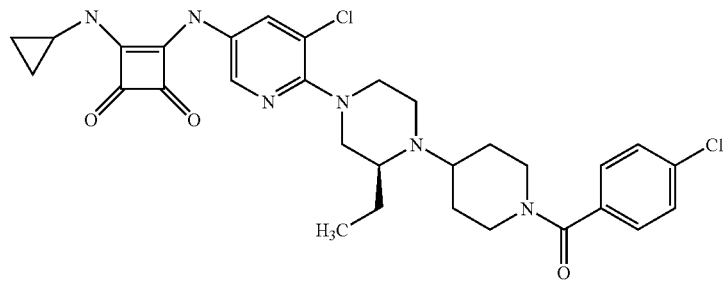 |
| 103 | 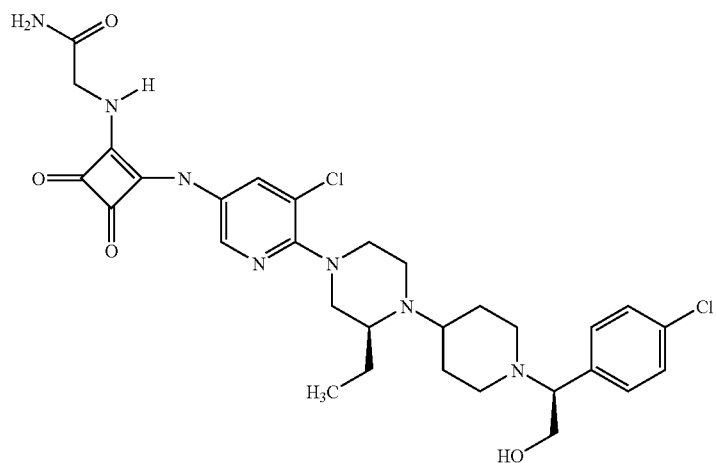 |
| 104 | 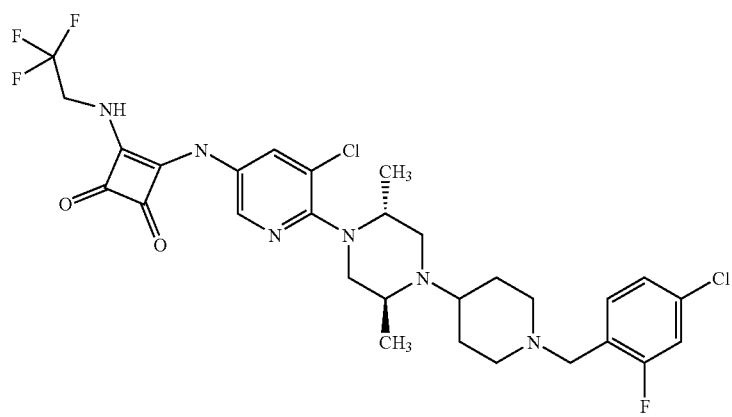 |
| 107 | 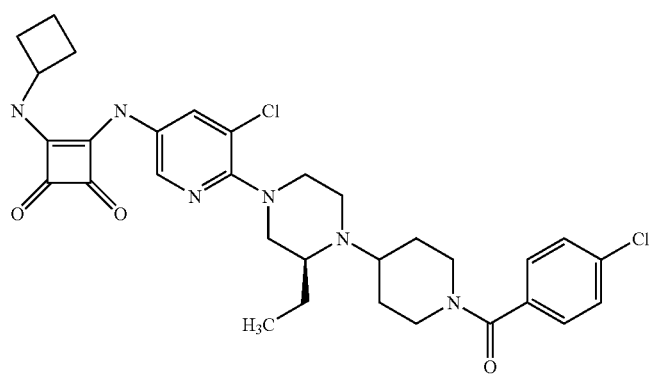 |

| Compound No. | STRUCTURE |
|---|---|
| 108 | 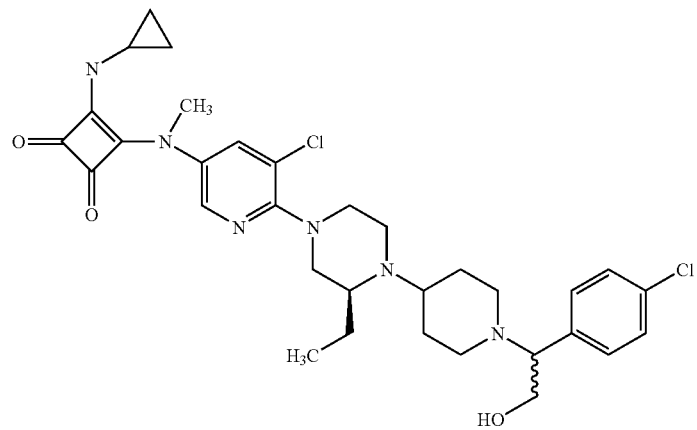 |
| 109 | 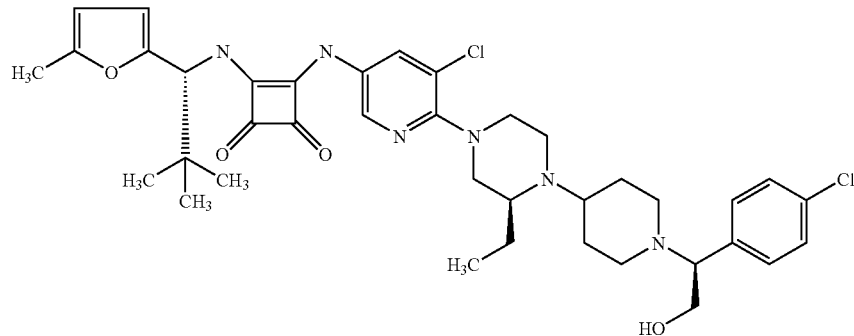 |
| 110 | 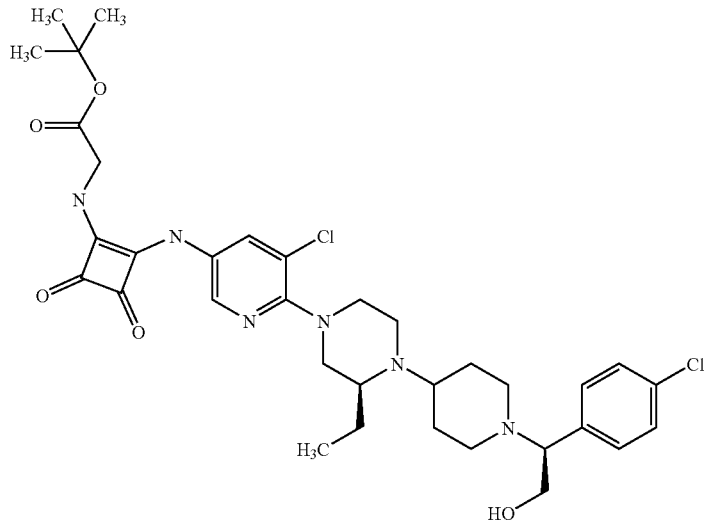 |
| 111 | 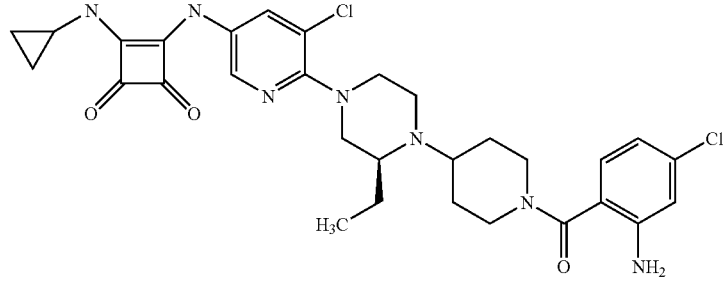 |

-continued
| Compound No. | STRUCTURE |
|---|---|
| 112 | 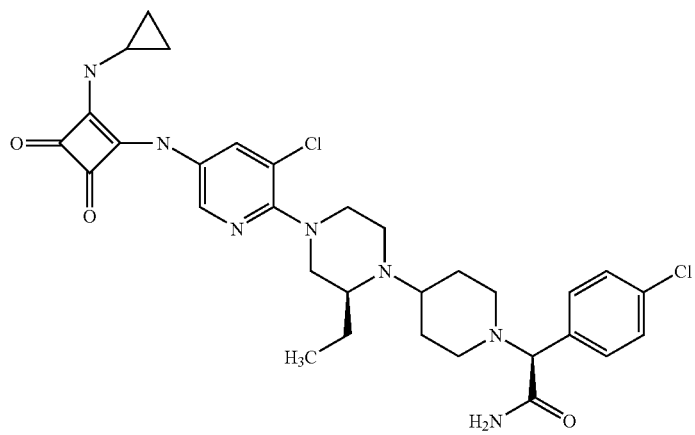 |
| 113 | 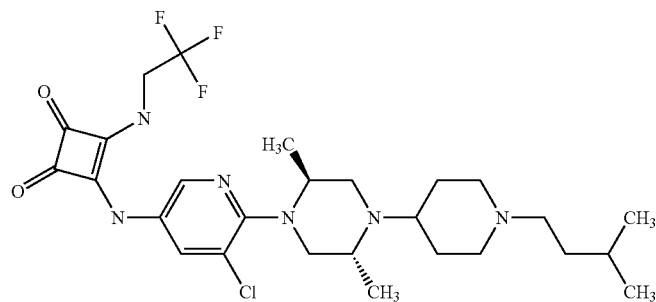 |
| 114 | 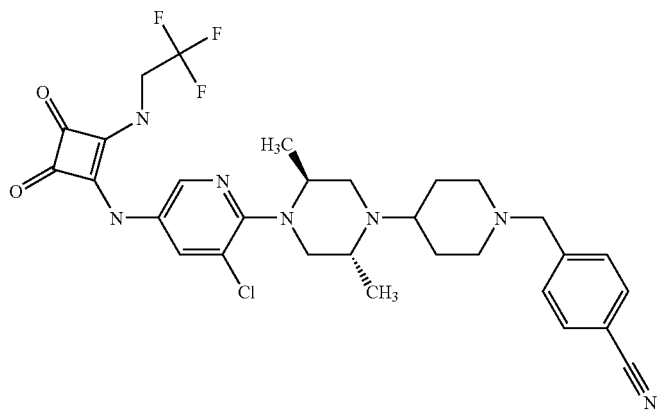 |
| 115 | 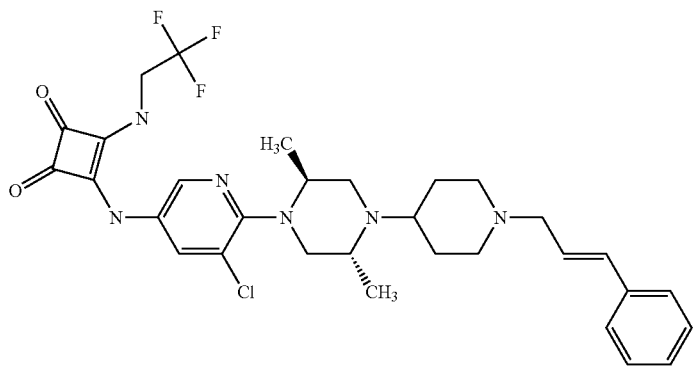 |

| Compound No. | STRUCTURE |
|---|---|
| 116 | 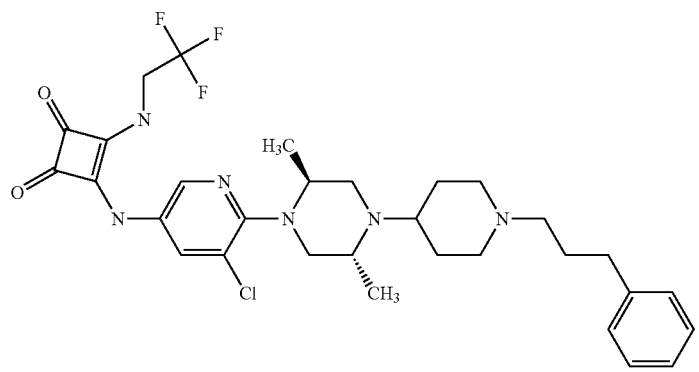 |
| 117 | 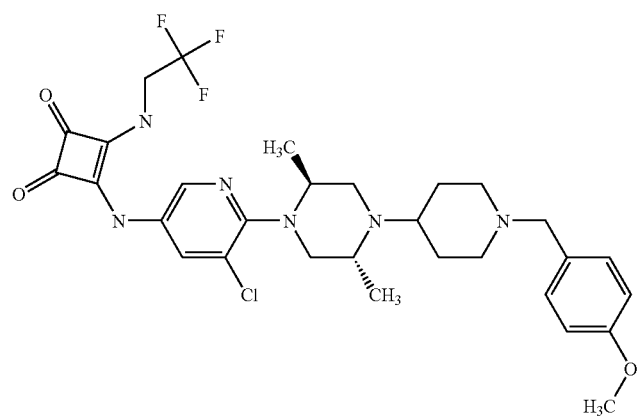 |
| 118 | 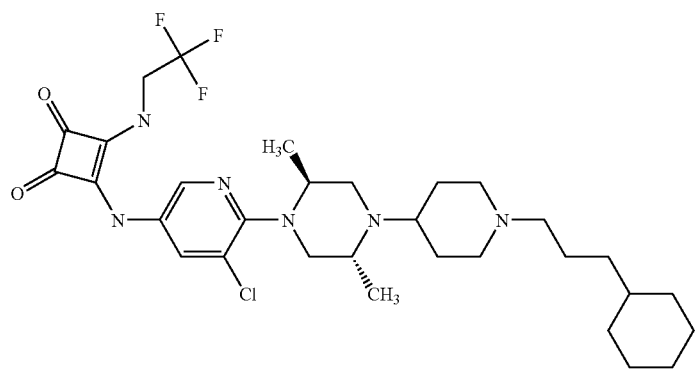 |
| 119 | 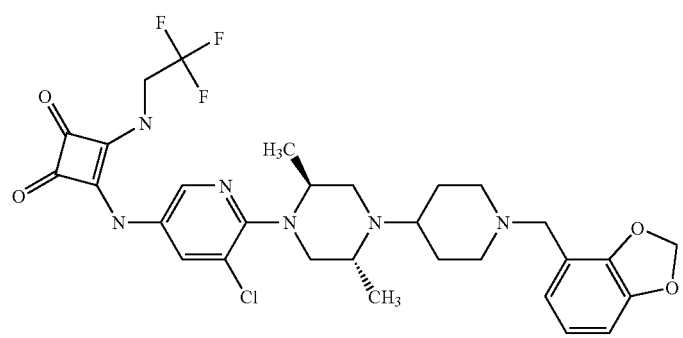 |

| Compound No. | STRUCTURE |
|---|---|
| 120 | 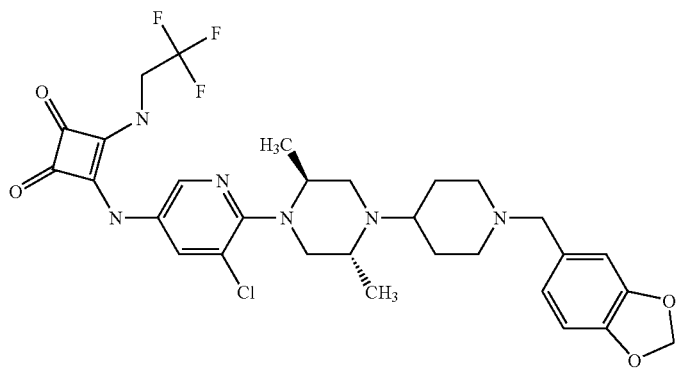 |
| 121 | 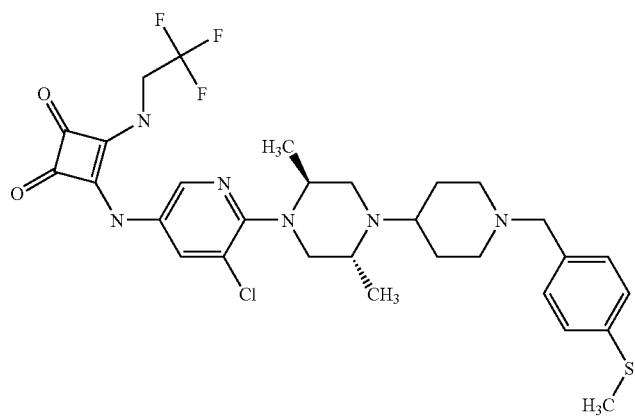 |
| 122 | 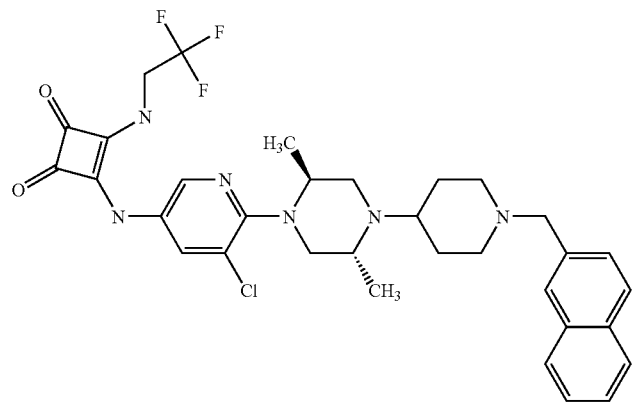 |

-continued
| Compound No. | STRUCTURE |
|---|---|
| 123 | 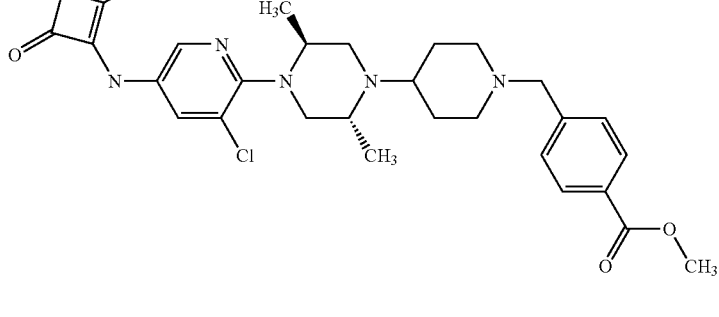 |
| 124 | 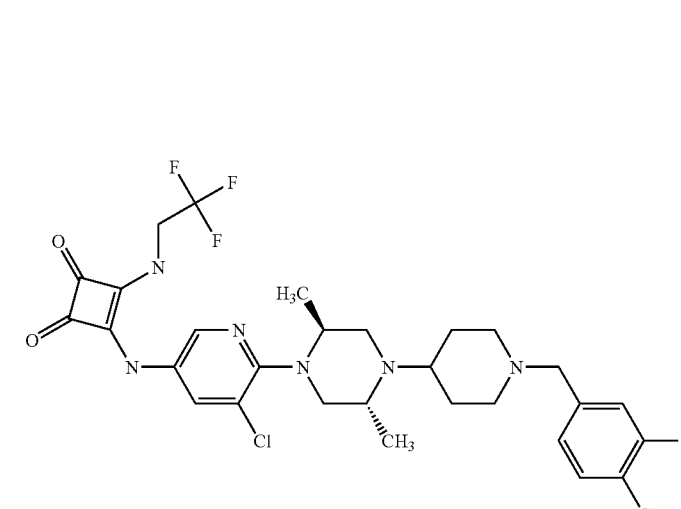 |
| 125 | 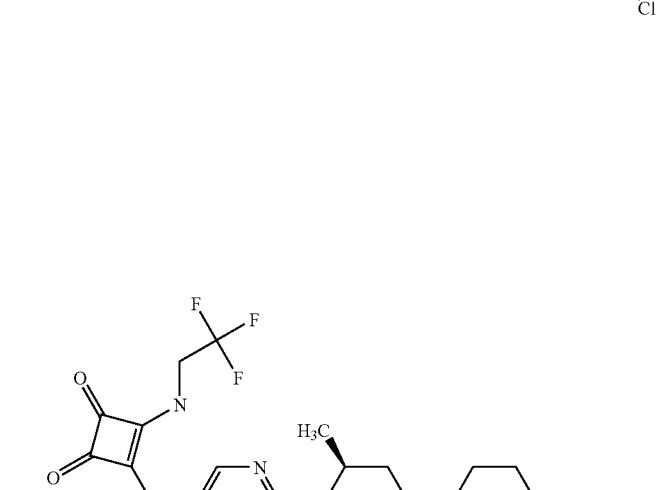 |

| Compound No. | STRUCTURE |
|---|---|
| 126 | 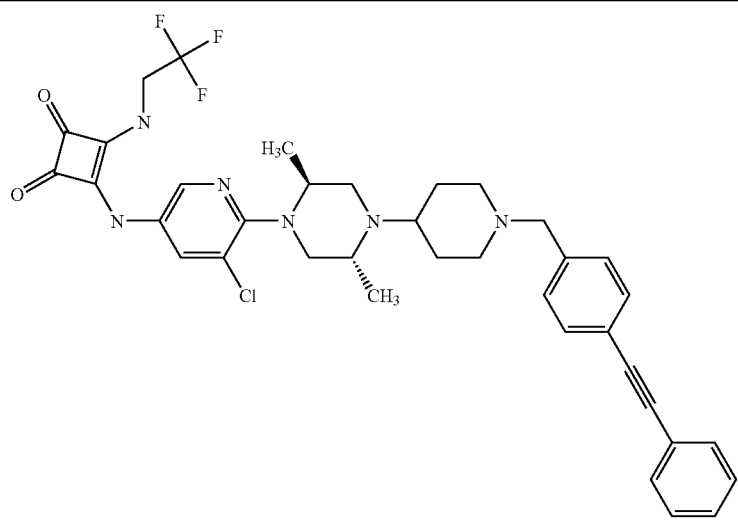 |
| 127 | 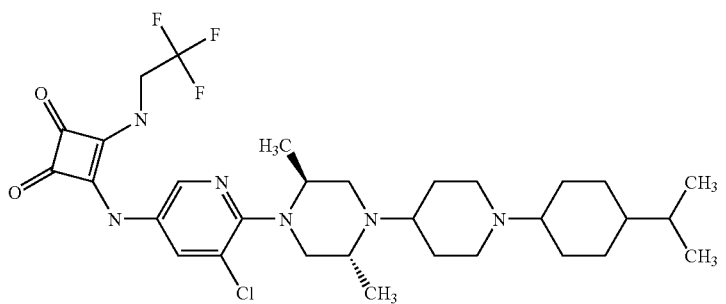 |
| 128 | 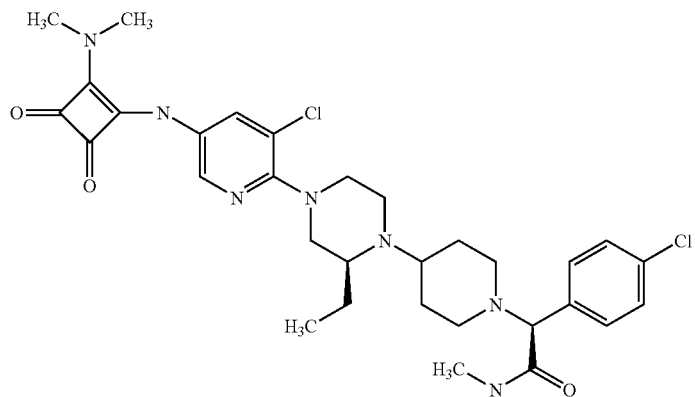 |

-continued
| Compound No. | STRUCTURE |
|---|---|
| 129 | 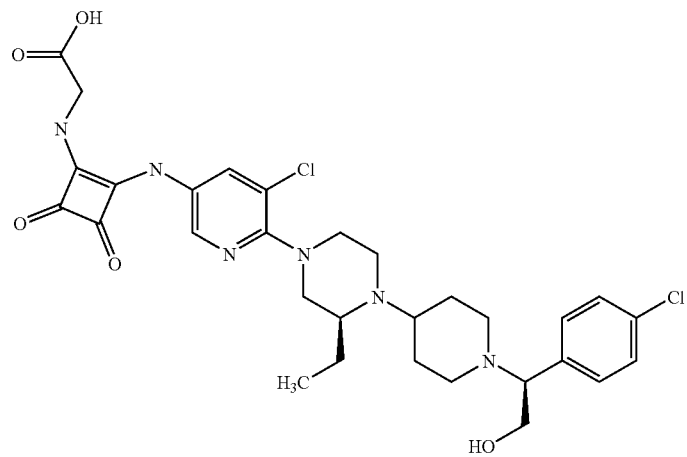 |
| 130 | 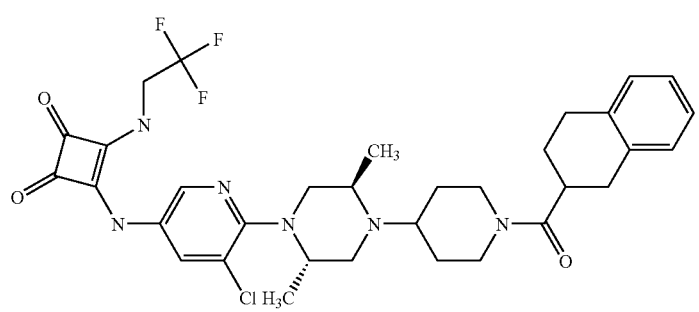 |
| 131 | 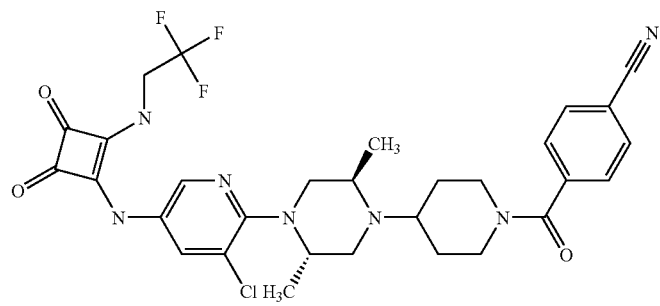 |
| 132 | 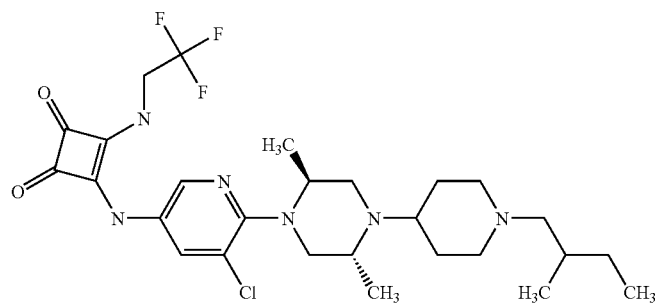 |

| Compound No. | STRUCTURE |
|---|---|
| 133 | 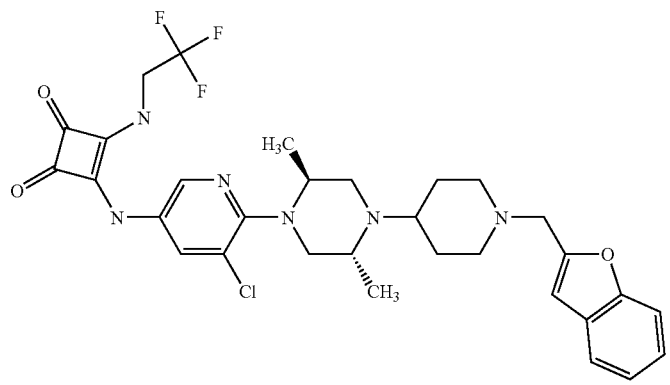 |
| 134 | 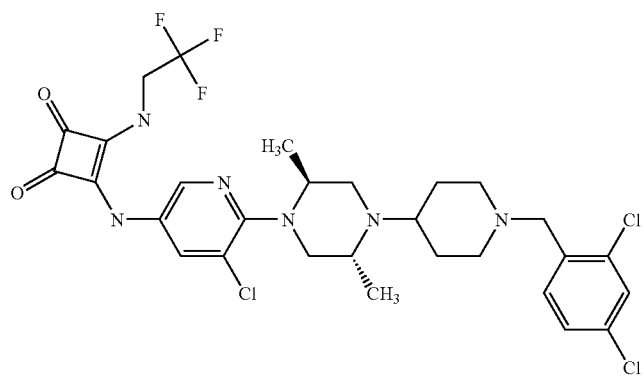 |
| 135 | 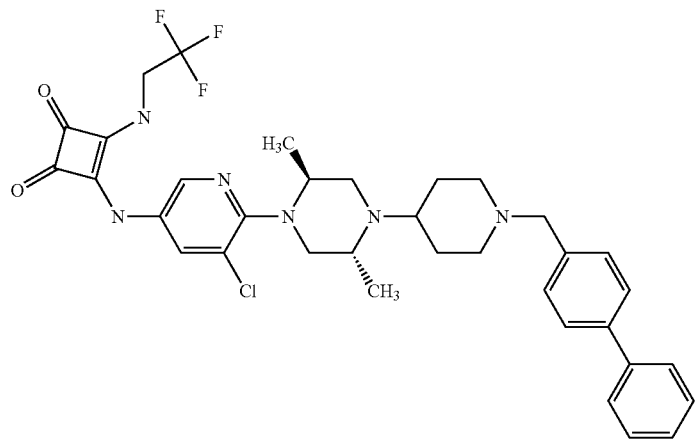 |
| 136 | 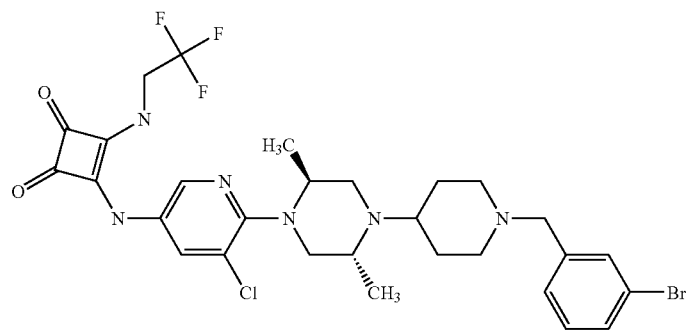 |

-continued
| Compound No. | STRUCTURE |
|---|---|
| 137 | 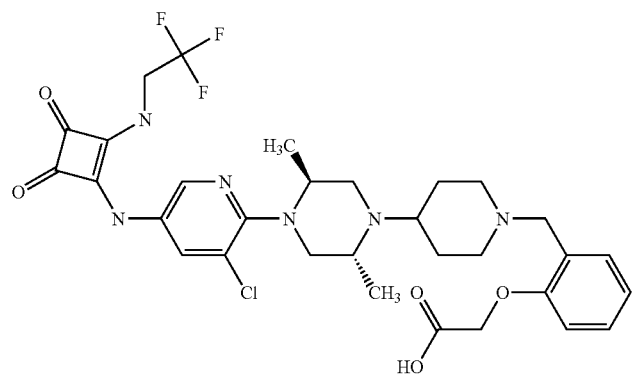 |
| 138 | 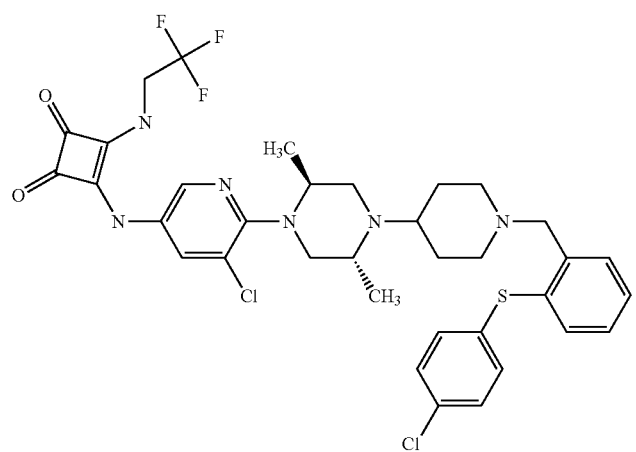 |
| 139 | 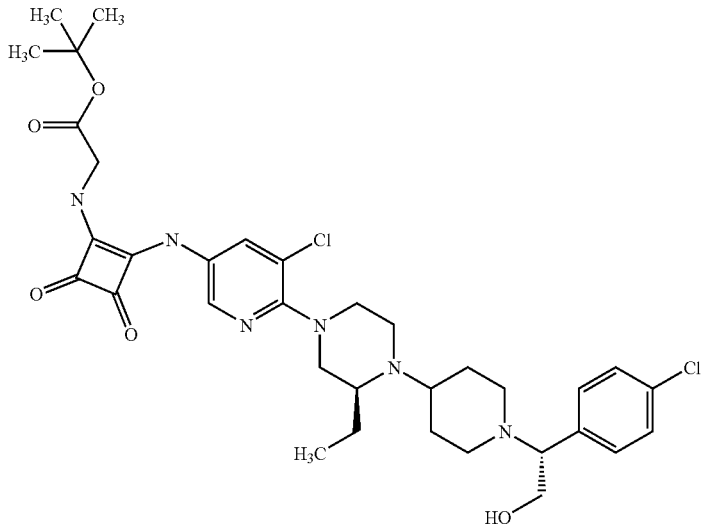 |

-continued
| Compound No. | STRUCTURE |
|---|---|
| 140 | 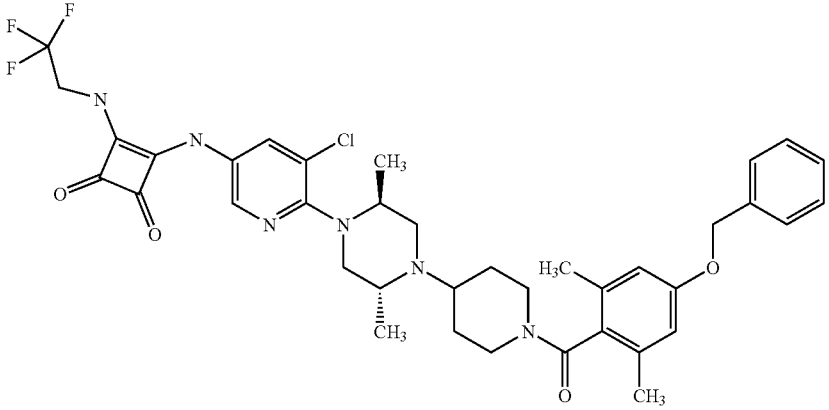 |
| 141 | 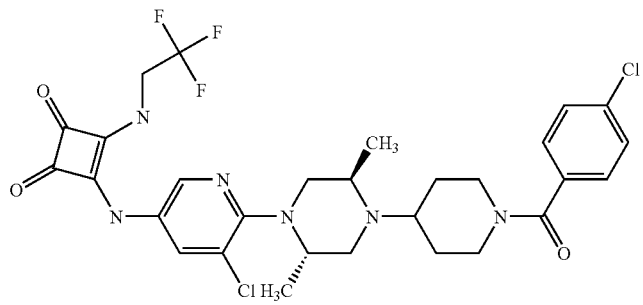 |
| 142 | 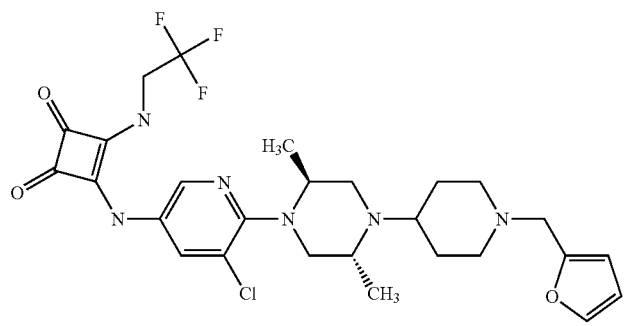 |
| 143 | 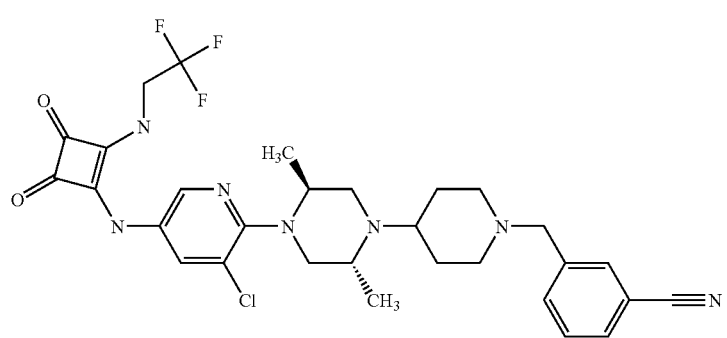 |

-continued
| Compound No. | STRUCTURE |
|---|---|
| 144 | 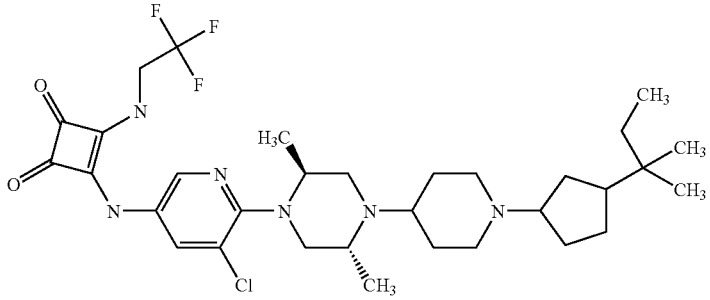 |
| 145 | 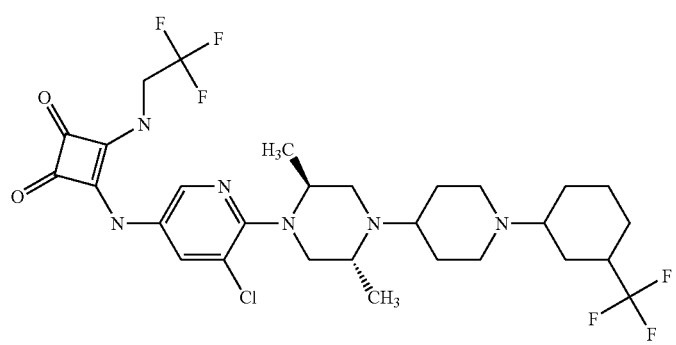 |
| 146 | 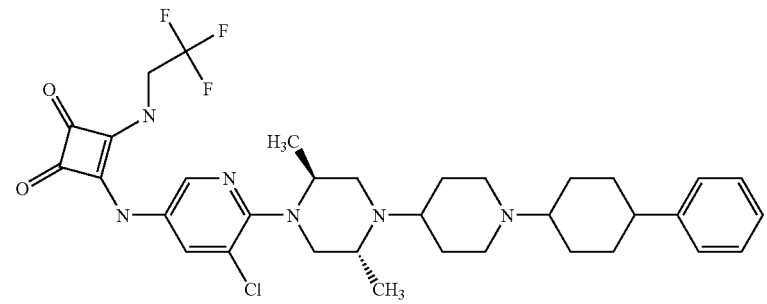 |
| 147 | 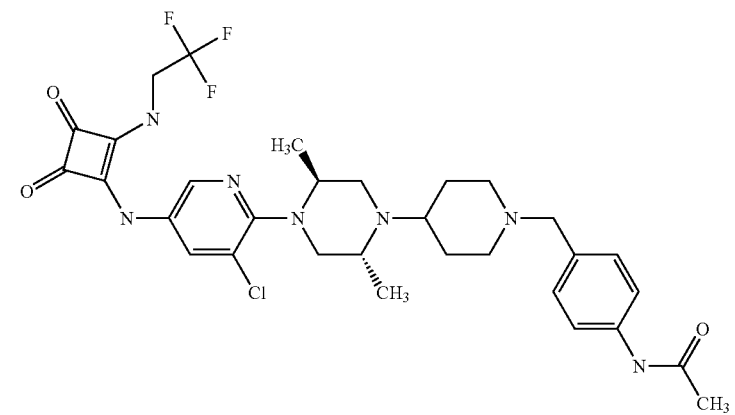 |

| Compound No. | STRUCTURE |
|---|---|
| 148 | 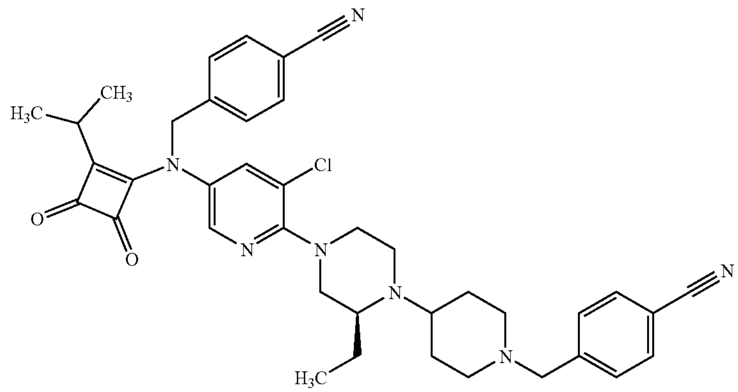 |
| 149 | 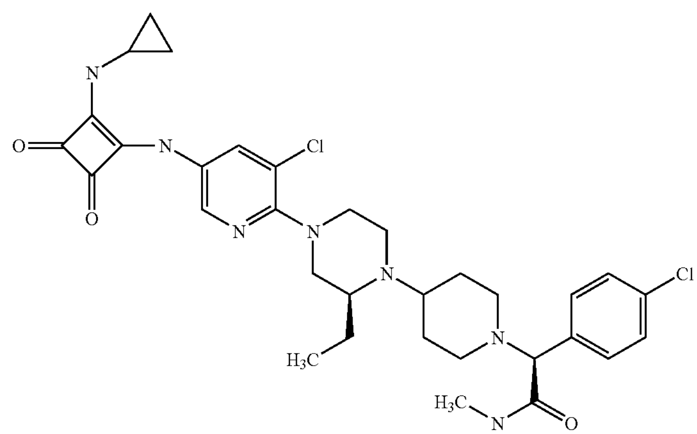 |
| 150 | 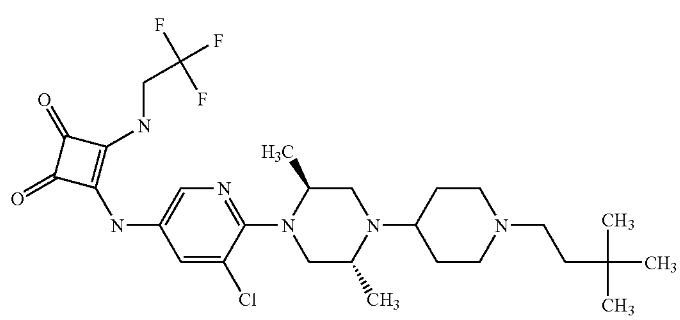 |
| 151 | 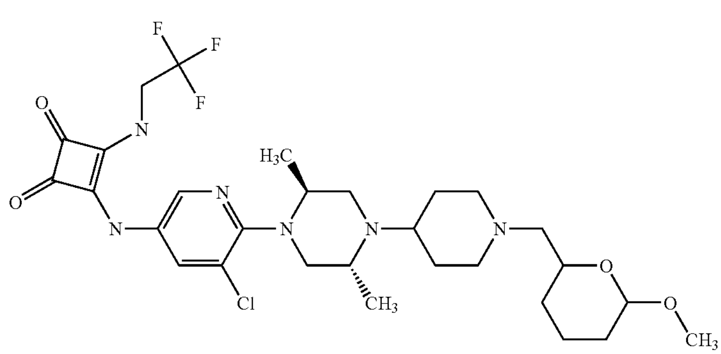 |

-continued

| Compound No. | STRUCTURE |
|---|---|
| 152 | 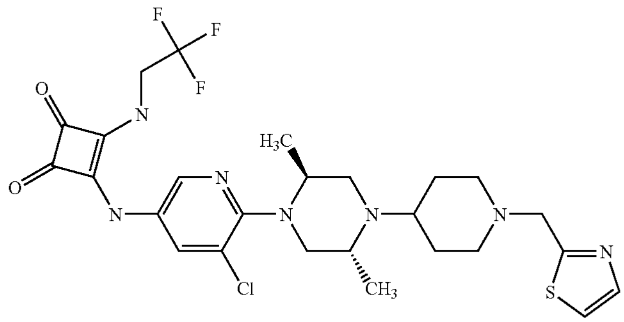 |
| 153 | 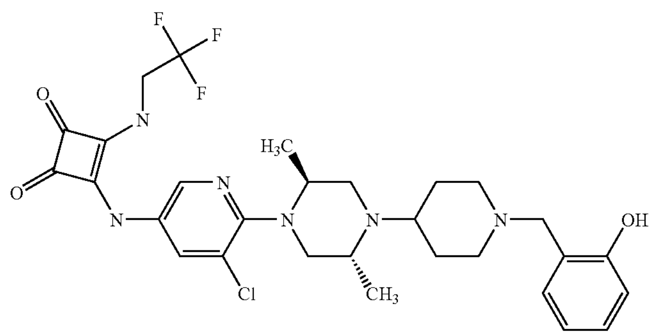 |
| 154 | 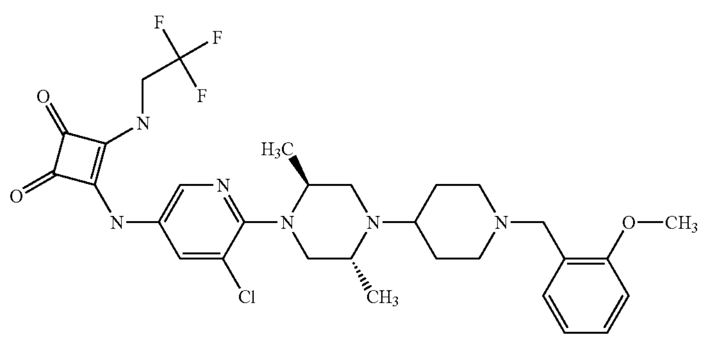 |
| 155 | 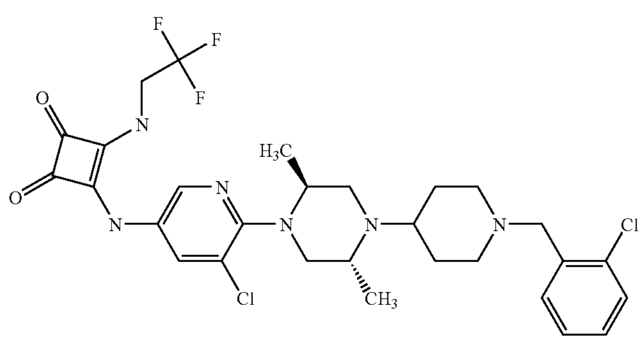 |

| Compound No. | STRUCTURE |
|---|---|
| 156 | 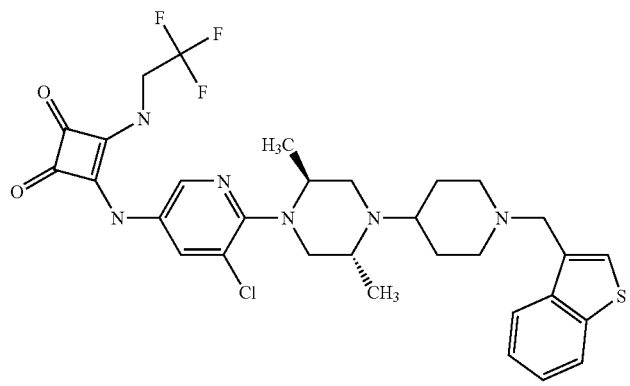 |
| 157 | 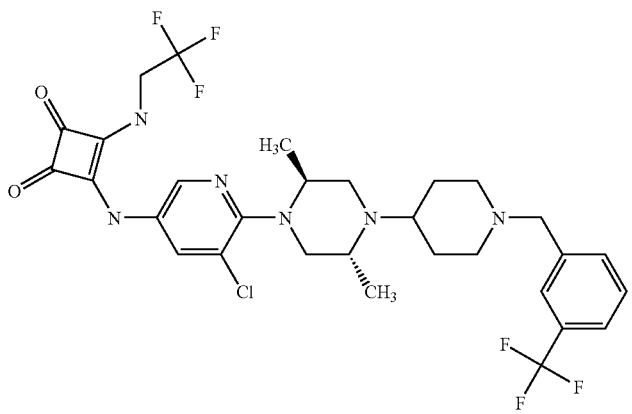 |
| 158 | 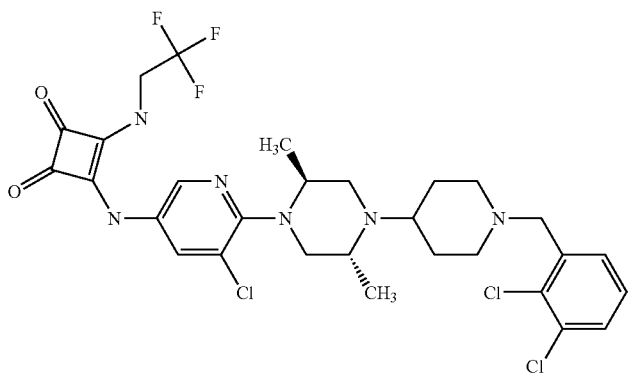 |
| 159 | 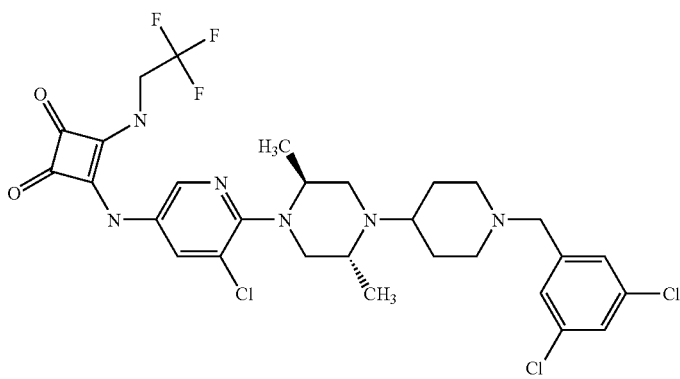 |

-continued
| Compound No. | STRUCTURE |
|---|---|
| 160 | 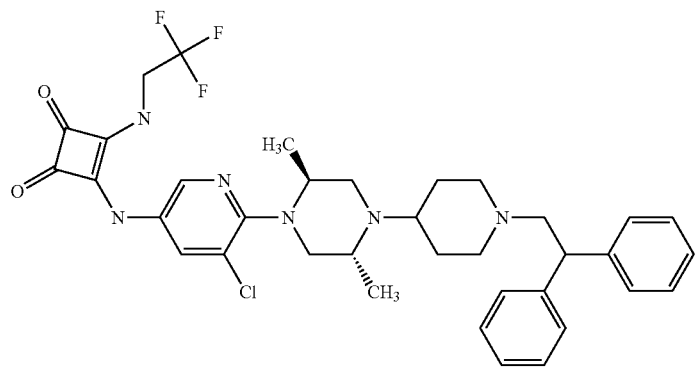 |
| 161 | 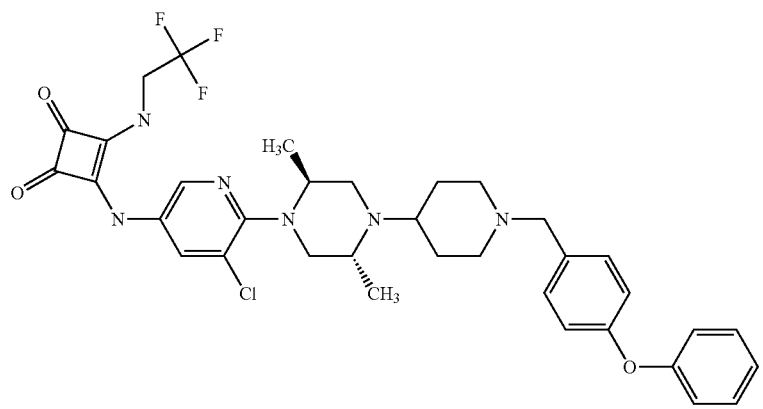 |
| 162 | 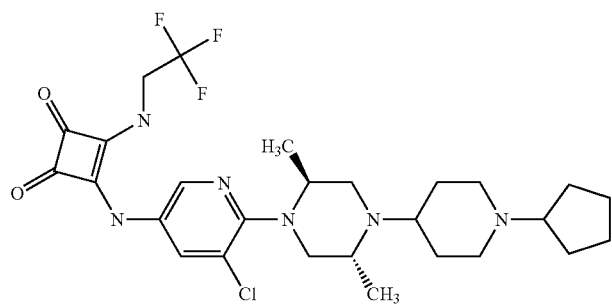 |
| 163 | 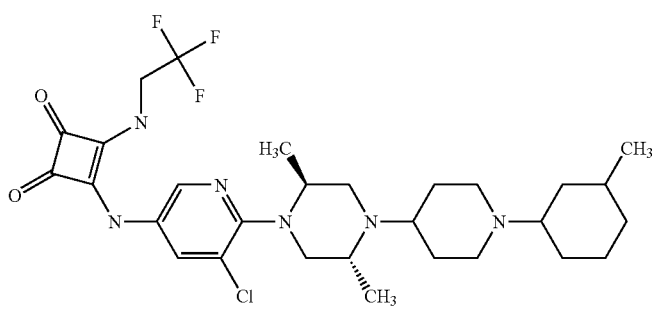 |

| Compound No. | STRUCTURE |
|---|---|
| 164 | 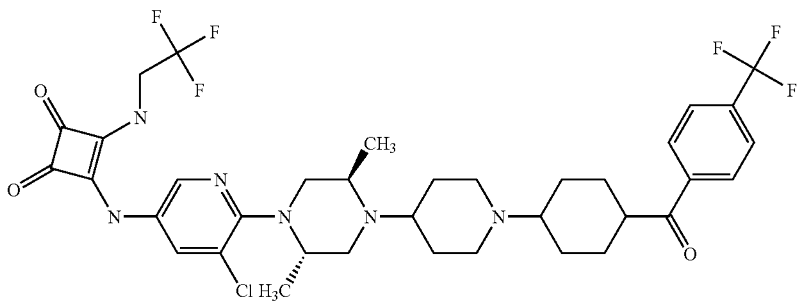 |
| 165 | 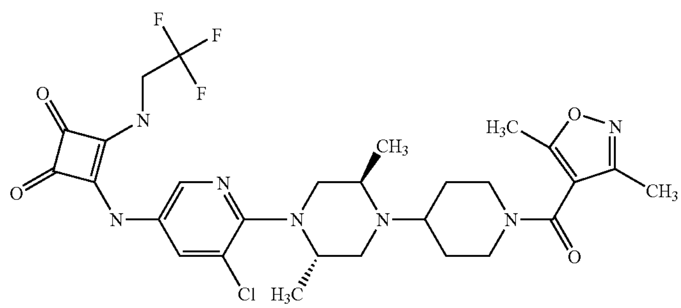 |
| 166 | 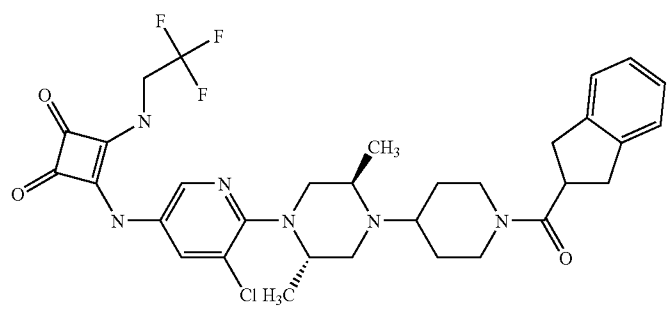 |
| 167 | 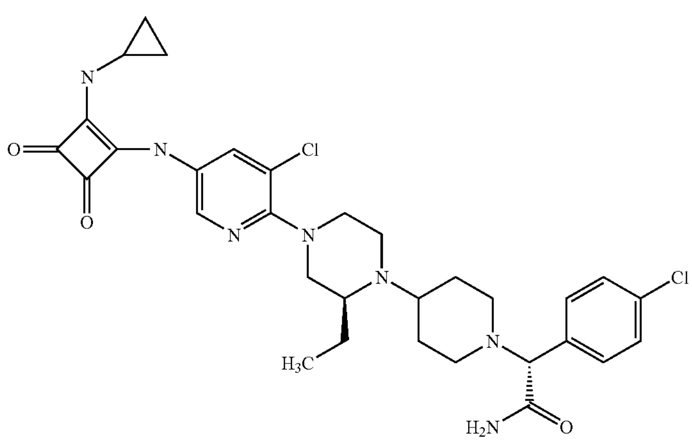 |

-continued
| Compound No. | STRUCTURE |
|---|---|
| 168 | 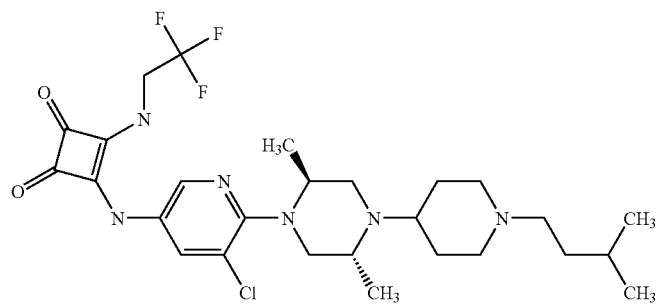 |
| 169 | 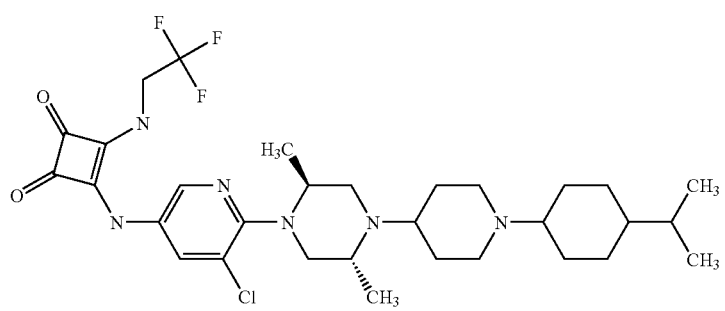 |
| 170 | 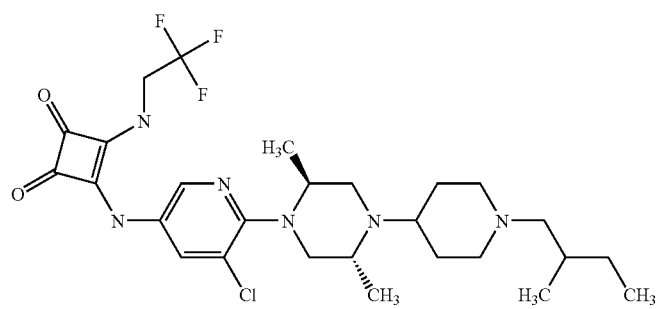 |
| 171 | 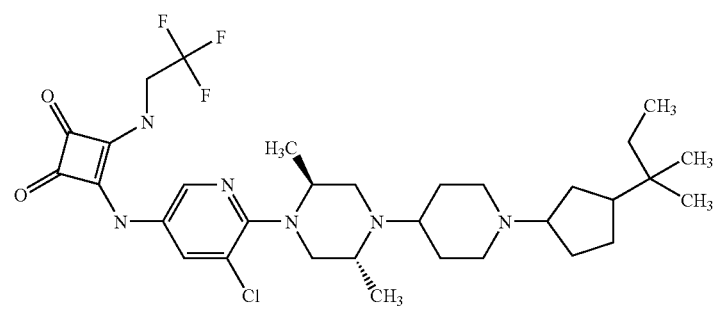 |
| 172 | 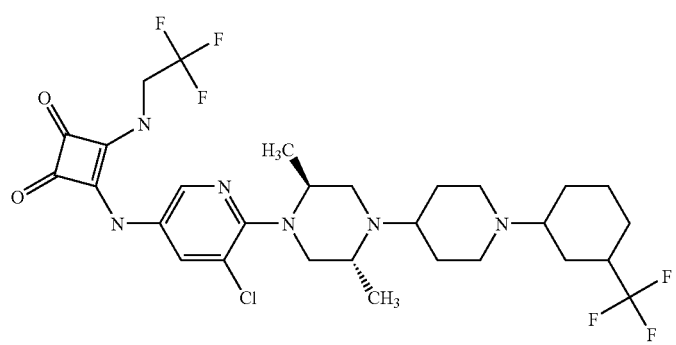 |

| Compound No. | STRUCTURE |
|---|---|
| 173 | 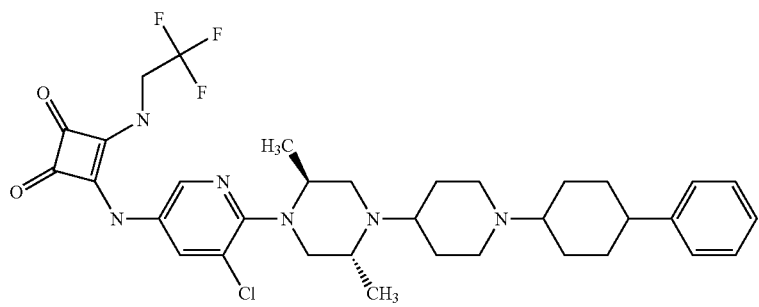 |
| 174 | 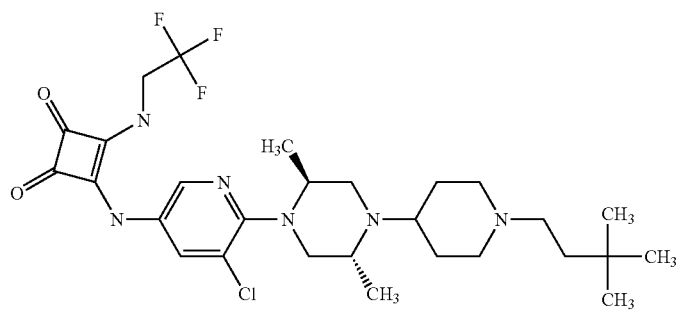 |
| 175 | 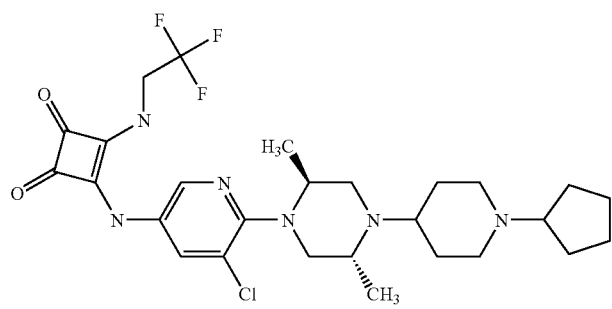 |
| 176 | 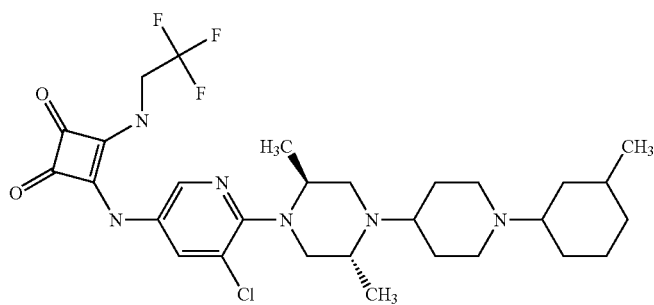 |

| Compound No. | STRUCTURE |
|---|---|
| 177 | 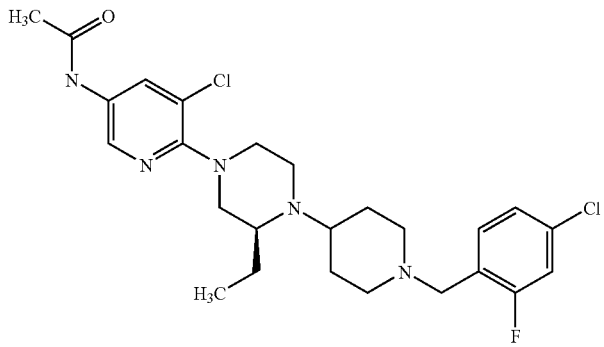 |
| 178 | 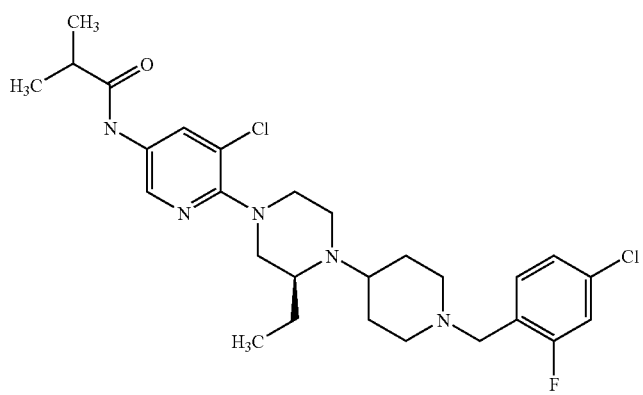 |
| 179 | 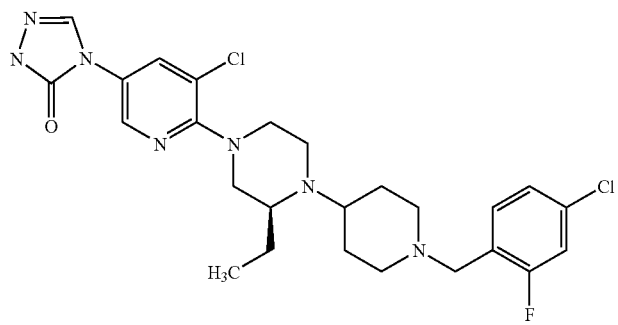 |
| 180 | 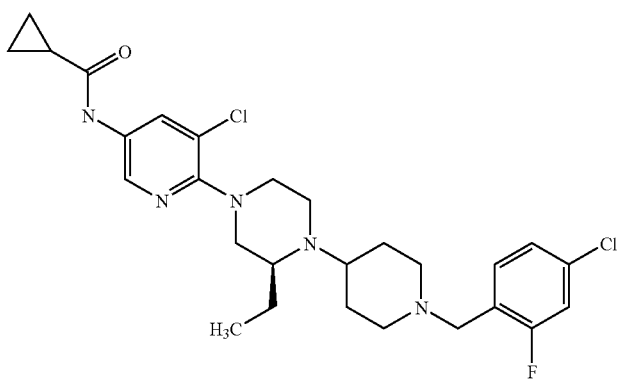 |

|Compound No.|STRUCTURE|
|---|---|
|181|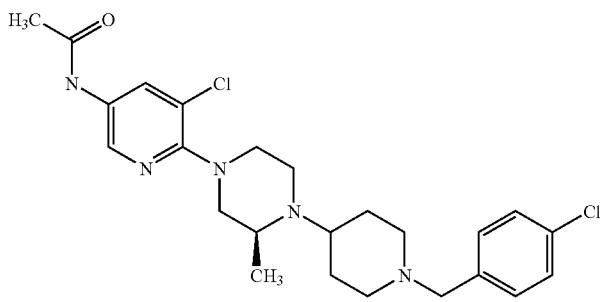|
|182|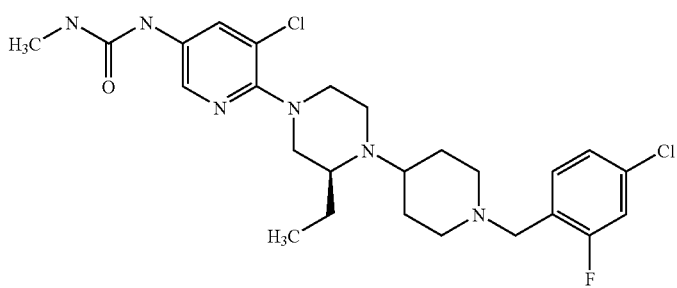|
|183|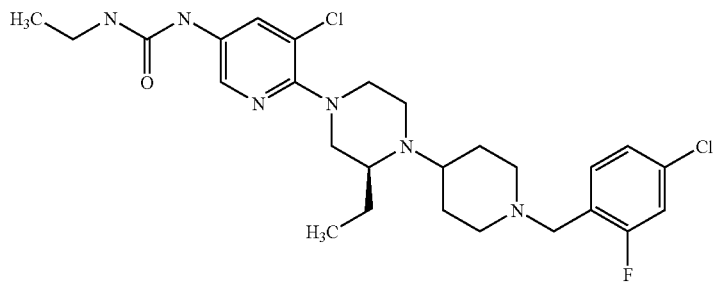|
|184|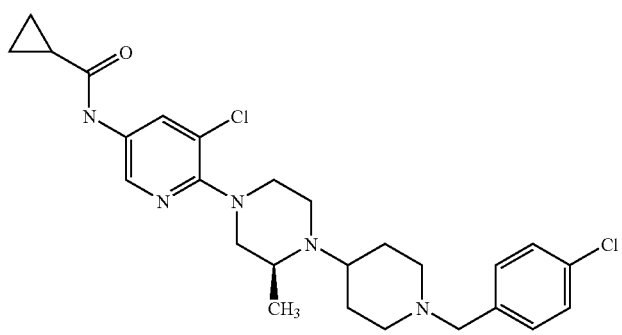|
|185|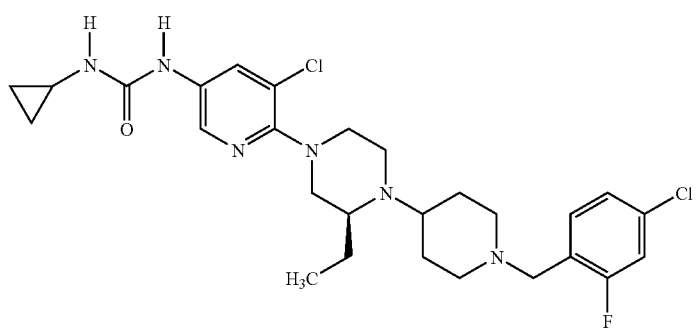|

| Compound No. | STRUCTURE |
|---|---|
| 186 | 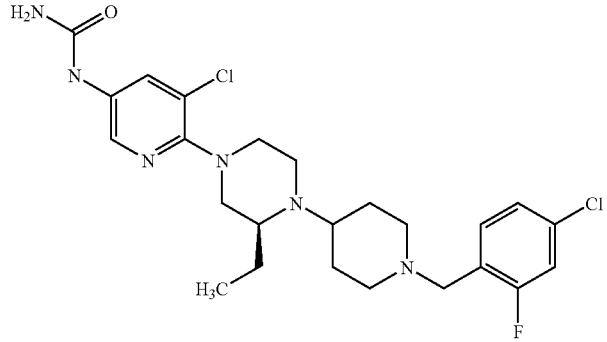 |
| 187 | 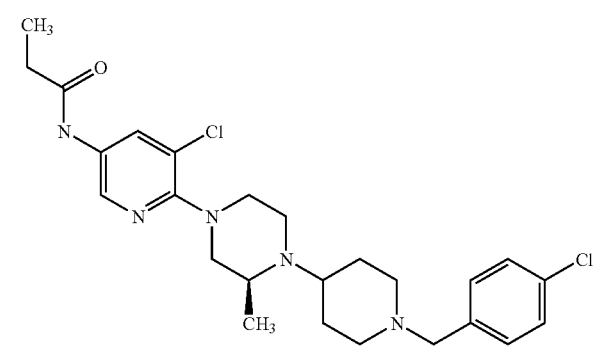 |
| 188 | 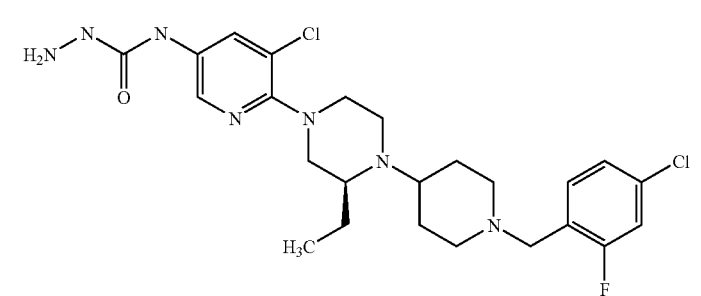 |
| 189 | 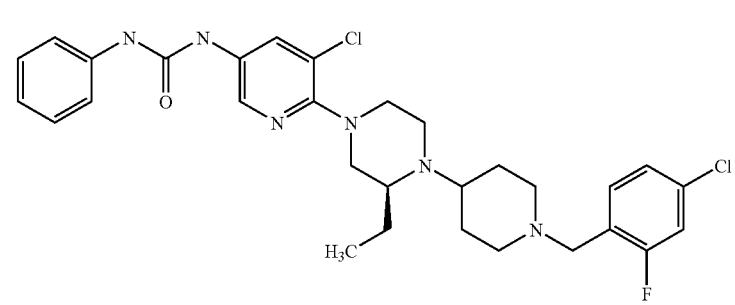 |

-continued
| Compound No. | STRUCTURE |
|---|---|
| 190 | 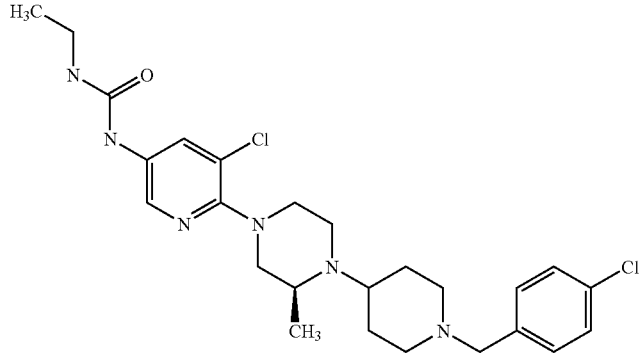 |
| 191 | 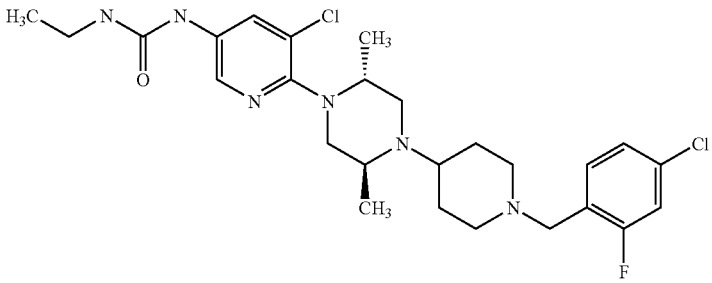 |
| 194 | 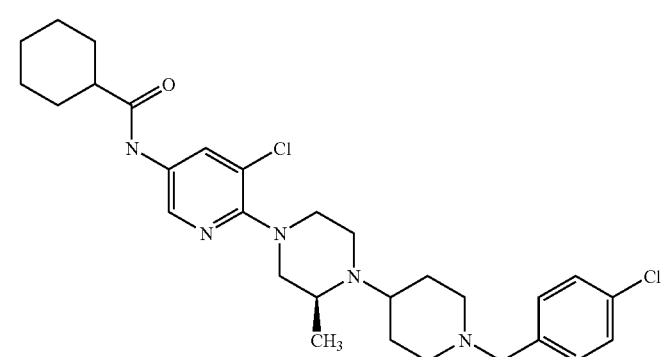 |
| 195 | 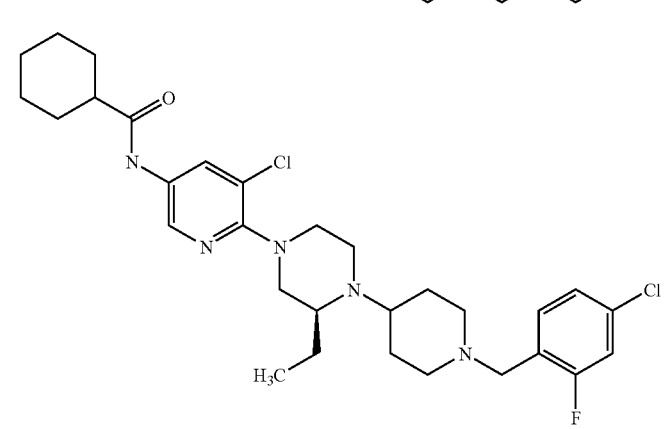 |

| Compound No. | STRUCTURE |
|---|---|
| 196 | 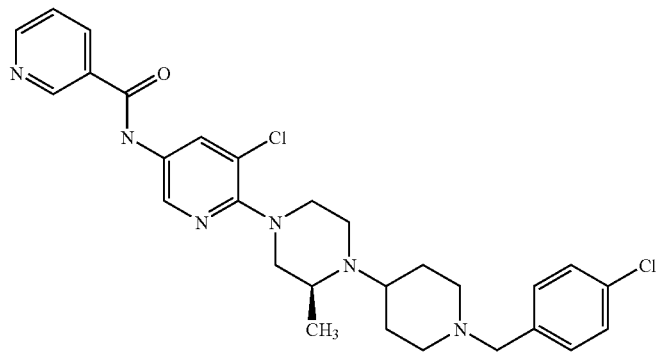 |
| 197 | 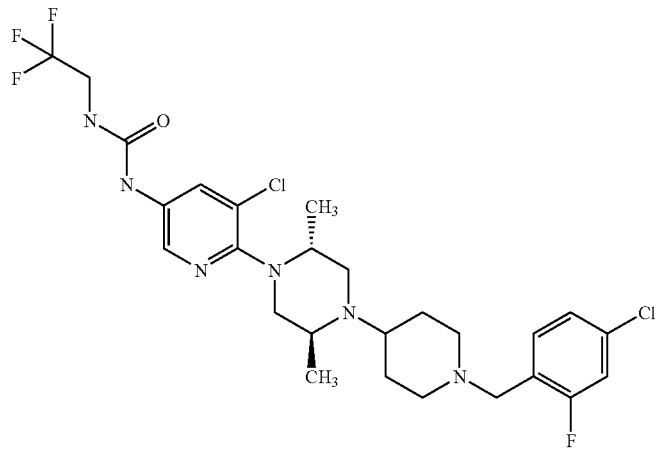 |
| 198 | 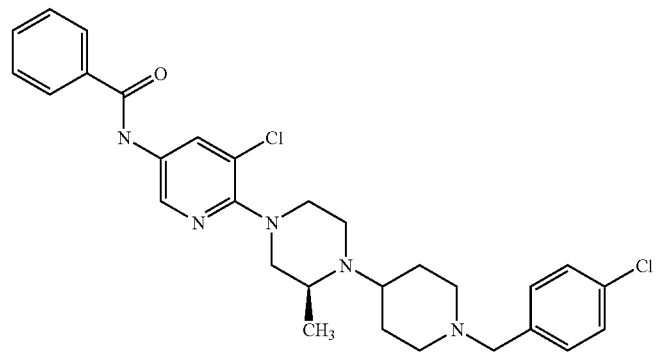 |

| Compound No. | STRUCTURE |
|---|---|
| 199 | 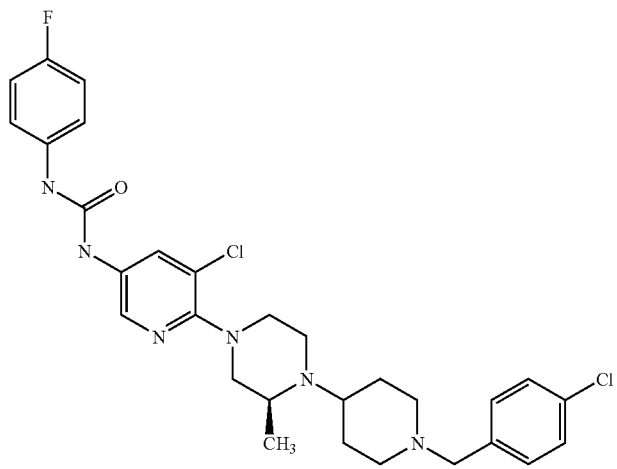 |
| 200 | 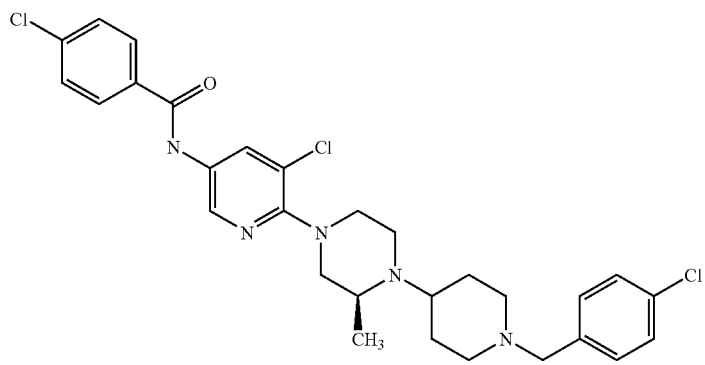 |
| 201 | 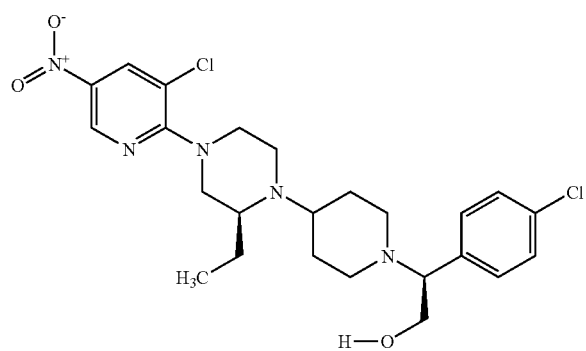 |
| 202 | 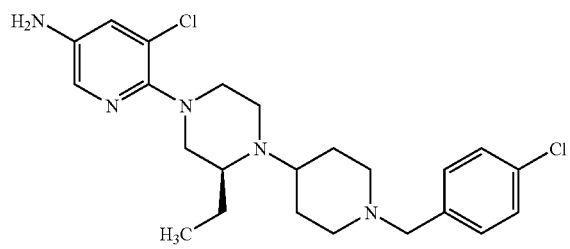 |

| Compound No. | STRUCTURE |
| --- | --- |
| 203 | (5-amino-3-chloro-pyridin-2-yl)-piperazine with ethyl substituent, linked to piperidine N-CH2-(4-chloro-2-fluorophenyl) |
| 204 | 5-(4,4,4-trifluorobutylamino)-3-chloro-pyridin-2-yl piperazine (ethyl), piperidine N-CH2-(4-chlorophenyl) |
| 205 | N-methyl-N'-cyano-guanidino-substituted 3-chloro-pyridin-2-yl piperazine (ethyl), piperidine N-CH2-(4-chloro-2-fluorophenyl) |
| 206 | (5-amino-3-chloro-pyridin-2-yl)-piperazine (ethyl), piperidine N-CH2-(4-chloro-2-fluorophenyl) |
| 207 | (6-amino-3-chloro-5-nitro-pyridin-2-yl)-piperazine (ethyl), piperidine N-CH2-(4-chloro-2-fluorophenyl) |

-continued
| Compound No. | STRUCTURE |
|---|---|
| 208 | 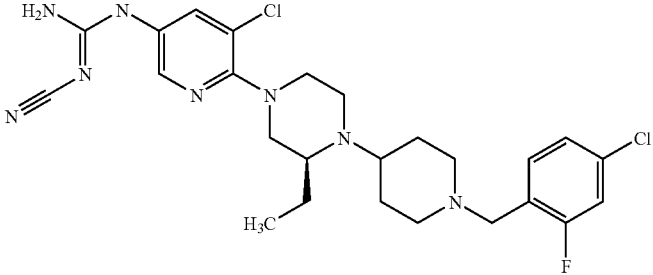 |
| 209 | 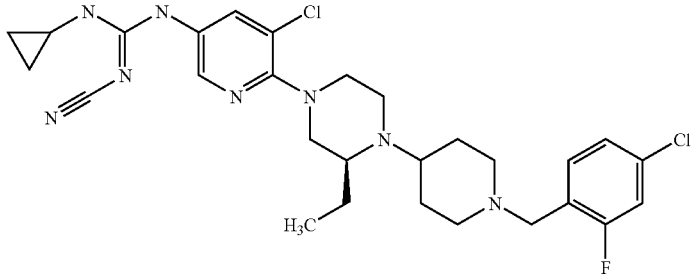 |
| 210 | 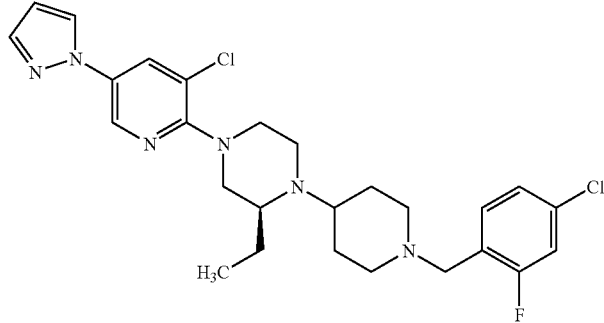 |
| 211 | 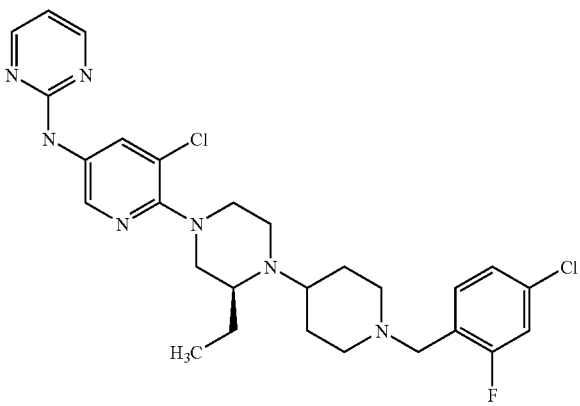 |

-continued
| Compound No. | STRUCTURE |
|---|---|
| 212 | 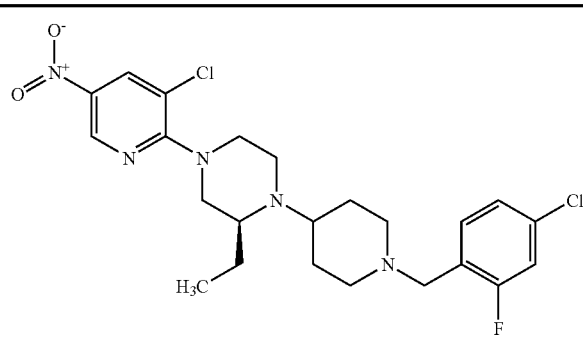 |
| 213 | 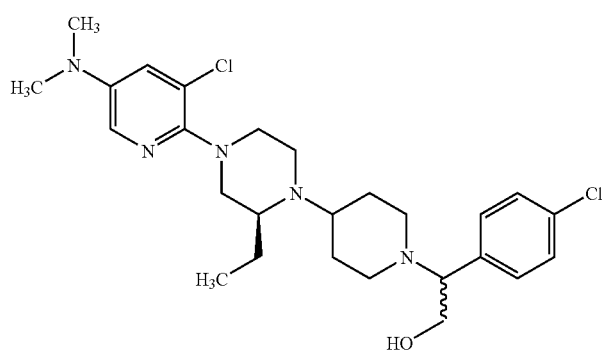 |
| 214 | 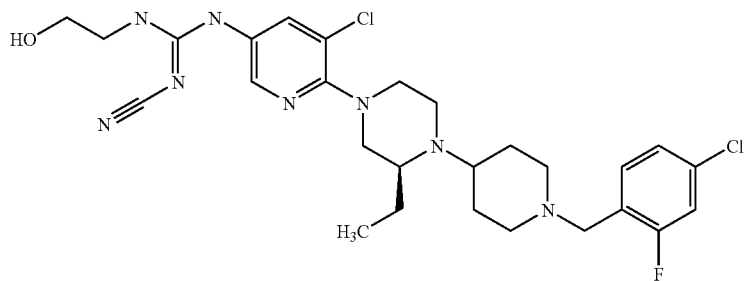 |
| 215 | 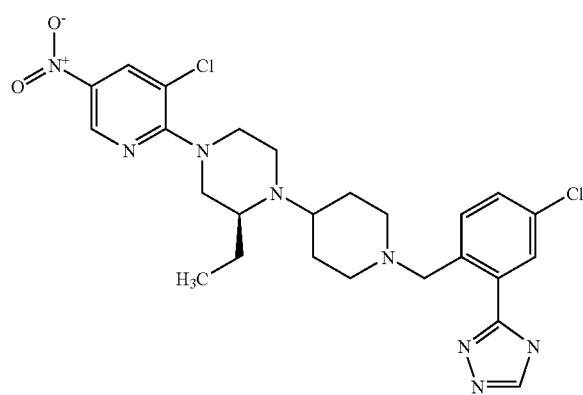 |

-continued

| Compound No. | STRUCTURE |
|---|---|
| 217 | 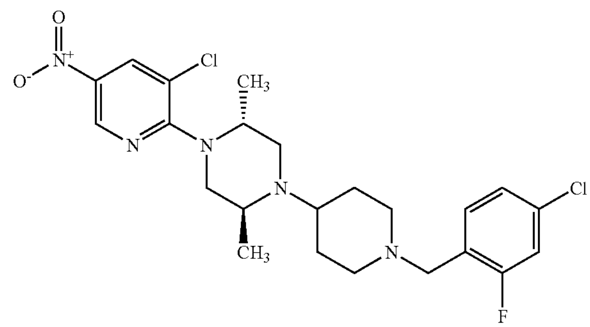 |
| 218 | 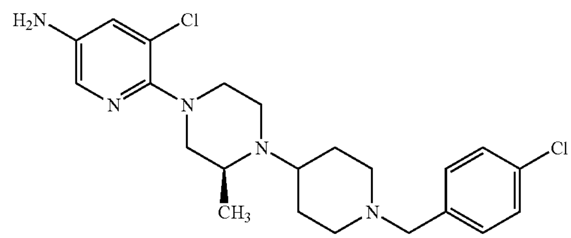 |
| 219 | 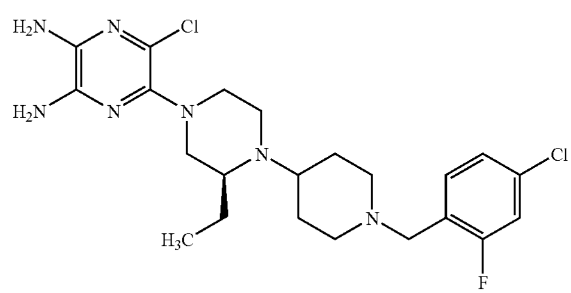 |
| 221 | 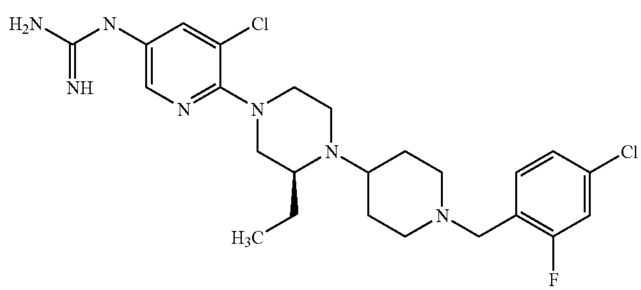 |
| 222 | 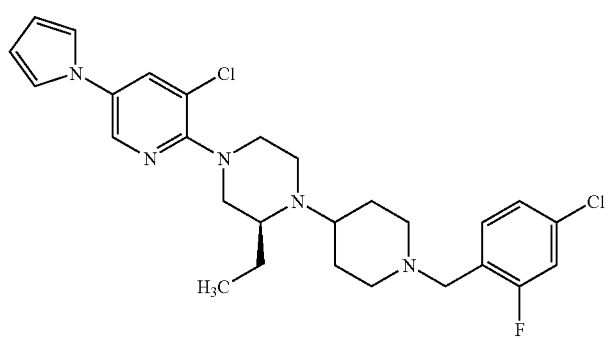 |

| Compound No. | STRUCTURE |
|---|---|
| 223 | 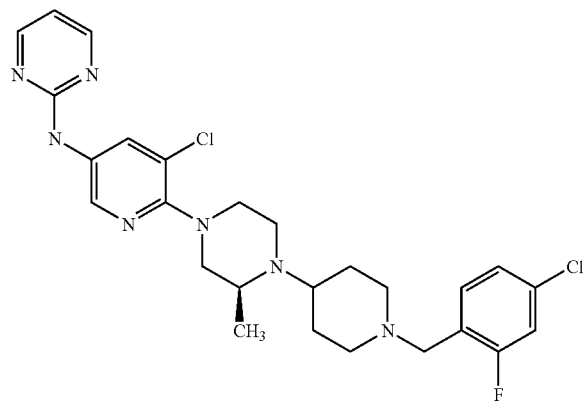 |
| 224 | 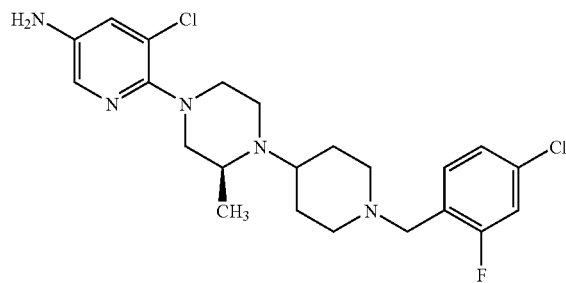 |
| 225 | 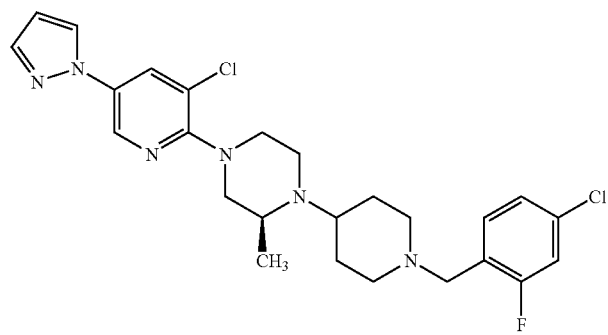 |
| 227 | 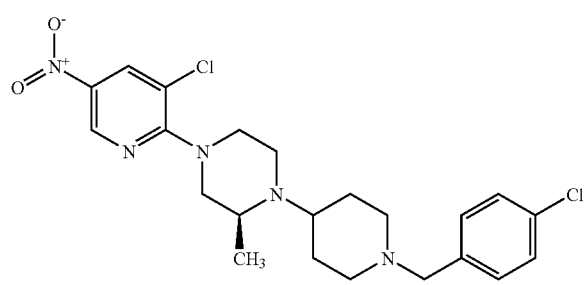 |

-continued
| Compound No. | STRUCTURE |
|---|---|
| 228 | 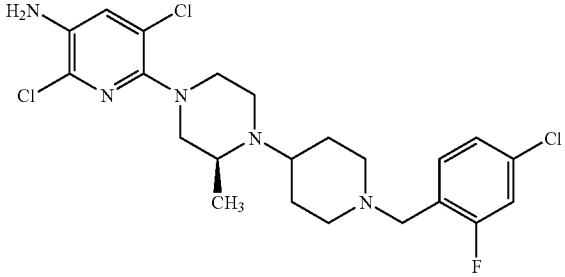 |
| 229 | 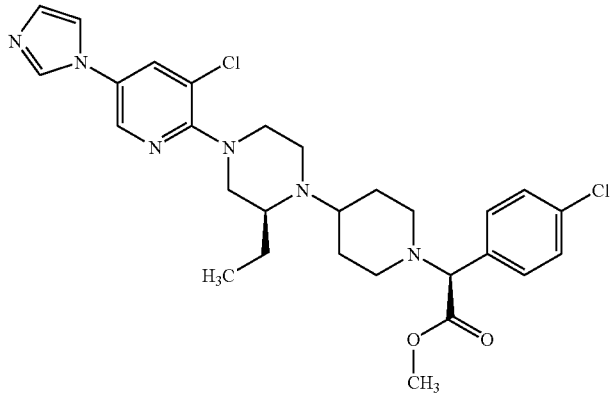 |
| 230 | 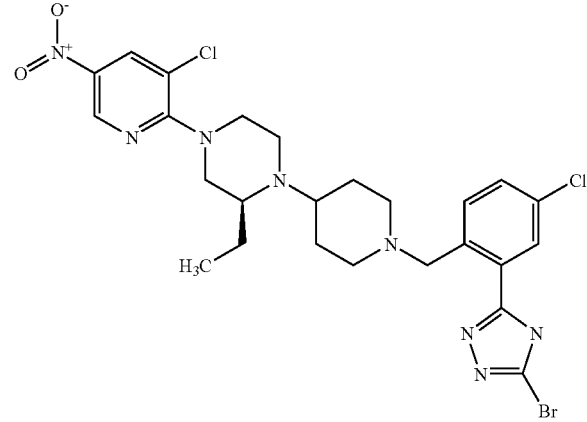 |
| 231 | 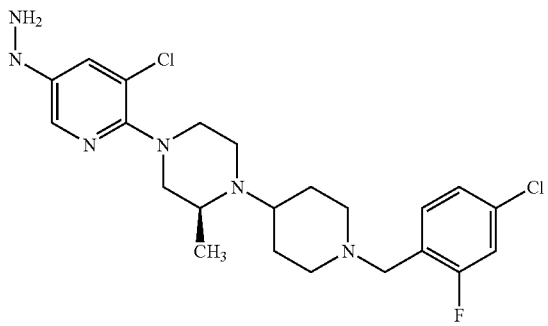 |

-continued
| Compound No. | STRUCTURE |
|---|---|
| 232 | 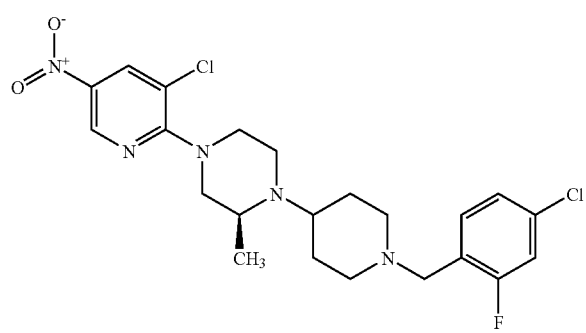 |
| 233 | 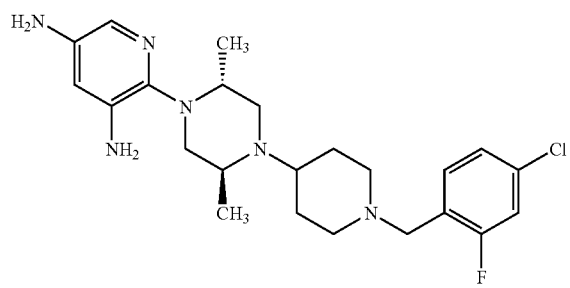 |
| 234 | 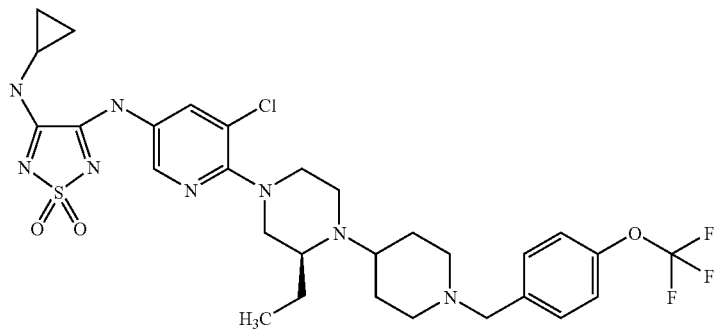 |
| 235 | 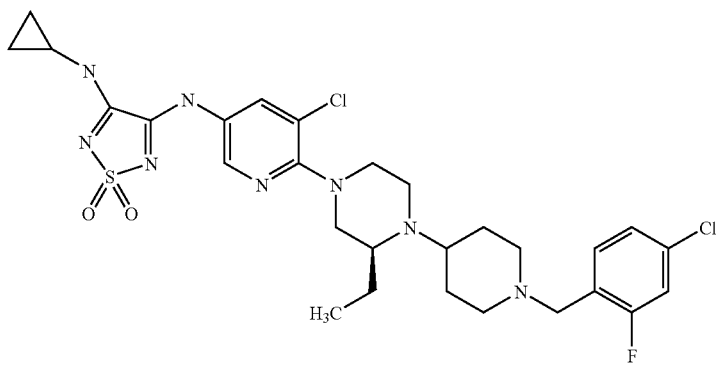 |

-continued

| Compound No. | STRUCTURE |
|---|---|
| 236 | 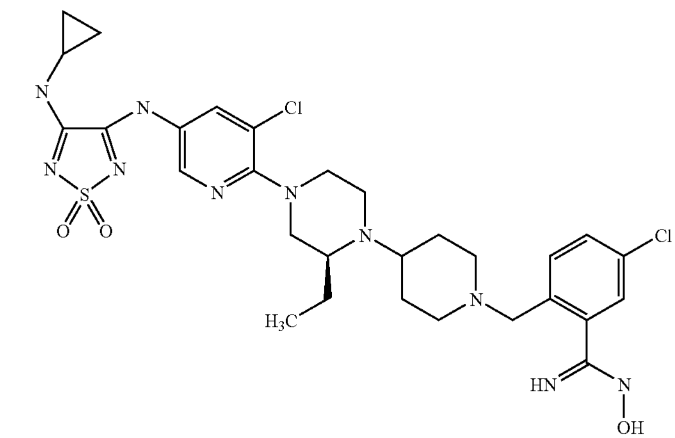 |
| 237 | 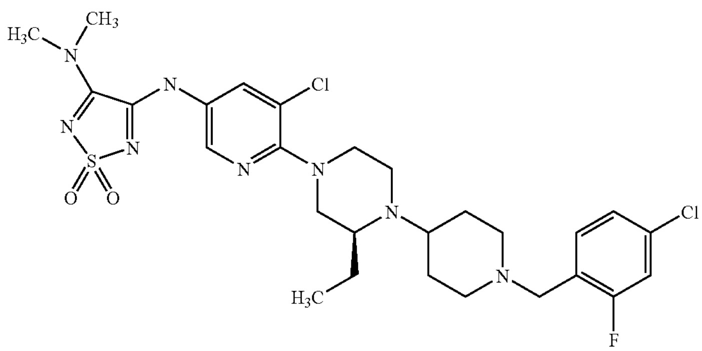 |
| 238 | 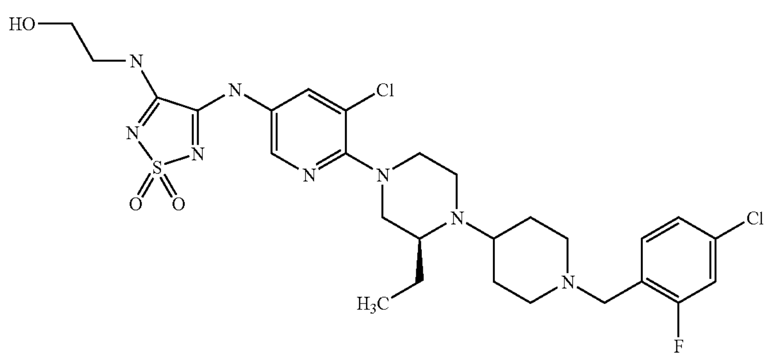 |
| 239 | 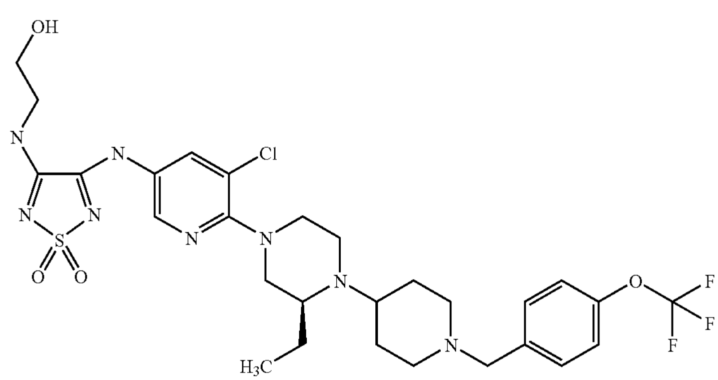 |

|Compound No.|STRUCTURE|
|---|---|
|240|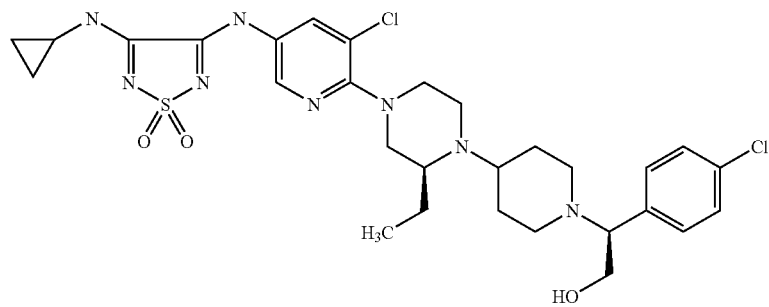|
|241|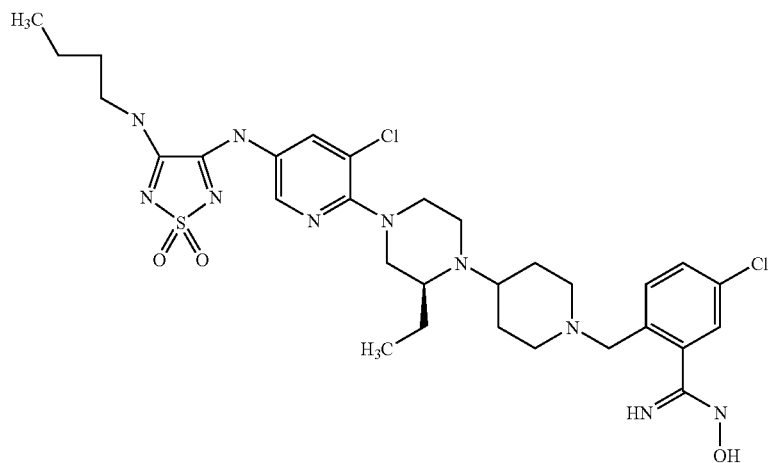|
|242|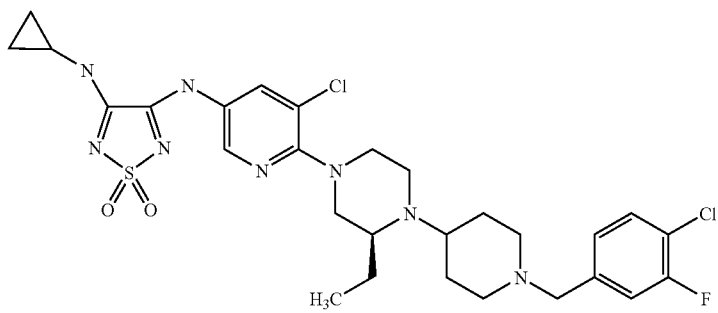|
|243|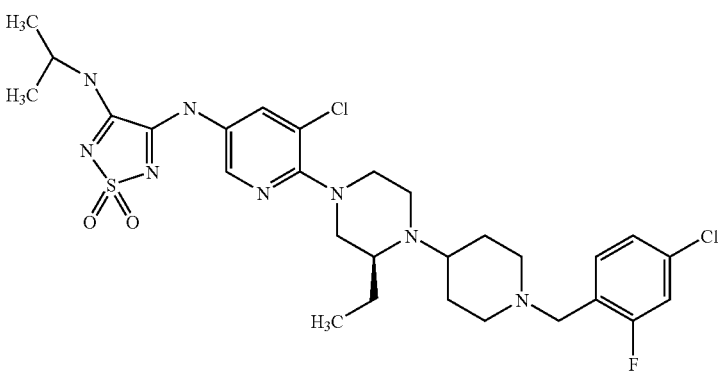|

-continued
| Compound No. | STRUCTURE |
|---|---|
| 244 | 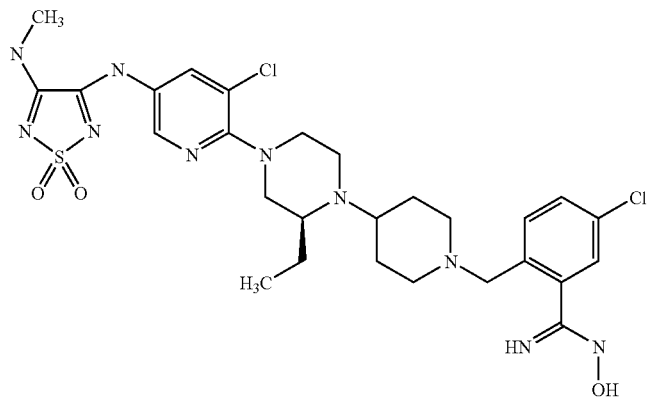 |
| 245 | 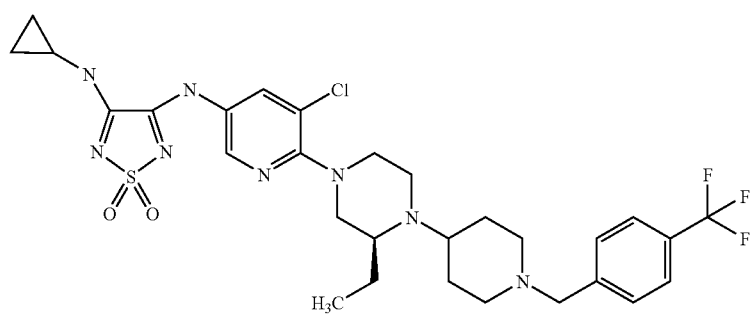 |
| 246 | 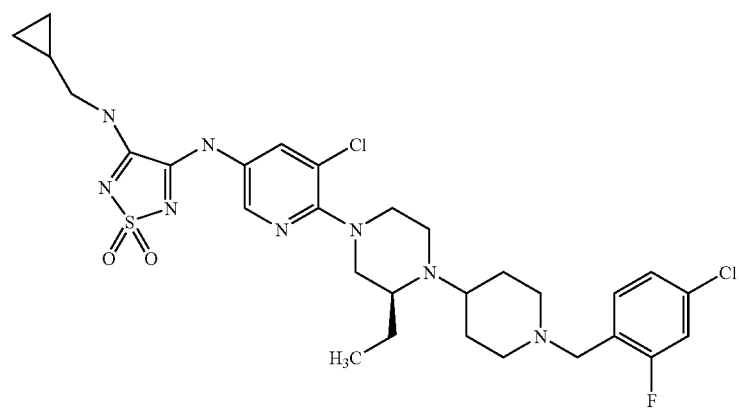 |
| 247 | 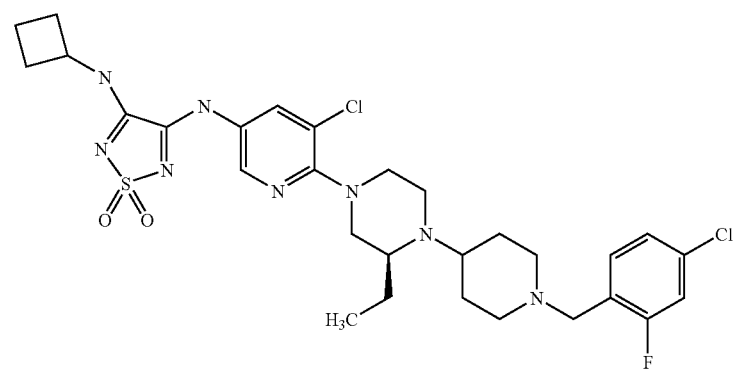 |

-continued
| Compound No. | STRUCTURE |
|---|---|
| 248 | 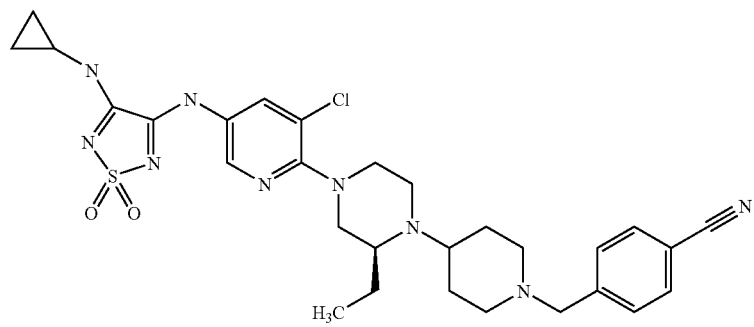 |
| 249 | 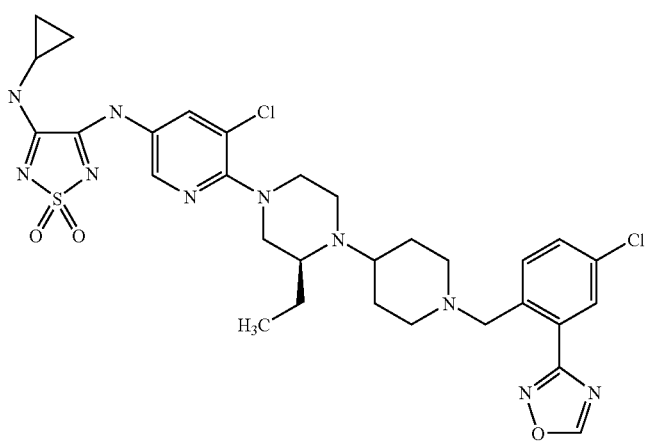 |
| 250 | 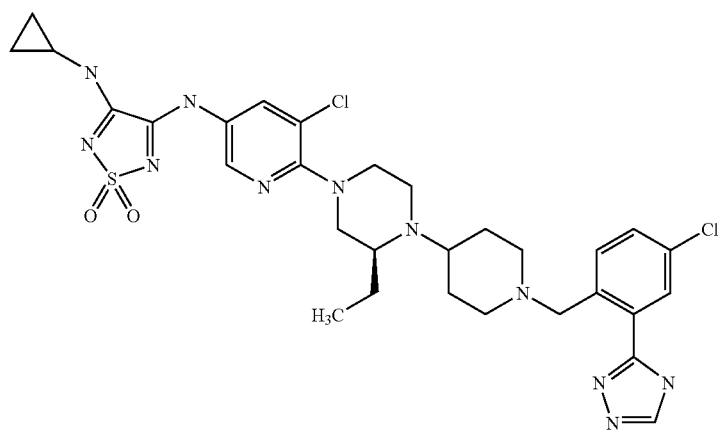 |
| 251 | 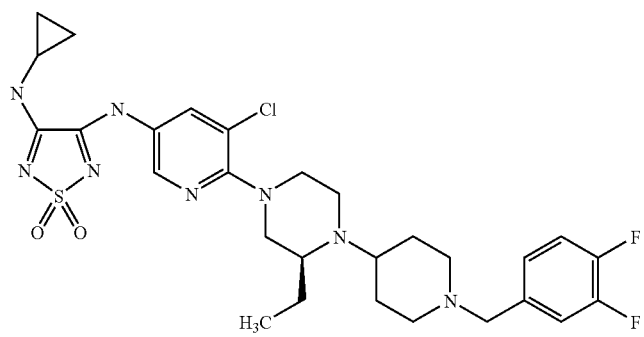 |

-continued
| Compound No. | STRUCTURE |
|---|---|
| 252 | 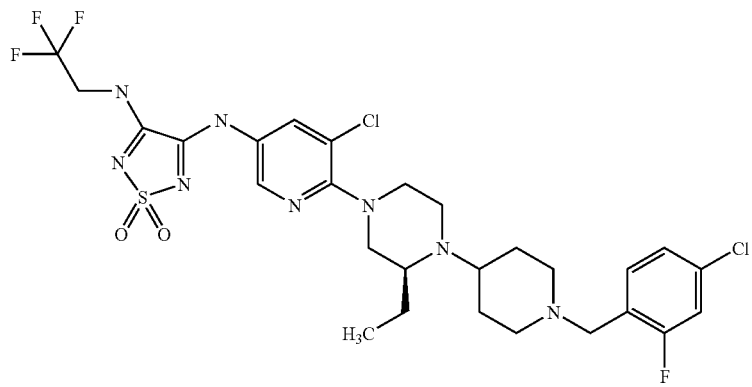 |
| 253 | 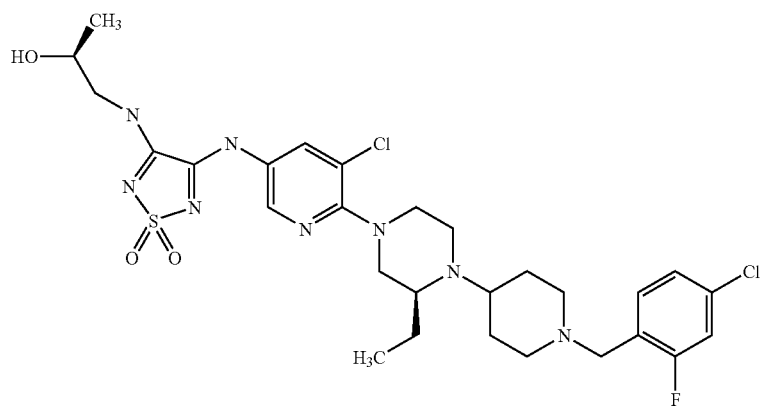 |
| 254 | 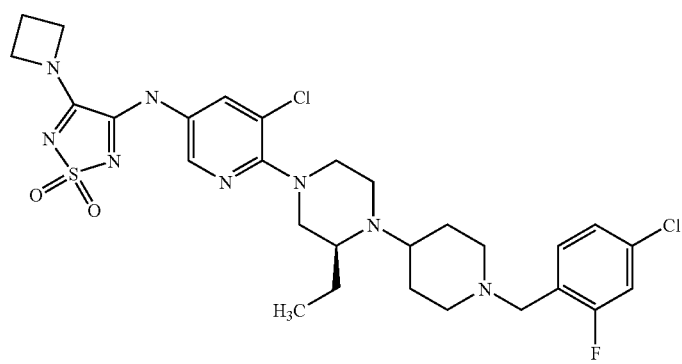 |
| 255 | 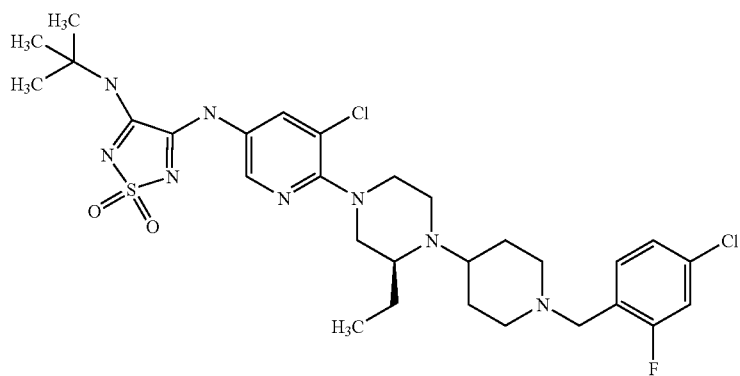 |

| Compound No. | STRUCTURE |
|---|---|
| 256 | 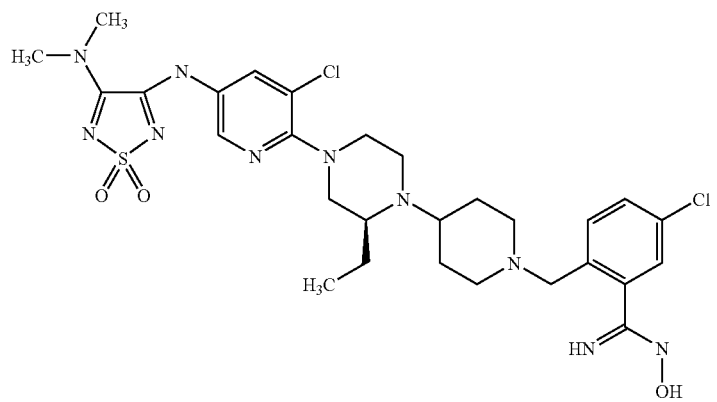 |
| 257 | 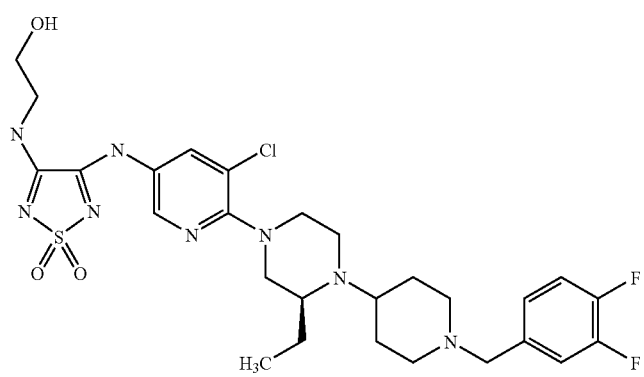 |
| 258 | 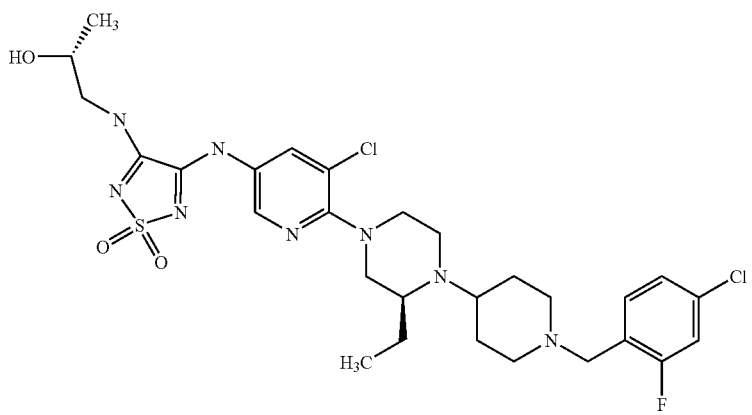 |
| 259 | 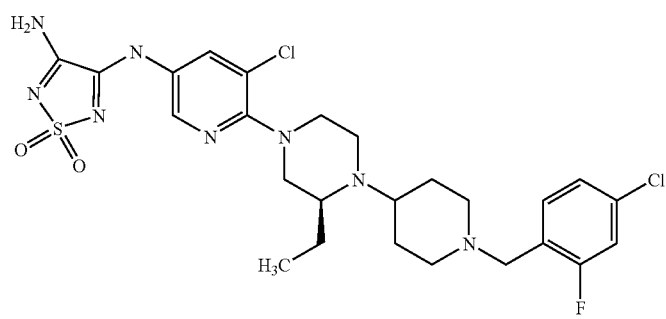 |

| Compound No. | STRUCTURE |
|---|---|
| 260 | 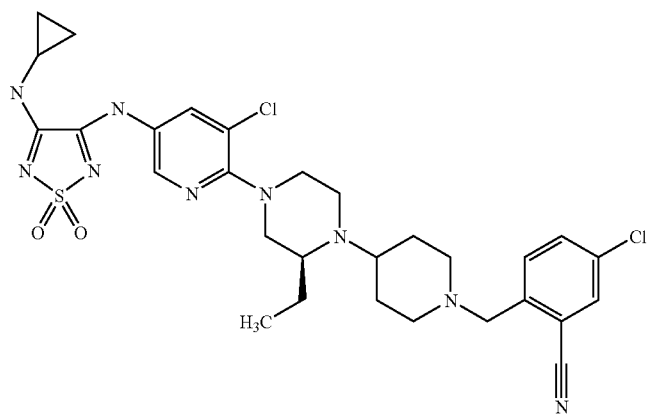 |
| 261 | 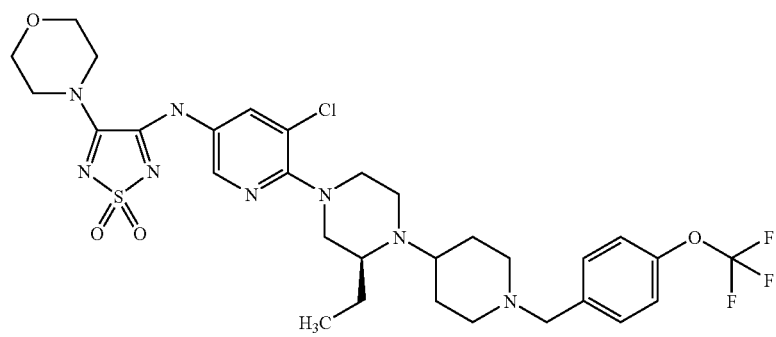 |
| 262 | 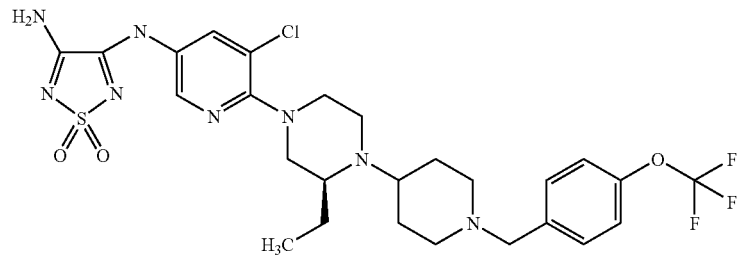 |
| 263 | 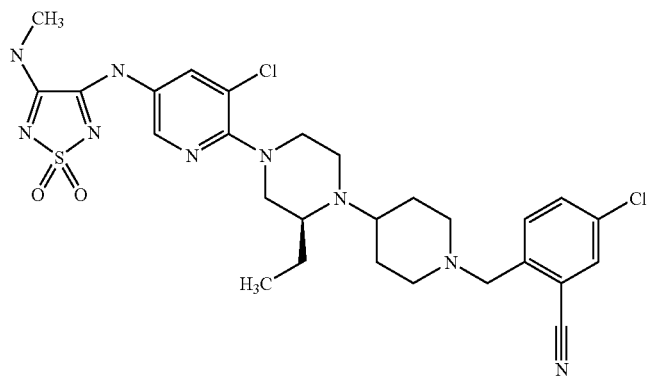 |

| Compound No. | STRUCTURE |
|---|---|
| 264 | 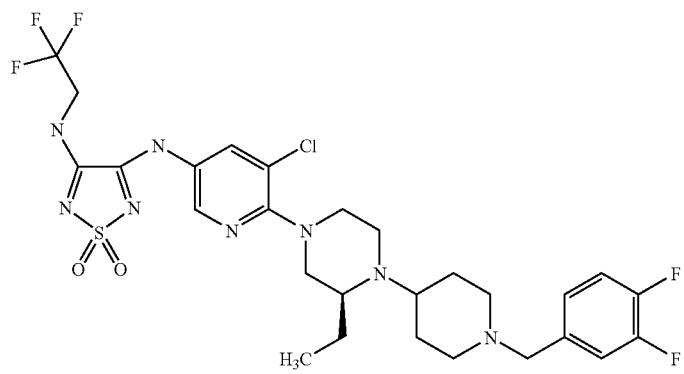 |
| 265 | 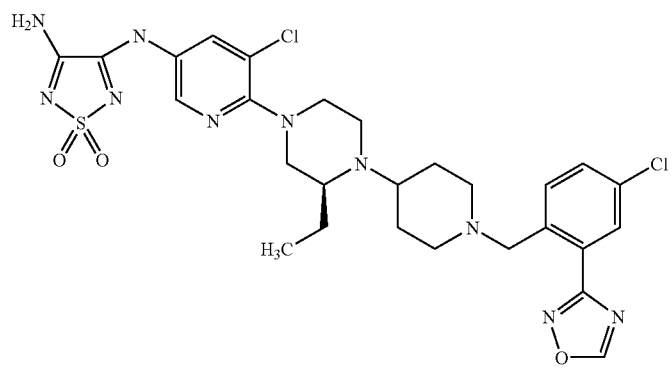 |
| 266 | 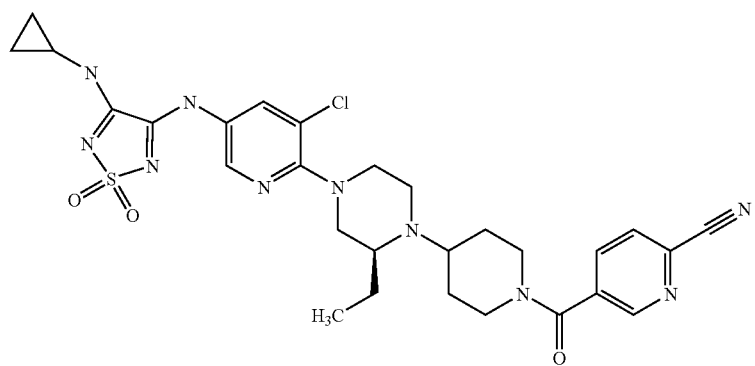 |
| 267 | 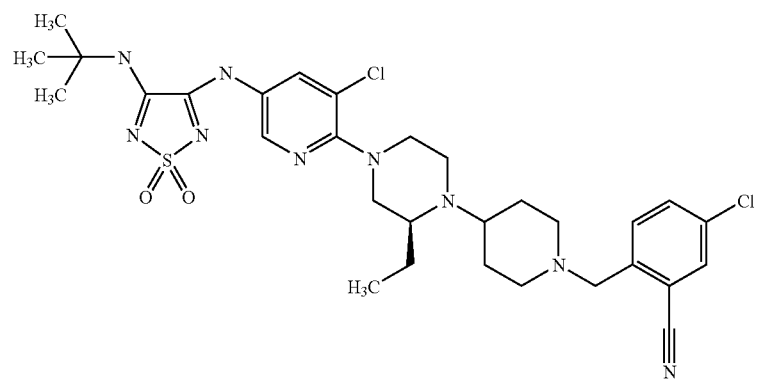 |

-continued
| Compound No. | STRUCTURE |
|---|---|
| 268 | 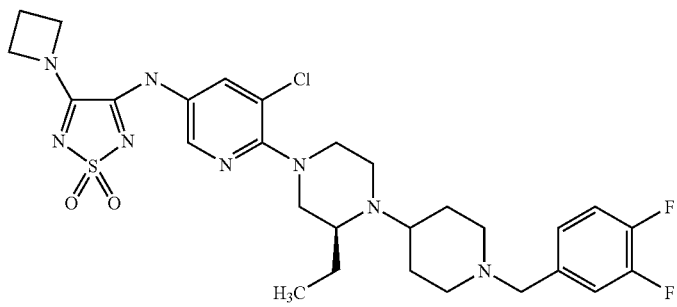 |
| 269 | 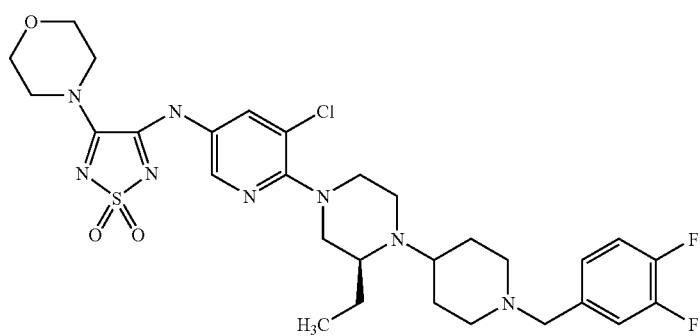 |
| 270 | 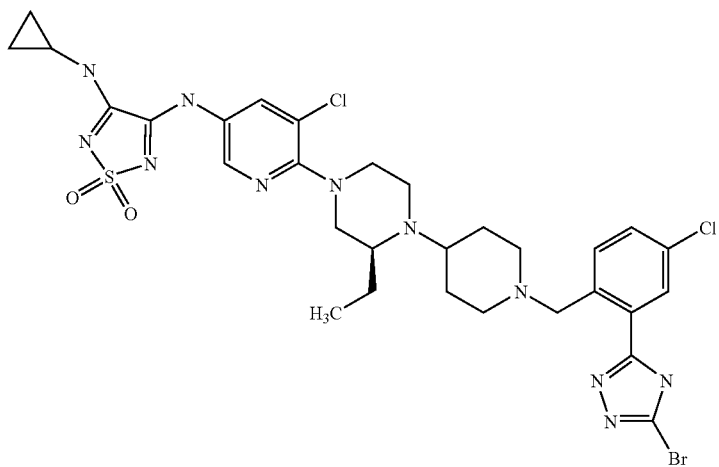 |
| 271 | 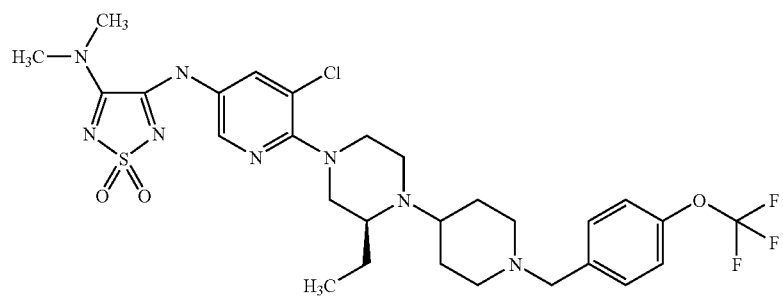 |

| Compound No. | STRUCTURE |
|---|---|
| 272 | 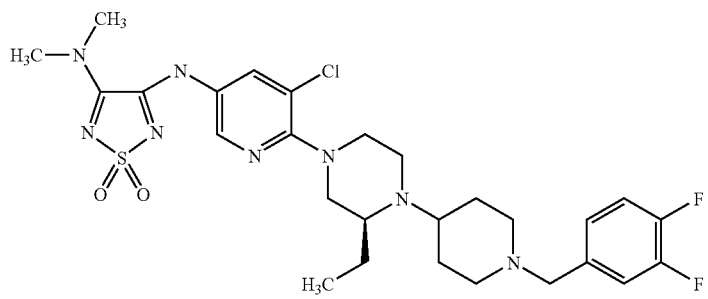 |
| 273 | 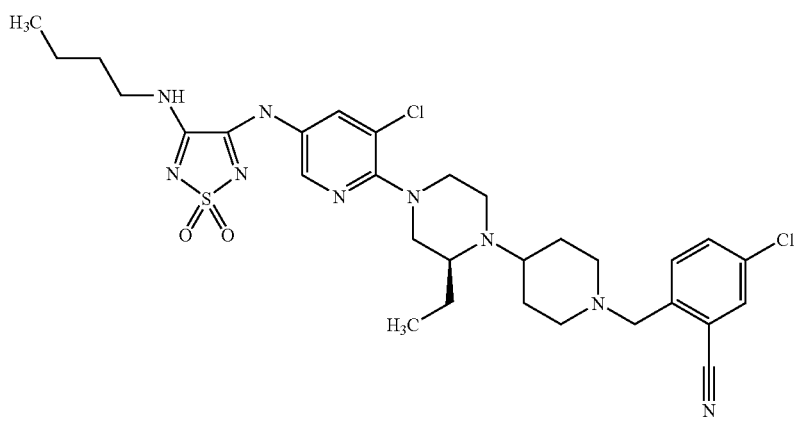 |
| 274 | 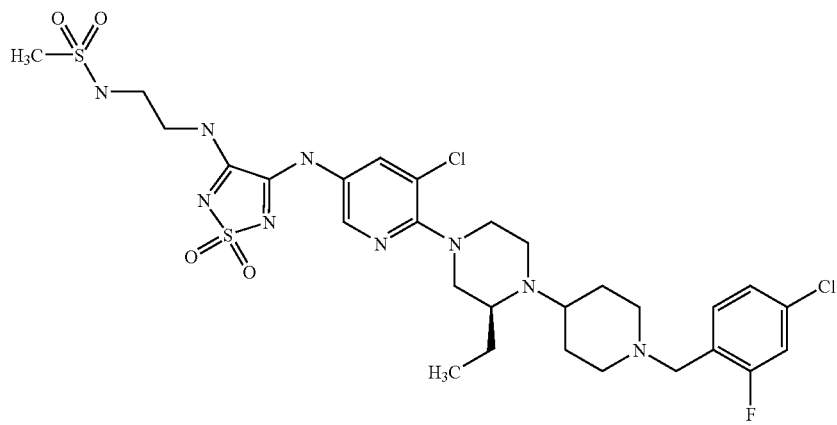 |
| 275 | 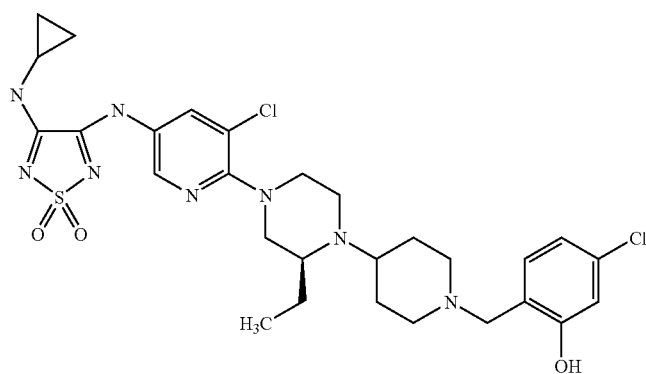 |

| Compound No. | STRUCTURE |
|---|---|
| 276 | 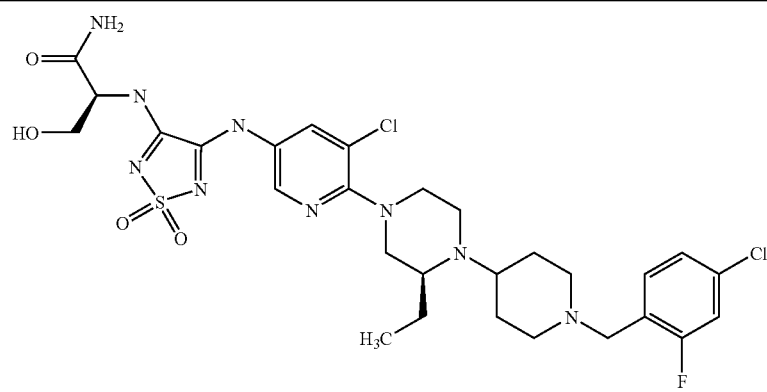 |
| 277 | 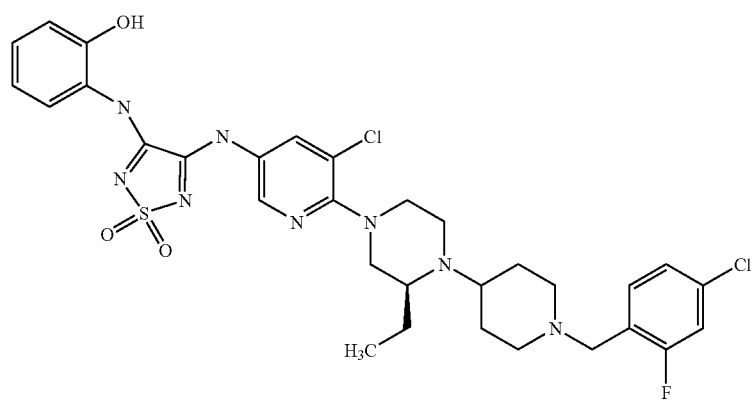 |
| 278 | 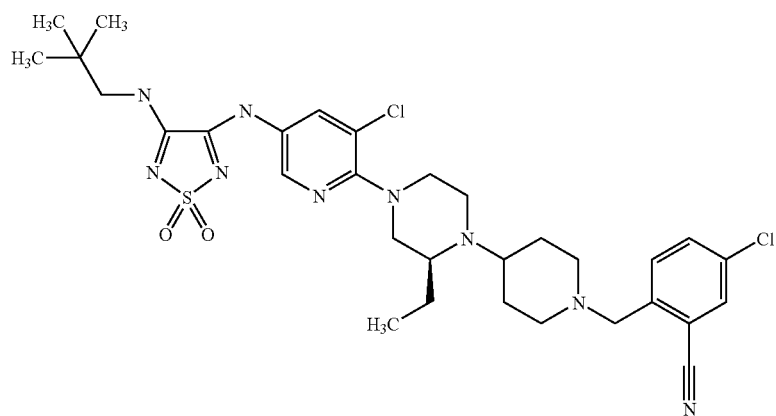 |
| 279 | 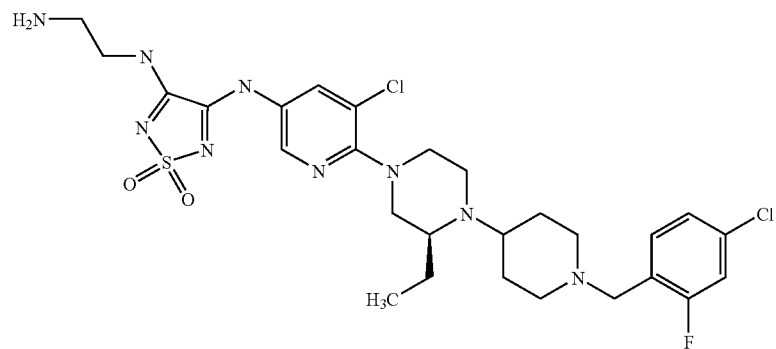 |
and

| Compound No. | STRUCTURE |
|---|---|
| 280 | 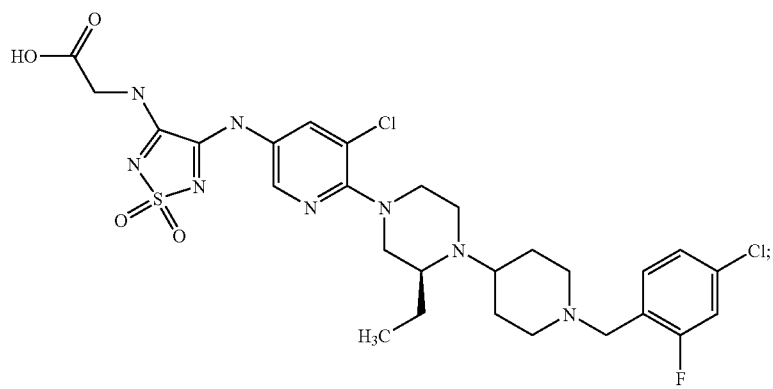 |
or a pharmaceutically acceptable salt thereof.
38. The compound according to 37, selected from the group consisting of:
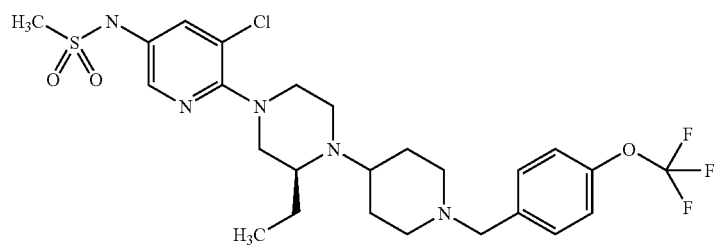
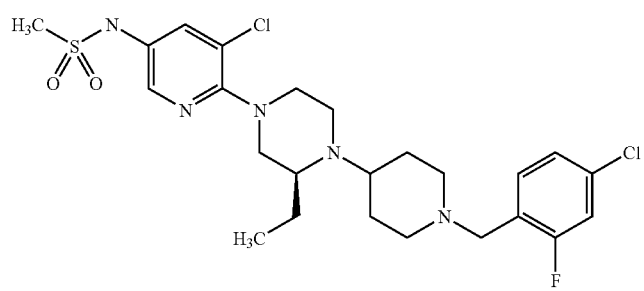
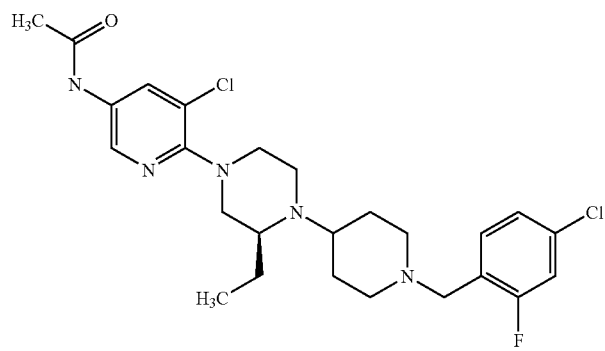

-continued

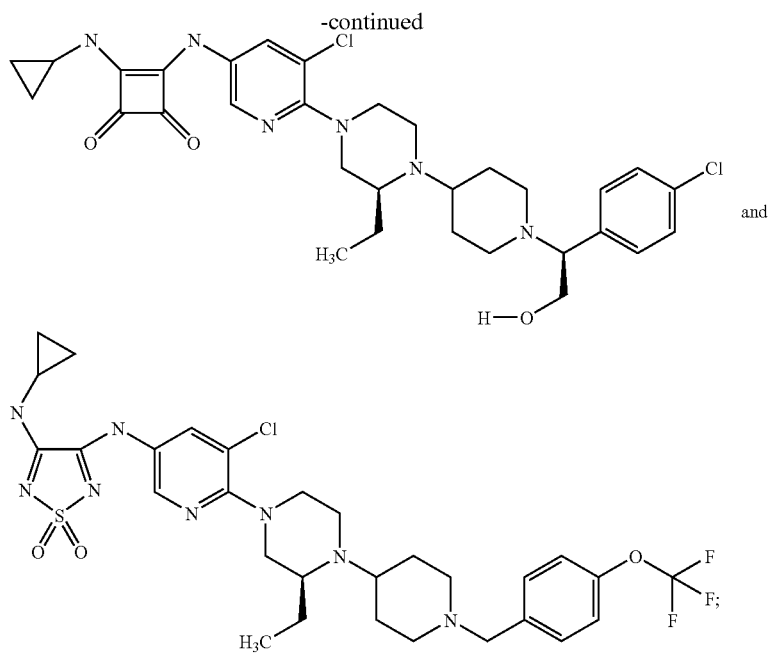

and or a pharmaceutically acceptable salt thereof.

39. A pharmaceutical composition comprising at least one compound of claim 1 or a pharmaceutically acceptable salt, thereof, in combination with at least one pharmaceutically acceptable carrier.

40. The pharmaceutical composition of claim 39, further comprising at least one additional agent, drug, medicament, antibody and/or inhibitor for treating a CXCR3 chemokine receptor mediated disease.

41. A pharmaceutical composition comprising at least one compound of claim 37 or a pharmaceutically acceptable salt or ester thereof, in combination with at least one pharmaceutically acceptable carrier.

* * * * *